(12) United States Patent
Kameda et al.

(10) Patent No.: US 9,464,077 B2
(45) Date of Patent: Oct. 11, 2016

(54) NITROGEN-CONTAINING AROMATIC HETEROCYCLIC COMPOUND

(71) Applicants: Astellas Pharma Inc., Tokyo (JP); KOTOBUKI PHARMACEUTICAL CO., LTD., Nagano (JP)

(72) Inventors: Minoru Kameda, Tokyo (JP); Ikumi Kuriwaki, Tokyo (JP); Kazuhiko Iikubo, Tokyo (JP); Hiroyuki Hisamichi, Tokyo (JP); Yuichiro Kawamoto, Tokyo (JP); Hiroyuki Moritomo, Tokyo (JP); Tomoyuki Suzuki, Tokyo (JP); Takashi Futami, Tokyo (JP); Atsushi Suzuki, Tokyo (JP); Kazuhisa Tsunoyama, Tokyo (JP); Makoto Asaumi, Tokyo (JP); Hiroshi Tomiyama, Nagano (JP); Atsushi Noda, Nagano (JP); Yoshinori Iwai, Nagano (JP); Kazuo Tokuzaki, Nagano (JP); Haruki Okada, Nagano (JP); Kozo Miyasaka, Nagano (JP)

(73) Assignees: Astellas Pharma Inc., Tokyo (JP); KOTOBUKI PHARMACEUTICAL CO., LTD., Nagano (JP)

( * ) Notice: Subject to any disclaimer, the term of this patent is extended or adjusted under 35 U.S.C. 154(b) by 413 days.

(21) Appl. No.: 13/979,327

(22) PCT Filed: Feb. 26, 2013

(86) PCT No.: PCT/JP2013/054878
§ 371 (c)(1),
(2) Date: Jul. 11, 2013

(87) PCT Pub. No.: WO2013/129369
PCT Pub. Date: Sep. 6, 2013

(65) Prior Publication Data
US 2014/0142084 A1    May 22, 2014

(30) Foreign Application Priority Data
Feb. 28, 2012 (JP) .............................. 2012-042065

(51) Int. Cl.
| | | |
|---|---|---|
| C07D 413/12 | (2006.01) |
| C07D 403/12 | (2006.01) |
| C07D 401/14 | (2006.01) |
| C07D 405/14 | (2006.01) |
| C07D 401/12 | (2006.01) |
| C07D 239/42 | (2006.01) |
| C07D 239/47 | (2006.01) |
| C07D 471/10 | (2006.01) |
| C07D 403/14 | (2006.01) |
| C07D 405/12 | (2006.01) |
| C07D 417/12 | (2006.01) |
| C07D 417/14 | (2006.01) |
| C07D 451/02 | (2006.01) |
| C07D 451/04 | (2006.01) |
| C07D 453/02 | (2006.01) |
| C07D 487/10 | (2006.01) |
| C07D 491/107 | (2006.01) |
| A61K 31/506 | (2006.01) |

(52) U.S. Cl.
CPC ........... *C07D 413/12* (2013.01); *C07D 239/42* (2013.01); *C07D 239/47* (2013.01); *C07D 401/12* (2013.01); *C07D 401/14* (2013.01); *C07D 403/12* (2013.01); *C07D 403/14* (2013.01); *C07D 405/12* (2013.01); *C07D 405/14* (2013.01); *C07D 417/12* (2013.01); *C07D 417/14* (2013.01); *C07D 451/02* (2013.01); *C07D 451/04* (2013.01); *C07D 453/02* (2013.01); *C07D 471/10* (2013.01); *C07D 487/10* (2013.01); *C07D 491/107* (2013.01)

(58) Field of Classification Search
None
See application file for complete search history.

(56) References Cited

FOREIGN PATENT DOCUMENTS

| | | |
|---|---|---|
| CN | 101155799 A | 4/2008 |
| CN | 101611014 A | 12/2009 |
| TW | 200819439 A | 5/2008 |
| WO | 03 066601 | 8/2003 |
| WO | 2005 002673 | 1/2005 |
| WO | 2006 101977 | 9/2006 |
| WO | 2007 022380 | 2/2007 |
| WO | 2007 056075 | 5/2007 |
| WO | 2007 071752 | 6/2007 |

(Continued)

OTHER PUBLICATIONS

Database Registry Chemical Abstracts Service, Columbus, Ohio, Accession No. RN 780809-21-4, Entered STN: Nov. 15, 2004.*

(Continued)

*Primary Examiner* — Samantha Shterengarts
(74) *Attorney, Agent, or Firm* — Oblon, McClelland, Maier & Neustadt, L.L.P.

(57) ABSTRACT

Provided is a compound useful as a prophylactic and/or therapeutic agent for bladder cancer.
As a result of studies on compounds having FGFR inhibitory action, the present inventors have found that the nitrogen-containing aromatic heterocyclic compounds of the present invention have inhibitory action on FGFR1, FGFR2, and/or FGFR3, particularly, mutant FGFR3, and thus, the present invention has been accomplished. The nitrogen-containing aromatic heterocyclic compound of the present invention can be used as a therapeutic agent for various cancers related to FGFR1, FGFR2, and/or FGFR3, such as lung cancer and hormone therapy-resistant breast cancer, stomach cancer, triple negative breast cancer, endometrial cancer, bladder cancer, and glioblastoma, particularly as a prophylactic and/or therapeutic agent for mutant FGFR3-positive bladder cancer.

20 Claims, No Drawings

(56) References Cited

FOREIGN PATENT DOCUMENTS

| WO | 2008 008234 | 1/2008 |
|----|-------------|--------|
| WO | 2008 075068 | 6/2008 |
| WO | 2009 046784 | 4/2009 |
| WO | 2009 056886 | 5/2009 |
| WO | 2009 153592 | 12/2009 |

OTHER PUBLICATIONS

International Search Report issued Apr. 2, 2013, in PCT/JP2013/054878.

Extended European Search Report issued on Jul. 22, 2015 in European Patent Application No. 13754501.8.
Combined Office Action and Search Report issued May 12, 2015 in Chinese Patent Application No. 2013800114237.
Office Action issued Dec. 14, 2015 in Chinese Patent Application No. 2013800114237.
Office Action issued Sep. 21, 2015 in Eurasian Patent Application No. 201491595.
Office Action dated Aug. 4, 2016 issued in corresponding European patent application No. 13 754 501.8.

* cited by examiner

```
                        SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 1
cctggactac tccttcgaca                                              20

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 2
tcttctccat cttggagatg agg                                          23

<210> SEQ ID NO 3
```

```
<211> LENGTH: 23
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 3
tgtttgaccg agtctacact cac                                            23

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 4
ttctccatgg agttcagatc tgtg                                           24

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 5
tcctgctctg ccggtcgcac                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 6
cagcggctcc gtggaggtca                                                20

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 7
ggatccgcca ccatgggcgc ccctgcc                                        27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 8
gaattctcag atcttctcca tcttgg                                         26

<210> SEQ ID NO 9
<211> LENGTH: 2856
```

<212> TYPE: DNA
<213> ORGANISM: Homo sapiens
<220> FEATURE:
<221> NAME/KEY: CDS
<222> LOCATION: (1)..(2856)

<400> SEQUENCE: 9

```
atg ggc gcc cct gcc tgc gcc ctc gcg ctc tgc gtg gcc gtg gcc atc      48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg      96
Val Ala Gly Ala Ser Ser Glu Ser Leu Gly Thr Glu Gln Arg Val Val
                20                  25                  30 ggg cga gcg gca gaa gtc ccg ggc cca gag ccc ggc cag cag gag cag     144
Gly Arg Ala Ala Glu Val Pro Gly Pro Glu Pro Gly Gln Gln Glu Gln
            35                  40                  45 ttg gtc ttc ggc agc ggg gat gct gtg gag ctg agc tgt ccc ccg ccc     192
Leu Val Phe Gly Ser Gly Asp Ala Val Glu Leu Ser Cys Pro Pro Pro
        50                  55                  60 ggg ggt ggt ccc atg ggg ccc act gtc tgg gtc aag gat ggc aca ggg     240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg     288
Leu Val Pro Ser Glu Arg Val Leu Val Gly Pro Gln Arg Leu Gln Val
                85                  90                  95 ctg aat gcc tcc cac gag gac tcc ggg gcc tac agc tgc cgg cag cgg     336
Leu Asn Ala Ser His Glu Asp Ser Gly Ala Tyr Ser Cys Arg Gln Arg
                100                 105                 110 ctc acg cag cgc gta ctg tgc cac ttc agt gtg cgg gtg aca gac gct     384
Leu Thr Gln Arg Val Leu Cys His Phe Ser Val Arg Val Thr Asp Ala
            115                 120                 125 cca tcc tcg gga gat gac gaa gac ggg gag gac gag gct gag gac aca     432
Pro Ser Ser Gly Asp Asp Glu Asp Gly Glu Asp Glu Ala Glu Asp Thr
        130                 135                 140 ggt gtg gac aca ggg gcc cct tac tgg aca cgg ccc gag cgg atg gac     480
Gly Val Asp Thr Gly Ala Pro Tyr Trp Thr Arg Pro Glu Arg Met Asp
145                 150                 155                 160 aag aag ctg ctg gcc gtg ccg gcc gcc aac acc gtc cgc ttc cgc tgc     528
Lys Lys Leu Leu Ala Val Pro Ala Ala Asn Thr Val Arg Phe Arg Cys
                165                 170                 175 cca gcc gct ggc aac ccc act ccc tcc atc tcc tgg ctg aag aac ggc     576
Pro Ala Ala Gly Asn Pro Thr Pro Ser Ile Ser Trp Leu Lys Asn Gly
                180                 185                 190 agg gag ttc cgc ggc gag cac cgc att gga ggc atc aag ctg cgg cat     624
Arg Glu Phe Arg Gly Glu His Arg Ile Gly Gly Ile Lys Leu Arg His
            195                 200                 205 cag cag tgg agc ctg gtc atg gaa agc gtg gtg ccc tcg gac cgc ggc     672
Gln Gln Trp Ser Leu Val Met Glu Ser Val Val Pro Ser Asp Arg Gly
        210                 215                 220 aac tac acc tgc gtc gtg gag aac aag ttt ggc agc atc cgg cag acg     720
Asn Tyr Thr Cys Val Val Glu Asn Lys Phe Gly Ser Ile Arg Gln Thr
225                 230                 235                 240 tac acg ctg gac gtg ctg gag cgc tcc ccg cac cgg ccc atc ctg cag     768
Tyr Thr Leu Asp Val Leu Glu Arg Ser Pro His Arg Pro Ile Leu Gln
                245                 250                 255 gcg ggg ctg ccg gcc aac cag acg gcg gtg ctg ggc agc gac gtg gag     816
Ala Gly Leu Pro Ala Asn Gln Thr Ala Val Leu Gly Ser Asp Val Glu
                260                 265                 270 ttc cac tgc aag gtg tac agt gac gca cag ccc cac atc cag tgg ctc     864
Phe His Cys Lys Val Tyr Ser Asp Ala Gln Pro His Ile Gln Trp Leu
            275                 280                 285
```

| | | |
|---|---|---|
| aag cac gtg gag gtg aat ggc agc aag gtg ggc ccg gac ggc aca ccc<br>Lys His Val Glu Val Asn Gly Ser Lys Val Gly Pro Asp Gly Thr Pro<br>290                            295                        300 | 912 |
| tac gtt acc gtg ctc aag tcc tgg atc agt gag agt gtg gag gcc gac<br>Tyr Val Thr Val Leu Lys Ser Trp Ile Ser Glu Ser Val Glu Ala Asp<br>305                          310                     315                 320 | 960 |
| gtg cgc ctc cgc ctg gcc aat gtg tcg gag cgg gac ggg ggc gag tac<br>Val Arg Leu Arg Leu Ala Asn Val Ser Glu Arg Asp Gly Gly Glu Tyr<br>                       325                     330                     335 | 1008 |
| ctc tgt cga gcc acc aat ttc ata ggc gtg gcc gag aag gcc ttt tgg<br>Leu Cys Arg Ala Thr Asn Phe Ile Gly Val Ala Glu Lys Ala Phe Trp<br>                   340                     345                     350 | 1056 |
| ctg agc gtt cac ggg ccc cga gca gcc gag gag gag ctg gtg gag gct<br>Leu Ser Val His Gly Pro Arg Ala Ala Glu Glu Glu Leu Val Glu Ala<br>                 355                     360                     365 | 1104 |
| gac gag gcg ggc agt gtg tat gca ggc atc ctc agc tac ggg gtg ggc<br>Asp Glu Ala Gly Ser Val Tyr Ala Gly Ile Leu Ser Tyr Gly Val Gly<br>370                            375                     380 | 1152 |
| ttc ttc ctg ttc atc ctg gtg gtg gcg gct gtg acg ctc tgc cgc ctg<br>Phe Phe Leu Phe Ile Leu Val Val Ala Ala Val Thr Leu Cys Arg Leu<br>385                            390                     395                 400 | 1200 |
| cgc agc ccc ccc aag aaa ggc ctg ggc tcc ccc acc gtg cac aag atc<br>Arg Ser Pro Pro Lys Lys Gly Leu Gly Ser Pro Thr Val His Lys Ile<br>                   405                     410                     415 | 1248 |
| tcc cgc ttc ccg ctc aag cga cag gtg tcc ctg gag tcc aac gcg tcc<br>Ser Arg Phe Pro Leu Lys Arg Gln Val Ser Leu Glu Ser Asn Ala Ser<br>                 420                     425                     430 | 1296 |
| atg agc tcc aac aca cca ctg gtg cgc atc gca agg ctg tcc tca ggg<br>Met Ser Ser Asn Thr Pro Leu Val Arg Ile Ala Arg Leu Ser Ser Gly<br>                 435                     440                     445 | 1344 |
| gag ggc ccc acg ctg gcc aat gtc tcc gag ctc gag ctg cct gcc gac<br>Glu Gly Pro Thr Leu Ala Asn Val Ser Glu Leu Glu Leu Pro Ala Asp<br>450                            455                     460 | 1392 |
| ccc aaa tgg gag ctg tct cgg gcc cgg ctg acc ctg ggc aag ccc ctt<br>Pro Lys Trp Glu Leu Ser Arg Ala Arg Leu Thr Leu Gly Lys Pro Leu<br>465                            470                     475                 480 | 1440 |
| ggg gag ggc tgc ttc ggc cag gtg gtc atg gcg gag gcc atc ggc att<br>Gly Glu Gly Cys Phe Gly Gln Val Val Met Ala Glu Ala Ile Gly Ile<br>                   485                     490                     495 | 1488 |
| gac aag gac cgg gcc gcc aag cct gtc acc gta gcc gtg aag atg ctg<br>Asp Lys Asp Arg Ala Ala Lys Pro Val Thr Val Ala Val Lys Met Leu<br>                 500                     505                     510 | 1536 |
| aaa gac gat gcc act gac aag gac ctg tcg gac ctg gtg tct gag atg<br>Lys Asp Asp Ala Thr Asp Lys Asp Leu Ser Asp Leu Val Ser Glu Met<br>                 515                     520                     525 | 1584 |
| gag atg atg aag atg atc ggg aaa cac aaa aac atc atc aac ctg ctg<br>Glu Met Met Lys Met Ile Gly Lys His Lys Asn Ile Ile Asn Leu Leu<br>530                            535                     540 | 1632 |
| ggc gcc tgc acg cag ggc ggg ccc ctg tac gtg ctg gtg gag tac gcg<br>Gly Ala Cys Thr Gln Gly Gly Pro Leu Tyr Val Leu Val Glu Tyr Ala<br>545                            550                     555                 560 | 1680 |
| gcc aag ggt aac ctg cgg gag ttt ctg cgg gcg cgg cgg ccc ccg ggc<br>Ala Lys Gly Asn Leu Arg Glu Phe Leu Arg Ala Arg Arg Pro Pro Gly<br>                   565                     570                     575 | 1728 |
| ctg gac tac tcc ttc gac acc tgc aag ccg ccc gag gag cag ctc acc<br>Leu Asp Tyr Ser Phe Asp Thr Cys Lys Pro Pro Glu Glu Gln Leu Thr<br>                 580                     585                     590 | 1776 |
| ttc aag gac ctg gtg tcc tgt gcc tac cag gtg gcc cgg ggc atg gag<br>Phe Lys Asp Leu Val Ser Cys Ala Tyr Gln Val Ala Arg Gly Met Glu | 1824 |

```
                    595                  600                  605
tac ttg gcc tcc cag aag tgc atc cac agg gac ctg gct gcc cgc aat     1872
Tyr Leu Ala Ser Gln Lys Cys Ile His Arg Asp Leu Ala Ala Arg Asn
    610                 615                 620 gtg ctg gtg acc gag gac aac gtg atg aag atc gca gac ttc ggg ctg     1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc     1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc     2016
Arg Leu Pro Val Lys Trp Met Ala Pro Glu Ala Leu Phe Asp Arg Val
            660                 665                 670 tac act cac cag agt gac gtc tgg tcc ttt ggg gtc ctg ctc tgg gag     2064
Tyr Thr His Gln Ser Asp Val Trp Ser Phe Gly Val Leu Leu Trp Glu
        675                 680                 685 atc ttc acg ctg ggg ggc tcc ccg tac ccc ggc atc cct gtg gag gag     2112
Ile Phe Thr Leu Gly Gly Ser Pro Tyr Pro Gly Ile Pro Val Glu Glu
    690                 695                 700 ctc ttc aag ctg ctg aag gag ggc cac cgc atg gac aag ccc gcc aac     2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg     2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt     2256
Pro Ser Gln Arg Pro Thr Phe Lys Gln Leu Val Glu Asp Leu Asp Arg
            740                 745                 750 gtc ctt acc gtg acg tcc acc gac gta aag gcg aca cag gag gag aac     2304
Val Leu Thr Val Thr Ser Thr Asp Val Lys Ala Thr Gln Glu Glu Asn
        755                 760                 765 cgg gag ctg agg agc agg tgt gag gag ctc cac ggg aag aac ctg gaa     2352
Arg Glu Leu Arg Ser Arg Cys Glu Glu Leu His Gly Lys Asn Leu Glu
    770                 775                 780 ctg ggg aag atc atg gac agg ttc gaa gag gtt gtg tac cag gcc atg     2400
Leu Gly Lys Ile Met Asp Arg Phe Glu Glu Val Val Tyr Gln Ala Met
785                 790                 795                 800 gag gaa gtt cag aag cag aag gaa ctt tcc aaa gct gaa atc cag aaa     2448
Glu Glu Val Gln Lys Gln Lys Glu Leu Ser Lys Ala Glu Ile Gln Lys
                805                 810                 815 gtt cta aaa gaa aaa gac caa ctt acc aca gat ctg aac tcc atg gag     2496
Val Leu Lys Glu Lys Asp Gln Leu Thr Thr Asp Leu Asn Ser Met Glu
            820                 825                 830 aag tcc ttc tcc gac ctc ttc aag cgt ttt gag aaa cag aaa gag gtg     2544
Lys Ser Phe Ser Asp Leu Phe Lys Arg Phe Glu Lys Gln Lys Glu Val
        835                 840                 845 atc gag ggc tac cgc aag aac gaa gag tca ctg aag aag tgc gtg gag     2592
Ile Glu Gly Tyr Arg Lys Asn Glu Glu Ser Leu Lys Lys Cys Val Glu
    850                 855                 860 gat tac ctg gca agg atc acc cag gag ggc cag agg tac caa gcc ctg     2640
Asp Tyr Leu Ala Arg Ile Thr Gln Glu Gly Gln Arg Tyr Gln Ala Leu
865                 870                 875                 880 aag gcc cac gcg gag gag aag ctg cag ctg gca aac gag gag atc gcc     2688
Lys Ala His Ala Glu Glu Lys Leu Gln Leu Ala Asn Glu Glu Ile Ala
                885                 890                 895 cag gtc cgg agc aag gcc cag gcg gaa gcg ttg gcc ctc cag gcc agc     2736
Gln Val Arg Ser Lys Ala Gln Ala Glu Ala Leu Ala Leu Gln Ala Ser
            900                 905                 910 ctg agg aag gag cag atg cgc atc cag tcg ctg gag aag aca gtg gag     2784
```

| Leu | Arg | Lys | Glu | Gln | Met | Arg | Ile | Gln | Ser | Leu | Glu | Lys | Thr | Val | Glu |
|---|---|---|---|---|---|---|---|---|---|---|---|---|---|---|---|
| | 915 | | | | 920 | | | | 925 | | | | | | |

```
cag aag act aaa gag aac gag gag ctg acc agg atc tgc gac gac ctc    2832
Gln Lys Thr Lys Glu Asn Glu Glu Leu Thr Arg Ile Cys Asp Asp Leu
    930                 935                 940 atc tcc aag atg gag aag atc tga                                    2856
Ile Ser Lys Met Glu Lys Ile
945                 950
```

<210> SEQ ID NO 10
<211> LENGTH: 951
<212> TYPE: PRT
<213> ORGANISM: Homo sapiens

<400> SEQUENCE: 10

| Met | Gly | Ala | Pro | Ala | Cys | Ala | Leu | Ala | Leu | Cys | Val | Ala | Val | Ala | Ile |
|---|---|---|---|---|---|---|---|---|---|---|---|---|---|---|---|
| 1 | | | | 5 | | | | | 10 | | | | | 15 | |

| Val | Ala | Gly | Ala | Ser | Ser | Glu | Ser | Leu | Gly | Thr | Glu | Gln | Arg | Val | Val |
|---|---|---|---|---|---|---|---|---|---|---|---|---|---|---|---|
| | | | 20 | | | | | 25 | | | | | 30 | | |

| Gly | Arg | Ala | Ala | Glu | Val | Pro | Gly | Pro | Glu | Pro | Gly | Gln | Gln | Glu | Gln |
|---|---|---|---|---|---|---|---|---|---|---|---|---|---|---|---|
| | | 35 | | | | | 40 | | | | | 45 | | | |

| Leu | Val | Phe | Gly | Ser | Gly | Asp | Ala | Val | Glu | Leu | Ser | Cys | Pro | Pro | Pro |
|---|---|---|---|---|---|---|---|---|---|---|---|---|---|---|---|
| | 50 | | | | | 55 | | | | | 60 | | | | |

| Gly | Gly | Gly | Pro | Met | Gly | Pro | Thr | Val | Trp | Val | Lys | Asp | Gly | Thr | Gly |
|---|---|---|---|---|---|---|---|---|---|---|---|---|---|---|---|
| 65 | | | | | 70 | | | | | 75 | | | | | 80 |

| Leu | Val | Pro | Ser | Glu | Arg | Val | Leu | Val | Gly | Pro | Gln | Arg | Leu | Gln | Val |
|---|---|---|---|---|---|---|---|---|---|---|---|---|---|---|---|
| | | | | 85 | | | | | 90 | | | | | 95 | |

| Leu | Asn | Ala | Ser | His | Glu | Asp | Ser | Gly | Ala | Tyr | Ser | Cys | Arg | Gln | Arg |
|---|---|---|---|---|---|---|---|---|---|---|---|---|---|---|---|
| | | | 100 | | | | | 105 | | | | | 110 | | |

| Leu | Thr | Gln | Arg | Val | Leu | Cys | His | Phe | Ser | Val | Arg | Val | Thr | Asp | Ala |
|---|---|---|---|---|---|---|---|---|---|---|---|---|---|---|---|
| | | 115 | | | | | 120 | | | | | 125 | | | |

| Pro | Ser | Ser | Gly | Asp | Asp | Glu | Asp | Gly | Glu | Asp | Glu | Ala | Glu | Asp | Thr |
|---|---|---|---|---|---|---|---|---|---|---|---|---|---|---|---|
| | 130 | | | | | 135 | | | | | 140 | | | | |

| Gly | Val | Asp | Thr | Gly | Ala | Pro | Tyr | Trp | Thr | Arg | Pro | Glu | Arg | Met | Asp |
|---|---|---|---|---|---|---|---|---|---|---|---|---|---|---|---|
| 145 | | | | | 150 | | | | | 155 | | | | | 160 |

| Lys | Lys | Leu | Leu | Ala | Val | Pro | Ala | Ala | Asn | Thr | Val | Arg | Phe | Arg | Cys |
|---|---|---|---|---|---|---|---|---|---|---|---|---|---|---|---|
| | | | | 165 | | | | | 170 | | | | | 175 | |

| Pro | Ala | Ala | Gly | Asn | Pro | Thr | Pro | Ser | Ile | Ser | Trp | Leu | Lys | Asn | Gly |
|---|---|---|---|---|---|---|---|---|---|---|---|---|---|---|---|
| | | | 180 | | | | | 185 | | | | | 190 | | |

| Arg | Glu | Phe | Arg | Gly | Glu | His | Arg | Ile | Gly | Gly | Ile | Lys | Leu | Arg | His |
|---|---|---|---|---|---|---|---|---|---|---|---|---|---|---|---|
| | | 195 | | | | | 200 | | | | | 205 | | | |

| Gln | Gln | Trp | Ser | Leu | Val | Met | Glu | Ser | Val | Val | Pro | Ser | Asp | Arg | Gly |
|---|---|---|---|---|---|---|---|---|---|---|---|---|---|---|---|
| | 210 | | | | | 215 | | | | | 220 | | | | |

| Asn | Tyr | Thr | Cys | Val | Val | Glu | Asn | Lys | Phe | Gly | Ser | Ile | Arg | Gln | Thr |
|---|---|---|---|---|---|---|---|---|---|---|---|---|---|---|---|
| 225 | | | | | 230 | | | | | 235 | | | | | 240 |

| Tyr | Thr | Leu | Asp | Val | Leu | Glu | Arg | Ser | Pro | His | Arg | Pro | Ile | Leu | Gln |
|---|---|---|---|---|---|---|---|---|---|---|---|---|---|---|---|
| | | | | 245 | | | | | 250 | | | | | 255 | |

| Ala | Gly | Leu | Pro | Ala | Asn | Gln | Thr | Ala | Val | Leu | Gly | Ser | Asp | Val | Glu |
|---|---|---|---|---|---|---|---|---|---|---|---|---|---|---|---|
| | | | 260 | | | | | 265 | | | | | 270 | | |

| Phe | His | Cys | Lys | Val | Tyr | Ser | Asp | Ala | Gln | Pro | His | Ile | Gln | Trp | Leu |
|---|---|---|---|---|---|---|---|---|---|---|---|---|---|---|---|
| | | 275 | | | | | 280 | | | | | 285 | | | |

| Lys | His | Val | Glu | Val | Asn | Gly | Ser | Lys | Val | Gly | Pro | Asp | Gly | Thr | Pro |
|---|---|---|---|---|---|---|---|---|---|---|---|---|---|---|---|
| | 290 | | | | | 295 | | | | | 300 | | | | |

| Tyr | Val | Thr | Val | Leu | Lys | Ser | Trp | Ile | Ser | Glu | Ser | Val | Glu | Ala | Asp |
|---|---|---|---|---|---|---|---|---|---|---|---|---|---|---|---|
| 305 | | | | | 310 | | | | | 315 | | | | | 320 |

```
Val Arg Leu Arg Leu Ala Asn Val Ser Glu Arg Asp Gly Gly Glu Tyr
            325                 330                 335

Leu Cys Arg Ala Thr Asn Phe Ile Gly Val Ala Glu Lys Ala Phe Trp
        340                 345                 350

Leu Ser Val His Gly Pro Arg Ala Ala Glu Glu Leu Val Glu Ala
    355                 360                 365

Asp Glu Ala Gly Ser Val Tyr Ala Gly Ile Leu Ser Tyr Gly Val Gly
370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
            405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
            435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
            515                 520                 525

Glu Met Met Lys Met Ile Gly Lys His Lys Asn Ile Ile Asn Leu Leu
530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
            565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
            595                 600                 605

Tyr Leu Ala Ser Gln Lys Cys Ile His Arg Asp Leu Ala Ala Arg Asn
            610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
            645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
            675                 680                 685

Ile Phe Thr Leu Gly Gly Ser Pro Tyr Pro Gly Ile Pro Val Glu Glu
            690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
            725                 730                 735

Pro Ser Gln Arg Pro Thr Phe Lys Gln Leu Val Glu Asp Leu Asp Arg
```

```
                    740                 745                 750
Val Leu Thr Val Thr Ser Thr Asp Val Lys Ala Thr Gln Glu Glu Asn
                755                 760                 765

Arg Glu Leu Arg Ser Arg Cys Glu Glu Leu His Gly Lys Asn Leu Glu
            770                 775                 780

Leu Gly Lys Ile Met Asp Arg Phe Glu Glu Val Val Tyr Gln Ala Met
785                 790                 795                 800

Glu Glu Val Gln Lys Gln Lys Glu Leu Ser Lys Ala Glu Ile Gln Lys
                805                 810                 815

Val Leu Lys Glu Lys Asp Gln Leu Thr Thr Asp Leu Asn Ser Met Glu
            820                 825                 830

Lys Ser Phe Ser Asp Leu Phe Lys Arg Phe Glu Lys Gln Lys Glu Val
            835                 840                 845

Ile Glu Gly Tyr Arg Lys Asn Glu Glu Ser Leu Lys Lys Cys Val Glu
            850                 855                 860

Asp Tyr Leu Ala Arg Ile Thr Gln Glu Gly Gln Arg Tyr Gln Ala Leu
865                 870                 875                 880

Lys Ala His Ala Glu Glu Lys Leu Gln Leu Ala Asn Glu Glu Ile Ala
                885                 890                 895

Gln Val Arg Ser Lys Ala Gln Ala Glu Ala Leu Ala Leu Gln Ala Ser
            900                 905                 910

Leu Arg Lys Glu Gln Met Arg Ile Gln Ser Leu Glu Lys Thr Val Glu
            915                 920                 925

Gln Lys Thr Lys Glu Asn Glu Glu Leu Thr Arg Ile Cys Asp Asp Leu
            930                 935                 940

Ile Ser Lys Met Glu Lys Ile
945                 950

<210> SEQ ID NO 11
<211> LENGTH: 2961
<212> TYPE: DNA
<213> ORGANISM: Homo sapiens
<220> FEATURE:
<221> NAME/KEY: CDS
<222> LOCATION: (1)..(2961)

<400> SEQUENCE: 11 atg ggc gcc cct gcc tgc gcc ctc gcg ctc tgc gtg gcc gtg gcc atc      48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg      96
Val Ala Gly Ala Ser Ser Glu Ser Leu Gly Thr Glu Gln Arg Val Val
                20                  25                  30 ggg cga gcg gca gaa gtc ccg ggc cca gag ccc ggc cag cag gag cag     144
Gly Arg Ala Ala Glu Val Pro Gly Pro Glu Pro Gly Gln Gln Glu Gln
            35                  40                  45 ttg gtc ttc ggc agc ggg gat gct gtg gag ctg agc tgt ccc ccg ccc     192
Leu Val Phe Gly Ser Gly Asp Ala Val Glu Leu Ser Cys Pro Pro Pro
        50                  55                  60 ggg ggt ggt ccc atg ggg ccc act gtc tgg gtc aag gat ggc aca ggg     240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg     288
Leu Val Pro Ser Glu Arg Val Leu Val Gly Pro Gln Arg Leu Gln Val
                85                  90                  95 ctg aat gcc tcc cac gag gac tcc ggg gcc tac agc tgc cgg cag cgg     336
Leu Asn Ala Ser His Glu Asp Ser Gly Ala Tyr Ser Cys Arg Gln Arg
                100                 105                 110
```

| | | |
|---|---|---|
| ctc acg cag cgc gta ctg tgc cac ttc agt gtg cgg gtg aca gac gct<br>Leu Thr Gln Arg Val Leu Cys His Phe Ser Val Arg Val Thr Asp Ala<br>     115                    120                   125 | 384 |
| cca tcc tcg gga gat gac gaa gac ggg gag gac gag gct gag gac aca<br>Pro Ser Ser Gly Asp Asp Glu Asp Gly Glu Asp Glu Ala Glu Asp Thr<br>130                   135                    140 | 432 |
| ggt gtg gac aca ggg gcc cct tac tgg aca cgg ccc gag cgg atg gac<br>Gly Val Asp Thr Gly Ala Pro Tyr Trp Thr Arg Pro Glu Arg Met Asp<br>145                   150                    155                 160 | 480 |
| aag aag ctg ctg gcc gtg ccg gcc gcc aac acc gtc cgc ttc cgc tgc<br>Lys Lys Leu Leu Ala Val Pro Ala Ala Asn Thr Val Arg Phe Arg Cys<br>                 165                    170                 175 | 528 |
| cca gcc gct ggc aac ccc act ccc tcc atc tcc tgg ctg aag aac ggc<br>Pro Ala Ala Gly Asn Pro Thr Pro Ser Ile Ser Trp Leu Lys Asn Gly<br>                 180                    185                 190 | 576 |
| agg gag ttc cgc ggc gag cac cgc att gga ggc atc aag ctg cgg cat<br>Arg Glu Phe Arg Gly Glu His Arg Ile Gly Gly Ile Lys Leu Arg His<br>          195                    200                    205 | 624 |
| cag cag tgg agc ctg gtc atg gaa agc gtg gtg ccc tcg gac cgc ggc<br>Gln Gln Trp Ser Leu Val Met Glu Ser Val Val Pro Ser Asp Arg Gly<br>     210                    215                    220 | 672 |
| aac tac acc tgc gtc gtg gag aac aag ttt ggc agc atc cgg cag acg<br>Asn Tyr Thr Cys Val Val Glu Asn Lys Phe Gly Ser Ile Arg Gln Thr<br>225                   230                    235                 240 | 720 |
| tac acg ctg gac gtg ctg gag cgc tcc ccg cac cgg ccc atc ctg cag<br>Tyr Thr Leu Asp Val Leu Glu Arg Ser Pro His Arg Pro Ile Leu Gln<br>                 245                    250                 255 | 768 |
| gcg ggg ctg ccg gcc aac cag acg gcg gtg ctg ggc agc gac gtg gag<br>Ala Gly Leu Pro Ala Asn Gln Thr Ala Val Leu Gly Ser Asp Val Glu<br>                 260                    265                 270 | 816 |
| ttc cac tgc aag gtg tac agt gac gca cag ccc cac atc cag tgg ctc<br>Phe His Cys Lys Val Tyr Ser Asp Ala Gln Pro His Ile Gln Trp Leu<br>         275                    280                    285 | 864 |
| aag cac gtg gag gtg aat ggc agc aag gtg ggc ccg gac ggc aca ccc<br>Lys His Val Glu Val Asn Gly Ser Lys Val Gly Pro Asp Gly Thr Pro<br>     290                    295                    300 | 912 |
| tac gtt acc gtg ctc aag tcc tgg atc agt gag agt gtg gag gcc gac<br>Tyr Val Thr Val Leu Lys Ser Trp Ile Ser Glu Ser Val Glu Ala Asp<br>305                   310                    315                 320 | 960 |
| gtg cgc ctc cgc ctg gcc aat gtg tcg gag cgg gac ggg ggc gag tac<br>Val Arg Leu Arg Leu Ala Asn Val Ser Glu Arg Asp Gly Gly Glu Tyr<br>                 325                    330                 335 | 1008 |
| ctc tgt cga gcc acc aat ttc ata ggc gtg gcc gag aag gcc ttt tgg<br>Leu Cys Arg Ala Thr Asn Phe Ile Gly Val Ala Glu Lys Ala Phe Trp<br>                 340                    345                 350 | 1056 |
| ctg agc gtt cac ggg ccc cga gca gcc gag gag gag ctg gtg gag gct<br>Leu Ser Val His Gly Pro Arg Ala Ala Glu Glu Glu Leu Val Glu Ala<br>         355                    360                    365 | 1104 |
| gac gag gcg ggc agt gtg tat gca ggc atc ctc agc tac ggg gtg ggc<br>Asp Glu Ala Gly Ser Val Tyr Ala Gly Ile Leu Ser Tyr Gly Val Gly<br>370                   375                    380 | 1152 |
| ttc ctc ctg ttc atc ctg gtg gtg gcg gct gtg acg ctc tgc cgc ctg<br>Phe Leu Leu Phe Ile Leu Val Val Ala Ala Val Thr Leu Cys Arg Leu<br>385                   390                    395                 400 | 1200 |
| cgc agc ccc ccc aag aaa ggc ctg ggc tcc ccc acc gtg cac aag atc<br>Arg Ser Pro Pro Lys Lys Gly Leu Gly Ser Pro Thr Val His Lys Ile<br>                 405                    410                 415 | 1248 |
| tcc cgc ttc ccg ctc aag cga cag gtg tcc ctg gag tcc aac gcg tcc<br>Ser Arg Phe Pro Leu Lys Arg Gln Val Ser Leu Glu Ser Asn Ala Ser | 1296 |

-continued

```
                420                 425                 430
atg agc tcc aac aca cca ctg gtg cgc atc gca agg ctg tcc tca ggg      1344
Met Ser Ser Asn Thr Pro Leu Val Arg Ile Ala Arg Leu Ser Ser Gly
        435                 440                 445 gag ggc ccc acg ctg gcc aat gtc tcc gag ctc gag ctg cct gcc gac      1392
Glu Gly Pro Thr Leu Ala Asn Val Ser Glu Leu Glu Leu Pro Ala Asp
    450                 455                 460 ccc aaa tgg gag ctg tct cgg gcc cgg ctg acc ctg ggc aag ccc ctt      1440
Pro Lys Trp Glu Leu Ser Arg Ala Arg Leu Thr Leu Gly Lys Pro Leu
465                 470                 475                 480 ggg gag ggc tgc ttc ggc cag gtg gtc atg gcg gag gcc atc ggc att      1488
Gly Glu Gly Cys Phe Gly Gln Val Val Met Ala Glu Ala Ile Gly Ile
                485                 490                 495 gac aag gac cgg gcc gcc aag cct gtc acc gta gcc gtg aag atg ctg      1536
Asp Lys Asp Arg Ala Ala Lys Pro Val Thr Val Ala Val Lys Met Leu
            500                 505                 510 aaa gac gat gcc act gac aag gac ctg tcg gac ctg gtg tct gag atg      1584
Lys Asp Asp Ala Thr Asp Lys Asp Leu Ser Asp Leu Val Ser Glu Met
        515                 520                 525 gag atg atg aag atg atc ggg aaa cac aaa aac atc atc aac ctg ctg      1632
Glu Met Met Lys Met Ile Gly Lys His Lys Asn Ile Ile Asn Leu Leu
    530                 535                 540 ggc gcc tgc acg cag ggc ggg ccc ctg tac gtg ctg gtg gag tac gcg      1680
Gly Ala Cys Thr Gln Gly Gly Pro Leu Tyr Val Leu Val Glu Tyr Ala
545                 550                 555                 560 gcc aag ggt aac ctg cgg gag ttt ctg cgg gcg cgg cgg ccc ccg ggc      1728
Ala Lys Gly Asn Leu Arg Glu Phe Leu Arg Ala Arg Arg Pro Pro Gly
                565                 570                 575 ctg gac tac tcc ttc gac acc tgc aag ccg ccc gag gag cag ctc acc      1776
Leu Asp Tyr Ser Phe Asp Thr Cys Lys Pro Pro Glu Glu Gln Leu Thr
            580                 585                 590 ttc aag gac ctg gtg tcc tgt gcc tac cag gtg gcc cgg ggc atg gag      1824
Phe Lys Asp Leu Val Ser Cys Ala Tyr Gln Val Ala Arg Gly Met Glu
        595                 600                 605 tac ttg gcc tcc cag aag tgc atc cac agg gac ctg gct gcc cgc aat      1872
Tyr Leu Ala Ser Gln Lys Cys Ile His Arg Asp Leu Ala Ala Arg Asn
    610                 615                 620 gtg ctg gtg acc gag gac aac gtg atg aag atc gca gac ttc ggg ctg      1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc      1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc      2016
Arg Leu Pro Val Lys Trp Met Ala Pro Glu Ala Leu Phe Asp Arg Val
            660                 665                 670 tac act cac cag agt gac gtc tgg tcc ttt ggg gtc ctg ctc tgg gag      2064
Tyr Thr His Gln Ser Asp Val Trp Ser Phe Gly Val Leu Leu Trp Glu
        675                 680                 685 atc ttc acg ctg ggg ggc tcc ccg tac ccc ggc atc cct gtg gag gag      2112
Ile Phe Thr Leu Gly Gly Ser Pro Tyr Pro Gly Ile Pro Val Glu Glu
    690                 695                 700 ctc ttc aag ctg ctg aag gag ggc cac cgc atg gac aag ccc gcc aac      2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg      2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt      2256
```

```
Pro Ser Gln Arg Pro Thr Phe Lys Gln Leu Val Glu Asp Leu Asp Arg
                740                 745                 750 gtc ctt acc gtg acg tcc acc gac gtg cca ggc cca ccc cca ggt gtt         2304
Val Leu Thr Val Thr Ser Thr Asp Val Pro Gly Pro Pro Pro Gly Val
        755                 760                 765 ccc gcg cct ggg ggc cca ccc ctg tcc acc gga cct ata gtg gac ctg         2352
Pro Ala Pro Gly Gly Pro Pro Leu Ser Thr Gly Pro Ile Val Asp Leu
770                 775                 780 ctc cag tac agc cag aag gac ctg gat gca gtg gta aag gcg aca cag         2400
Leu Gln Tyr Ser Gln Lys Asp Leu Asp Ala Val Val Lys Ala Thr Gln
785                 790                 795                 800 gag gag aac cgg gag ctg agg agc agg tgt gag gag ctc cac ggg aag         2448
Glu Glu Asn Arg Glu Leu Arg Ser Arg Cys Glu Glu Leu His Gly Lys
                805                 810                 815 aac ctg gaa ctg ggg aag atc atg gac agg ttc gaa gag gtt gtg tac         2496
Asn Leu Glu Leu Gly Lys Ile Met Asp Arg Phe Glu Glu Val Val Tyr
        820                 825                 830 cag gcc atg gag gaa gtt cag aag cag aag gaa ctt tcc aaa gct gaa         2544
Gln Ala Met Glu Glu Val Gln Lys Gln Lys Glu Leu Ser Lys Ala Glu
835                 840                 845 atc cag aaa gtt cta aaa gaa aaa gac caa ctt acc aca gat ctg aac         2592
Ile Gln Lys Val Leu Lys Glu Lys Asp Gln Leu Thr Thr Asp Leu Asn
850                 855                 860 tcc atg gag aag tcc ttc tcc gac ctc ttc aag cgt ttt gag aaa cag         2640
Ser Met Glu Lys Ser Phe Ser Asp Leu Phe Lys Arg Phe Glu Lys Gln
865                 870                 875                 880 aaa gag gtg atc gag ggc tac cgc aag aac gaa gag tca ctg aag aag         2688
Lys Glu Val Ile Glu Gly Tyr Arg Lys Asn Glu Glu Ser Leu Lys Lys
                885                 890                 895 tgc gtg gag gat tac ctg gca agg atc acc cag gag ggc cag agg tac         2736
Cys Val Glu Asp Tyr Leu Ala Arg Ile Thr Gln Glu Gly Gln Arg Tyr
        900                 905                 910 caa gcc ctg aag gcc cac gcg gag gag aag ctg cag ctg gca aac gag         2784
Gln Ala Leu Lys Ala His Ala Glu Glu Lys Leu Gln Leu Ala Asn Glu
915                 920                 925 gag atc gcc cag gtc cgg agc aag gcc cag gcg gaa gcg ttg gcc ctc         2832
Glu Ile Ala Gln Val Arg Ser Lys Ala Gln Ala Glu Ala Leu Ala Leu
930                 935                 940 cag gcc agc ctg agg aag gag cag atg cgc atc cag tcg ctg gag aag         2880
Gln Ala Ser Leu Arg Lys Glu Gln Met Arg Ile Gln Ser Leu Glu Lys
945                 950                 955                 960 aca gtg gag cag aag act aaa gag aac gag gag ctg acc agg atc tgc         2928
Thr Val Glu Gln Lys Thr Lys Glu Asn Glu Glu Leu Thr Arg Ile Cys
                965                 970                 975 gac gac ctc atc tcc aag atg gag aag atc tga                             2961
Asp Asp Leu Ile Ser Lys Met Glu Lys Ile
        980                 985

<210> SEQ ID NO 12
<211> LENGTH: 986
<212> TYPE: PRT
<213> ORGANISM: Homo sapiens

<400> SEQUENCE: 12

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
        35                  40                  45
```

```
Leu Val Phe Gly Ser Gly Asp Ala Val Glu Leu Ser Cys Pro Pro
        50                  55                  60
Gly Gly Gly Pro Met Gly Pro Thr Val Trp Val Lys Asp Gly Thr Gly
 65              70                  75                  80
Leu Val Pro Ser Glu Arg Val Leu Val Gly Pro Gln Arg Leu Gln Val
                 85                  90                  95
Leu Asn Ala Ser His Glu Asp Ser Gly Ala Tyr Ser Cys Arg Gln Arg
            100                 105                 110
Leu Thr Gln Arg Val Leu Cys His Phe Ser Val Arg Val Thr Asp Ala
        115                 120                 125
Pro Ser Ser Gly Asp Asp Glu Asp Gly Glu Asp Glu Ala Glu Asp Thr
    130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
            180                 185                 190
Arg Glu Phe Arg Gly Glu His Arg Ile Gly Gly Ile Lys Leu Arg His
        195                 200                 205
Gln Gln Trp Ser Leu Val Met Glu Ser Val Val Pro Ser Asp Arg Gly
    210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
            260                 265                 270
Phe His Cys Lys Val Tyr Ser Asp Ala Gln Pro His Ile Gln Trp Leu
        275                 280                 285
Lys His Val Glu Val Asn Gly Ser Lys Val Gly Pro Asp Gly Thr Pro
    290                 295                 300
Tyr Val Thr Val Leu Lys Ser Trp Ile Ser Glu Ser Val Glu Ala Asp
305                 310                 315                 320
Val Arg Leu Arg Leu Ala Asn Val Ser Glu Arg Asp Gly Gly Glu Tyr
                325                 330                 335
Leu Cys Arg Ala Thr Asn Phe Ile Gly Val Ala Glu Lys Ala Phe Trp
            340                 345                 350
Leu Ser Val His Gly Pro Arg Ala Ala Glu Glu Glu Leu Val Glu Ala
        355                 360                 365
Asp Glu Ala Gly Ser Val Tyr Ala Gly Ile Leu Ser Tyr Gly Val Gly
    370                 375                 380
Phe Leu Leu Phe Ile Leu Val Val Ala Ala Val Thr Leu Cys Arg Leu
385                 390                 395                 400
Arg Ser Pro Pro Lys Lys Gly Leu Gly Ser Pro Thr Val His Lys Ile
                405                 410                 415
Ser Arg Phe Pro Leu Lys Arg Gln Val Ser Leu Glu Ser Asn Ala Ser
            420                 425                 430
Met Ser Ser Asn Thr Pro Leu Val Arg Ile Ala Arg Leu Ser Ser Gly
        435                 440                 445
Glu Gly Pro Thr Leu Ala Asn Val Ser Glu Leu Glu Leu Pro Ala Asp
    450                 455                 460
```

```
Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
                500                 505                 510

Lys Asp Asp Ala Thr Asp Lys Asp Leu Ser Asp Leu Val Ser Glu Met
            515                 520                 525

Glu Met Met Lys Met Ile Gly Lys His Lys Asn Ile Ile Asn Leu Leu
        530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Val Pro Gly Pro Pro Gly Val
        755                 760                 765

Pro Ala Pro Gly Gly Pro Pro Leu Ser Thr Gly Pro Ile Val Asp Leu
770                 775                 780

Leu Gln Tyr Ser Gln Lys Asp Leu Asp Ala Val Val Lys Ala Thr Gln
785                 790                 795                 800

Glu Glu Asn Arg Glu Leu Arg Ser Arg Cys Glu Glu Leu His Gly Lys
                805                 810                 815

Asn Leu Glu Leu Gly Lys Ile Met Asp Arg Phe Glu Glu Val Val Tyr
            820                 825                 830

Gln Ala Met Glu Glu Val Gln Lys Gln Lys Glu Leu Ser Lys Ala Glu
        835                 840                 845

Ile Gln Lys Val Leu Lys Glu Lys Asp Gln Leu Thr Thr Asp Leu Asn
850                 855                 860

Ser Met Glu Lys Ser Phe Ser Asp Leu Phe Lys Arg Phe Glu Lys Gln
865                 870                 875                 880

Lys Glu Val Ile Glu Gly Tyr Arg Lys Asn Glu Glu Ser Leu Lys Lys
```

-continued

```
                            885                 890                 895
        Cys Val Glu Asp Tyr Leu Ala Arg Ile Thr Gln Glu Gly Gln Arg Tyr
                        900                 905                 910

Gln Ala Leu Lys Ala His Ala Glu Glu Lys Leu Gln Leu Ala Asn Glu
                        915                 920                 925

Glu Ile Ala Gln Val Arg Ser Lys Ala Gln Ala Glu Ala Leu Ala Leu
                        930                 935                 940

Gln Ala Ser Leu Arg Lys Glu Gln Met Arg Ile Gln Ser Leu Glu Lys
        945                 950                 955                 960

Thr Val Glu Gln Lys Thr Lys Glu Asn Glu Glu Leu Thr Arg Ile Cys
                        965                 970                 975

Asp Asp Leu Ile Ser Lys Met Glu Lys Ile
                        980                 985

<210> SEQ ID NO 13
<211> LENGTH: 3003
<212> TYPE: DNA
<213> ORGANISM: Homo sapiens
<220> FEATURE:
<221> NAME/KEY: CDS
<222> LOCATION: (1)..(3003)

<400> SEQUENCE: 13 atg ggc gcc cct gcc tgc gcc ctc gcg ctc tgc gtg gcc gtg gcc atc        48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg        96
Val Ala Gly Ala Ser Ser Glu Ser Leu Gly Thr Glu Gln Arg Val Val
            20                  25                  30 ggg cga gcg gca gaa gtc ccg ggc cca gag ccc ggc cag cag gag cag       144
Gly Arg Ala Ala Glu Val Pro Gly Pro Glu Pro Gly Gln Gln Glu Gln
        35                  40                  45 ttg gtc ttc ggc agc ggg gat gct gtg gag ctg agc tgt ccc ccg ccc       192
Leu Val Phe Gly Ser Gly Asp Ala Val Glu Leu Ser Cys Pro Pro Pro
    50                  55                  60 ggg ggt ggt ccc atg ggg ccc act gtc tgg gtc aag gat ggc aca ggg       240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg       288
Leu Val Pro Ser Glu Arg Val Leu Val Gly Pro Gln Arg Leu Gln Val
                85                  90                  95 ctg aat gcc tcc cac gag gac tcc ggg gcc tac agc tgc cgg cag cgg       336
Leu Asn Ala Ser His Glu Asp Ser Gly Ala Tyr Ser Cys Arg Gln Arg
            100                 105                 110 ctc acg cag cgc gta ctg tgc cac ttc agt gtg cgg gtg aca gac gct       384
Leu Thr Gln Arg Val Leu Cys His Phe Ser Val Arg Val Thr Asp Ala
        115                 120                 125 cca tcc tcg gga gat gac gaa gac ggg gag gac gag gct gag gac aca       432
Pro Ser Ser Gly Asp Asp Glu Asp Gly Glu Asp Glu Ala Glu Asp Thr
    130                 135                 140 ggt gtg gac aca ggg gcc cct tac tgg aca cgg ccc gag cgg atg gac       480
Gly Val Asp Thr Gly Ala Pro Tyr Trp Thr Arg Pro Glu Arg Met Asp
145                 150                 155                 160 aag aag ctg ctg gcc gtg ccg gcc gcc aac acc gtc cgc ttc cgc tgc       528
Lys Lys Leu Leu Ala Val Pro Ala Ala Asn Thr Val Arg Phe Arg Cys
                165                 170                 175 cca gcc gct ggc aac ccc act ccc tcc atc tcc tgg ctg aag aac ggc       576
Pro Ala Ala Gly Asn Pro Thr Pro Ser Ile Ser Trp Leu Lys Asn Gly
            180                 185                 190
```

```
agg gag ttc cgc ggc gag cac cgc att gga ggc atc aag ctg cgg cat    624
Arg Glu Phe Arg Gly Glu His Arg Ile Gly Gly Ile Lys Leu Arg His
        195                 200                 205 cag cag tgg agc ctg gtc atg gaa agc gtg gtg ccc tcg gac cgc ggc    672
Gln Gln Trp Ser Leu Val Met Glu Ser Val Val Pro Ser Asp Arg Gly
    210                 215                 220 aac tac acc tgc gtc gtg gag aac aag ttt ggc agc atc cgg cag acg    720
Asn Tyr Thr Cys Val Val Glu Asn Lys Phe Gly Ser Ile Arg Gln Thr
225                 230                 235                 240 tac acg ctg gac gtg ctg gag cgc tcc ccg cac cgg ccc atc ctg cag    768
Tyr Thr Leu Asp Val Leu Glu Arg Ser Pro His Arg Pro Ile Leu Gln
                245                 250                 255 gcg ggg ctg ccg gcc aac cag acg gcg gtg ctg ggc agc gac gtg gag    816
Ala Gly Leu Pro Ala Asn Gln Thr Ala Val Leu Gly Ser Asp Val Glu
            260                 265                 270 ttc cac tgc aag gtg tac agt gac gca cag ccc cac atc cag tgg ctc    864
Phe His Cys Lys Val Tyr Ser Asp Ala Gln Pro His Ile Gln Trp Leu
        275                 280                 285 aag cac gtg gag gtg aat ggc agc aag gtg ggc ccg gac ggc aca ccc    912
Lys His Val Glu Val Asn Gly Ser Lys Val Gly Pro Asp Gly Thr Pro
    290                 295                 300 tac gtt acc gtg ctc aag tcc tgg atc agt gag agt gtg gag gcc gac    960
Tyr Val Thr Val Leu Lys Ser Trp Ile Ser Glu Ser Val Glu Ala Asp
305                 310                 315                 320 gtg cgc ctc cgc ctg gcc aat gtg tcg gag cgg gac ggg ggc gag tac   1008
Val Arg Leu Arg Leu Ala Asn Val Ser Glu Arg Asp Gly Gly Glu Tyr
                325                 330                 335 ctc tgt cga gcc acc aat ttc ata ggc gtg gcc gag aag gcc ttt tgg   1056
Leu Cys Arg Ala Thr Asn Phe Ile Gly Val Ala Glu Lys Ala Phe Trp
            340                 345                 350 ctg agc gtt cac ggg ccc cga gca gcc gag gag gag ctg gtg gag gct   1104
Leu Ser Val His Gly Pro Arg Ala Ala Glu Glu Glu Leu Val Glu Ala
        355                 360                 365 gac gag gcg ggc agt gtg tat gca ggc atc ctc agc tac ggg gtg ggc   1152
Asp Glu Ala Gly Ser Val Tyr Ala Gly Ile Leu Ser Tyr Gly Val Gly
    370                 375                 380 ttc ttc ctg ttc atc ctg gtg gtg gcg gct gtg acg ctc tgc cgc ctg   1200
Phe Phe Leu Phe Ile Leu Val Val Ala Ala Val Thr Leu Cys Arg Leu
385                 390                 395                 400 cgc agc ccc ccc aag aaa ggc ctg ggc tcc ccc acc gtg cac aag atc   1248
Arg Ser Pro Pro Lys Lys Gly Leu Gly Ser Pro Thr Val His Lys Ile
                405                 410                 415 tcc cgc ttc ccg ctc aag cga cag gtg tcc ctg gag tcc aac gcg tcc   1296
Ser Arg Phe Pro Leu Lys Arg Gln Val Ser Leu Glu Ser Asn Ala Ser
            420                 425                 430 atg agc tcc aac aca cca ctg gtg cgc atc gca agg ctg tcc tca ggg   1344
Met Ser Ser Asn Thr Pro Leu Val Arg Ile Ala Arg Leu Ser Ser Gly
        435                 440                 445 gag ggc ccc acg ctg gcc aat gtc tcc gag ctc gag ctg cct gcc gac   1392
Glu Gly Pro Thr Leu Ala Asn Val Ser Glu Leu Glu Leu Pro Ala Asp
    450                 455                 460 ccc aaa tgg gag ctg tct cgg gcc cgg ctg acc ctg ggc aag ccc ctt   1440
Pro Lys Trp Glu Leu Ser Arg Ala Arg Leu Thr Leu Gly Lys Pro Leu
465                 470                 475                 480 ggg gag ggc tgc ttc ggc cag gtg gtc atg gcg gag gcc atc ggc att   1488
Gly Glu Gly Cys Phe Gly Gln Val Val Met Ala Glu Ala Ile Gly Ile
                485                 490                 495 gac aag gac cgg gcc gcc aag cct gtc acc gta gcc gtg aag atg ctg   1536
Asp Lys Asp Arg Ala Ala Lys Pro Val Thr Val Ala Val Lys Met Leu
            500                 505                 510
```

```
aaa gac gat gcc act gac aag gac ctg tcg gac ctg gtg tct gag atg     1584
Lys Asp Asp Ala Thr Asp Lys Asp Leu Ser Asp Leu Val Ser Glu Met
            515                 520                 525 gag atg atg aaa atg atc ggg aaa cac aaa aac atc atc aac ctg ctg     1632
Glu Met Met Lys Met Ile Gly Lys His Lys Asn Ile Ile Asn Leu Leu
        530                 535                 540 ggc gcc tgc acg cag ggc ggg ccc ctg tac gtg ctg gtg gag tac gcg     1680
Gly Ala Cys Thr Gln Gly Gly Pro Leu Tyr Val Leu Val Glu Tyr Ala
545                 550                 555                 560 gcc aag ggt aac ctg cgg gag ttt ctg cgg gcg cgg cgg ccc ccg ggc     1728
Ala Lys Gly Asn Leu Arg Glu Phe Leu Arg Ala Arg Arg Pro Pro Gly
                565                 570                 575 ctg gac tac tcc ttc gac acc tgc aag ccg ccc gag gag cag ctc acc     1776
Leu Asp Tyr Ser Phe Asp Thr Cys Lys Pro Pro Glu Glu Gln Leu Thr
            580                 585                 590 ttc aag gac ctg gtg tcc tgt gcc tac cag gtg gcc cgg ggc atg gag     1824
Phe Lys Asp Leu Val Ser Cys Ala Tyr Gln Val Ala Arg Gly Met Glu
        595                 600                 605 tac ttg gcc tcc cag aag tgc atc cac agg gac ctg gct gcc cgc aat     1872
Tyr Leu Ala Ser Gln Lys Cys Ile His Arg Asp Leu Ala Ala Arg Asn
610                 615                 620 gtg ctg gtg acc gag gac aac gtg atg aag atc gca gac ttc ggg ctg     1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc     1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc     2016
Arg Leu Pro Val Lys Trp Met Ala Pro Glu Ala Leu Phe Asp Arg Val
            660                 665                 670 tac act cac cag agt gac gtc tgg tcc ttt ggg gtc ctc tgg gag         2064
Tyr Thr His Gln Ser Asp Val Trp Ser Phe Gly Val Leu Leu Trp Glu
        675                 680                 685 atc ttc acg ctg ggg ggc tcc ccg tac ccc ggc atc cct gtg gag gag     2112
Ile Phe Thr Leu Gly Gly Ser Pro Tyr Pro Gly Ile Pro Val Glu Glu
        690                 695                 700 ctc ttc aag ctg ctg aag gag ggc cac cgc atg gac aag ccc gcc aac     2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg     2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt     2256
Pro Ser Gln Arg Pro Thr Phe Lys Gln Leu Val Glu Asp Leu Asp Arg
            740                 745                 750 gtc ctt acc gtg acg tcc acc gac gag tac ctg gac ctg tcg gcg cct     2304
Val Leu Thr Val Thr Ser Thr Asp Glu Tyr Leu Asp Leu Ser Ala Pro
        755                 760                 765 ttc gag cag tac tcc ccg ggt ggc cag gac acc ccc agc tcc agc tcc     2352
Phe Glu Gln Tyr Ser Pro Gly Gly Gln Asp Thr Pro Ser Ser Ser Ser
770                 775                 780 tca ggg gac gac tcc gag gtc ctg gga ggg tca gtc tgg ccc gcc tgc     2400
Ser Gly Asp Asp Ser Glu Val Leu Gly Gly Ser Val Trp Pro Ala Cys
785                 790                 795                 800 ctg ctg act tgg gtg tgg cct gag cag gta aag gca aca cag gag gag     2448
Leu Leu Thr Trp Val Trp Pro Glu Gln Val Lys Ala Thr Gln Glu Glu
                805                 810                 815 aac cgg gag ctg agg agc agg tgt gag gag ctc cac ggg aag aac ctg     2496
Asn Arg Glu Leu Arg Ser Arg Cys Glu Glu Leu His Gly Lys Asn Leu
```

-continued

```
                820                 825                 830
gaa ctg ggg aag atc atg gac agg ttc gaa gag gtt gtg tac cag gcc     2544
Glu Leu Gly Lys Ile Met Asp Arg Phe Glu Glu Val Val Tyr Gln Ala
        835                 840                 845 atg gag gaa gtt cag aag cag aag gaa ctt tcc aaa gct gaa atc cag     2592
Met Glu Glu Val Gln Lys Gln Lys Glu Leu Ser Lys Ala Glu Ile Gln
850                 855                 860 aaa gtt cta aaa gaa aaa gac caa ctt acc aca gat ctg aac tcc atg     2640
Lys Val Leu Lys Glu Lys Asp Gln Leu Thr Thr Asp Leu Asn Ser Met
865                 870                 875                 880 gag aag tcc ttc tcc gac ctc ttc aag cgt ttt gag aaa cag aaa gag     2688
Glu Lys Ser Phe Ser Asp Leu Phe Lys Arg Phe Glu Lys Gln Lys Glu
                885                 890                 895 gtg atc gag ggc tac cgc aag aac gaa gag tca ctg aag aag tgc gtg     2736
Val Ile Glu Gly Tyr Arg Lys Asn Glu Glu Ser Leu Lys Lys Cys Val
            900                 905                 910 gag gat tac ctg gca agg atc acc cag gag ggc cag agg tac caa gcc     2784
Glu Asp Tyr Leu Ala Arg Ile Thr Gln Glu Gly Gln Arg Tyr Gln Ala
        915                 920                 925 ctg aag gcc cac gcg gag gag aag ctg cag ctg gca aac gag gag atc     2832
Leu Lys Ala His Ala Glu Glu Lys Leu Gln Leu Ala Asn Glu Glu Ile
930                 935                 940 gcc cag gtc cgg agc aag gcc cag gcg gaa gcg ttg gcc ctc cag gcc     2880
Ala Gln Val Arg Ser Lys Ala Gln Ala Glu Ala Leu Ala Leu Gln Ala
945                 950                 955                 960 agc ctg agg aag gag cag atg cgc atc cag tcg ctg gag aag aca gtg     2928
Ser Leu Arg Lys Glu Gln Met Arg Ile Gln Ser Leu Glu Lys Thr Val
                965                 970                 975 gag cag aag act aaa gag aac gag gag ctg acc agg atc tgc gac gac     2976
Glu Gln Lys Thr Lys Glu Asn Glu Glu Leu Thr Arg Ile Cys Asp Asp
            980                 985                 990 ctc atc tcc aag atg gag aag atc  tga                                3003
Leu Ile Ser Lys Met Glu Lys Ile
        995                 1000

<210> SEQ ID NO 14
<211> LENGTH: 1000
<212> TYPE: PRT
<213> ORGANISM: Homo sapiens

<400> SEQUENCE: 14

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
```

-continued

```
                130                 135                 140
Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Ile Lys Leu Arg His
                195                 200                 205

Gln Gln Trp Ser Leu Val Met Glu Ser Val Val Pro Ser Asp Arg Gly
                210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
                275                 280                 285

Lys His Val Glu Val Asn Gly Ser Lys Val Gly Pro Asp Gly Thr Pro
                290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
                340                 345                 350

Leu Ser Val His Gly Pro Arg Ala Ala Glu Glu Leu Val Glu Ala
                355                 360                 365

Asp Glu Ala Gly Ser Val Tyr Ala Gly Ile Leu Ser Tyr Gly Val Gly
                370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
                420                 425                 430

Met Ser Ser Asn Thr Pro Leu Val Arg Ile Ala Arg Leu Ser Ser Gly
                435                 440                 445

Glu Gly Pro Thr Leu Ala Asn Val Ser Glu Leu Glu Leu Pro Ala Asp
                450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
                500                 505                 510

Lys Asp Asp Ala Thr Asp Lys Asp Leu Ser Asp Leu Val Ser Glu Met
                515                 520                 525

Glu Met Met Lys Met Ile Gly Lys His Lys Asn Ile Ile Asn Leu Leu
                530                 535                 540

Gly Ala Cys Thr Gln Gly Gly Pro Leu Tyr Val Leu Val Glu Tyr Ala
545                 550                 555                 560
```

-continued

```
Ala Lys Gly Asn Leu Arg Glu Phe Leu Arg Ala Arg Pro Pro Gly
            565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
            595                 600                 605

Tyr Leu Ala Ser Gln Lys Cys Ile His Arg Asp Leu Ala Ala Arg Asn
            610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
            645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
            675                 680                 685

Ile Phe Thr Leu Gly Gly Ser Pro Tyr Pro Gly Ile Pro Val Glu Glu
690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
            725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
            755                 760                 765

Phe Glu Gln Tyr Ser Pro Gly Gly Gln Asp Thr Pro Ser Ser Ser Ser
            770                 775                 780

Ser Gly Asp Asp Ser Glu Val Leu Gly Gly Ser Val Trp Pro Ala Cys
785                 790                 795                 800

Leu Leu Thr Trp Val Trp Pro Glu Gln Val Lys Ala Thr Gln Glu Glu
            805                 810                 815

Asn Arg Glu Leu Arg Ser Arg Cys Glu Glu Leu His Gly Lys Asn Leu
            820                 825                 830

Glu Leu Gly Lys Ile Met Asp Arg Phe Glu Glu Val Val Tyr Gln Ala
            835                 840                 845

Met Glu Glu Val Gln Lys Gln Lys Glu Leu Ser Lys Ala Glu Ile Gln
850                 855                 860

Lys Val Leu Lys Glu Lys Asp Gln Leu Thr Thr Asp Leu Asn Ser Met
865                 870                 875                 880

Glu Lys Ser Phe Ser Asp Leu Phe Lys Arg Phe Glu Lys Gln Lys Glu
            885                 890                 895

Val Ile Glu Gly Tyr Arg Lys Asn Glu Glu Ser Leu Lys Lys Cys Val
            900                 905                 910

Glu Asp Tyr Leu Ala Arg Ile Thr Gln Glu Gly Gln Arg Tyr Gln Ala
            915                 920                 925

Leu Lys Ala His Ala Glu Glu Lys Leu Gln Leu Ala Asn Glu Glu Ile
            930                 935                 940

Ala Gln Val Arg Ser Lys Ala Gln Ala Glu Ala Leu Ala Leu Gln Ala
945                 950                 955                 960

Ser Leu Arg Lys Glu Gln Met Arg Ile Gln Ser Leu Glu Lys Thr Val
            965                 970                 975
```

```
Glu Gln Lys Thr Lys Glu Asn Glu Glu Leu Thr Arg Ile Cys Asp Asp
            980                 985                 990
Leu Ile Ser Lys Met Glu Lys Ile
        995                 1000

<210> SEQ ID NO 15
<211> LENGTH: 4467
<212> TYPE: DNA
<213> ORGANISM: Homo sapiens
<220> FEATURE:
<221> NAME/KEY: CDS
<222> LOCATION: (1)..(4467)

<400> SEQUENCE: 15 atg ggc gcc cct gcc tgc gcc ctc gcg ctc tgc gtg gcc gtg gcc atc       48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg       96
Val Ala Gly Ala Ser Ser Glu Ser Leu Gly Thr Glu Gln Arg Val Val
                20                  25                  30 ggg cga gcg gca gaa gtc ccg ggc cca gag ccc ggc cag cag gag cag      144
Gly Arg Ala Ala Glu Val Pro Gly Pro Glu Pro Gly Gln Gln Glu Gln
            35                  40                  45 ttg gtc ttc ggc agc ggg gat gct gtg gag ctg agc tgt ccc ccg ccc      192
Leu Val Phe Gly Ser Gly Asp Ala Val Glu Leu Ser Cys Pro Pro Pro
        50                  55                  60 ggg ggt ggt ccc atg ggg ccc act gtc tgg gtc aag gat ggc aca ggg      240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg      288
Leu Val Pro Ser Glu Arg Val Leu Val Gly Pro Gln Arg Leu Gln Val
                85                  90                  95 ctg aat gcc tcc cac gag gac tcc ggg gcc tac agc tgc cgg cag cgg      336
Leu Asn Ala Ser His Glu Asp Ser Gly Ala Tyr Ser Cys Arg Gln Arg
                100                 105                 110 ctc acg cag cgc gta ctg tgc cac ttc agt gtg cgg gtg aca gac gct      384
Leu Thr Gln Arg Val Leu Cys His Phe Ser Val Arg Val Thr Asp Ala
            115                 120                 125 cca tcc tcg gga gat gac gaa gac ggg gag gac gag gct gag gac aca      432
Pro Ser Ser Gly Asp Asp Glu Asp Gly Glu Asp Glu Ala Glu Asp Thr
        130                 135                 140 ggt gtg gac aca ggg gcc cct tac tgg aca cgg ccc gag cgg atg gac      480
Gly Val Asp Thr Gly Ala Pro Tyr Trp Thr Arg Pro Glu Arg Met Asp
145                 150                 155                 160 aag aag ctg ctg gcc gtg ccg gcc gcc aac acc gtc cgc ttc cgc tgc      528
Lys Lys Leu Leu Ala Val Pro Ala Ala Asn Thr Val Arg Phe Arg Cys
                165                 170                 175 cca gcc gct ggc aac ccc act ccc tcc atc tcc tgg ctg aag aac ggc      576
Pro Ala Ala Gly Asn Pro Thr Pro Ser Ile Ser Trp Leu Lys Asn Gly
                180                 185                 190 agg gag ttc cgc ggc gag cac cgc att gga ggc atc aag ctg cgg cat      624
Arg Glu Phe Arg Gly Glu His Arg Ile Gly Gly Ile Lys Leu Arg His
            195                 200                 205 cag cag tgg agc ctg gtc atg gaa agc gtg gtg ccc tcg gac cgc ggc      672
Gln Gln Trp Ser Leu Val Met Glu Ser Val Val Pro Ser Asp Arg Gly
        210                 215                 220 aac tac acc tgc gtc gtg gag aac aag ttt ggc agc atc cgg cag acg      720
Asn Tyr Thr Cys Val Val Glu Asn Lys Phe Gly Ser Ile Arg Gln Thr
225                 230                 235                 240 tac acg ctg gac gtg ctg gag cgc tcc ccg cac cgg ccc atc ctg cag      768
Tyr Thr Leu Asp Val Leu Glu Arg Ser Pro His Arg Pro Ile Leu Gln
```

|  |  |
|---|---|
| gcg ggg ctg ccg gcc aac cag acg gcg gtg ctg ggc agc gac gtg gag<br>Ala Gly Leu Pro Ala Asn Gln Thr Ala Val Leu Gly Ser Asp Val Glu<br>260 265 270 | 816 |
| ttc cac tgc aag gtg tac agt gac gca cag ccc cac atc cag tgg ctc<br>Phe His Cys Lys Val Tyr Ser Asp Ala Gln Pro His Ile Gln Trp Leu<br>275 280 285 | 864 |
| aag cac gtg gag gtg aac ggc agc aag gtg ggc ccg gac ggc aca ccc<br>Lys His Val Glu Val Asn Gly Ser Lys Val Gly Pro Asp Gly Thr Pro<br>290 295 300 | 912 |
| tac gtt acc gtg ctc aag tcc tgg atc agt gag agt gtg gag gcc gac<br>Tyr Val Thr Val Leu Lys Ser Trp Ile Ser Glu Ser Val Glu Ala Asp<br>305 310 315 320 | 960 |
| gtg cgc ctc cgc ctg gcc aat gtg tcg gag cgg gac ggg ggc gag tac<br>Val Arg Leu Arg Leu Ala Asn Val Ser Glu Arg Asp Gly Gly Glu Tyr<br>325 330 335 | 1008 |
| ctc tgt cga gcc acc aat ttc ata ggc gtg gcc gag aag gcc ttt tgg<br>Leu Cys Arg Ala Thr Asn Phe Ile Gly Val Ala Glu Lys Ala Phe Trp<br>340 345 350 | 1056 |
| ctg agc gtt cac ggg ccc cga gca gcc gag gag gag ctg gtg gag gct<br>Leu Ser Val His Gly Pro Arg Ala Ala Glu Glu Glu Leu Val Glu Ala<br>355 360 365 | 1104 |
| gac gag gcg ggc agt gtg tat gca ggc atc ctc agc tac ggg gtg ggc<br>Asp Glu Ala Gly Ser Val Tyr Ala Gly Ile Leu Ser Tyr Gly Val Gly<br>370 375 380 | 1152 |
| ttc ttc ctg ttc atc ctg gtg gtg gcg gct gtg acg ctc tgc cgc ctg<br>Phe Phe Leu Phe Ile Leu Val Val Ala Ala Val Thr Leu Cys Arg Leu<br>385 390 395 400 | 1200 |
| cgc agc ccc ccc aag aaa ggc ctg ggc tcc ccc acc gtg cac aag atc<br>Arg Ser Pro Pro Lys Lys Gly Leu Gly Ser Pro Thr Val His Lys Ile<br>405 410 415 | 1248 |
| tcc cgc ttc ccg ctc aag cga cag gtg tcc ctg gag tcc aac gcg tcc<br>Ser Arg Phe Pro Leu Lys Arg Gln Val Ser Leu Glu Ser Asn Ala Ser<br>420 425 430 | 1296 |
| atg agc tcc aac aca cca ctg gtg cgc atc gca agg ctg tcc tca ggg<br>Met Ser Ser Asn Thr Pro Leu Val Arg Ile Ala Arg Leu Ser Ser Gly<br>435 440 445 | 1344 |
| gag ggc ccc acg ctg gcc aat gtc tcc gag ctc gag ctg cct gcc gac<br>Glu Gly Pro Thr Leu Ala Asn Val Ser Glu Leu Glu Leu Pro Ala Asp<br>450 455 460 | 1392 |
| ccc aaa tgg gag ctg tct cgg gcc cgg ctg acc ctg ggc aag ccc ctt<br>Pro Lys Trp Glu Leu Ser Arg Ala Arg Leu Thr Leu Gly Lys Pro Leu<br>465 470 475 480 | 1440 |
| ggg gag ggc tgc ttc ggc cag gtg gtc atg gcg gag gcc atc ggc att<br>Gly Glu Gly Cys Phe Gly Gln Val Val Met Ala Glu Ala Ile Gly Ile<br>485 490 495 | 1488 |
| gac aag gac cgg gcc gcc aag cct gtc acc gta gcc gtg aag atg ctg<br>Asp Lys Asp Arg Ala Ala Lys Pro Val Thr Val Ala Val Lys Met Leu<br>500 505 510 | 1536 |
| aaa gac gat gcc act gac aag gac ctg tcg gac ctg gtg tct gag atg<br>Lys Asp Asp Ala Thr Asp Lys Asp Leu Ser Asp Leu Val Ser Glu Met<br>515 520 525 | 1584 |
| gag atg atg aag atg atc ggg aaa cac aaa aac atc atc aac ctg ctg<br>Glu Met Met Lys Met Ile Gly Lys His Lys Asn Ile Ile Asn Leu Leu<br>530 535 540 | 1632 |
| ggc gcc tgc acg cag ggc ggg ccc ctg tac gtg ctg gtg gag tac gcg<br>Gly Ala Cys Thr Gln Gly Gly Pro Leu Tyr Val Leu Val Glu Tyr Ala<br>545 550 555 560 | 1680 |
| gcc aag ggt aac ctg cgg gag ttt ctg cgg gcg cgg cgg ccc ccg ggc<br> | 1728 |

```
Ala Lys Gly Asn Leu Arg Glu Phe Leu Arg Ala Arg Arg Pro Pro Gly
            565                 570                 575 ctg gac tac tcc ttc gac acc tgc aag ccg ccc gag gag cag ctc acc    1776
Leu Asp Tyr Ser Phe Asp Thr Cys Lys Pro Pro Glu Glu Gln Leu Thr
        580                 585                 590 ttc aag gac ctg gtg tcc tgt gcc tac cag gtg gcc cgg ggc atg gag    1824
Phe Lys Asp Leu Val Ser Cys Ala Tyr Gln Val Ala Arg Gly Met Glu
            595                 600                 605 tac ttg gcc tcc cag aag tgc atc cac agg gac ctg gct gcc cgc aat    1872
Tyr Leu Ala Ser Gln Lys Cys Ile His Arg Asp Leu Ala Ala Arg Asn
610                 615                 620 gtg ctg gtg acc gag gac aac gtg atg aag atc gca gac ttc ggg ctg    1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc    1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc    2016
Arg Leu Pro Val Lys Trp Met Ala Pro Glu Ala Leu Phe Asp Arg Val
            660                 665                 670 tac act cac cag agt gac gtc tgg tcc ttt ggg gtc ctg ctc tgg gag    2064
Tyr Thr His Gln Ser Asp Val Trp Ser Phe Gly Val Leu Leu Trp Glu
        675                 680                 685 atc ttc acg ctg ggg ggc tcc ccg tac ccc ggc atc cct gtg gag gag    2112
Ile Phe Thr Leu Gly Gly Ser Pro Tyr Pro Gly Ile Pro Val Glu Glu
690                 695                 700 ctc ttc aag ctg ctg aag gag ggc cac cgc atg gac aag ccc gcc aac    2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg    2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt    2256
Pro Ser Gln Arg Pro Thr Phe Lys Gln Leu Val Glu Asp Leu Asp Arg
            740                 745                 750 gtc ctt acc gtg acg tcc acc gac gtg agt gct ggc tct ggc ctg gtg    2304
Val Leu Thr Val Thr Ser Thr Asp Val Ser Ala Gly Ser Gly Leu Val
        755                 760                 765 cca ccc gcc tat gcc cct ccc cct gcc gtc ccc ggc cat cct gcc ccc    2352
Pro Pro Ala Tyr Ala Pro Pro Pro Ala Val Pro Gly His Pro Ala Pro
770                 775                 780 cag agt gct gag gtg tgg ggc ggg cct tct ggc cca ggt gcc ctg gct    2400
Gln Ser Ala Glu Val Trp Gly Gly Pro Ser Gly Pro Gly Ala Leu Ala
785                 790                 795                 800 gac ctg gac tgc tca agc tct tcc cag agc cca gga agt tct gag aac    2448
Asp Leu Asp Cys Ser Ser Ser Ser Gln Ser Pro Gly Ser Ser Glu Asn
                805                 810                 815 caa atg gtg tct cca gga aaa gtg tct ggc agc cct gag caa gcc gtg    2496
Gln Met Val Ser Pro Gly Lys Val Ser Gly Ser Pro Glu Gln Ala Val
            820                 825                 830 gag gaa aac ctt agt tcc tat tcc tta gac aga aga gtg aca ccc gcc    2544
Glu Glu Asn Leu Ser Ser Tyr Ser Leu Asp Arg Arg Val Thr Pro Ala
        835                 840                 845 tct gag acc tta gaa gac cct tgc agg aca gag tcc cag cac aaa gcg    2592
Ser Glu Thr Leu Glu Asp Pro Cys Arg Thr Glu Ser Gln His Lys Ala
850                 855                 860 gag act ccg cac gga gcc gag gaa gaa tgc aaa gcg gag act ccg cac    2640
Glu Thr Pro His Gly Ala Glu Glu Glu Cys Lys Ala Glu Thr Pro His
865                 870                 875                 880
```

```
gga gcc gag gag gaa tgc cgg cac ggt ggg gtc tgt gct ccc gca gca      2688
Gly Ala Glu Glu Glu Cys Arg His Gly Gly Val Cys Ala Pro Ala Ala
                885                 890                 895 gtg gcc act tcg cct cct ggt gca atc cct aag gaa gcc tgc gga gga      2736
Val Ala Thr Ser Pro Pro Gly Ala Ile Pro Lys Glu Ala Cys Gly Gly
                900                 905                 910 gca ccc ctg cag ggt ctg cct ggc gaa gcc ctg ggc tgc cct gcg ggt      2784
Ala Pro Leu Gln Gly Leu Pro Gly Glu Ala Leu Gly Cys Pro Ala Gly
                915                 920                 925 gtg ggc acc ccc gtg cca gca gat ggc act cag acc ctt acc tgt gca      2832
Val Gly Thr Pro Val Pro Ala Asp Gly Thr Gln Thr Leu Thr Cys Ala
                930                 935                 940 cac acc tct gct cct gag agc aca gcc cca acc aac cac ctg gtg gct      2880
His Thr Ser Ala Pro Glu Ser Thr Ala Pro Thr Asn His Leu Val Ala
945                 950                 955                 960 ggc agg gcc atg acc ctg agt cct cag gaa gaa gtg gct gca ggc caa      2928
Gly Arg Ala Met Thr Leu Ser Pro Gln Glu Glu Val Ala Ala Gly Gln
                965                 970                 975 atg gcc agc tcc tcg agg agc gga cct gta aaa cta gaa ttt gat gta      2976
Met Ala Ser Ser Ser Arg Ser Gly Pro Val Lys Leu Glu Phe Asp Val
                980                 985                 990 tct gat ggc gcc acc agc aaa agg  gca ccc cca cca agg  aga ctg gga    3024
Ser Asp Gly Ala Thr Ser Lys Arg  Ala Pro Pro Pro Arg  Arg Leu Gly
                995                 1000                1005 gag agg  tcc ggc ctc aag cct  ccc ttg agg aaa gca  gca gtg agg       3069
Glu Arg  Ser Gly Leu Lys Pro  Pro Leu Arg Lys Ala  Ala Val Arg
1010                 1015                1020 cag caa  aag gcc ccg cag gag  gtg gag gag gac gac  ggt agg agc       3114
Gln Gln  Lys Ala Pro Gln Glu  Val Glu Glu Asp Asp  Gly Arg Ser
1025                 1030                1035 gga gca  gga gag gac ccc ccc  atg cca gct tct cgg  ggc tct tac       3159
Gly Ala  Gly Glu Asp Pro Pro  Met Pro Ala Ser Arg  Gly Ser Tyr
1040                 1045                1050 cac ctc  gac tgg gac aaa atg  gat gac cca aac ttc  atc ccg ttc       3204
His Leu  Asp Trp Asp Lys Met  Asp Asp Pro Asn Phe  Ile Pro Phe
1055                 1060                1065 gga ggt  gac acc aag tct ggt  tgc agt gag gcc cag  ccc cca gaa       3249
Gly Gly  Asp Thr Lys Ser Gly  Cys Ser Glu Ala Gln  Pro Pro Glu
1070                 1075                1080 agc cct  gag acc agg ctg ggc  cag cca gcg gct gaa  cag ttg cat       3294
Ser Pro  Glu Thr Arg Leu Gly  Gln Pro Ala Ala Glu  Gln Leu His
1085                 1090                1095 gct ggg  cct gcc acg gag gag  cca ggt ccc tgt ctg  agc cag cag       3339
Ala Gly  Pro Ala Thr Glu Glu  Pro Gly Pro Cys Leu  Ser Gln Gln
1100                 1105                1110 ctg cat  tca gcc tca gcg gag  gac acg cct gtg gtg  cag ttg gca       3384
Leu His  Ser Ala Ser Ala Glu  Asp Thr Pro Val Val  Gln Leu Ala
1115                 1120                1125 gcc gag  acc cca aca gca gag  agc aag gag aga gcc  ttg aac tct       3429
Ala Glu  Thr Pro Thr Ala Glu  Ser Lys Glu Arg Ala  Leu Asn Ser
1130                 1135                1140 gcc agc  acc tcg ctt ccc aca  agc tgt cca ggc agt  gag cca gtg       3474
Ala Ser  Thr Ser Leu Pro Thr  Ser Cys Pro Gly Ser  Glu Pro Val
1145                 1150                1155 ccc acc  cat cag cag ggg cag  cct gcc ttg gag ctg  aaa gag gag       3519
Pro Thr  His Gln Gln Gly Gln  Pro Ala Leu Glu Leu  Lys Glu Glu
1160                 1165                1170 agc ttc  aga gac ccc gct gag  gtt cta ggc acg ggc  gcg gag gtg       3564
Ser Phe  Arg Asp Pro Ala Glu  Val Leu Gly Thr Gly  Ala Glu Val
1175                 1180                1185
```

```
gat tac ctg gag cag ttt gga act tcc tcg ttt aag gag tcg gcc      3609
Asp Tyr Leu Glu Gln Phe Gly Thr Ser Ser Phe Lys Glu Ser Ala
    1190                1195                1200 ttg agg aag cag tcc tta tac ctc aag ttc gac ccc ctc ctg agg      3654
Leu Arg Lys Gln Ser Leu Tyr Leu Lys Phe Asp Pro Leu Leu Arg
    1205                1210                1215 gac agt cct ggt aga cca gtg ccc gtg gcc acc gag acc agc agc      3699
Asp Ser Pro Gly Arg Pro Val Pro Val Ala Thr Glu Thr Ser Ser
    1220                1225                1230 atg cac ggt gca aat gag act ccc tca gga cgt ccg cgg gaa gcc      3744
Met His Gly Ala Asn Glu Thr Pro Ser Gly Arg Pro Arg Glu Ala
    1235                1240                1245 aag ctt gtg gag ttc gat ttc ttg gga gca ctg gac att cct gtg      3789
Lys Leu Val Glu Phe Asp Phe Leu Gly Ala Leu Asp Ile Pro Val
    1250                1255                1260 cca ggc cca ccc cca ggt gtt ccc gcg cct ggg ggc cca ccc ctg      3834
Pro Gly Pro Pro Pro Gly Val Pro Ala Pro Gly Gly Pro Pro Leu
    1265                1270                1275 tcc acc gga cct ata gtg gac ctg ctc cag tac agc cag aag gac      3879
Ser Thr Gly Pro Ile Val Asp Leu Leu Gln Tyr Ser Gln Lys Asp
    1280                1285                1290 ctg gat gca gtg gta aag gcg aca cag gag gag aac cgg gag ctg      3924
Leu Asp Ala Val Val Lys Ala Thr Gln Glu Glu Asn Arg Glu Leu
    1295                1300                1305 agg agc agg tgt gag gag ctc cac ggg aag aac ctg gaa ctg ggg      3969
Arg Ser Arg Cys Glu Glu Leu His Gly Lys Asn Leu Glu Leu Gly
    1310                1315                1320 aag atc atg gac agg ttc gaa gag gtt gtg tac cag gcc atg gag      4014
Lys Ile Met Asp Arg Phe Glu Glu Val Val Tyr Gln Ala Met Glu
    1325                1330                1335 gaa gtt cag aag cag aag gaa ctt tcc aaa gct gaa atc cag aaa      4059
Glu Val Gln Lys Gln Lys Glu Leu Ser Lys Ala Glu Ile Gln Lys
    1340                1345                1350 gtt cta aaa gaa aaa gac caa ctt acc aca gat ctg aac tcc atg      4104
Val Leu Lys Glu Lys Asp Gln Leu Thr Thr Asp Leu Asn Ser Met
    1355                1360                1365 gag aag tcc ttc tcc gac ctc ttc aag cgt ttt gag aaa cag aaa      4149
Glu Lys Ser Phe Ser Asp Leu Phe Lys Arg Phe Glu Lys Gln Lys
    1370                1375                1380 gag gtg atc gag ggc tac cgc aag aac gaa gag tca ctg aag aag      4194
Glu Val Ile Glu Gly Tyr Arg Lys Asn Glu Glu Ser Leu Lys Lys
    1385                1390                1395 tgc gtg gag gat tac ctg gca agg atc acc cag gag ggc cag agg      4239
Cys Val Glu Asp Tyr Leu Ala Arg Ile Thr Gln Glu Gly Gln Arg
    1400                1405                1410 tac caa gcc ctg aag gcc cac gcg gag gag aag ctg cag ctg gca      4284
Tyr Gln Ala Leu Lys Ala His Ala Glu Glu Lys Leu Gln Leu Ala
    1415                1420                1425 aac gag gag atc gcc cag gtc cgg agc aag gcc cag gcg gaa gcg      4329
Asn Glu Glu Ile Ala Gln Val Arg Ser Lys Ala Gln Ala Glu Ala
    1430                1435                1440 ttg gcc ctc cag gcc agc ctg agg aag gag cag atg cgc atc cag      4374
Leu Ala Leu Gln Ala Ser Leu Arg Lys Glu Gln Met Arg Ile Gln
    1445                1450                1455 tcg ctg gag aag aca gtg gag cag aag act aaa gag aac gag gag      4419
Ser Leu Glu Lys Thr Val Glu Gln Lys Thr Lys Glu Asn Glu Glu
    1460                1465                1470 ctg acc agg atc tgc gac gac ctc atc tcc aag atg gag aag atc      4464
Leu Thr Arg Ile Cys Asp Asp Leu Ile Ser Lys Met Glu Lys Ile
```

-continued

```
           1475                1480               1485
tga                                                                  4467
```

<210> SEQ ID NO 16
<211> LENGTH: 1488
<212> TYPE: PRT
<213> ORGANISM: Homo sapiens

<400> SEQUENCE: 16

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala

```
                355                 360                 365
Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Gly Leu Gly Ser Pro Thr Val His Lys Ile
            405                 410                 415

Ser Arg Phe Pro Leu Lys Arg Gln Val Ser Leu Glu Ser Asn Ala Ser
                420                 425                 430

Met Ser Ser Asn Thr Pro Leu Val Arg Ile Ala Arg Leu Ser Ser Gly
            435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
                515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
                595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
                675                 680                 685

Ile Phe Thr Leu Gly Gly Ser Pro Tyr Pro Gly Ile Pro Val Glu Glu
    690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Val Ser Ala Gly Ser Gly Leu Val
                755                 760                 765

Pro Pro Ala Tyr Ala Pro Pro Ala Val Pro Gly His Pro Ala Pro
    770                 775                 780
```

```
Gln Ser Ala Glu Val Trp Gly Gly Pro Ser Gly Pro Gly Ala Leu Ala
785                 790                 795                 800

Asp Leu Asp Cys Ser Ser Ser Gln Ser Pro Gly Ser Ser Glu Asn
            805                 810                 815

Gln Met Val Ser Pro Gly Lys Val Ser Gly Ser Pro Glu Gln Ala Val
            820                 825                 830

Glu Glu Asn Leu Ser Ser Tyr Ser Leu Asp Arg Arg Val Thr Pro Ala
            835                 840                 845

Ser Glu Thr Leu Glu Asp Pro Cys Arg Thr Glu Ser Gln His Lys Ala
    850                 855                 860

Glu Thr Pro His Gly Ala Glu Glu Cys Lys Ala Glu Thr Pro His
865                 870                 875                 880

Gly Ala Glu Glu Cys Arg His Gly Gly Val Cys Ala Pro Ala Ala
            885                 890                 895

Val Ala Thr Ser Pro Pro Gly Ala Ile Pro Lys Glu Ala Cys Gly Gly
            900                 905                 910

Ala Pro Leu Gln Gly Leu Pro Gly Glu Ala Leu Gly Cys Pro Ala Gly
            915                 920                 925

Val Gly Thr Pro Val Pro Ala Asp Gly Thr Gln Thr Leu Thr Cys Ala
    930                 935                 940

His Thr Ser Ala Pro Glu Ser Thr Ala Pro Thr Asn His Leu Val Ala
945                 950                 955                 960

Gly Arg Ala Met Thr Leu Ser Pro Gln Glu Glu Val Ala Ala Gly Gln
            965                 970                 975

Met Ala Ser Ser Ser Arg Ser Gly Pro Val Lys Leu Glu Phe Asp Val
            980                 985                 990

Ser Asp Gly Ala Thr Ser Lys Arg Ala Pro Pro Pro Arg Arg Leu Gly
    995                 1000                1005

Glu Arg Ser Gly Leu Lys Pro Pro Leu Arg Lys Ala Ala Val Arg
    1010                1015                1020

Gln Gln Lys Ala Pro Gln Glu Val Glu Asp Asp Gly Arg Ser
    1025                1030                1035

Gly Ala Gly Glu Asp Pro Pro Met Pro Ala Ser Arg Gly Ser Tyr
    1040                1045                1050

His Leu Asp Trp Asp Lys Met Asp Asp Pro Asn Phe Ile Pro Phe
    1055                1060                1065

Gly Gly Asp Thr Lys Ser Gly Cys Ser Glu Ala Gln Pro Pro Glu
    1070                1075                1080

Ser Pro Glu Thr Arg Leu Gly Gln Pro Ala Ala Glu Gln Leu His
    1085                1090                1095

Ala Gly Pro Ala Thr Glu Glu Pro Gly Pro Cys Leu Ser Gln Gln
    1100                1105                1110

Leu His Ser Ala Ser Ala Glu Asp Thr Pro Val Val Gln Leu Ala
    1115                1120                1125

Ala Glu Thr Pro Thr Ala Glu Ser Lys Glu Arg Ala Leu Asn Ser
    1130                1135                1140

Ala Ser Thr Ser Leu Pro Thr Ser Cys Pro Gly Ser Glu Pro Val
    1145                1150                1155

Pro Thr His Gln Gln Gly Gln Pro Ala Leu Glu Leu Lys Glu Glu
    1160                1165                1170

Ser Phe Arg Asp Pro Ala Glu Val Leu Gly Thr Gly Ala Glu Val
    1175                1180                1185
```

Asp Tyr Leu Glu Gln Phe Gly Thr Ser Ser Phe Lys Glu Ser Ala
1190                1195                1200

Leu Arg Lys Gln Ser Leu Tyr Leu Lys Phe Asp Pro Leu Leu Arg
1205                1210                1215

Asp Ser Pro Gly Arg Pro Val Pro Val Ala Thr Glu Thr Ser Ser
1220                1225                1230

Met His Gly Ala Asn Glu Thr Pro Ser Gly Arg Pro Arg Glu Ala
1235                1240                1245

Lys Leu Val Glu Phe Asp Phe Leu Gly Ala Leu Asp Ile Pro Val
1250                1255                1260

Pro Gly Pro Pro Pro Gly Val Pro Ala Pro Gly Gly Pro Pro Leu
1265                1270                1275

Ser Thr Gly Pro Ile Val Asp Leu Leu Gln Tyr Ser Gln Lys Asp
1280                1285                1290

Leu Asp Ala Val Val Lys Ala Thr Gln Glu Glu Asn Arg Glu Leu
1295                1300                1305

Arg Ser Arg Cys Glu Glu Leu His Gly Lys Asn Leu Glu Leu Gly
1310                1315                1320

Lys Ile Met Asp Arg Phe Glu Glu Val Val Tyr Gln Ala Met Glu
1325                1330                1335

Glu Val Gln Lys Gln Lys Glu Leu Ser Lys Ala Glu Ile Gln Lys
1340                1345                1350

Val Leu Lys Glu Lys Asp Gln Leu Thr Thr Asp Leu Asn Ser Met
1355                1360                1365

Glu Lys Ser Phe Ser Asp Leu Phe Lys Arg Phe Glu Lys Gln Lys
1370                1375                1380

Glu Val Ile Glu Gly Tyr Arg Lys Asn Glu Glu Ser Leu Lys Lys
1385                1390                1395

Cys Val Glu Asp Tyr Leu Ala Arg Ile Thr Gln Glu Gly Gln Arg
1400                1405                1410

Tyr Gln Ala Leu Lys Ala His Ala Glu Glu Lys Leu Gln Leu Ala
1415                1420                1425

Asn Glu Glu Ile Ala Gln Val Arg Ser Lys Ala Gln Ala Glu Ala
1430                1435                1440

Leu Ala Leu Gln Ala Ser Leu Arg Lys Glu Gln Met Arg Ile Gln
1445                1450                1455

Ser Leu Glu Lys Thr Val Glu Gln Lys Thr Lys Glu Asn Glu Glu
1460                1465                1470

Leu Thr Arg Ile Cys Asp Asp Leu Ile Ser Lys Met Glu Lys Ile
1475                1480                1485

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 17
ggatccgcca ccatggacta caaggacgac gatgacaagg gcgcccctgc ctgcgccctc    60

<210> SEQ ID NO 18
<211> LENGTH: 20
<212> TYPE: DNA
<213> ORGANISM: Artificial Sequence
<220> FEATURE:

```
<223> OTHER INFORMATION: Description of Artificial Sequence: an
      artificially synthesized primer sequence

<400> SEQUENCE: 18
tcctgctctg ccggtcgcac                                                    20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 19
aggatgcgcc catcattccg ca                                                 22

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 20
ggatccgcca ccatgggcgc ccctgcctg                                          29

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 21
gcggccgctc atcgaatgat gggtgccg                                           28

<210> SEQ ID NO 22
<211> LENGTH: 3765
<212> TYPE: DNA
<213> ORGANISM: Homo sapiens
<220> FEATURE:
<221> NAME/KEY: CDS
<222> LOCATION: (1)..(3765)

<400> SEQUENCE: 22 atg ggc gcc cct gcc tgc gcc ctc gcg ctc tgc gtg gcc gtg gcc atc          48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg          96
Val Ala Gly Ala Ser Ser Glu Ser Leu Gly Thr Glu Gln Arg Val Val
                20                  25                  30 ggg cga gcg gca gaa gtc ccg ggc cca gag ccc ggc cag cag gag cag         144
Gly Arg Ala Ala Glu Val Pro Gly Pro Glu Pro Gly Gln Gln Glu Gln
            35                  40                  45 ttg gtc ttc ggc agc ggg gat gct gtg gag ctg agc tgt ccc ccg ccc         192
Leu Val Phe Gly Ser Gly Asp Ala Val Glu Leu Ser Cys Pro Pro Pro
        50                  55                  60 ggg ggt ggt ccc atg ggg ccc act gtc tgg gtc aag gat ggc aca ggg         240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg         288
Leu Val Pro Ser Glu Arg Val Leu Val Gly Pro Gln Arg Leu Gln Val
```

```
                    85                  90                  95
ctg aat gcc tcc cac gag gac tcc ggg gcc tac agc tgc cgg cag cgg      336
Leu Asn Ala Ser His Glu Asp Ser Gly Ala Tyr Ser Cys Arg Gln Arg
        100                 105                 110 ctc acg cag cgc gta ctg tgc cac ttc agt gtg cgg gtg aca gac gct      384
Leu Thr Gln Arg Val Leu Cys His Phe Ser Val Arg Val Thr Asp Ala
        115                 120                 125 cca tcc tcg gga gat gac gaa gac ggg gag gac gag gct gag gac aca      432
Pro Ser Ser Gly Asp Asp Glu Asp Gly Glu Asp Glu Ala Glu Asp Thr
130                 135                 140 ggt gtg gac aca ggg gcc cct tac tgg aca cgg ccc gag cgg atg gac      480
Gly Val Asp Thr Gly Ala Pro Tyr Trp Thr Arg Pro Glu Arg Met Asp
145                 150                 155                 160 aag aag ctg ctg gcc gtg ccg gcc gcc aac acc gtc cgc ttc cgc tgc      528
Lys Lys Leu Leu Ala Val Pro Ala Ala Asn Thr Val Arg Phe Arg Cys
                165                 170                 175 cca gcc gct ggc aac ccc act ccc tcc atc tcc tgg ctg aag aac ggc      576
Pro Ala Ala Gly Asn Pro Thr Pro Ser Ile Ser Trp Leu Lys Asn Gly
        180                 185                 190 agg gag ttc cgc ggc gag cac cgc att gga ggc atc aag ctg cgg cat      624
Arg Glu Phe Arg Gly Glu His Arg Ile Gly Gly Ile Lys Leu Arg His
        195                 200                 205 cag cag tgg agc ctg gtc atg gaa agc gtg gtg ccc tcg gac cgc ggc      672
Gln Gln Trp Ser Leu Val Met Glu Ser Val Val Pro Ser Asp Arg Gly
        210                 215                 220 aac tac acc tgc gtc gtg gag aac aag ttt ggc agc atc cgg cag acg      720
Asn Tyr Thr Cys Val Val Glu Asn Lys Phe Gly Ser Ile Arg Gln Thr
225                 230                 235                 240 tac acg ctg gac gtg ctg gag cgc tcc ccg cac cgg ccc atc ctg cag      768
Tyr Thr Leu Asp Val Leu Glu Arg Ser Pro His Arg Pro Ile Leu Gln
                245                 250                 255 gcg ggg ctg ccg gcc aac cag acg gcg gtg ctg ggc agc gac gtg gag      816
Ala Gly Leu Pro Ala Asn Gln Thr Ala Val Leu Gly Ser Asp Val Glu
        260                 265                 270 ttc cac tgc aag gtg tac agt gac gca cag ccc cac atc cag tgg ctc      864
Phe His Cys Lys Val Tyr Ser Asp Ala Gln Pro His Ile Gln Trp Leu
        275                 280                 285 aag cac gtg gag gtg aat ggc agc aag gtg ggc ccg gac ggc aca ccc      912
Lys His Val Glu Val Asn Gly Ser Lys Val Gly Pro Asp Gly Thr Pro
        290                 295                 300 tac gtt acc gtg ctc aag tcc tgg atc agt gag agt gtg gag gcc gac      960
Tyr Val Thr Val Leu Lys Ser Trp Ile Ser Glu Ser Val Glu Ala Asp
305                 310                 315                 320 gtg cgc ctc cgc ctg gcc aat gtg tcg gag cgg gac ggg ggc gag tac     1008
Val Arg Leu Arg Leu Ala Asn Val Ser Glu Arg Asp Gly Gly Glu Tyr
                325                 330                 335 ctc tgt cga gcc acc aat ttc ata ggc gtg gcc gag aag gcc ttt tgg     1056
Leu Cys Arg Ala Thr Asn Phe Ile Gly Val Ala Glu Lys Ala Phe Trp
        340                 345                 350 ctg agc gtt cac ggg ccc cga gca gcc gag gag gag ctg gtg gag gct     1104
Leu Ser Val His Gly Pro Arg Ala Ala Glu Glu Glu Leu Val Glu Ala
        355                 360                 365 gac gag gcg ggc agt gtg tat gca ggc atc ctc agc tac ggg gtg ggc     1152
Asp Glu Ala Gly Ser Val Tyr Ala Gly Ile Leu Ser Tyr Gly Val Gly
        370                 375                 380 ttc ttc ctg ttc atc ctg gtg gtg gcg gct gtg acg ctc tgc cgc ctg     1200
Phe Phe Leu Phe Ile Leu Val Val Ala Ala Val Thr Leu Cys Arg Leu
385                 390                 395                 400 cgc agc ccc ccc aag aaa ggc ctg ggc tcc ccc acc gtg cac aag atc     1248
```

|  |  |  |  |  |  |  |  |  |  |  |  |  |  |
|---|---|---|---|---|---|---|---|---|---|---|---|---|---|
| Arg | Ser | Pro | Pro | Lys | Lys | Gly | Leu | Gly | Ser | Pro | Thr | Val | His | Lys | Ile |
|  |  |  | 405 |  |  |  | 410 |  |  |  |  | 415 |

```
tcc cgc ttc ccg ctc aag cga cag gtg tcc ctg gag tcc aac gcg tcc          1296
Ser Arg Phe Pro Leu Lys Arg Gln Val Ser Leu Glu Ser Asn Ala Ser
            420                 425                 430 atg agc tcc aac aca cca ctg gtg cgc atc gca agg ctg tcc tca ggg          1344
Met Ser Ser Asn Thr Pro Leu Val Arg Ile Ala Arg Leu Ser Ser Gly
            435                 440                 445 gag ggc ccc acg ctg gcc aat gtc tcc gag ctc gag ctg cct gcc gac          1392
Glu Gly Pro Thr Leu Ala Asn Val Ser Glu Leu Glu Leu Pro Ala Asp
        450                 455                 460 ccc aaa tgg gag ctg tct cgg gcc cgg ctg acc ctg ggc aag ccc ctt          1440
Pro Lys Trp Glu Leu Ser Arg Ala Arg Leu Thr Leu Gly Lys Pro Leu
465                 470                 475                 480 ggg gag ggc tgc ttc ggc cag gtg gtc atg gcg gag gcc atc ggc att          1488
Gly Glu Gly Cys Phe Gly Gln Val Val Met Ala Glu Ala Ile Gly Ile
                    485                 490                 495 gac aag gac cgg gcc gcc aag cct gtc acc gta gcc gtg aag atg ctg          1536
Asp Lys Asp Arg Ala Ala Lys Pro Val Thr Val Ala Val Lys Met Leu
            500                 505                 510 aaa gac gat gcc act gac aag gac ctg tcg gac ctg gtg tct gag atg          1584
Lys Asp Asp Ala Thr Asp Lys Asp Leu Ser Asp Leu Val Ser Glu Met
            515                 520                 525 gag atg atg aag atg atc ggg aaa cac aaa aac atc atc aac ctg ctg          1632
Glu Met Met Lys Met Ile Gly Lys His Lys Asn Ile Ile Asn Leu Leu
530                 535                 540 ggc gcc tgc acg cag ggc ggg ccc ctg tac gtg ctg gtg gag tac gcg          1680
Gly Ala Cys Thr Gln Gly Gly Pro Leu Tyr Val Leu Val Glu Tyr Ala
545                 550                 555                 560 gcc aag ggt aac ctg cgg gag ttt ctg cgg gcg cgg cgg ccc ccg ggc          1728
Ala Lys Gly Asn Leu Arg Glu Phe Leu Arg Ala Arg Arg Pro Pro Gly
                565                 570                 575 ctg gac tac tcc ttc gac acc tgc aag ccg ccc gag gag cag ctc acc          1776
Leu Asp Tyr Ser Phe Asp Thr Cys Lys Pro Pro Glu Glu Gln Leu Thr
            580                 585                 590 ttc aag gac ctg gtg tcc tgt gcc tac cag gtg gcc cgg ggc atg gag          1824
Phe Lys Asp Leu Val Ser Cys Ala Tyr Gln Val Ala Arg Gly Met Glu
            595                 600                 605 tac ttg gcc tcc cag aag tgc atc cac agg gac ctg gct gcc cgc aat          1872
Tyr Leu Ala Ser Gln Lys Cys Ile His Arg Asp Leu Ala Ala Arg Asn
        610                 615                 620 gtg ctg gtg acc gag gac aac gtg atg aag atc gca gac ttc ggg ctg          1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc          1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc          2016
Arg Leu Pro Val Lys Trp Met Ala Pro Glu Ala Leu Phe Asp Arg Val
            660                 665                 670 tac act cac cag agt gac gtc tgg tcc ttt ggg gtc ctg ctc tgg gag          2064
Tyr Thr His Gln Ser Asp Val Trp Ser Phe Gly Val Leu Leu Trp Glu
            675                 680                 685 atc ttc acg ctg ggg ggc tcc ccg tac ccc ggc atc cct gtg gag gag          2112
Ile Phe Thr Leu Gly Gly Ser Pro Tyr Pro Gly Ile Pro Val Glu Glu
        690                 695                 700 ctc ttc aag ctg ctg aag gag ggc cac cgc atg gac aag ccc gcc aac          2160
Leu Phe Lys Leu Leu Lys Glu Gly His Arg Met Asp Lys Pro Ala Asn
705                 710                 715                 720
```

-continued

| | | |
|---|---|---|
| tgc aca cac gac ctg tac atg atc atg cgg gag tgc tgg cat gcc gcg<br>Cys Thr His Asp Leu Tyr Met Ile Met Arg Glu Cys Trp His Ala Ala<br>725 730 735 | | 2208 |
| ccc tcc cag agg ccc acc ttc aag cag ctg gtg gag gac ctg gac cgt<br>Pro Ser Gln Arg Pro Thr Phe Lys Gln Leu Val Glu Asp Leu Asp Arg<br>740 745 750 | | 2256 |
| gtc ctt acc gtg acg tcc acc gac aat gtt atg gaa cag ttc aat cct<br>Val Leu Thr Val Thr Ser Thr Asp Asn Val Met Glu Gln Phe Asn Pro<br>755 760 765 | | 2304 |
| ggg ctg cga aat tta ata aac ctg ggg aaa aat tat gag aaa gct gta<br>Gly Leu Arg Asn Leu Ile Asn Leu Gly Lys Asn Tyr Glu Lys Ala Val<br>770 775 780 | | 2352 |
| aac gct atg atc ctg gca gga aaa gcc tac tac gat gga gtg gcc aag<br>Asn Ala Met Ile Leu Ala Gly Lys Ala Tyr Tyr Asp Gly Val Ala Lys<br>785 790 795 800 | | 2400 |
| atc ggt gag att gcc act ggg tcc ccc gtg tca act gaa ctg gga cat<br>Ile Gly Glu Ile Ala Thr Gly Ser Pro Val Ser Thr Glu Leu Gly His<br>805 810 815 | | 2448 |
| gtc ctc ata gag att tca agt acc cac aag aaa ctc aac gag agt ctt<br>Val Leu Ile Glu Ile Ser Ser Thr His Lys Lys Leu Asn Glu Ser Leu<br>820 825 830 | | 2496 |
| gat gaa aat ttt aaa aaa ttc cac aaa gag att atc cat gag ctg gag<br>Asp Glu Asn Phe Lys Lys Phe His Lys Glu Ile Ile His Glu Leu Glu<br>835 840 845 | | 2544 |
| aag aag ata gaa ctt gac gtg aaa tat atg aac gca act cta aaa aga<br>Lys Lys Ile Glu Leu Asp Val Lys Tyr Met Asn Ala Thr Leu Lys Arg<br>850 855 860 | | 2592 |
| tac caa aca gaa cac aag aat aaa tta gag tct ttg gag aaa tcc caa<br>Tyr Gln Thr Glu His Lys Asn Lys Leu Glu Ser Leu Glu Lys Ser Gln<br>865 870 875 880 | | 2640 |
| gct gag ttg aag aag atc aga agg aaa agc caa gga agc cga aac gca<br>Ala Glu Leu Lys Lys Ile Arg Arg Lys Ser Gln Gly Ser Arg Asn Ala<br>885 890 895 | | 2688 |
| ctc aaa tat gaa cac aaa gaa att gag tat gtg gag acc gtt act tct<br>Leu Lys Tyr Glu His Lys Glu Ile Glu Tyr Val Glu Thr Val Thr Ser<br>900 905 910 | | 2736 |
| cgt cag agt gaa atc cag aaa ttc att gca gat ggt tgc aaa gag gct<br>Arg Gln Ser Glu Ile Gln Lys Phe Ile Ala Asp Gly Cys Lys Glu Ala<br>915 920 925 | | 2784 |
| ctg ctt gaa gag aag agg cgc ttc tgc ttt ctg gtt gat aag cac tgt<br>Leu Leu Glu Glu Lys Arg Arg Phe Cys Phe Leu Val Asp Lys His Cys<br>930 935 940 | | 2832 |
| ggc ttt gca aac cac ata cat tat tat cac tta cag tct gca gaa cta<br>Gly Phe Ala Asn His Ile His Tyr Tyr His Leu Gln Ser Ala Glu Leu<br>945 950 955 960 | | 2880 |
| ctg aat tcc aag ctg cct cgg tgg cag gag acc tgt gtt gat gcc atc<br>Leu Asn Ser Lys Leu Pro Arg Trp Gln Glu Thr Cys Val Asp Ala Ile<br>965 970 975 | | 2928 |
| aaa gtg cca gag aaa atc atg aat atg atc gaa gaa ata aag acc cca<br>Lys Val Pro Glu Lys Ile Met Asn Met Ile Glu Glu Ile Lys Thr Pro<br>980 985 990 | | 2976 |
| gcc tct acc ccc gtg tct gga act cct cag gct tca ccc atg atc gag<br>Ala Ser Thr Pro Val Ser Gly Thr Pro Gln Ala Ser Pro Met Ile Glu<br>995 1000 1005 | | 3024 |
| aga agc aat gtg gtt agg aaa gat tac gac acc ctt tct aaa tgc<br>Arg Ser Asn Val Val Arg Lys Asp Tyr Asp Thr Leu Ser Lys Cys<br>1010 1015 1020 | | 3069 |
| tca cca aag atg ccc ccc gct cct tca ggc aga gca tat acc agt<br>Ser Pro Lys Met Pro Pro Ala Pro Ser Gly Arg Ala Tyr Thr Ser<br>1025 1030 1035 | | 3114 |

-continued

```
ccc ttg atc gat atg ttt aat aac cca gcc acg gct gcc ccg aat       3159
Pro Leu Ile Asp Met Phe Asn Asn Pro Ala Thr Ala Ala Pro Asn
    1040            1045                1050 tca caa agg gta aat aat tca aca ggt act tcc gaa gat ccc agt       3204
Ser Gln Arg Val Asn Asn Ser Thr Gly Thr Ser Glu Asp Pro Ser
1055                1060                1065 tta cag cga tca gtt tcg gtt gca acg gga ctg aac atg atg aag       3249
Leu Gln Arg Ser Val Ser Val Ala Thr Gly Leu Asn Met Met Lys
    1070            1075                1080 aag cag aaa gtg aag acc atc ttc ccg cac act gcg ggc tcc aac       3294
Lys Gln Lys Val Lys Thr Ile Phe Pro His Thr Ala Gly Ser Asn
1085                1090                1095 aag acc tta ctc agc ttt gca cag gga gat gtc atc acg ctg ctc       3339
Lys Thr Leu Leu Ser Phe Ala Gln Gly Asp Val Ile Thr Leu Leu
    1100            1105                1110 atc ccc gag gag aag gat ggc tgg ctc tat gga gaa cac gac gtg       3384
Ile Pro Glu Glu Lys Asp Gly Trp Leu Tyr Gly Glu His Asp Val
1115                1120                1125 tcc aag gcg agg ggt tgg ttc ccg tcg tcg tac acg aag ttg ctg       3429
Ser Lys Ala Arg Gly Trp Phe Pro Ser Ser Tyr Thr Lys Leu Leu
    1130            1135                1140 gaa gaa aat gag aca gaa gca gtg acc gtg ccc acg cca agc ccc       3474
Glu Glu Asn Glu Thr Glu Ala Val Thr Val Pro Thr Pro Ser Pro
1145                1150                1155 aca cca gtg aga agc atc agc acc gtg aac ttg tct gag aat agc       3519
Thr Pro Val Arg Ser Ile Ser Thr Val Asn Leu Ser Glu Asn Ser
    1160            1165                1170 agt gtt gtc atc ccc cca ccc gac tac ttg gaa tgc tta tcc atg       3564
Ser Val Val Ile Pro Pro Pro Asp Tyr Leu Glu Cys Leu Ser Met
1175                1180                1185 ggg gca gct gcc gac agg aga gca gat tcg gcc agg acg aca tcc       3609
Gly Ala Ala Ala Asp Arg Arg Ala Asp Ser Ala Arg Thr Thr Ser
    1190            1195                1200 acc ttt aag gcc cca gcg tcc aag ccc gag acc gcg gct cct aac       3654
Thr Phe Lys Ala Pro Ala Ser Lys Pro Glu Thr Ala Ala Pro Asn
1205                1210                1215 gat gcc aac ggg act gca aag ccg cct ttt ctc agc gga gaa aac       3699
Asp Ala Asn Gly Thr Ala Lys Pro Pro Phe Leu Ser Gly Glu Asn
    1220            1225                1230 ccc ttt gcc act gtg aaa ctc cgt ccg act gtg acg aat gat cgc       3744
Pro Phe Ala Thr Val Lys Leu Arg Pro Thr Val Thr Asn Asp Arg
1235                1240                1245 tca gca ccc atc att cga tga                                       3765
Ser Ala Pro Ile Ile Arg
    1250
```

<210> SEQ ID NO 23
<211> LENGTH: 1254
<212> TYPE: PRT
<213> ORGANISM: Homo sapiens

<400> SEQUENCE: 23

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro

-continued

```
                50                  55                  60
Gly Gly Gly Pro Met Gly Pro Thr Val Trp Val Lys Asp Gly Thr Gly
 65                  70                  75                  80
Leu Val Pro Ser Glu Arg Val Leu Val Gly Pro Gln Arg Leu Gln Val
                 85                  90                  95
Leu Asn Ala Ser His Glu Asp Ser Gly Ala Tyr Ser Cys Arg Gln Arg
                100                 105                 110
Leu Thr Gln Arg Val Leu Cys His Phe Ser Val Arg Val Thr Asp Ala
                115                 120                 125
Pro Ser Ser Gly Asp Asp Glu Asp Gly Glu Asp Glu Ala Glu Asp Thr
                130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
                180                 185                 190
Arg Glu Phe Arg Gly Glu His Arg Ile Gly Gly Ile Lys Leu Arg His
                195                 200                 205
Gln Gln Trp Ser Leu Val Met Glu Ser Val Val Pro Ser Asp Arg Gly
                210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
                260                 265                 270
Phe His Cys Lys Val Tyr Ser Asp Ala Gln Pro His Ile Gln Trp Leu
                275                 280                 285
Lys His Val Glu Val Asn Gly Ser Lys Val Gly Pro Asp Gly Thr Pro
                290                 295                 300
Tyr Val Thr Val Leu Lys Ser Trp Ile Ser Glu Ser Val Glu Ala Asp
305                 310                 315                 320
Val Arg Leu Arg Leu Ala Asn Val Ser Glu Arg Asp Gly Gly Glu Tyr
                325                 330                 335
Leu Cys Arg Ala Thr Asn Phe Ile Gly Val Ala Glu Lys Ala Phe Trp
                340                 345                 350
Leu Ser Val His Gly Pro Arg Ala Ala Glu Glu Leu Val Glu Ala
                355                 360                 365
Asp Glu Ala Gly Ser Val Tyr Ala Gly Ile Leu Ser Tyr Gly Val Gly
                370                 375                 380
Phe Phe Leu Phe Ile Leu Val Val Ala Ala Val Thr Leu Cys Arg Leu
385                 390                 395                 400
Arg Ser Pro Pro Lys Lys Gly Leu Gly Ser Pro Thr Val His Lys Ile
                405                 410                 415
Ser Arg Phe Pro Leu Lys Arg Gln Val Ser Leu Glu Ser Asn Ala Ser
                420                 425                 430
Met Ser Ser Asn Thr Pro Leu Val Arg Ile Ala Arg Leu Ser Ser Gly
                435                 440                 445
Glu Gly Pro Thr Leu Ala Asn Val Ser Glu Leu Glu Leu Pro Ala Asp
                450                 455                 460
Pro Lys Trp Glu Leu Ser Arg Ala Arg Leu Thr Leu Gly Lys Pro Leu
465                 470                 475                 480
```

```
Gly Glu Gly Cys Phe Gly Gln Val Val Met Ala Glu Ala Ile Gly Ile
            485                 490                 495
Asp Lys Asp Arg Ala Ala Lys Pro Val Thr Val Ala Val Lys Met Leu
        500                 505                 510
Lys Asp Asp Ala Thr Lys Asp Leu Ser Asp Leu Val Ser Glu Met
        515                 520                 525
Glu Met Met Lys Met Ile Gly Lys His Lys Asn Ile Ile Asn Leu Leu
        530                 535                 540
Gly Ala Cys Thr Gln Gly Gly Pro Leu Tyr Val Leu Val Glu Tyr Ala
545                 550                 555                 560
Ala Lys Gly Asn Leu Arg Glu Phe Leu Arg Ala Arg Pro Pro Gly
            565                 570                 575
Leu Asp Tyr Ser Phe Asp Thr Cys Lys Pro Pro Glu Glu Gln Leu Thr
            580                 585                 590
Phe Lys Asp Leu Val Ser Cys Ala Tyr Gln Val Ala Arg Gly Met Glu
            595                 600                 605
Tyr Leu Ala Ser Gln Lys Cys Ile His Arg Asp Leu Ala Ala Arg Asn
            610                 615                 620
Val Leu Val Thr Glu Asp Asn Val Met Lys Ile Ala Asp Phe Gly Leu
625                 630                 635                 640
Ala Arg Asp Val His Asn Leu Asp Tyr Tyr Lys Lys Thr Thr Asn Gly
            645                 650                 655
Arg Leu Pro Val Lys Trp Met Ala Pro Glu Ala Leu Phe Asp Arg Val
            660                 665                 670
Tyr Thr His Gln Ser Asp Val Trp Ser Phe Gly Val Leu Leu Trp Glu
            675                 680                 685
Ile Phe Thr Leu Gly Gly Ser Pro Tyr Pro Gly Ile Pro Val Glu Glu
            690                 695                 700
Leu Phe Lys Leu Leu Lys Glu Gly His Arg Met Asp Lys Pro Ala Asn
705                 710                 715                 720
Cys Thr His Asp Leu Tyr Met Ile Met Arg Glu Cys Trp His Ala Ala
            725                 730                 735
Pro Ser Gln Arg Pro Thr Phe Lys Gln Leu Val Glu Asp Leu Asp Arg
            740                 745                 750
Val Leu Thr Val Thr Ser Thr Asp Asn Val Met Glu Gln Phe Asn Pro
            755                 760                 765
Gly Leu Arg Asn Leu Ile Asn Leu Gly Lys Asn Tyr Glu Lys Ala Val
            770                 775                 780
Asn Ala Met Ile Leu Ala Gly Lys Ala Tyr Tyr Asp Gly Val Ala Lys
785                 790                 795                 800
Ile Gly Glu Ile Ala Thr Gly Ser Pro Val Ser Thr Glu Leu Gly His
            805                 810                 815
Val Leu Ile Glu Ile Ser Ser Thr His Lys Lys Leu Asn Glu Ser Leu
            820                 825                 830
Asp Glu Asn Phe Lys Lys Phe His Lys Glu Ile Ile His Glu Leu Glu
            835                 840                 845
Lys Lys Ile Glu Leu Asp Val Lys Tyr Met Asn Ala Thr Leu Lys Arg
            850                 855                 860
Tyr Gln Thr Glu His Lys Asn Lys Leu Glu Ser Leu Glu Lys Ser Gln
865                 870                 875                 880
Ala Glu Leu Lys Lys Ile Arg Arg Lys Ser Gln Gly Ser Arg Asn Ala
            885                 890                 895
```

```
Leu Lys Tyr Glu His Lys Glu Ile Glu Tyr Val Glu Thr Val Thr Ser
            900                 905                 910

Arg Gln Ser Glu Ile Gln Lys Phe Ile Ala Asp Gly Cys Lys Glu Ala
        915                 920                 925

Leu Leu Glu Glu Lys Arg Arg Phe Cys Phe Leu Val Asp Lys His Cys
    930                 935                 940

Gly Phe Ala Asn His Ile His Tyr Tyr His Leu Gln Ser Ala Glu Leu
945                 950                 955                 960

Leu Asn Ser Lys Leu Pro Arg Trp Gln Glu Thr Cys Val Asp Ala Ile
                965                 970                 975

Lys Val Pro Glu Lys Ile Met Asn Met Ile Glu Glu Ile Lys Thr Pro
            980                 985                 990

Ala Ser Thr Pro Val Ser Gly Thr Pro Gln Ala Ser Pro Met Ile Glu
        995                 1000                1005

Arg Ser Asn Val Val Arg Lys Asp Tyr Asp Thr Leu Ser Lys Cys
    1010                1015                1020

Ser Pro Lys Met Pro Pro Ala Pro Ser Gly Arg Ala Tyr Thr Ser
    1025                1030                1035

Pro Leu Ile Asp Met Phe Asn Asn Pro Ala Thr Ala Ala Pro Asn
    1040                1045                1050

Ser Gln Arg Val Asn Asn Ser Thr Gly Thr Ser Glu Asp Pro Ser
    1055                1060                1065

Leu Gln Arg Ser Val Ser Val Ala Thr Gly Leu Asn Met Met Lys
    1070                1075                1080

Lys Gln Lys Val Lys Thr Ile Phe Pro His Thr Ala Gly Ser Asn
    1085                1090                1095

Lys Thr Leu Leu Ser Phe Ala Gln Gly Asp Val Ile Thr Leu Leu
    1100                1105                1110

Ile Pro Glu Glu Lys Asp Gly Trp Leu Tyr Gly Glu His Asp Val
    1115                1120                1125

Ser Lys Ala Arg Gly Trp Phe Pro Ser Ser Tyr Thr Lys Leu Leu
    1130                1135                1140

Glu Glu Asn Glu Thr Glu Ala Val Thr Val Pro Thr Pro Ser Pro
    1145                1150                1155

Thr Pro Val Arg Ser Ile Ser Thr Val Asn Leu Ser Glu Asn Ser
    1160                1165                1170

Ser Val Val Ile Pro Pro Asp Tyr Leu Glu Cys Leu Ser Met
    1175                1180                1185

Gly Ala Ala Ala Asp Arg Arg Ala Asp Ser Ala Arg Thr Thr Ser
    1190                1195                1200

Thr Phe Lys Ala Pro Ala Ser Lys Pro Glu Thr Ala Ala Pro Asn
    1205                1210                1215

Asp Ala Asn Gly Thr Ala Lys Pro Pro Phe Leu Ser Gly Glu Asn
    1220                1225                1230

Pro Phe Ala Thr Val Lys Leu Arg Pro Thr Val Thr Asn Asp Arg
    1235                1240                1245

Ser Ala Pro Ile Ile Arg
    1250

<210> SEQ ID NO 24
<211> LENGTH: 27
<212> TYPE: DNA
<213> ORGANISM: Artificial Sequence
```

```
<220> FEATURE:
<223> OTHER INFORMATION: Description of Artificial Sequence: an
      artificially synthesized FLAG tag sequence

<400> SEQUENCE: 24
atggactaca aggacgacga tgacaag                                         27
```

NITROGEN-CONTAINING AROMATIC HETEROCYCLIC COMPOUND

TECHNICAL FIELD

The present invention relates to compounds useful as active ingredients in pharmaceutical compositions, particularly in pharmaceutical compositions for the treatment of mutant FGFR3-positive bladder cancer.

BACKGROUND ART

The signaling pathway induced by fibroblast growth factors (FGFs) and their receptors, fibroblast growth factor receptors (FGFRs), is one of signaling pathways having the most important functions in the course of development from early embryogenesis to the formation of various organs. There are 18 genes of FGF ligands and four FGFR genes (FGFR1 to FGFR4), which are expressed in various cells and involved in cell growth, differentiation, and survival. In recent years, the importance of FGF signaling in the pathogenesis of diverse tumor types has been reported, and clinical reagents that specifically target the FGFs or FGF receptors are being developed (Nature Reviews Cancer 2010; 10, 116-129, J. Med. Chem. 2011; 54, 7066-7083, AACR 2011, No. 1643 AstraZeneca).

As for FGFR1, it is reported that FGFR1 gene is amplified in lung cancer (in particular, squamous cell cancer) and hormone therapy-resistant breast cancer, and it is also reported that these cell lines exhibit FGFR1-dependent cell growth (Sci. Transl. Med. 2010; 2(62): 62ra93, Breast Cancer Res. 2007; 9(2): R23, Cancer Res. 2010, 70 (5), 2085-2094).

As for FGFR2, the gene amplification in stomach cancer and triple negative breast cancer and the activating mutation in endometrial cancer are reported (Laboratory Investigation 1998, 78(9); 1143-1153, Virchows Arch. 1997, 431; 383-389, J. Cancer Res. Clin. Oncol., 1993, 119, 265-272, AACR 2011, No. 1643 AstraZeneca, Oncogene 2010; 29, 2013-2023). These cancer cells have been also confirmed to exhibit FGFR2-dependent growth.

Further, FGFR3 exhibits activating gene mutation in about 50% of cases of bladder cancer. Bladder cancer is largely divided into three types: non-invasive, invasive, and metastatic types. There have been issues on them that although non-invasive bladder cancer has a high 5-year survival rate of 70% or above, it frequently recurs or partly progresses to invasive cancer, and that invasive or metastatic bladder cancer has a low 5-year survival rate of 50% or below. Current therapies for non-invasive bladder cancer with FGFR3 mutation are transurethral resection of bladder tumor (TUR-BT) and postoperative BCG therapy or intravesical instillation of chemotherapeutic agents. However, their recurrence-preventing effect remains unsatisfactory, and their adverse effects such as hematuria and irritable bladder have been at issue. Meanwhile, total cystectomy and the systemic administration of chemotherapeutic agents have been used for the treatment of invasive or metastatic bladder cancer. However, there are issues on their effectiveness, and adverse effects. Bladder cancer is known to be characterized in that part of the cancer cells sloughs off from bladder tissues into urine, and, based on this characteristic, urine cytology is used for the diagnostic of bladder cancer. It was recently reported that FGFR3 mutation can be detected using the sediments in urine (Biochem. Biophys. Res. Commun. Nov. 3, 2007; 362(4): 865-71). Based on the presence or absence of this FGFR3 mutation, patients with FGFR3 mutation-positive bladder cancer can be selected, and the creation of an FGFR3 selective inhibitor has been demanded.

It is also reported that fusion genes combining FGFR genes and TACC (Transforming Acidic Coiled-coil) genes (FGFR3-TACC3 and FGFR1-TACC1) are expressed in the tumor of some glioblastoma patients (Science, Sep. 7, 2012; 337(6099): 1231-5). According to this report, the forced expression of FGFR3-TACC3 and FGFR1-TACC1 in astrocytes led to transformation and this result showed the oncogenicity of these fusion genes. It was also shown that FGFR3-TACC3 is localized in mitotic spindle poles and induces kinase activity-dependent chromosomal aneuploidy. Further, treatment of FGFR3-TACC3-expressing cells with an FGFR inhibitor suppressed chromosomal aneuploidy, thereby suppressing the growth of the cells. Thus, it is suggested that FGFR inhibitors might be effective for the treatment of glioblastoma patients with FGFR-TACC fusion genes.

It is also reported that human bladder cancer cell lines RT112, RT4, and LUCC2 express FGFR3-TACC3 fusion gene and that human bladder cancer cell line SW780 also expresses FGFR3-BAIAP2L1 fusion gene (Hum Mol Genet., 2013 Feb. 15, 22(4), 795-803). According to this report, the anchorage-independent growth of these fusion genes has been confirmed as a result of their introduction into NIH3T3 cells. Given that the growth of the foregoing bladder cancer cell lines expressing these FGFR3 fusion genes is inhibited by FGFR inhibitors, the detection of the presence of the fusion genes can be useful to select patients who can be treated effectively with FGFR inhibitors.

It is reported that the compounds of formula (A) shown below exhibit inhibition of various kinases and are useful as therapeutic agents for cancer and vascular disorders including myocardial infarction (Patent Document 1). Table 2 of the document discloses the test results of inhibition of kinases Yes, VEGFR, EphB4, PDGFRβ, and FGFR1 by some of the compounds, which discloses that IC$_{50}$ values for the FGFR1 inhibitory activity were higher than 1000 nM, showing that the activity was also lower than in the case of inhibition of the activity of the other kinases. Further, in the document, there is no specific disclosure about the compounds of formula (I) of the present invention described below.

[Formula 1]

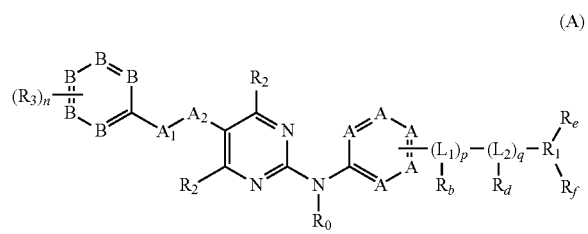

(A)

(In this formula, each of A is CH, N, or the like; each of B is CH or the like; $A_1$ is O, $CR_2$, or the like; $R_0$ is H or the like; $A_2$ is NR, O, or the like; $L_1$ is a bond, O, or the like; $L_2$ is a bond, $C_1$-$C_6$ alkyl, or the like; $R_1$ is a 3- to 6-membered heterocyclic ring or the like; and each of $R_e$ and $R_f$ is H, $C_1$-$C_6$ alkyl, hydroxyalkyl, or the like. For the other symbols, refer to the publication.)

It is reported that the compounds of formula (B) shown below exhibit Abl inhibitory action and are useful against various cancers (Patent Document 2). However, in the document, there is no specific description about FGFR inhibitory action. Further, the compounds of formula (I) of the present invention described below have group $(R^1)_p$ which differentiate the compounds in structure from the compounds of formula (B).

[Formula 2]

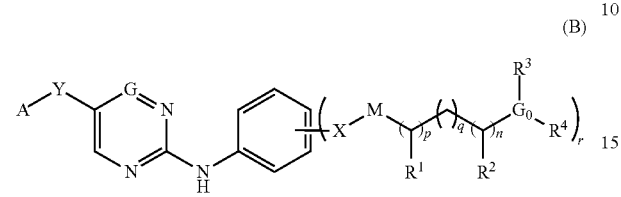

(B)

(In this formula, G is CH or the like; A is 3-hydroxyphenyl or the like; and Y is vinyl or ethylene. For the other symbols, refer to the publication.)

It is reported that the compounds of formula (C) shown below have inhibitory action on various kinases including Src, VEGFR2, Yes, Fyn, Lck, Abl, PDGFR, EGFR, and RET and are usable for the treatment of cancer, vascular disorders, and the like (Patent Document 3). However, there is no disclosure about FGFR inhibitory action in the document. In the document, there is also no specific disclosure about the compounds of formula (I) of the present invention described below.

[Formula 3]

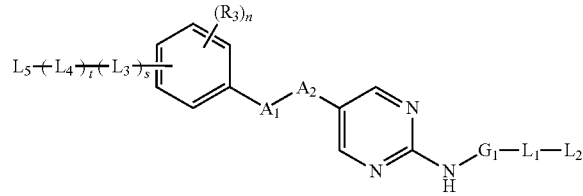

(C)

(In this formula, $G_1$ is aryl optionally having a substituent, heteroaryl optionally having a substituent, or the like; $L_1$ is O, SO, $SO_2$, optionally substituted alkyl, or the like; $L_2$ is optionally substituted alkyl, heterocyclic ring, or the like; $A_1$ is a bond, O, $C(R_a)_2$, or the like; and $A_2$ is $NR_a$, O, or the like. For the other symbols, refer to the publication.)

It is reported that the compounds of formula (D) shown below have TIE-2 and/or VEGFR-2 kinase inhibitory action and are useful in treatment of angiogenesis-related diseases including cancer (Patent Document 4). However, there is no specific description about FGFR inhibition in the document. Further, the compounds of formula (I) of the present invention described below differ in structure from the compounds of formula (D) in that the compounds of formula (I) have a group $L^1$ having no amino group and that the compounds also have two bonds positioned para to each other on a ring comprising X and Y.

[Formula 4]

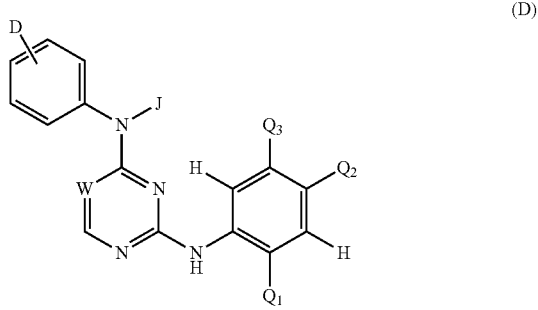

(D)

(In this formula, W is N or CR; R is H or the like. For the other symbols, refer to the publication.)

It is reported that the compounds of formula (E) shown below exhibit inhibitory action on the activity of many receptor protein tyrosine kinases, particularly, FGFRs, and can be used for the treatment of various diseases related to aberrant or excessive activity of these enzymes (Patent Document 5). However, the compounds of formula (I) of the present invention described below differ in structure from the compounds of formula (E) in that the compounds of formula (I) have a group $L^1$ which does not represent a N atom and that the compounds also have two bonds positioned para to each other on a ring comprising X and Y.

[Formula 5]

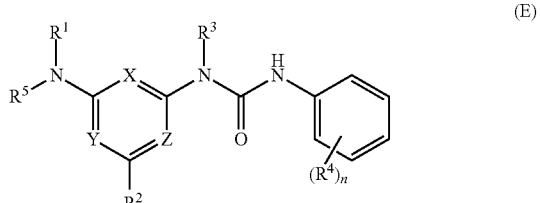

(E)

(In this formula, two of X, Y, and Z are N and the third is CH or N. For the other symbols, refer to the publication.)

It is reported that the compounds of formula (F) shown below exhibit inhibitory action on various kinases and are useful against inflammation and autoimmune diseases (Patent Document 6). On the other hand, the compounds of formula (I) of the present invention described below differ in structure from the compounds of formula (F) in that the compounds of formula (I) have a group $L^1$ which is not amide and that the compounds also have two bonds positioned para to each other on a ring comprising X and Y.

[Formula 6]

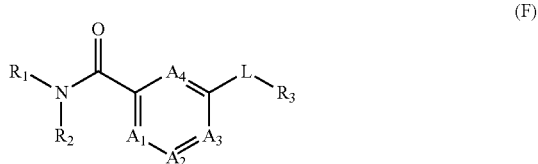

(F)

(In this formula, $A^1$, $A^2$, $A^3$, and $A^4$ are $CR^4$, $CR^5$, $CR^6$, and $CR^7$, respectively, or are N; L is —C(O)$NR^7$—, —$NR^7$C(O)—, or the like. For the other symbols, refer to the publication.)

It is reported that the compounds of formula (G) and those of formula (H) shown below exhibit FGFR inhibitory action and can be used for the treatment of various cancers (Patent Documents 7 and 8).

[Formula 7]

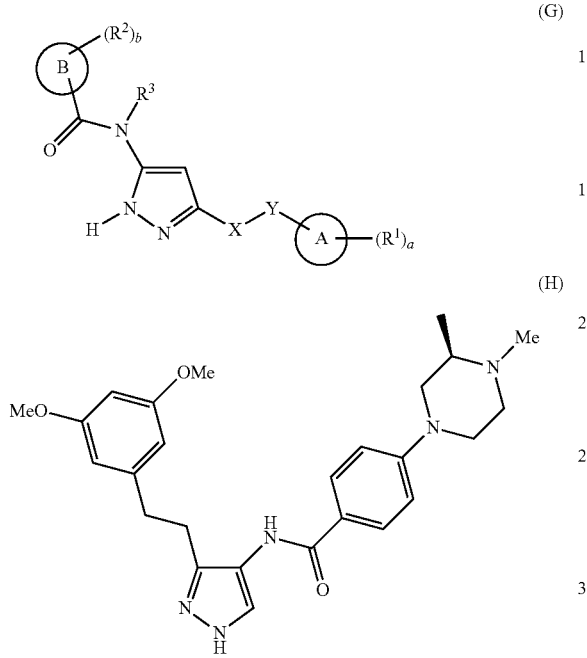

(In formula (G), ring B represents a 5- or 6-membered aromatic group that may comprise at least one heteroatom selected from O, S, and N. For the other symbols, refer to the publication.)

It is reported that the compounds of formula (J) shown below exhibit glucokinase activating effects and can be used for the treatment of diseases related to diabetes mellitus (Patent Document 9), and the structural feature is substitution with amino at the 2 position of the pyridine.

[Formula 8]

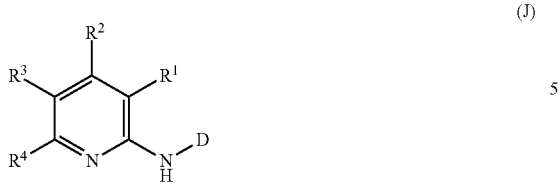

(For the symbols in this formula, refer to the publication.)

Also, the known compounds having the structures shown below are registered on the database as 1371065-79-0 and 1317903-92-6 in CAS registry number, respectively.

[Formula 9]

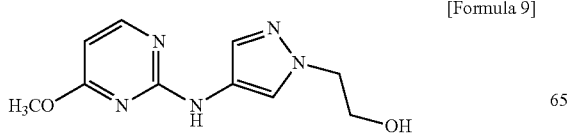

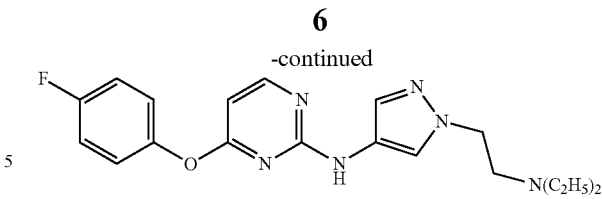

CITATION LIST

Patent Documents

Patent Document 1: International Publication No. WO 2006/101977
Patent Document 2: International Publication No. WO 2007/056075
Patent Document 3: International Publication No. WO 2008/008234
Patent Document 4: International Publication No. WO 2003/066601
Patent Document 5: International Publication No. WO 2007/071752
Patent Document 6: International Publication No. WO 2007/022380
Patent Document 7: International Publication No. WO 2008/075068
Patent Document 8: International Publication No. WO 2009/153592
Patent Document 9: International Publication No. WO 2009/046784

SUMMARY OF INVENTION

Technical Problem

The present invention provides compounds useful as active ingredients in pharmaceutical compositions, particularly in pharmaceutical compositions for the treatment of mutant FGFR3-positive bladder cancer.

Solution to Problem

As a result of intensive and extensive studies on compounds having FGFR inhibitory action, the present inventors have found that the nitrogen-containing aromatic heterocyclic compound of the present invention has inhibitory action on FGFR1, FGFR2, and FGFR3, particularly, good inhibitory action on mutant FGFR3. The present invention has been thus accomplished.

More specifically, the present invention relates to a compound of formula (I) or a salt thereof as well as to a pharmaceutical composition comprising a compound of formula (I) or a salt thereof and a pharmaceutically acceptable excipient.

[Formula 10]

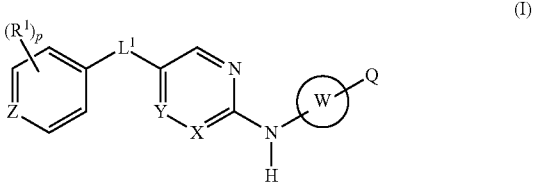

(wherein
X and Y, the same or different from each other, are CH or N, with the proviso that X and Y are not N simultaneously;
$L^1$ is -lower alkylene-, -lower alkylene-O—, —O-lower alkylene-, or -lower alkynylene-;
Z is N or CH;
$R^1$, the same or different from one another, are lower alkyl optionally substituted with halogen, —O-(lower alkyl optionally substituted with halogen), halogen, cyano, or —N(lower alkyl)$_2$;
p is an integer of 2 to 4;
ring W is an optionally substituted aromatic carbocyclic ring, an optionally substituted aromatic heterocyclic ring, or an optionally substituted non-aromatic heterocyclic ring;
Q is -$L^2$-$R^2$ or $R^3$;
$L^2$ is an optionally substituted aromatic heterocyclic ring or an optionally substituted non-aromatic heterocyclic ring;
$R^2$ is a non-aromatic heterocyclic group optionally substituted with lower alkyl, optionally substituted cycloalkyl, lower alkyl optionally substituted with one or more groups selected from the group consisting of —OH and —O-lower alkyl, —C(O)—$R^0$, —C(O)-optionally substituted cycloalkyl, —NH—$R^0$, —N(lower alkyl)-$R^0$, -$L^3$-optionally substituted non-aromatic heterocyclic group, or H;
$R^0$ is lower alkyl optionally substituted with —OH;
$R^3$ is
(1) lower alkyl optionally substituted with one or more groups selected from the group consisting of —C(O)OH, —OH, —O—$R^0$, amino optionally substituted with one or two $R^0$, carbamoyl optionally substituted with one or two $R^0$, an optionally substituted aromatic heterocyclic group, an optionally substituted non-aromatic heterocyclic group, and a —C(O)-optionally substituted non-aromatic heterocyclic group;
(2) —O-(lower alkyl optionally substituted with one or more groups selected from the group consisting of —C(O)OH, —OH, —O—$R^0$, carbamoyl optionally substituted with one or two $R^0$, an optionally substituted non-aromatic heterocyclic group, and a —C(O)-optionally substituted non-aromatic heterocyclic group);
(3) —NH-(lower alkyl optionally substituted with one or more groups selected from the group consisting of —OH, a non-aromatic heterocyclic group optionally substituted with lower alkyl, and carbamoyl optionally substituted with one or two $R^0$);
(4) —N(lower alkyl)-(lower alkyl optionally substituted with one or more groups selected from the group consisting of —OH, a non-aromatic heterocyclic group optionally substituted with lower alkyl, and carbamoyl optionally substituted with one or two $R^0$);
(5) —C(O)OH;
(6) —C(O)-optionally substituted non-aromatic heterocyclic group;
(7) —O-(a non-aromatic heterocyclic group optionally substituted with lower alkyl); or
(8) carbamoyl optionally substituted with one or two $R^0$; and
$L^3$ is a bond, —NH—, —N(lower alkyl)-, or lower alkylene.)

Unless otherwise specified, when symbols used in one chemical formula herein are also used in another chemical formula, the same symbols have identical meanings.

The present invention also relates to a pharmaceutical composition that comprises a compound of formula (I) or a salt thereof and a pharmaceutically acceptable excipient and which is available for the treatment of various cancers related to FGFR1, FGFR2, and/or FGFR3, such as FGFR1-related lung cancer and hormone therapy-resistant breast cancer, FGFR2-related stomach cancer, triple negative breast cancer, and endometrial cancer, and FGFR3-related bladder cancer and glioblastoma. It is to be noted that the pharmaceutical composition includes therapeutic agents for various cancers related to FGFR1, FGFR2, and/or FGFR3. One embodiment is a pharmaceutical composition for the treatment of FGFR3-related bladder cancer, which comprises a compound of formula (I) or a salt thereof and a pharmaceutically acceptable excipient. Another embodiment is a pharmaceutical composition for the treatment of mutant FGFR3-positive bladder cancer, which comprises a compound of formula (I) or a salt thereof and a pharmaceutically acceptable excipient. In the present specification, "mutant" includes point mutation, fusion mutation, deletion mutation and insertion mutation, and in an embodiment, "mutant" means general idea including point mutation and fusion mutation. In another embodiment, "mutant" means point mutation, and in yet another embodiment, "mutant" means fusion mutation.

Further, the present invention relates to: use of a compound of formula (I) or a salt thereof, for the manufacture of a pharmaceutical composition for the treatment of various cancers related to FGFR1, FGFR2, and/or FGFR3; use of a compound of formula (I) or a salt thereof, for the treatment of various cancers related to FGFR1, FGFR2, and/or FGFR3; a compound of formula (I) or a salt thereof, for the treatment of various cancers related to FGFR1, FGFR2, and/or FGFR3; and a method for treating various cancers related to FGFR1, FGFR2, and/or FGFR3, which comprises administering an effective amount of a compound of formula (I) or a salt thereof to a subject. The present invention also relates to: use of a compound of formula (I) or a salt thereof, for the manufacture of a pharmaceutical composition for the treatment of mutant FGFR3-positive bladder cancer; use of a compound of formula (I) or a salt thereof, for the treatment of mutant FGFR3-positive bladder cancer; a compound of formula (I) or a salt thereof, for the treatment of mutant FGFR3-positive bladder cancer; and a method for treating mutant FGFR3-positive bladder cancer, which comprises administering an effective amount of a compound of formula (I) or a salt thereof to a subject. It is to be noted that the "subject" referred to above is a human or another animal in need of the treatment, and is a human in need of the treatment in one embodiment.

Advantageous Effects of Invention

A compound of formula (I) or a salt thereof has inhibitory action on FGFR1, FGFR2, and/or FGFR3, particularly, mutant FGFR3, and can be used as a therapeutic agent for various cancers related to FGFR1, FGFR2, and/or FGFR3, such as lung cancer and hormone therapy-resistant breast cancer, stomach cancer, triple negative breast cancer, endometrial cancer, bladder cancer, and glioblastoma, particularly as a therapeutic agent for mutant FGFR3-positive bladder cancer.

DESCRIPTION OF EMBODIMENTS

The present invention is described in detail below.

As used herein, the term "lower alkyl" refers to linear or branched alkyl having 1 to 8 carbon atoms (hereinafter abbreviated as $C_{1-8}$) including methyl, ethyl, n-propyl, isopropyl, n-butyl, isobutyl, sec-butyl, tert-butyl, n-pentyl, n-hexyl, n-heptyl, n-octyl, and the like. Another embodiment is $C_{1-4}$ alkyl, and yet another embodiment is methyl. Yet another embodiment is ethyl.

The term "lower alkylene" refers to linear or branched $C_{1-8}$ alkylene including methylene, ethylene, trimethylene, tetramethylene, pentamethylene, hexamethylene, heptamethylene, octamethylene, propylene, methylmethylene, ethylethylene, 1,2-dimethylethylene, 1,1,2,2-tetramethylethylene, and the like. Another embodiment is $C_{1-4}$ alkylene, and yet another embodiment is methylene. Yet another embodiment is ethylene.

The term "lower alkynylene" refers to linear or branched $C_{2-6}$ alkynylene including ethynylene, propynylene, butynylene, pentinylene, hexynylene, 1,3-butadiynylene, 1,3-pentadiynylene, and the like. Another embodiment is $C_{2-4}$ alkynylene, and yet another embodiment is ethynylene.

The term "cycloalkyl" refers to a $C_{3-10}$ saturated hydrocarbon ring group and it may be bridged. Examples include cyclopropyl, cyclobutyl, cyclopentyl, cyclohexyl, cycloheptyl, cyclooctyl, adamantyl, and the like. Another embodiment is $C_{3-8}$ cycloalkyl, and yet another embodiment is $C_{3-6}$ cycloalkyl. Yet another embodiment is cyclopropyl.

The term "aromatic carbocyclic ring" refers to a $C_{6-14}$ monocyclic to tricyclic aromatic hydrocarbon ring. Examples include benzene, naphthalene, and anthracene, and another embodiment is benzene.

The term "aromatic heterocyclic ring" refers to a 5- to 10-membered aromatic heterocyclic ring which has 1 to 4 heteroatoms selected from the group consisting of nitrogen, oxygen, and sulfur. Examples include pyridine, pyrrole, pyrazine, pyrimidine, pyridazine, imidazole, pyrazole, thiazole, oxazole, isoxazole, thiophene, isothiazole, furan, oxadiazole, thiadiazole, indole, isoindole, indazole, benzofuran, benzothiophene, benzimidazole, benzoxazole, benzothiazole, quinoline, isoquinoline, cinnoline, phthalazine, quinazoline, quinoxaline, thienopyridine, thienopyrimidine, thienopyrazine, and the like. Another embodiment is pyridine, pyrrole, pyrazine, pyrimidine, pyridazine, imidazole, pyrazole, thiazole, oxazole, thiophene, furan, oxadiazole, and indazole. Yet another embodiment is pyridine, pyrimidine, imidazole, pyrazole, thiazole, and indazole. Yet another embodiment is pyridine, imidazole, and pyrazole. Yet another embodiment is pyridine. Yet another embodiment is pyrazole. Yet another embodiment is imidazole.

The term "aromatic heterocyclic group" refers to a monovalent group of the "aromatic heterocyclic ring" described above. Examples include pyridyl, pyrrolyl, pyrazinyl, pyrimidinyl, pyridazinyl, imidazolyl, pyrazolyl, thiazolyl, oxazolyl, thienyl, furyl, 1,2,4-oxadiazolyl, and the like. Another embodiment is a 5- or 6-membered aromatic heterocyclic group which has 1 or 2 nitrogen atoms, and yet another embodiment is pyridyl.

The term "non-aromatic heterocyclic ring" refers to a 3- to 10-membered non-aromatic heterocyclic ring (or a 4- to 8-membered non-aromatic heterocyclic ring in one embodiment) having 1 to 4 heteroatoms which are selected from the group consisting of nitrogen, oxygen, and sulfur and which are the same or different. The non-aromatic heterocyclic ring may be fused to a benzene ring or a thiophene ring, be bridged by lower alkylene, be combined with another non-aromatic heterocyclic ring to form a spiro ring, or have an unsaturated bond on part of the own ring. The sulfur atom or nitrogen atom which is a ring-forming atom may be oxidized. Examples include aziridine, oxetane, azetidine, pyrrolidine, piperidine, azepane, diazepane, azocane, piperazine, 4-oxidopiperazine, homopiperazine, morpholine, oxazepane, thiomorpholine, 1,1-dioxidothiomorpholine, 1,1-dioxidotetrahydrothiopyran, 1,1-dioxidothiazolidine, thiazepane, 1-azabicyclo[2,2,2]octane, 7-oxabicyclo[2.2.1]heptane, 2,5-diazabicyclo[2.2.1]heptane, 3-azabicyclo[3.2.1]octane, 8-azabicyclo[3.2.1]octane, 9-azabicyclo[3.3.1]nonane, 3,9-diazabicyclo[3.3.1]nonane, 3,9-diazaspiro[5.5]undecane, 2,6-diazaspiro[3.3]heptane, 2-oxa-6-azaspiro[3.3]heptane, 2-oxa-7-azaspiro[3.5]nonane, tetrahydropyran, tetrahydrofuran, dioxane, dioxolan, tetrahydrothiophene, tetrahydrothiopyran, tetrahydrothienopyridine, tetrahydrobenzoazepine, tetrahydrobenzodiazepine, dihydrobenzofuran, dihydrobenzothiophene, dihydrobenzopyran, dihydrobenzodioxane, benzodioxane, dihydropyran, dihydropyrrole, dihydropyridine, tetrahydropyridine, tetrahydropyrazine, and the like. Another embodiment is a 5- to 7-membered non-aromatic heterocyclic ring having 1 or 2 heteroatoms which are selected from the group consisting of nitrogen, oxygen, and sulfur and which are the same or different. Yet another embodiment is a 5- to 7-membered nitrogen-containing non-aromatic heterocyclic ring which may have at least one nitrogen atom and have one additional heteroatom selected from the group consisting of nitrogen, oxygen, and sulfur. Yet another embodiment is a 6-membered nitrogen-containing non-aromatic heterocyclic ring. Examples include piperazine, piperidine, morpholine, thiomorpholine, 1,1-dioxidothiomorpholine, and the like. Yet another embodiment is oxetane, piperidine, piperazine, morpholine, thiomorpholine, 4-oxidopiperazine, 1,1-dioxidothiomorpholine, tetrahydropyran, tetrahydrofuran, tetrahydrothiophene, tetrahydropyridine, 1-azabicyclo[2.2.2]octane, 8-azabicyclo[3.2.1]octane, 3,9-diazaspiro[5.5]undecane, 2,6-diazaspiro[3.3]heptane, 2-oxa-6-azaspiro[3.3]heptane, or 2-oxa-7-azaspiro[3.5]nonane. Yet another embodiment is morpholine, piperidine, piperazine, 4-oxidopiperazine, 3,9-diazaspiro[5.5]undecane, or 2,6-diazaspiro[3.3]heptane. Yet another embodiment is piperidine. Yet another embodiment is piperazine.

The term "non-aromatic heterocyclic group" refers to a monovalent group of a non-aromatic heterocyclic ring. The non-aromatic heterocyclic group is a 3- to 10-membered non-aromatic heterocyclic group having 1 to 4 heteroatoms which are selected from the group consisting of nitrogen, oxygen, and sulfur and which are the same or different. The non-aromatic heterocyclic group may be bridged by lower alkylene, have an unsaturated bond on part of the ring, or be combined with another non-aromatic heterocyclic ring to form a spiro ring. The sulfur atom or nitrogen atom which is a ring-forming atom may be oxidized. Examples include aziridinyl, azetidinyl, oxetanyl, pyrrolidinyl, piperidinyl, azepanyl, diazepanyl, azocanyl, piperazinyl, homopiperazinyl, morpholinyl, oxazepanyl, thiomorpholinyl, 1,1-dioxidothiomorpholinyl, thiazepanyl, tetrahydropyranyl, tetrahydrofuryl, dioxanyl, dioxolanyl, tetrahydrothienyl, tetrahydrothiopyranyl, 7-oxabicyclo[2.2.1]heptyl, 2,5-diazabicyclo[2.2.1]heptyl, 3-azabicyclo[3.2.1]octyl, 8-azabicyclo[3.2.1]octyl, 9-azabicyclo[3.3.1]nonyl, 3,9-diazabicyclo[3.3.1]nonyl, dihydropyranyl, dihydropyrrolyl, dihydropyridyl, tetrahydropyridyl, tetrahydropyrazyl, 9-diazaspiro[5.5]undec-3-yl, 1,9-diazaspiro[5.5]undec-9-yl, 2,8-diazaspiro[4.5]dec-8-yl, 1,4-dioxa-8-azaspiro[4.5]dec-8-yl, and the like. Another embodiment is a 5- to 7-membered non-aromatic heterocyclic group having 1 or 2 heteroatoms which are selected from the group consisting of nitrogen, oxygen, and sulfur and which are the same or different. Yet another embodiment is a 5- to 7-membered non-aromatic heterocyclic group having at least one nitrogen atom. Yet another embodiment is a 6-membered nitrogen-containing non-aromatic heterocyclic group. Examples include piperazinyl, piperidinyl, morpholinyl, thiomorpholinyl, 1,1-dioxidothiomorpholinyl, and the like. Yet another embodiment is oxetanyl, piperidinyl, piperazinyl, morpholinyl, thiomorpholinyl, 4-oxidopiperazinyl, 1,1-dioxidothiomorpholinyl, tetrahydropyranyl, tetrahydrofuryl, tetrahydrothienyl, tetrahydropyridyl, 1-azabicyclo[2.2.2]octyl, 8-azabicyclo[3.2.1]octyl, 3,9-diazaspiro[5.5]undec-3-yl, 2,6-diazaspiro[3.3]hept-2-yl, or 2-oxa-6-azaspiro[3.3]hept-6-yl. Yet another embodiment is piperidinyl or piperazinyl. Yet another embodiment is piperidinyl. Yet another embodiment is piperazinyl.

The term "halogen" refers to —F, —Cl, —Br, or —I. Another embodiment is —F, and yet another embodiment is —Cl.

A compound of formula (I) or a salt thereof, wherein $L^1$ in formula (I) is -lower alkylene-O—, means a compound of formula (II) or a salt thereof.

[Formula 11]

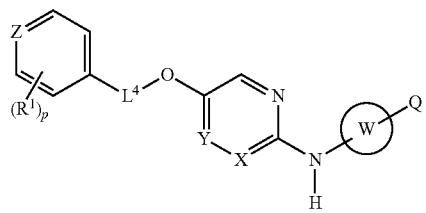

(II)

(In this formula, $L^4$ represents lower alkylene. The same applies hereinafter.)

Further, two to four $R^1$ in $(R^1)_p$ may be the same or different from one another.

The phrase "optionally substituted" as used herein means "unsubstituted" or "having 1 to 5 substituents". When a plurality of substituents are contained, these substituents may be the same or different from one another. Further, for example, two $R^0$ on the nitrogen in the "carbamoyl optionally substituted with one or two $R^{0}$" may be the same lower alkyl or different lower alkyl from each other. Each $R^0$ may be substituted with —OH, or alternatively, either one may be substituted or neither one may be substituted.

As referred to herein, a substituent in "an optionally substituted aromatic carbocyclic ring", "an optionally substituted aromatic heterocyclic ring", or "an optionally substituted non-aromatic heterocyclic ring" as ring W in formula (I) is, for example, a group shown in group D1 described below.

Group D1 is a group consisting of:
(1) an aromatic heterocyclic group optionally substituted with one or more substituents selected from —OH and lower alkyl;
(2) a non-aromatic heterocyclic group optionally substituted with one or more substituents selected from —OH and lower alkyl;
(3) halogens;
(4) —O-lower alkyl, —S-lower alkyl, —OH, and —SH;
(5) —CN and —NO$_2$;
(6) —CO$_2$H and —CO$_2$-lower alkyl; and
(7) lower alkyl or —O-lower alkyl, each of which is optionally substituted with one or more groups selected from the group consisting of the groups shown in (1) to (6) above.

Another embodiment of group D1 is a group consisting of:
(1) an aromatic heterocyclic group optionally substituted with —OH;

(2) halogens;
(3) —OH;
(4) —CN;
(5) —CO$_2$H; and
(6) lower alkyl or —O-lower alkyl, each of which is optionally substituted with one or more substituents selected from the group consisting of the substituents shown in (1) to (5) above.

Yet another embodiment of group D1 is a group consisting of:
(1) lower alkyl optionally substituted with halogen;
(2) —O-lower alkyl optionally substituted with an aromatic heterocyclic group optionally substituted with —OH;
(3) halogens; and
(4) —CN Yet another embodiment of group D1 is a group consisting of lower alkyl optionally substituted with halogen; —O-(lower alkyl optionally substituted with one or more substituents selected from the group consisting of a non-aromatic heterocyclic group optionally substituted with oxo, an aromatic heterocyclic group optionally substituted with —OH, and halogens), halogens, cyano, and oxo.

A substituent acceptable in "an optionally substituted aromatic heterocyclic ring" or "an optionally substituted non-aromatic heterocyclic ring" referred to as $L^2$ in formula (I), "optionally substituted cycloalkyl" or "an optionally substituted non-aromatic heterocyclic group" referred to as $R^2$ in formula (I), and "an optionally substituted aromatic heterocyclic group" or "an optionally substituted non-aromatic heterocyclic group" referred to in $R^3$ in formula (I) is, for example, a substituent selected from group D2.

Group D2 is a group consisting of:
(1) halogens;
(2) —OH and —SH;
(3) —CN; and
(4) lower alkyl optionally substituted with one or more substituents selected from the group consisting of the substituents shown in (1) to (3) above.

Another embodiment of group D2 is a group consisting of:
(1) lower alkyl optionally substituted with —OH; and
(2) —OH Some embodiments of the compounds of formula (I) or salts thereof are given below.

(1) A compound or a salt thereof, wherein X is N and Y is CH. Another embodiment is a compound or a salt thereof, wherein X is CH and Y is N. Yet another embodiment is a compound or a salt thereof, wherein X is CH and Y is CH.

(2) A compound or a salt thereof, wherein $L^1$ is lower alkylene or -lower alkylene-O—. Another embodiment is a compound or a salt thereof, wherein $L^1$ is -lower alkylene-. Yet another embodiment is a compound or a salt thereof, wherein $L^1$ is -lower alkylene-O—. Yet another embodiment is a compound or a salt thereof, wherein $L^1$ is ethylene or -methylene-O—. Yet another embodiment is a compound or a salt thereof, wherein $L^1$ is ethylene. Yet another embodiment is a compound or a salt thereof, wherein $L^1$ is -methylene-O—. Yet another embodiment is a compound or a salt thereof, wherein $L^1$ is ethynylene.

(3) A compound or a salt thereof, wherein Z is CH. Another embodiment is a compound or a salt thereof, wherein Z is N.

(4-1) A compound or a salt thereof, wherein p is 2 or 4. Another embodiment is a compound or a salt thereof, wherein p is 2. Yet another embodiment is a compound or a salt thereof, wherein p is 4.

(4-2) A compound or a salt thereof, wherein $R^1$, the same or different from one another, are —O-lower alkyl or halogen. Another embodiment is a compound or a salt thereof, wherein $R^1$, the same or different from one another, are —O-lower alkyl. Yet another embodiment is a compound or a salt thereof, wherein $R^1$, the same or different from one another, are halogen. Yet another embodiment is a compound or a salt thereof, wherein $R^1$, the same or different from one another, are —O-methyl or F. Yet another embodiment is a compound or a salt thereof, wherein R', the same or different from one another, are —O-methyl or Cl. Yet another embodiment is a compound or a salt thereof, wherein all of $R^1$ are F.

(5) A compound or a salt thereof, wherein the 6-membered aromatic ring in formula (I) which is substituted with $(R^1)_p$ and which has Z as a ring-forming atom is 2,6-dichloro-3,5-dimethoxyphenyl or 2,6-difluoro-3,5-dimethoxyphenyl. Another embodiment is a compound or a salt thereof, wherein the 6-membered aromatic ring in formula (I) which is substituted with $(R^1)_p$ and which has Z as a ring-forming atom is 2,6-dichloro-3,5-dimethoxyphenyl. Another embodiment is a compound or a salt thereof, wherein the 6-membered aromatic ring in formula (I) which is substituted with $(R^1)_p$ and which has Z as a ring-forming atom is 2,6-difluoro-3,5-dimethoxyphenyl.

(6) A compound or a salt thereof, wherein ring W is an aromatic carbocyclic ring optionally substituted with one or more substituents selected from group D1 or is an aromatic heterocyclic ring optionally substituted with one or more substituents selected from group D1. Another embodiment is a compound or a salt thereof, wherein ring W is a benzene ring substituted with one or more substituents selected from group D1 or is pyrazole, pyridine, pyrimidine, thiazole, indazole, or imidazole which in each case is optionally substituted with one or more substituents selected from group D1. Yet another embodiment is a compound or a salt thereof, wherein ring W is a benzene ring optionally substituted with one or more substituents selected from group D1 or is pyrazole optionally substituted with one or more substituents selected from group D1. Yet another embodiment is a compound or a salt thereof, wherein ring W is a benzene ring optionally substituted with one or more substituents selected from group D1. Yet another embodiment is a compound or a salt thereof, wherein ring W is a benzene ring optionally substituted with one or more substituents selected from the group consisting of lower alkyl, —O-lower alkyl, and halogens. Yet another embodiment is a compound or a salt thereof, wherein ring W is a benzene ring optionally substituted with one or more substituents selected from the group consisting of methyl, —O-methyl, and halogens. Yet another embodiment is a compound or a salt thereof, wherein ring W is a benzene ring optionally substituted with —O-methyl. Yet another embodiment is a compound or a salt thereof, wherein ring W is pyrazole optionally substituted with one or more substituents selected from group D1. Yet another embodiment is a compound or a salt thereof, wherein ring W is pyrazole optionally substituted with lower alkyl. Yet another embodiment is a compound or a salt thereof, wherein ring W is pyrazole optionally substituted with methyl. Yet another embodiment is a compound or a salt thereof, wherein ring W is pyrazole substituted with methyl. Yet another embodiment is a compound or a salt thereof, wherein ring W is pyrazole.

(7) A compound or a salt thereof, wherein Q is -$L^2$-$R^2$. Another embodiment is a compound or a salt thereof, wherein Q is $R^3$.

(8) A compound or a salt thereof, wherein $L^2$ is a non-aromatic heterocyclic ring optionally substituted with one or more substituents selected from group D2. Another embodiment is a compound or a salt thereof, wherein $L^2$ is a nitrogen-containing non-aromatic heterocyclic ring optionally substituted with one or more substituents selected from group D2. Yet another embodiment is a compound or a salt thereof, wherein $L^2$ is piperazine, 4-oxidopiperazine, piperidine, morpholine, azetidine, 3,9-diazaspiro[5.5]undecane, 2,6-diazaspiro[3.3]heptane, 2-oxa-6-azaspiro[3.3]heptane, 2-oxa-7-azaspiro[3.5]nonane, 8-azabicyclo[3.2.1]octane, or 1-azabicyclo[2.2.2]octane which in each case is optionally substituted with one or more substituents selected from group D2. Yet another embodiment is a compound or a salt thereof, wherein $L^2$ is piperazine optionally substituted with one or more methyl, piperidine optionally substituted with one or more methyl, or 3,9-diazaspiro[5.5]undecane. Yet another embodiment is a compound or a salt thereof, wherein $L^2$ is piperidine or 4-methylpyperazine.

(9) A compound or a salt thereof, wherein $R^2$ is lower alkyl optionally substituted with one or more groups selected from the group consisting of —OH and —O-lower alkyl, —NH-(lower alkyl optionally substituted with —OH), a non-aromatic heterocyclic group optionally substituted with one or more substituents selected from group D2, -lower alkylene-(a non-aromatic heterocyclic group optionally substituted with one or more substituents selected from the group D2), or H. Another embodiment is a compound or a salt thereof, wherein $R^2$ is lower alkyl optionally substituted with one or more groups selected from the group consisting of —OH and —O-lower alkyl, —NH-(lower alkyl optionally substituted with —OH), a non-aromatic heterocyclic group optionally substituted with lower alkyl (the lower alkyl is optionally substituted with —OH), or H. Yet another embodiment is a compound or a salt thereof, wherein $R^2$ is piperazine optionally substituted with methyl, piperidine optionally substituted with methyl, 2-hydroxyethylamino, or H. Yet another embodiment is a compound or a salt thereof, wherein $R^2$ is 4-methylpiperazine, 2-hydroxyethylamino, or H. Yet another embodiment is a compound or a salt thereof, wherein $R^2$ is 4-methylpiperazine. Yet another embodiment is a compound or a salt thereof, wherein $R^2$ is 2-hydroxyethylamino. Yet another embodiment is a compound or a salt thereof, wherein $R^2$ is H.

(10) A compound or a salt thereof, wherein $R^3$ is lower alkyl optionally substituted with one or more groups selected from the group consisting of —C(O)OH, carbamoyl optionally substituted with one or two $R^0$, —OH, a non-aromatic heterocyclic group optionally substituted with one or more substituents selected from group D2, and —C(O)-(a non-aromatic heterocyclic group optionally substituted with one or more substituents selected from group D2) or wherein $R^3$ is —O-(lower alkyl optionally substituted with one or more groups selected from the group consisting of —C(O)OH, carbamoyl optionally substituted with one or two $R^0$, —OH, a non-aromatic heterocyclic group optionally substituted with one or more substituents selected from group D2, and —C(O)-(a non-aromatic heterocyclic group optionally substituted with one or more substituents selected from group D2)). Another embodiment is a compound or a salt thereof, wherein $R^3$ is lower alkyl substituted with one or more groups selected from the group consisting of —C(O)OH, carbamoyl optionally substituted with one or two $R^0$, —OH, a non-aromatic heterocyclic group optionally substituted with one or more substituents selected from group D2, and —C(O)-(a non-aromatic heterocyclic group optionally substituted with one or more substituents selected from group D2). Yet another embodiment is a compound or a salt thereof, wherein $R^3$ is lower alkyl substituted with one or more substituents selected from the group consisting of —OH, a non-aromatic heterocyclic group optionally substituted with one or more substituents selected from —OH and lower alkyl, and —C(O)-(a non-aromatic heterocyclic group optionally substituted with one or more substituents selected from the group consisting of —OH and lower alkyl). Yet another embodiment is a compound or a salt thereof, wherein $R^3$ is lower alkyl substituted with one or more substituents selected from the group consisting of —OH, a non-aromatic heterocyclic group optionally substituted with lower alkyl, and —C(O)-(a non-aromatic heterocyclic group optionally substituted with —OH). Yet another embodiment is a compound or a salt thereof, wherein $R^3$ is lower alkyl substituted with one or more groups selected from the group consisting of —OH, piperazinyl optionally substituted with methyl, and —C(O)-(azetidinyl optionally substituted with —OH). Yet another embodiment is a compound or a salt thereof, wherein $R^3$ is 2-hydroxyethyl, 2,3-dihydroxypropyl, or 4-methylpiperazin-1-ylmethyl. Yet another embodiment is a compound or a salt thereof, wherein $R^3$ is 4-methylpiperazin-1-ylmethyl. Yet another embodiment is a compound or a salt thereof, wherein $R^3$ is lower alkyl optionally substituted with one or more —OH. Yet another embodiment is a compound or a salt thereof, wherein $R^3$ is 2-hydroxyethyl or 2,3-dihydroxypropyl.

(11) A compound or a salt thereof, which is a consistent combination of any two or more of the embodiments described in (1) to (10) above.

The present invention encompasses a compound or a salt thereof, which is a combination of any two or more of the embodiments described in (1) to (10) above, as described in (11) above. Specific examples include the embodiments described below.

(12) A compound or a salt thereof, wherein X is N; Y is CH; and $L^1$ is lower alkylene or -lower alkylene-O—.

(13) The compound according to (12) or a salt thereof, wherein Z is CH; $R^1$, the same or different from one another, are —O-lower alkyl or halogen; p is 2 or 4; ring W is an optionally substituted aromatic carbocyclic ring or an optionally substituted aromatic heterocyclic ring.

(14) The compound according to (13) or a salt thereof, wherein $L^1$ is ethylene or -methylene-O—; p is 4; ring W is an optionally substituted benzene ring or optionally substituted pyrazole.

(15) The compound according to any one of (12) to (14) or a salt thereof, wherein Q is -$L^2$-$R^2$; $L^2$ is an optionally substituted non-aromatic heterocyclic ring; $R^2$ is lower alkyl optionally substituted with one or more groups selected from the group consisting of —OH and —O-lower alkyl, —NH-(lower alkyl optionally substituted with —OH), an optionally substituted non-aromatic heterocyclic group, -lower alkylene-(an optionally substituted non-aromatic heterocyclic group), or H.

(16) The compound according to (15) or a salt thereof, wherein p is 4; $L^2$ is piperazine optionally substituted with one or more methyl, piperidine optionally substituted with one or more methyl, or 3,9-diazaspiro[5.5]undecane; $R^2$ is piperazine optionally substituted with methyl, piperidine optionally substituted with methyl, 2-hydroxyethylamino, or H.

(17) The compound according to (16) or a salt thereof, wherein $R^1$, the same or different from one another, are —O-methyl or F; $L^1$ is -methylene-O—; ring W is a benzene ring optionally substituted with —O-methyl; $L^2$ is piperidine or 4-methylpiperazine; $R^2$ is 4-methylpiperazine, 2-hydroxyethylamino, or H.

(18) The compound according to any one of (12) to (14) or a salt thereof, wherein ring W is optionally substituted pyrazole; Q is $R^3$; $R^3$ is lower alkyl substituted with one or more groups selected from the group consisting of —C(O)OH, carbamoyl optionally substituted with one or two $R^0$, —OH, an optionally substituted non-aromatic heterocyclic group, and —C(O)-(an optionally substituted non-aromatic heterocyclic group).

(19) The compound according to (18) or a salt thereof, wherein p is 4 and $R^3$ is lower alkyl substituted with one or more substituents selected from the group consisting of —OH, a non-aromatic heterocyclic group optionally substituted with lower alkyl, and —C(O)-(a non-aromatic heterocyclic group optionally substituted with —OH).

(20) The compound according to (19) or a salt thereof, wherein $R^1$, the same or different from one another, are —O-methyl or F; $L^1$ is -methylene-O—; ring W is pyrazole optionally substituted with methyl; $R^3$ is 2-hydroxyethyl, 2,3-dihydroxypropyl, or 4-methylpiperazin-1-ylmethyl.

Another embodiment of the compound of formula (I) or salt thereof is, for example, a compound or a salt thereof, wherein X and Y, the same or different from each other, are CH or N, with the proviso that X and Y are not N simultaneously;

$L^1$ is -lower alkylene-, -lower alkylene-O—, —O-lower alkylene-, or lower alkynylene; Z is N or CH;

$R^1$, the same or different from one another, are lower alkyl optionally substituted with halogen, —O-(lower alkyl optionally substituted with halogen), halogen, cyano, or —N(lower alkyl)$_2$;

p is an integer of 2 to 4;

ring W is an optionally substituted aromatic carbocyclic ring, an optionally substituted aromatic heterocyclic ring, or an optionally substituted non-aromatic heterocyclic ring;

Q is -$L^2$-$R^2$ or $R^3$;

$L^2$ is an optionally substituted aromatic heterocyclic ring or an optionally substituted non-aromatic heterocyclic ring;

$R^2$ is lower alkyl optionally substituted with one or more groups selected from the group consisting of —OH and —O-lower alkyl, —C(O)-optionally substituted cycloalkyl, —NH-(lower alkyl optionally substituted with —OH), an -$L^3$-optionally substituted non-aromatic heterocyclic group, or H;

$R^3$ is lower alkyl optionally substituted with one or more groups selected from the group consisting of —C(O)OH, —OH, —NH-lower alkyl, —N(lower alkyl)$_2$, —C(O)—NH-lower alkyl, —C(O)—N(lower alkyl)$_2$, an optionally substituted aromatic heterocyclic group, an optionally substituted non-aromatic heterocyclic group, and a —C(O)-optionally substituted non-aromatic heterocyclic group, —O-(lower alkyl optionally substituted with one or more groups selected from the group consisting of —OH, —C(O)—NH-lower alkyl, and —C(O)—N(lower alkyl)$_2$), —NH-(lower alkyl optionally substituted with one or more groups selected from the group consisting of —OH, —C(O)—NH-lower alkyl, and —C(O)—N(lower alkyl)$_2$), —N(lower alkyl)-(lower alkyl optionally substituted with one or more groups selected from the group consisting of —OH, —C(O)—NH-lower alkyl, and —C(O)—N(lower alkyl)$_2$), —C(O)OH, or a —C(O)-optionally substituted non-aromatic heterocyclic group; and $L^3$ is a bond or lower alkylene.

Examples of specific compounds falling within the scope of the compound of formula (I) or a salt thereof include the following compounds:

5-[2-(2,6-difluoro-3,5-dimethoxyphenyl)ethyl]-N-[3-methoxy-4-(4-methylpiperazin-1-yl)phenyl]pyrimidin-2-amine,
(2S)-3-[4-({5-[(2,6-difluoro-3,5-dimethoxybenzyl)oxy]pyrimidin-2-yl}amino)-1H-pyrazol-1-yl]propane-1,2-diol,
5-[2-(2,6-difluoro-3,5-dimethoxyphenyl)ethyl]-N-{3-methoxy-4-[4-(4-methylpiperazin-1-yl)piperidin-1-yl]phenyl}pyrimidin-2-amine,
5-[2-(2,6-difluoro-3,5-dimethoxyphenyl)ethyl]-N-{3-fluoro-4-[4-(4-methylpiperazin-1-yl)piperidin-1-yl]phenyl}pyrimidin-2-amine,
5-[(2,6-difluoro-3,5-dimethoxybenzyl)oxy]-N-{3-methoxy-4-[4-(4-methylpiperazin-1-yl)piperidin-1-yl]phenyl}pyrimidin-2-amine,
5-[(2,6-difluoro-3,5-dimethoxybenzyl)oxy]-N-[3-methoxy-4-(4-methylpiperazin-1-yl)phenyl]pyrimidin-2-amine,
5-[(2,6-dichloro-3,5-dimethoxybenzyl)oxy]-N-[1-(1-methylpiperidin-4-yl)-1H-pyrazol-4-yl]pyrimidin-2-amine,
5-[(2,6-dichloro-3,5-dimethoxybenzyl)oxy]-N-[1-(piperidin-4-yl)-1H-pyrazol-4-yl]pyrimidin-2-amine,
5-[(2,6-difluoro-3,5-dimethoxybenzyl)oxy]-N-{3-methoxy-4-[4-(1-methylpiperidin-4-yl)piperazin-1-yl]phenyl}pyrimidin-2-amine,
5-[(2,6-difluoro-3,5-dimethoxybenzyl)oxy]-N-{3-methyl-4-[4-(4-methylpiperazin-1-yl)piperidin-1-yl]phenyl}pyrimidin-2-amine,
5-[(2,6-difluoro-3,5-dimethoxybenzyl)oxy]-N-{4-[(3R,5S)-3,5-dimethylpiperazin-1-yl]-3-methoxyphenyl}pyrimidin-2-amine,
N-[4-(3,9-diazaspiro[5.5]undec-3-yl)-3-methoxyphenyl]-5-[(2,6-difluoro-3,5-dimethoxybenzyl)oxy]pyrimidin-2-amine,
2-[4-({5-[(2,6-difluoro-3,5-dimethoxybenzyl)oxy]pyrimidin-2-yl}amino)-1H-pyrazol-1-yl]ethanol,
5-[(2,6-difluoro-3,5-dimethoxybenzyl)oxy]-N-{1-[2-(4-methylpiperazin-1-yl)ethyl]-1H-pyrazol-4-yl}pyrimidin-2-amine,
2-[4-({5-[(2,6-difluoro-3,5-dimethoxybenzyl)oxy]pyrimidin-2-yl}amino)-1H-pyrazol-1-yl]-1-(3-hydroxyazetidin-1-yl)ethanone,
(2R)-3-[4-({5-[(2,6-difluoro-3,5-dimethoxybenzyl)oxy]pyrimidin-2-yl}amino)-1H-pyrazol-1-yl]propane-1,2-diol,
2-({1-[4-({5-[(2,6-difluoro-3,5-dimethoxybenzyl)oxy]pyrimidin-2-yl}amino)phenyl]piperidin-4-yl}amino)ethanol,
5-[(2,6-difluoro-3,5-dimethoxybenzyl)oxy]-N-{1-methyl-5-[(4-methylpiperazin-1-yl)methyl]-1H-pyrazol-3-yl}pyrimidin-2-amine, and
5-[(2,6-difluoro-3,5-dimethoxybenzyl)oxy]-N-[4-(4-methylpiperazin-1-yl)phenyl]pyrimidin-2-amine, and salts thereof.

In another embodiment, examples of specific compounds falling within the scope of the compound of formula (I) or a salt thereof include the following compounds:

5-[2-(2,6-difluoro-3,5-dimethoxyphenyl)ethyl]-N-[3-methoxy-4-(4-methylpiperazin-1-yl)phenyl]pyrimidin-2-amine,
(2S)-3-[4-({5-[(2,6-difluoro-3,5-dimethoxybenzyl)oxy]pyrimidin-2-yl}amino)-1H-pyrazol-1-yl]propane-1,2-diol,
5-[2-(2,6-difluoro-3,5-dimethoxyphenyl)ethyl]-N-{3-methoxy-4-[4-(4-methylpiperazin-1-yl)piperidin-1-yl]phenyl}pyrimidin-2-amine,
5-[2-(2,6-difluoro-3,5-dimethoxyphenyl)ethyl]-N-{3-fluoro-4-[4-(4-methylpiperazin-1-yl)piperidin-1-yl]phenyl}pyrimidin-2-amine,
5-[(2,6-difluoro-3,5-dimethoxybenzyl)oxy]-N-{3-methoxy-4-[4-(4-methylpiperazin-1-yl)piperidin-1-yl]phenyl}pyrimidin-2-amine,
5-[(2,6-difluoro-3,5-dimethoxybenzyl)oxy]-N-[3-methoxy-4-(4-methylpiperazin-1-yl)phenyl]pyrimidin-2-amine,
5-[(2,6-dichloro-3,5-dimethoxybenzyl)oxy]-N-[1-(1-methylpiperidin-4-yl)-1H-pyrazol-4-yl]pyrimidin-2-amine,
5-[(2,6-dichloro-3,5-dimethoxybenzyl)oxy]-N-[1-(piperidin-4-yl)-1H-pyrazol-4-yl]pyrimidin-2-amine,
5-[(2,6-difluoro-3,5-dimethoxybenzyl)oxy]-N-{3-methoxy-4-[4-(1-methylpiperidin-4-yl)piperazin-1-yl]phenyl}pyrimidin-2-amine,
5-[(2,6-difluoro-3,5-dimethoxybenzyl)oxy]-N-{3-methyl-4-[4-(4-methylpiperazin-1-yl)piperidin-1-yl]phenyl}pyrimidin-2-amine,
5-[(2,6-difluoro-3,5-dimethoxybenzyl)oxy]-N-{4-[(3R,5S)-3,5-dimethylpiperazin-1-yl]-3-methoxyphenyl}pyrimidin-2-amine,
N-[4-(3,9-diazaspiro[5.5]undec-3-yl)-3-methoxyphenyl]-5-[(2,6-difluoro-3,5-dimethoxybenzyl)oxy]pyrimidin-2-amine,
2-[4-({5-[(2,6-difluoro-3,5-dimethoxybenzyl)oxy]pyrimidin-2-yl}amino)-1H-pyrazol-1-yl]ethanol,
5-[(2,6-difluoro-3,5-dimethoxybenzyl)oxy]-N-{1-[2-(4-methylpiperazin-1-yl)ethyl]-1H-pyrazol-4-yl}pyrimidin-2-amine,
2-[4-({5-[(2,6-difluoro-3,5-dimethoxybenzyl)oxy]pyrimidin-2-yl}amino)-1H-pyrazol-1-yl]-1-(3-hydroxyazetidin-1-yl)ethanone, and
(2R)-3-[4-({5-[(2,6-difluoro-3,5-dimethoxybenzyl)oxy]pyrimidin-2-yl}amino)-1H-pyrazol-1-yl]propane-1,2-diol, and salts thereof.

In yet another embodiment, examples of specific compounds falling within the scope of the compound of formula (I) or a salt thereof include the following compounds:

5-[(2,6-difluoro-3,5-dimethoxybenzyl)oxy]-N-{3-methoxy-4-[4-(4-methylpiperazin-1-yl)piperidin-1-yl]phenyl}pyrimidin-2-amine,
2-[4-({5-[(2,6-difluoro-3,5-dimethoxybenzyl)oxy]pyrimidin-2-yl}amino)-1H-pyrazol-1-yl]ethanol,
(2R)-3-[4-({5-[(2,6-difluoro-3,5-dimethoxybenzyl)oxy]pyrimidin-2-yl}amino)-1H-pyrazol-1-yl]propane-1,2-diol,
2-({1-[4-({5-[(2,6-difluoro-3,5-dimethoxybenzyl)oxy]pyrimidin-2-yl}amino)phenyl]piperidin-4-yl}amino)ethanol,
5-[(2,6-difluoro-3,5-dimethoxybenzyl)oxy]-N-{1-methyl-5-[(4-methylpiperazin-1-yl)methyl]-1H-pyrazol-3-yl}pyrimidin-2-amine, and
5-[(2,6-difluoro-3,5-dimethoxybenzyl)oxy]-N-[4-(4-methylpiperazin-1-yl)phenyl]pyrimidin-2-amine, and salts thereof.

In yet another embodiment, examples of specific compounds falling within the scope of the compound of formula (I) or a salt thereof include the following compounds:

5-[(2,6-difluoro-3,5-dimethoxybenzyl)oxy]-N-{3-methoxy-4-[4-(4-methylpiperazin-1-yl)piperidin-1-yl]phenyl}pyrimidin-2-amine,
2-[4-({15-[(2,6-difluoro-3,5-dimethoxybenzyl)oxy]pyrimidin-2-yl}amino)-1H-pyrazol-1-yl]ethanol, and (2R)-3-[4-({5-[(2,6-difluoro-3,5-dimethoxybenzyl)oxy]pyrimidin-2-yl}amino)-1H-pyrazol-1-yl]propane-1,2-diol, and salts thereof.

In yet another embodiment, examples of specific compounds falling within the scope of the compound of formula (I) or a salt thereof include the following compounds:

2-({1-[4-({5-[2,6-difluoro-3,5-dimethoxybenzyl)oxy]pyrimidin-2-yl}amino)phenyl]piperidin-4-yl}amino)ethanol, 5-[(2,6-difluoro-3,5-dimethoxybenzyl)oxy]-N-{1-methyl-5-[(4-methylpiperazin-1-yl)methyl]-1H-pyrazol-3-yl}pyrimidin-2-amine, and 5-[(2,6-difluoro-3,5-dimethoxybenzyl)oxy]-N-[4-(4-methylpiperazin-1-yl)phenyl]pyrimidin-2-amine, and salts thereof.

The compounds of formula (I) may have tautomers and/or geometrical isomers, depending on the type of substituents. Even when the compound of formula (I) appear herein only in one isomer form, the present invention encompasses the other isomers, and also encompasses separated isomers or mixtures thereof.

Further, since some compounds of formula (I) have an asymmetric carbon atom or axial asymmetry, optical isomers based on this asymmetry may also exist. The present invention also encompasses separated optical isomers of the compounds of formula (I) or mixtures thereof.

Furthermore, the present invention encompasses pharmaceutically acceptable prodrugs of the compounds represented by formula (I). The term "pharmaceutically acceptable prodrug" refers to a compound having a group that can be converted into an amino group, a hydroxyl group, a carboxyl group, or the like by solvolysis or under physiological conditions. Examples of a prodrug-forming group include those described in Prog. Med., 5, 2157-2161 (1985) and those described in "Development of Pharmaceuticals" (Hirokawa Publishing, 1990) vol. 7, Molecular Design, 163-198.

Likewise, salts of the compounds of formula (I) are pharmaceutically acceptable salts of the compounds of formula (I). The compounds of formula (I) may form acid addition salts or salts with bases, depending on the type of substituents. Specific examples include acid addition salts with inorganic acids (e.g., hydrochloric acid, hydrobromic acid, hydroiodic acid, sulfuric acid, nitric acid, phosphoric acid) or with organic acids (e.g., formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid), salts with inorganic bases (e.g., sodium, potassium, magnesium, calcium, aluminum) or with organic bases (e.g., methylamine, ethylamine, ethanolamine, lysine, ornithine), salts with various amino acids and amino acid derivatives (e.g., acetylleucine), ammonium salts, and the like.

Moreover, the present invention encompasses the compounds of formula (I) and salts thereof in the form of various hydrates, solvates, and crystalline polymorphic substances. The present invention also encompasses the compounds labeled with various radioactive or non-radioactive isotopes.

(Preparation Processes)

The compounds of formula (I) and salts thereof can be prepared by applying various known synthesis methods on the basis of characteristics derived from their basic structure or the type of their substituents. In some cases, depending on the type of functional group, it is technically effective to replace such a functional group with an appropriate protecting group (a group that can be easily converted into the original functional group) between the starting material stage and the intermediate stage. Examples of the protecting group include those described in Wuts (P. G. M. Wuts) and Greene (T. W. Greene), "Greene's Protective Groups in Organic Synthesis (fourth edition, 2006)", and the like, which may be selected and used as appropriate, depending on reaction conditions. In such a method, after introduction of the protecting group and subsequent reaction, the protecting group may be removed, if needed, to obtain a desired compound.

Likewise, a prodrug of the compound of formula (I) can be prepared by introducing a specific group between the starting material stage and the intermediate stage, as in the case of the above protecting group, or by subjecting the obtained compound of formula (I) to further reaction. The reaction may be accomplished by applying esterification, amidation, dehydration, or the like, which is a method that is common and known to those skilled in the art.

Described below are typical processes for preparing the compounds of formula (I). Each process may also be accomplished by reference to the documents cited in this description. It should be noted that the preparation processes of the present invention are not limited to the examples illustrated below.

(Preparation Process 1)

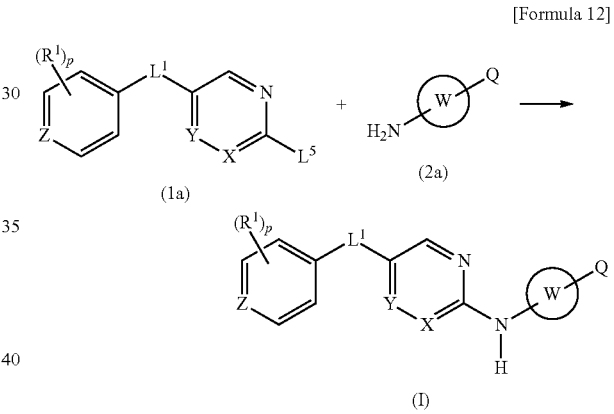

[Formula 12]

(In this formula, $L^5$ represents halogen, methylsulfinyl, or methylsulfonyl. The same applies hereinafter.)

The compound (I) of the present invention can be obtained by coupling reaction of compound (1a) and compound (2a).

In this reaction, compounds (1a) and (2a) are used in equal amounts or one of them is used in an excessive amount. A mixture of these compounds is stirred in the presence of a predetermined catalyst, in a solvent inert to the reaction or in the absence of a solvent, generally for 0.1 hour to 5 days under conditions between room temperature and heating to reflux. This reaction is preferably performed under an inert gas atmosphere. Examples of the solvent used in this process include, but are not particularly limited to, aromatic hydrocarbons (e.g., benzene, toluene, xylene), ethers (e.g., diethyl ether, tetrahydrofuran, dioxane, dimethoxyethane), halogenated hydrocarbons (e.g., dichloromethane, 1,2-dichloroethane, chloroform), N-methylpyrrolidone, N,N-dimethylformamide, N,N-dimethylacetamide, dimethyl sulfoxide, ethyl acetate, acetonitrile, tert-butanol, and mixtures thereof. Examples of the predetermined catalyst include palladium acetate, tris(dibenzylideneacetone)dipalladium, and the like. Further, when a palladium catalyst is used, a ligand used for the catalyst may be triphenylphosphine, 1,1'-binaphthalene-2,2'-diylbis(diphenylphosphine), 2-(dicyclohexylphosphino)-2',4',6'-triisopropyl-1,1'-biphenyl, or 4,5-bis(diphenylphosphino)-9,9-dimethylxanthene. The reaction may be performed in the presence of an organic base (e.g., triethylamine, N,N-diisopropylethylamine, or N-methylmorpholine) or an inorganic base (e.g., sodium tert-butoxide, potassium carbonate, sodium carbonate, cesium carbonate, or potassium hydroxide), because it is advantageous for smooth reaction in some cases. Heating the reaction mixture by microwave irradiation is advantageous for smooth reaction in some cases.

DOCUMENTS

S. R. Sandler and W. Karo, "Organic Functional Group Preparations", second edition, vol. 1, Academic Press Inc., 1991

The Chemical Society of Japan (ed.), "The Fifth Series of Experimental Chemistry", vol. 14, MARUZEN Co., Ltd., 2005

(Preparation Process 2)

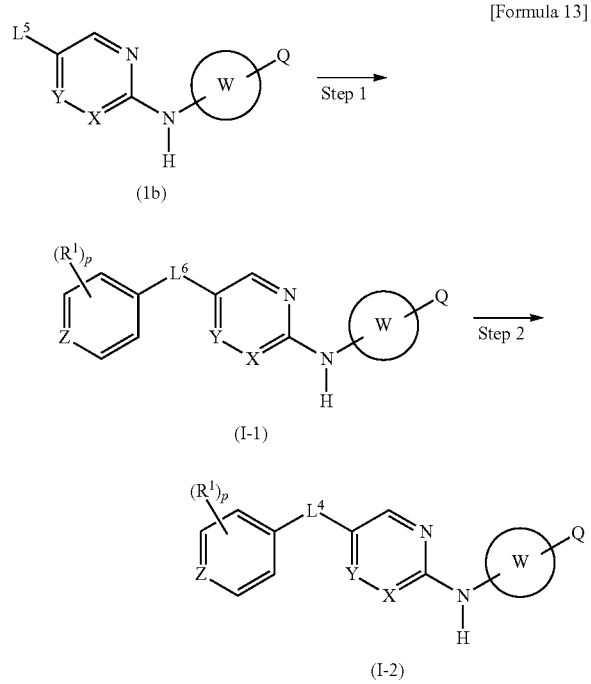

(In this formula, $L^6$ represents lower alkynylene. The same applies hereinafter.)

(Step 1)

This process is intended to prepare compound (I-1) of the present invention by Sonogashira coupling reaction of compound (1b) and a terminal alkyne derivative.

In this process, compound (1b) and a terminal alkyne derivative are used in equal amounts or one of them is used in an excessive amount. A mixture of these is stirred in the presence of a base, a palladium catalyst, and copper iodide, in a solvent inert to the reaction, generally for 0.1 hour to 5 days under conditions between room temperature and heating to reflux. This reaction is preferably performed under an inert gas atmosphere. Examples of the solvent used in this process include, but are not particularly limited to, aromatic hydrocarbons (e.g., benzene, toluene, xylene), ethers (e.g., diethyl ether, tetrahydrofuran, dioxane, dimethoxyethane), halogenated hydrocarbons (e.g., dichloromethane, 1,2-dichloroethane, or chloroform), alcohols (e.g., methanol, ethanol, 2-propanol, butanol), N,N-dimethylformamide, dimethyl sulfoxide, and mixtures thereof. The base is preferably an organic base (e.g., triethylamine, N,N-diisopropylethylamine, or N-methylmorpholine) or an inorganic base (e.g., potassium carbonate, sodium carbonate, cesium carbonate, or potassium hydroxide). The palladium catalyst is preferably tetrakis(triphenylphosphine)palladium, dichlorobis(triphenylphosphine)palladium, palladium chloride-1,1'-bis(diphenylphosphino)ferrocene, or the like. Heating the reaction mixture by microwave irradiation is advantageous for smooth reaction in some cases.

DOCUMENTS

A. d. Meijere and F. Diederich (ed.), "Metal-Catalyzed Cross-Coupling Reactions", first edition, VCH Publishers Inc., 1997

The Chemical Society of Japan (ed.), "The Fifth Series of Experimental Chemistry", vol. 13, MARUZEN Co., Ltd., 2005

(Step 2)

This process is intended to prepare compound (I-2) of the present invention by reducing the alkyne moiety of compound (I-1) of the present invention to alkylene by hydrogenation or diimide reduction.

In this process, compound (I-1) of the present invention and palladium carbon are used in equal amounts or one of them is used in an excessive amount. A mixture of these is stirred in a solvent inert to the reaction, under a hydrogen atmosphere, generally for 0.1 hour to 5 days under conditions between room temperature and heating to reflux. Examples of the solvent used in this process include, but are not particularly limited to, ethers (e.g., diethyl ether, tetrahydrofuran, dioxane, dimethoxyethane), alcohols (e.g., methanol, ethanol, 2-propanol, butanol), and mixtures thereof.

Other than the hydrogenation reaction, compound (I-1) of the present invention and predetermined diimide are used in equal amounts or one of them is used in an excessive amount. A mixture of these is stirred in a solvent inert to the reaction, generally for 0.1 hour to 5 days under conditions between room temperature and heating to reflux. Examples of the solvent used in this process are the same as shown above. The predetermined diimide is, for example, 4-methylbenzenesulfonyl hydrazide.

The substituent(s) on ring W in the compound of formula (I) can be easily converted into other functional groups by the reaction described below in the Examples, reaction obvious to those skilled in the art, or a modified process thereof, using a compound of formula (I) as a starting material. For example, the conversion can be achieved by combining any processes that can be applied generally by those skilled in the art, such as reduction, halogenation, deprotection, hydrolysis, amidation, amination, oxidation, reductive amination, acylation, O-alkylation, N-alkylation, reductive alkylation, and epoxidation.

(Preparation of Starting Compound)

The starting compound used in the preparation process described above can be prepared, for example, by a process described below, the process in the Preparation Examples described later, a known process, or a modified process thereof.

23

(Starting Material Synthesis 1)

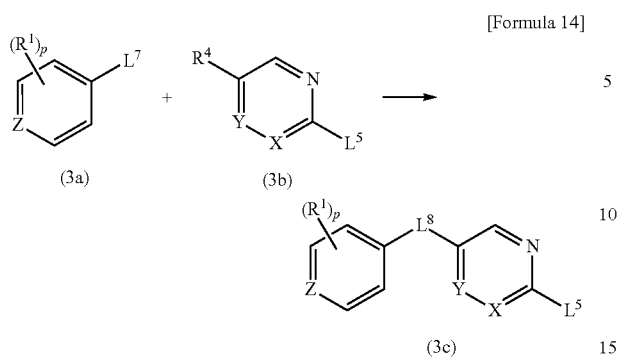

[Formula 14]

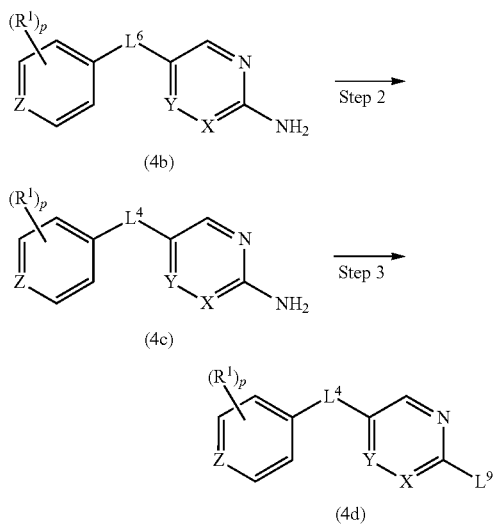

(In this formula, R⁴ represents —OH or -lower alkylene-OH; L⁷ represents halogen, —OH, -lower alkylene-OH, -lower alkylene-OMs, -lower alkylene-OTs, -lower alkylene-OTf, or -lower alkylene-halogen; L⁸ represents -lower alkylene-O— or —O-lower alkylene-. The same applies hereinafter.)

This preparation process is intended to prepare compound (3c) which is starting compound (1a) of the Preparation Process 1 wherein $L^1$ is —O-lower alkylene- or -lower alkylene-O—.

In the case of compound (3a) wherein $L^7$ is halogen, -lower alkylene-OMs, -lower alkylene-OTs, -lower alkylene-OTf, or -lower alkylene-halogen, compounds (3a) and (3b) are used in equal amounts or one of them is used in an excessive amount. A mixture of these is stirred in the presence of a base in a solvent inert to the reaction, generally for 0.1 hour to 5 days under conditions between room temperature and heating to reflux. Examples of the solvent used in this process include, but are not particularly limited to, N-methylpyrrolidone, N,N-dimethylformamide, dimethyl sulfoxide, and the like. The base is preferably an inorganic base such as potassium carbonate, sodium carbonate, cesium carbonate, or potassium hydroxide.

In the case of compound (3a) wherein $L^7$ is —OH or -lower alkylene-OH, compounds (3a) and (3b) are used in equal amounts or one of them is used in an excessive amount. A mixture of these is stirred in the presence of a predetermined phosphine reagent and a predetermined condensing agent in a solvent inert to the reaction, generally for 0.1 hour to 5 days under conditions between room temperature and heating to reflux. Examples of the solvent used in this process include, but are not particularly limited to, ethers such as diethyl ether, tetrahydrofuran, dioxane, and dimethoxyethane. Examples of the predetermined phosphine reagent include tributylphosphine, triphenylphosphine, and the like. Examples of the predetermined condensing agent include diethyl azodicarboxylate, 1,1'-(azodicarbonyl)dipiperidine, and the like. Use of (cyanomethylene)trimethylphosphorane, instead of the predetermined phosphine and the predetermined condensing agent, is advantageous for smooth reaction in some cases.

(Starting Material Synthesis 2)

24

(In this formula, $L^9$ represents halogen. The same applies hereinafter.)

This preparation process is intended to prepare compound (4d) which is starting compound (1a) of the Preparation Process 1 wherein $L^1$ is lower alkylene.

(Step 1)

This process is intended to prepare compound (4b) by Sonogashira coupling reaction of compound (4a) and a terminal alkyne derivative.

The reaction conditions are the same as in Step 1 of the Preparation Process 2.

(Step 2)

This process is intended to prepare compound (4c) by reducing the alkyne moiety of compound (4b) to lower alkylene by hydrogenation.

The reaction conditions are the same as in Step 2 of the Preparation Process 2.

(Step 3)

This process is intended to prepare compound (4d) by converting the amino group of compound (4c) into halogen.

In this process, compound (4c) and a combination of copper chloride (II) and n-pentyl nitrite are used in equal amounts or one of them is used in an excessive amount. A mixture of these is stirred in a solvent inert to the reaction, generally for 0.1 hour to 5 days under conditions between ice cooling and heating to reflux. Examples of the solvent used in this process include, but are not particularly limited to, halogenated hydrocarbons such as dichloromethane, 1,2-dichloroethane, and chloroform.

(Starting Material Synthesis 3)

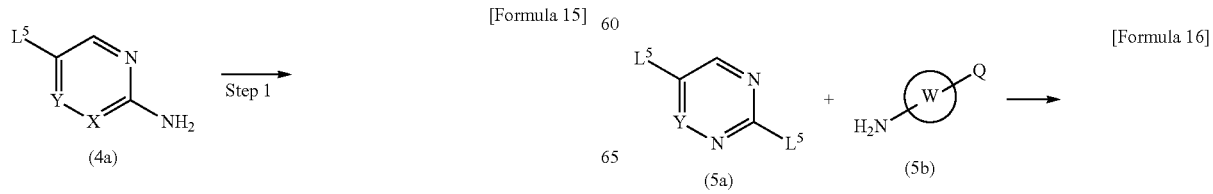

[Formula 15]

[Formula 16]

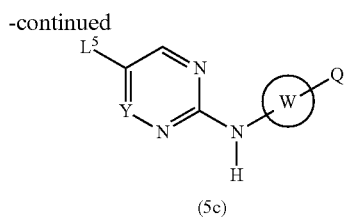

(5c)

This preparation process is intended to prepare compound (5c) which is starting compound (1b) of the Preparation Process 2 wherein X is N.

This reaction is intended to prepare compound (5c) by ipso-substitution reaction of compounds (5a) and (5b).

Compounds (5a) and (5b) are used in equal amounts or one of them is used in an excessive amount. A mixture of these is stirred in a solvent inert to the reaction under a hydrogen atmosphere, generally for 0.1 hour to 5 days under conditions between ice cooling and heating to reflux. Examples of the solvent used in this process include, but are not particularly limited to, alcohols (e.g., methanol, ethanol, 2-propanol, butanol), N-methylpyrrolidone, N,N-dimethylformamide, dimethyl sulfoxide, and mixtures thereof. Use of an acid such as methanesulfonic acid, acetic acid, trifluoroacetic acid, hydrogen chloride, or sulfuric acid is advantageous for smooth reaction in some cases.

The pharmacological activity of the compounds of formula (I) was confirmed in the tests described below.

Test Example 1

FGFR1, FGFR2, and FGFR3 Enzyme Assay

In the enzyme assay, human recombinant FGFR1, FGFR2, and FGFR3 (Cama Biosciences; Catalog Nos. 08-133, 08-134, and 08-135) were used, and reactions were performed at room temperature (FGFR1 and FGFR2) or 30° C. (FGFR3). The measurement method is outlined below.

The compound was diluted with a solution of dimethyl sulfoxide (DMSO) (10-fold common ratio, 4 portions) before dilution with a reaction buffer (100 mM HEPES (pH7.5), 0.003% Brij-35, 0.004% Tween 20, 0.5 mM DTT, and 10 mM $MgCl_2$) so that the final DMSO concentration was 2%. To 4 µL of the compound solution in a 384-well plate, 2 µL each of FGFR1 enzyme (2 or 3 ng/µL), FGFR2 enzyme (2 ng/µL), or FGFR3 enzyme (6 ng/µL) which were diluted with the reaction buffer was added. In 20 minutes, 4 µL of a substrate-ATP solution (100 mM HEPES (pH7.5), 0.003% Brij-35, 0.004% Tween 20, 0.5 mM DTT, 10 mM $MgCl_2$, 3.75 µM substrate-FL-peptide 22+ 500 µM (FGFR1) ATP, 188 µM (FGFR2) ATP, or 250 µM (FGFR3) ATP) was added before subsequent 30-minute reaction. After the reaction was stopped, the reaction mixture was measured with a LabChip EZ Reader. The $IC_{50}$ values were calculated by non-linear regression based on the inhibition rates obtained. The results of some compounds are shown in Table 1. The term "Ex" in the table denotes compound No. in the Examples described later.

TABLE 1

| Ex | FGFR1 $IC_{50}$ (nM) | FGFR2 $IC_{50}$ (nM) | FGFR3 $IC_{50}$ (nM) |
|---|---|---|---|
| 7 | 2 | 3 | 1 |
| 11 | 1 | — | 2 |

TABLE 1-continued

| Ex | FGFR1 $IC_{50}$ (nM) | FGFR2 $IC_{50}$ (nM) | FGFR3 $IC_{50}$ (nM) |
|---|---|---|---|
| 27 | 2 | 1 | <1 |
| 33 | 2 | 3 | 2 |
| 56 | 2 | 2 | 1 |
| 57 | 1 | 2 | 2 |
| 71 | 2 | 3 | 2 |
| 72 | — | 2 | 2 |
| 84 | 2 | 2 | 1 |
| 87 | — | 3 | 2 |
| 92 | — | 2 | 1 |
| 95 | — | 3 | 2 |
| 113 | 1 | — | 2 |
| 114 | 2 | — | 1 |
| 115 | 2 | — | 2 |
| 116 | 1 | — | 2 |
| 122 | — | 2 | 2 |
| 248 | 4 | — | 5 |
| 299 | <1 | — | 2 |

Test Example 2

Growth Assay of Cells with Forced Expression of Mutant FGFR3 (FGFR3_S249C/NIH3T3)

FGFR3_S249C/NIH3T3 cells were added to a 96-well spheroid plate (U bottom) at a concentration of 3000 cells/well/90 µL, and the compound solution (10 µL) was added thereto on the next day (final DMSO concentration: 0.1%). The compound solution was prepared by serially diluting the compound with DMSO at a 3-fold common ratio (9 portions and DMSO only) from the maximum concentration of 10 mM and then diluted 100-fold with a culture medium (D-MEM, 10% FBS). 5 days after the addition of the compound, the growth inhibition caused by the compound was evaluated by Promega (G7573) CellTiter-Glo™ Luminescent Cell Viability Assay. The $IC_{50}$ value was calculated by non-linear regression, using DMSO-added wells as control and assuming count 0 to be 100% inhibition. The results of some compounds are shown in Table 2.

TABLE 2

| Ex | $IC_{50}$ (nM) |
|---|---|
| 7 | 18 |
| 11 | 13 |
| 27 | 13 |
| 33 | 26 |
| 56 | 13 |
| 57 | 5 |
| 71 | 10 |
| 72 | 24 |
| 84 | 16 |
| 87 | 20 |
| 92 | 7 |
| 95 | 57 |
| 113 | 11 |
| 114 | 7 |
| 115 | 36 |
| 116 | 8 |
| 122 | 7 |
| 248 | 50 |
| 299 | 10 |

Test Example 3

Antitumor Test on UM-UC-14 (FGFR3_S249C-Positive Cells, Bladder Cancer)

$3 \times 10^6$ UM-UC-14 cells per 0.1 mL (PBS+matrigel, 1:1) were inoculated subcutaneously into the right flank of nude mice (CAnN, Cg-Foxn1nu/CrlCrlj (nu/nu), male, 4- to 5-week-old), and when their tumor size reached about 250 mm³, drug administration was started (Day 1). The drug was administered once a day and the tumor size was measured with a caliper and the body weight was also measured every two or three days. The antitumor effect was finally determined based on the tumor volume (mm³; minor axis (mm)× minor axis (mm)×major axis (mm)/2) at Day 11 (n=3-5). To the control group, 0.5% MC (methyl cellulose) was administered. For "% inhibition" in the table, for example, 100% inhibition indicates that the tumor growth of the control was inhibited to the level of the tumor volume at Day 1. "% regression" indicates what percentage of regression could be achieved compared with the tumor volume at Day 1. Here, the tumor volume at Day 1 means tumor volume immediately before drug administration. The results of some compounds administered orally (1 mg/kg/day for other than Ex 95 and 3 mg/kg/day for Ex 95) are shown in Table 3.

TABLE 3

| Ex | Antitumor Activity |
|---|---|
| 7 | 33% inhibition |
| 11 | 53% regression |
| 27 | 62% inhibition |
| 33 | 70% inhibition |
| 56 | 4% regression |
| 57 | 77% inhibition |
| 71 | 50% inhibition |
| 72 | 30% inhibition |
| 84 | 34% regression |
| 87 | 72% inhibition |
| 92 | 49% inhibition |
| 95 | 97% inhibition |
| 113 | 4% regression |
| 114 | 33% regression |
| 115 | 70% inhibition |
| 116 | 54% regression |
| 122 | 15% regression |
| 248 | 95% inhibition |
| 299 | 15% regression |

The test described above confirmed that the plural compounds of the Examples included in formula (I) of the present invention had inhibitory action on FGFR1, FGFR 2, and/or FGFR3. It was also confirmed that the plural compounds of the Examples included in formula (I) inhibited the growth of the cells with forced expression of mutant FGFR3 and that the compounds also inhibited the growth of bladder cancer or made bladder cancer itself regress, in the animal model bearing mutant FGFR3-positive bladder cancer. In light of the foregoing, the compound of formula (I) or a salt thereof can be used as a therapeutic agent for various cancers related to FGFR1, FGFR 2, and/or FGFR3, particularly, mutant FGFR3-positive bladder cancer.

Test Example 4

Isolation of FGFR3-TACC3_v1 cDNA was synthesized by reverse transcription reaction in 200 clinical specimens of lung cancer (Asterand plc.; US) using reverse transcriptase (SuperScriptIII, Life Technologies, Corp.) and random primers (random primers, Life Technologies Corp.) in accordance with the protocol of the kit.

Next, PCR (30 cycles of 98° C. for 10 seconds, 55° C. for 15 seconds, 68° C. for 1.5 minutes) was carried out using primers FGFR3_TACC3_RT_F represented by SEQ ID No: 1 and FGFR3_TACC3_RT_R represented by SEQ ID No: 2, the cDNA obtained above as a template, and DNA polymerase (TaKaRa Ex Taq; Takara Bio Inc.). Additional PCR (30 cycles of 98° C. for 15 seconds, 55° C. for 15 seconds, 68° C. for 1 minute) was carried out using the PCR product described above which was diluted 10-fold as a template, primers FGFR3_TACC3_nested_F represented by SEQ ID No: 3 and FGFR3_TACC3_nested_R represented by SEQ ID No: 4, and the same DNA polymerase as shown above. Electrophoresis performed after the PCR reaction showed that a PCR product of about 500 bases was obtained from only sample Lg344 specimen.

After that, the PCR product was sequenced by dideoxy sequencing (BigDye Terminator v3.1 Cycle Sequencing Kit; Life Technologies Corp.). As a result, the PCR product of about 500 bases was found to be a sequence obtained by fusion of the 3' end of exon 18 in the coding sequence (hereinafter, CDS) of FGFR3 (NM_001163213.1) registered in the NCBI to the 5' end of exon 11 in the CDS of TACC3 (NM_006342.1).

cDNA was synthesized by reverse transcription reaction in the Lg344 specimen RNA which is the lung cancer tissue-derived RNA of a squamous cell lung cancer patient (Asterand plc.; US) using reverse transcriptase (SuperScriptIII, Life Technologies, Corp.) and oligo(dT) primers (oligo (dT)20 primers, Life Technologies, Corp.) in accordance with the protocol of the kit.

Next, PCR (25 cycles of 98° C. for 15 seconds, 60° C. for 15 seconds, 68° C. for 3.5 minutes) was carried out using primers FGFR3-TACC3_cloning_F represented by SEQ ID No: 5 and FGFR3-TACC3_cloning_R represented by SEQ ID No: 6, the cDNA obtained above as a template, and DNA polymerase (KOD-plus-Ver. 2; Toyobo Co., Ltd.). Additional PCR (25 cycles of 98° C. for 15 seconds, 55° C. for 15 seconds, 68° C. for 3.5 minutes) was carried out using the PCR product described above which was diluted 10-fold as a template, primers FGFR3_TACC3_cloning_BamHI_F represented by SEQ ID No: 7 and FGFR3_TACC3_cloning_EcoRI_R represented by SEQ ID No: 8, and the same DNA polymerase as shown above. Electrophoresis performed after the PCR reaction showed that a PCR product of about 2.9 k bases was obtained. The PCR product was cloned into a cloning vector (TOPO XL PCR Cloning Kit; Life Technologies, Corp.). The insert was sequenced by dideoxy sequencing (BigDye Terminator v3.1 Cycle Sequencing Kit; Life Technologies, Corp.). As a result, it was found in the PCR product of about 2.9 k bases that there was a transcript obtained by fusion of the region between the 5'-terminus of the CDS of FGFR3 (NM_001163213.1) registered in the NCBI and the 3' end of exon 18 to the region between the 5' end of exon 11 in the CDS of TACC3 (NM_006342.1) and the 3'-terminus of the CDS (FGFR3-TACC3_v1) (SEQ ID No: 9). The polypeptide coded by SEQ ID No: 9 (FGFR3-TACC3_v1 fusion polypeptide) is shown in SEQ ID No: 10.

Test Example 5

Isolation of FGFR3-TACC3_v2 cDNA was synthesized by reverse transcription reaction in 59 specimens of bladder cancer (Asterand plc.; US) using reverse transcriptase (SuperScriptIII, Life Technologies, Corp.) and random primers (random primers, Life Technologies Corp.) in accordance with the protocol of the kit.

Next, PCR (30 cycles of 98° C. for 10 seconds, 55° C. for 15 seconds, 68° C. for 1.5 minutes) was carried out using primers FGFR3_TACC3_RT_F represented by SEQ ID No: 1 and FGFR3_TACC3_RT_R represented by SEQ ID No: 2, the cDNA obtained above as a template, and DNA polymerase (TaKaRa Ex Taq; Takara Bio Inc.). Additional PCR (30 cycles of 98° C. for 15 seconds, 55° C. for 15 seconds, 68° C. for 1 minute) was carried out using the PCR product described above which was diluted 10-fold as a template, primers FGFR3_TACC3_nested_F represented by SEQ ID No: 3 and FGFR3_TACC3_nested_R represented by SEQ ID No: 4, and the same DNA polymerase as shown above. Electrophoresis performed after the PCR reaction showed that a PCR product of about 600 bases was obtained from sample Bd106 specimen.

After that, the PCR product was sequenced by dideoxy sequencing (BigDye Terminator v3.1 Cycle Sequencing Kit; Life Technologies Corp.). As a result, the PCR product of about 600 bases was found to be a sequence obtained by fusion of the 3' end of exon 18 in the CDS of FGFR3 (NM_001163213.1) registered in the NCBI to the 5' end of exon 10 in the CDS of TACC3 (NM_006342.1). cDNA was synthesized by reverse transcription reaction in the Bd106 specimen RNA which is the bladder cancer tissue-derived RNA of a bladder cancer patient (Asterand plc.; US) using reverse transcriptase (SuperScriptIII, Life Technologies, Corp.) and oligo(dT) primers (oligo(dT)20 primers, Life Technologies, Corp.) in accordance with the protocol of the kit.

Next, PCR (25 cycles of 98° C. for 15 seconds, 60° C. for 15 seconds, 68° C. for 3.5 minutes) was carried out using primers FGFR3-TACC3_cloning_F represented by SEQ ID No: 5 and FGFR3-TACC3_cloning_R represented by SEQ ID No: 6, the cDNA obtained above as a template, and DNA polymerase (KOD-plus-Ver. 2; Toyobo Co., Ltd.). Additional PCR (25 cycles of 98° C. for 15 seconds, 55° C. for 15 seconds, 68° C. for 3.5 minutes) was carried out using the PCR product described above which was diluted 10-fold as a template, primers FGFR3_TACC3_cloning_BamHI_F represented by SEQ ID No: 7 and FGFR3_TACC3_cloning_EcoRI_R represented by SEQ ID No: 8, and the same DNA polymerase as shown above. Electrophoresis performed after the PCR reaction showed that a PCR product of about 3.0 k bases was obtained. The PCR product was cloned into a cloning vector (TOPO XL PCR Cloning Kit; Life Technologies, Corp.). The insert was sequenced by dideoxy sequencing (BigDye Terminator v3.1 Cycle Sequencing Kit; Life Technologies, Corp.). As a result, it was found in the PCR product of about 3.0 k bases that there was a transcript obtained by fusion of the region between the 5'-terminus of the CDS of FGFR3 (NM_001163213.1) registered in the NCBI and the 3' end of exon 18 to the region between the 5' end of exon 10 in the CDS of TACC3 (NM_006342.1) and the 3'-terminus of the CDS (FGFR3-TACC3_v2) (SEQ ID No: 11). The polypeptide coded by SEQ ID No: 11 (FGFR3-TACC3_v2 fusion polypeptide) is shown in SEQ ID No: 12.

Test Example 6

Isolation of FGFR3-TACC3_v3 cDNA was synthesized by reverse transcription reaction in 59 specimens of bladder cancer (Asterand plc.; US) using reverse transcriptase (SuperScriptIII, Life Technologies, Corp.) and random primers (random primers, Life Technologies Corp.) in accordance with the protocol of the kit.

Next, PCR (30 cycles of 98° C. for 10 seconds, 55° C. for 15 seconds, 68° C. for 1.5 minutes) was carried out using primers FGFR3_TACC3_RT_F represented by SEQ ID No: 1 and FGFR3_TACC3_RT_R represented by SEQ ID No: 2, the cDNA obtained above as a template, and DNA polymerase (TaKaRa Ex Taq; Takara Bio Inc.). Additional PCR (30 cycles of 98° C. for 15 seconds, 55° C. for 15 seconds, 68° C. for 1 minute) was carried out using the PCR product described above which was diluted 10-fold as a template, primers FGFR3_TACC3_nested_F represented by SEQ ID No: 3 and FGFR3_TACC3_nested_R represented by SEQ ID No: 4, and the same DNA polymerase as shown above. Electrophoresis performed after the PCR reaction showed that a PCR product of about 650 bases was obtained from sample Bd021 specimen.

After that, the PCR product was sequenced by dideoxy sequencing (BigDye Terminator v3.1 Cycle Sequencing Kit; Life Technologies Corp.). As a result, the PCR product of about 650 bases was found to be a sequence obtained by fusion of a certain sequence of exon 19 in the CDS of FGFR3 (NM_001163213.1) registered in the NCBI to a part of intron 10-11 of TACC3 (NM_006342.1) and to the 5' end of exon 11 in the CDS of TACC3.

cDNA was synthesized by reverse transcription reaction in the Bd021 specimen RNA which is the bladder cancer tissue-derived RNA of a bladder cancer patient (Asterand plc.; US) using reverse transcriptase (SuperScriptIII, Life Technologies, Corp.) and oligo(dT) primers (oligo(dT)20 primers, Life Technologies, Corp.) in accordance with the protocol of the kit.

Next, PCR (25 cycles of 98° C. for 15 seconds, 60° C. for 15 seconds, 68° C. for 3.5 minutes) was carried out using primers FGFR3-TACC3_cloning_F represented by SEQ ID No: 5 and FGFR3-TACC3_cloning_R represented by SEQ ID No: 6, the cDNA obtained above as a template, and DNA polymerase (KOD-plus-Ver. 2; Toyobo Co., Ltd.). Additional PCR (25 cycles of 98° C. for 15 seconds, 55° C. for 15 seconds, 68° C. for 3.5 minutes) was carried out using the PCR product described above which was diluted 10-fold as a template, primers FGFR3_TACC3_cloning_BamHI_F represented by SEQ ID No: 7 and FGFR3_TACC3_cloning_EcoRI_R represented by SEQ ID No: 8, and the same DNA polymerase as shown above. Electrophoresis performed after the PCR reaction showed that a PCR product of about 3.0 k bases was obtained. The PCR product was cloned into a cloning vector (TOPO XL PCR Cloning Kit; Life Technologies, Corp.). The insert was sequenced by dideoxy sequencing (BigDye Terminator v3.1 Cycle Sequencing Kit; Life Technologies, Corp.). As a result, it was found in the PCR product of about 3.0 k bases that there was a transcript obtained by fusion of the region between the 5'-terminus of the CDS of FGFR3 (NM_001163213.1) registered in the NCBI and a certain sequence of exon 19 to part of intron 10-11 of TACC3 (NM_006342.1) and further to the region between the 5' end of exon 11 in the CDS of TACC3 and the 3'-terminus of the CDS (FGFR3-TACC3_v3) (SEQ ID No: 13). The polypeptide coded by SEQ ID No: 13 (FGFR3-TACC3_v3 fusion polypeptide) is shown in SEQ ID No: 14.

Test Example 7

Isolation of FGFR3-TACC3 v1 from Bladder Cancer Patient-Derived Cell Line RT-112 cDNA was synthesized by reverse transcription reaction in RNA purified from bladder cancer patient-derived cell line RT-112 (purchased from Leibniz-Institut DSMZ-Deutsche Sammlung von Mikroorganismen and Zellkulturen GmbH) using reverse transcriptase (SuperScriptIII, Life Technologies, Corp.) and oligo(dT) primers (oligo(dT) 20 primers, Life Technologies, Corp.) in accordance with the protocol of the kit.

Next, PCR (25 cycles of 98° C. for 15 seconds, 60° C. for 15 seconds, 68° C. for 3.5 minutes) was carried out using primers FGFR3-TACC3_cloning_F represented by SEQ ID No: 5 and FGFR3-TACC3_cloning_R represented by SEQ ID No: 6, the cDNA obtained above as a template, and DNA polymerase (KOD-plus-Ver. 2; Toyobo Co., Ltd.). Additional PCR (25 cycles of 98° C. for 15 seconds, 55° C. for 15 seconds, 68° C. for 3.5 minutes) was carried out using the PCR product described above which was diluted 10-fold as a template, primers FGFR3_TACC3_cloning_BamHI_F represented by SEQ ID No: 7 and FGFR3_TACC3_cloning_EcoRI_R represented by SEQ ID No: 8, and the same DNA polymerase as shown above. Electrophoresis performed after the PCR reaction showed that a PCR product of about 2.9 k bases was obtained. The PCR product was cloned into a cloning vector (TOPO XL PCR Cloning Kit; Life Technologies, Corp.), and the insert was sequenced by dideoxy sequencing (BigDye Terminator v3.1 Cycle Sequencing Kit; Life Technologies, Corp.). As a result, it was found that a transcript obtained was the same as the transcript obtained by fusion of the region between the N-terminus of the CDS of FGFR3 (NM_001163213.1) registered in the NCBI and the 3' end of exon 18 to the region between the 5' end of exon 11 in the CDS of TACC3 (NM_006342.1) and the C-terminus of the CDS (FGFR3-TACC3_v1) (SEQ ID No: 9).

Test Example 8

Isolation of FGFR3-TACC3_v4 from Bladder Cancer Patient-Derived Cell Line RT4 cDNA was synthesized by reverse transcription reaction in RNA purified from bladder cancer patient-derived cell line RT4 (purchased from ECACC (European Collection of Cell Cultures)) using reverse transciptase (SuperScriptIII, Life Technologies, Corp.) and oligo(dT) primers (oligo(dT) 20 primers, Life Technologies, Corp.) in accordance with the protocol of the kit. Next, PCR (30 cycles of 98° C. for 15 seconds, 60° C. for 15 seconds, 68° C. for 5.5 minutes) was carried out using primers FGFR3-TACC3_cloning_F represented by SEQ ID No: 5 and FGFR3-TACC3_cloning_R represented by SEQ ID No: 6, the cDNA obtained above as a template, and DNA polymerase (KOD-plus-Ver. 2; Toyobo Co., Ltd.). Additional PCR (30 cycles of 98° C. for 15 seconds, 55° C. for 15 seconds, 68° C. for 5 minutes) was carried out using the PCR product described above which was diluted 10-fold as a template, primers FGFR3_TACC3_cloning_BamHI_F represented by SEQ ID No: 7 and FGFR3_TACC3_cloning_EcoRI_R represented by SEQ ID No: 8, and the same DNA polymerase as shown above. Electrophoresis performed after the PCR reaction showed that a PCR product of about 4.5 k bases was obtained. The PCR product was cloned into a cloning vector (TOPO XL PCR Cloning Kit; Life Technologies, Corp.), and the insert was sequenced by dideoxy sequencing (BigDye Terminator v3.1 Cycle Sequencing Kit; Life Technologies, Corp.). As a result, it was found that there was a transcript obtained by fusion of part of intron 18-19 sequence of FGFR3 (NM_001163213.1) registered in the NCBI to the region between the 5'-terminus of the CDS of the FGFR3 and the 3' end of exon 18 and further to the region between a certain sequence of exon 4 of TACC3 (NM_006342.1) and the 3'-terminus of the CDS of the TACC3 (FGFR3-TACC3_v4). In the confirmed sequence, T at base position 882 was replaced by C (SNPs registration No.; rs2234909), C at base position 2484 by T, and G at base position 2663 by A (SEQ ID No: 15). The polypeptide coded by SEQ ID No: 15 (FGFR3-TACC3_v4 fusion polypeptide) is shown in SEQ ID No: 16.

Test Example 9

Preparation of Retrovirus Solutions of FGFR3-TACC3_v1, FGFR3-TACC3_v2, FGFR3-TACC3_v3, and FGFR3-TACC3_v4

To express, as proteins, the ORF full lengths of FGFR3-TACC3_v1, FGFR3-TACC3_v2, FGFR3-TACC3_v3, and FGFR3-TACC3_v4, enzyme reaction was performed at 37° C. for 3 hours using the cloning vectors prepared in Test Examples 4, 5, 6, and 8 and restriction enzyme BamHI, and restriction enzyme digested DNA fragments were obtained and purified. Another enzyme reaction was performed at 37° C. for 3 hours using EcoRI and the DNA fragments, and restriction enzyme digested DNA fragments were obtained and purified. The ORF-containing DNA fragments were cloned into BamHI and EcoRI sites in the multicloning site of an expression vector (pMXs-puro; Cosmo Bio) to construct expression plasmids (FGFR3-TACC3_v1/pMXs-puro, FGFR3-TACC3_v2/pMXs-puro, FGFR3-TACC3_v3/pMXs-puro, and FGFR3-TACC3_v4/pMXs-puro).

9 µg each of FGFR3-TACC3_v1/pMXs-puro, FGFR3-TACC3_v2/pMXs-puro, FGFR3-TACC3_v3/pMXs-puro, and FGFR3-TACC3_v4/pMXs-puro was transfected into Platinum-E cells, using a transfection reagent (FUGENE® HD, Roche). At 24 hours after the transfection, D-MEM media (Dulbecco's Modified Eagle Medium; Invitrogen) containing 10% bovine serum (Nichirei Biosciences) were replaced, and the culture supernatants were collected after 24 hours to prepare retrovirus solutions.

Test Example 10

Investigation of Anchorage-Independent Growth-Promoting Action of FGFR3-TACC3_v1, FGFR3-TACC3_v2, FGFR3-TACC3_v3, and FGFR3-TACC3_v4

To the virus solutions prepared using FGFR3-TACC3_v1/pMXs-puro, FGFR3-TACC3_v2/pMXs-puro, FGFR3-TACC3_v3/pMXs-puro, and FGFR3-TACC3_v4/pMXs-puro in Test Example 9, 4 µg/mL of polybrene (Polybrene; Sigma) was added followed by addition of the resulting mixtures to NIH3T3 cells for infection. At 6 hours after the addition, the media used were replaced by D-MEM media containing 10% bovine serum (Nichirei Biosciences), and, on the day after the infection, the media were replaced by D-MEM media (Invitrogen) containing 10% bovine serum (Nichirei Biosciences) and 1 µg/mL of puromycin (Sigma). The culture was continued in the presence of 5% $CO_2$ at 37° C. for 4 weeks to obtain NIH3T3 cells stably expressing each of FGFR3-TACC3_v1, FGFR3-TACC3_v2, FGFR3-TACC3_v3, and FGFR3-TACC3_v4 (these cells were designated as FGFR3-TACC3_v1-expressing NIH3T3 cells, FGFR3-TACC3_v2-expressing NIH3T3 cells, FGFR3-TACC3_v3-expressing NIH3T3 cells, and FGFR3-TACC3_v4-expressing NIH3T3 cells, respectively.)

To investigate the anchorage-independent growth-promoting ability of FGFR3-TACC3_v1-expressing NIH3T3 cells, FGFR3-TACC3_v2-expressing NIH3T3 cells, FGFR3-TACC3_v3-expressing NIH3T3 cells, and FGFR3-TACC3_v4-expressing NIH3T3 cells, these cells and NIH3T3 cells infected with a blank vector pMXs-puro (Mock/NIH3T3 cells) were each seeded at 1×10³ cells per well in D-MEM media (Invitrogen) containing 10% bovine serum (Nichirei Biosciences) in a 96-well spheroid plate (Sumilon Celltight Spheroid 96U; Sumitomo Bakelite). The cells were cultured in the presence of 5% $CO_2$ at 37° C. and were counted on the next day (Day 1) and 4 days later (Day 4), using a cell counting reagent (CELLTITER-Glo™ Luminescent Cell Viability Assay; Promega) in accordance with the method described in the manual. A luminometer was used for detection. It was confirmed that the count of Mock/NIH3T3 cells did not increase between Day 1 and Day 4, while the counts of FGFR3-TACC3_v1-expressing NIH3T3 cells, FGFR3-TACC3_v2-expressing NIH3T3 cells, FGFR3-TACC3_v3-expressing NIH3T3 cells, and FGFR3-TACC3_v4-expressing NIH3T3 cells increased about 3.1-fold, about 2.8-fold, about 2.3-fold, and about 2.5-fold, respectively, between Day 1 and Day 4.

In light of the foregoing, it was found that FGFR3-TACC3_v1-expressing NIH3T3 cells, FGFR3-TACC3_v2-expressing NIH3T3 cells, FGFR3-TACC3_v3-expressing NIH3T3 cells, and FGFR3-TACC3_v4-expressing NIH3T3 cells exhibit anchorage-independent cell growth.

Test Example 11

Anchorage-Independent Cell Growth-Inhibitory Activity of Compounds on FGFR3-TACC3_v1-Expressing NIH3T3 Cells, FGFR3-TACC3_v2-Expressing NIH3T3 Cells, FGFR3-TACC3_v3-Expressing NIH3T3 Cells, FGFR3-TACC3_v4-Expressing NIH3T3 Cells, and Bladder Cancer Patient-Derived Cell Lines RT-112 and RT4

Measurement for anchorage-independent cell growth (colony method, etc.) is known to be a system for investigating the anticancer action (pharmacological effect) of compounds (Clinical Oncology, second edition, Cancer and Chemotherapy Publishers Inc.). As a method for measuring the non-adhesive growth of cells, there is the following method using a spheroid plate as referred to above in place of the colony method.

In a 96-well spheroid plate (Sumilon Celltight Spheroid 96U; Sumitomo Bakelite), FGFR3-TACC3_v1-expressing NIH3T3 cells, FGFR3-TACC3_v2-expressing NIH3T3 cells, FGFR3-TACC3_v3-expressing NIH3T3 cells, and FGFR3-TACC3_v4-expressing NIH3T3 cells were each seeded at 1×10³ cells per well in D-MEM media (Invitrogen) containing 10% fetal bovine serum. Likewise, bladder cancer patient-derived cell line RT-112 was seeded at 1×10³ cells per well in RPMI1640 medium containing 10% fetal bovine serum and 2 mM L-glutamine, and bladder cancer patient-derived cell line RT4 was seeded at 1×10³ cells per well in RPMI1640 medium containing 10% fetal bovine serum. A well supplemented with only medium was also prepared for a positive control. Culturing was performed overnight in the presence of 5% $CO_2$ at 37° C. followed by addition of test compounds (final concentrations: 100 nM, 10 nM, and 1 nM). As a negative control, DMSO used as a solvent for the compounds was added at the same concentration (0.1%) as in the case of addition of the compounds. Then, culturing was performed in the presence of 5% $CO_2$ at 37° C. for 4 days, and a cell counting reagent (CellTiter-Glo™ Luminescent Cell Viability Assay; Promega) was added and the resulting mixture was stirred for 20 minutes followed by measurement with a luminometer. Assuming that the values of the positive control and the negative control were 100% inhibition and 0% inhibition, respectively, the growth inhibition rate (%) was calculated for each compound. As shown in Table 4, it was found out that some compounds of the present invention inhibited the anchorage-independent growth of FGFR3-TACC3_v1-expressing NIH3T3 cells, FGFR3-TACC3_v2-expressing NIH3T3 cells, FGFR3-TACC3_v3-expressing NIH3T3 cells, FGFR3-TACC3_v4-expressing NIH3T3 cells, and bladder cancer patient-derived cell lines RT-112 and RT4.

The results described above showed that the growth of cancer cells and tumors that express FGFR3-TACC3_v1, FGFR3-TACC3_v2, FGFR3-TACC3_v3, and FGFR3-TACC3_v4 can be inhibited by the compounds of the present invention.

TABLE 4

| Ex | | v1 | v2 | v3 | v4 | RT-112 | RT4 |
| --- | --- | --- | --- | --- | --- | --- | --- |
| 56 | 100 nM | 92 | 91 | 91 | 90 | 90 | 64 |
|  | 10 nM | 84 | 79 | 78 | 82 | 83 | 42 |
|  | 1 nM | 22 | 21 | 20 | 22 | 29 | 5 |
| 113 | 100 nM | 91 | 91 | 87 | 88 | 89 | 64 |
|  | 10 nM | 53 | 42 | 32 | 73 | 77 | 39 |
|  | 1 nM | 4 | 2 | 3 | 13 | 23 | 8 |
| 116 | 100 nM | 91 | 90 | 86 | 89 | 89 | 63 |
|  | 10 nM | 44 | 31 | 24 | 70 | 72 | 39 |
|  | 1 nM | 5 | 0 | 3 | 11 | 21 | 8 |
| 122 | 100 nM | 90 | 88 | 89 | 89 | 89 | 63 |
|  | 10 nM | 84 | 79 | 79 | 82 | 80 | 43 |
|  | 1 nM | 26 | 23 | 25 | 19 | 23 | 6 |
| 248 | 100 nM | 84 | 79 | 81 | 83 | 81 | 43 |
|  | 10 nM | 28 | 29 | 20 | 26 | 33 | 10 |
|  | 1 nM | 7 | 11 | 6 | −5 | 5 | 3 |
| 299 | 100 nM | 92 | 91 | 89 | 90 | 89 | 63 |
|  | 10 nM | 77 | 63 | 51 | 82 | 84 | 45 |
|  | 1 nM | 9 | 4 | 5 | 16 | 31 | 8 |

Test Example 12

Inhibitory Activity of Compounds on the In Vitro Kinase Activity of FGFR3-TACC3 Fusion Polypeptide (1) Construction of FLAG-Tag Fusion Expression Plasmids (FGFR3-TACC3_v1 (N-FLAG)/pcDNA3.1/Zeo(+), FGFR3-TACC3_v2 (N-FLAG)/pcDNA3.1/Zeo(+), and FGFR3-TACC3_v3 (N-FLAG)/pcDNA3.1/Zeo(+))

To obtain 5'-terminally FLAG-tagged FGFR3-TACC3 fusion polynucleotide, PCR was carried out for 5'-terminal FLAG tagging using the vectors cloned in Test Examples 4, 5, and 6 as templates. PCR (12 cycles of 98° C. for 15 seconds, 55° C. for 15 seconds, 68° C. for 3.5 minutes) was carried out using primers FGFR3_N_FLAG_BamHI represented by SEQ ID No: 17 and FGFR3_TACC3_cloning_EcoRI_R represented by SEQ ID No: 8 and DNA polymerase (KOD-plus-Ver. 2; Toyobo Co., Ltd.). PCR products obtained were cloned into cloning vectors (TOPO XL PCR Cloning Kit; Life Technologies, Corp.). The inserts were sequenced by dideoxy sequencing (BigDye Terminator v3.1 Cycle Sequencing Kit; Life Technologies, Corp.). As a result, it was confirmed that the PCR products were nucleic acid sequences of SEQ ID Nos: 9, 11, and 13 in which the three bases coding for the first methionine (ATG) were deleted and start codon and a nucleic acid sequence coding for FLAG tag (SEQ ID No: 24) were added to the 5'-terminus. Polypeptides coded by the above are referred to FGFR3-TACC3_v1 (N-FLAG) fusion polypeptide, FGFR3-TACC3_v2 (N-FLAG) fusion polypeptide and FGFR3-TACC3_v3 (N-FLAG) fusion polypeptide, respectively, and these polypeptides are collectively referred to FGFR3-TACC3 (N-FLAG) fusion polypeptide. Further, to construct an expression vector expressing, as a protein, each of the ORF full lengths of FGFR3-TACC3_v1 (N-FLAG), FGFR3-TACC3_v2 (N-FLAG), and FGFR3-TACC3_v3 (N-FLAG) which contained these FLAG sequences added, enzyme reaction was performed at 37° C. for 3 hours using the cloning vectors described above and restriction enzyme BamHI, and restriction enzyme digested DNA fragments were obtained and purified. Further, enzyme reaction was performed at 37° C. for 3 hours using EcoRI and the DNA fragments, and restriction enzyme digested DNA fragments were obtained and purified. These ORF-containing DNA fragments were cloned into BamHI and EcoRI sites in the multicloning site of an expression vector (pcDNA3.1/Zeo (+); Life Technologies, Corp.) to construct expression plasmids (FGFR3-TACC3_v1 (N-FLAG)/pcDNA3.1/Zeo(+), FGFR3-TACC3_v2 (N-FLAG)/pcDNA3.1/Zeo(+), and FGFR3-TACC3_v3 (N-FLAG)/pcDNA3.1/Zeo(+)).

(2) Preparation of FGFR3-TACC3 (N-FLAG) Fusion Polypeptide

On the day before transfection, $0.5 \times 10^7$ HEK293 cells per collagen-coated 15-cm dish were cultured in D-MEM medium containing 10% fetal bovine serum to prepare 10 dishes. On the day of transfection, 27 μg each of FGFR3-TACC3_v1 (N-FLAG)/pcDNA3.1/Zeo(+), FGFR3-TACC3_v2 (N-FLAG)/pcDNA3.1/Zeo(+), and FGFR3-TACC3_v3 (N-FLAG)/pcDNA3.1/Zeo(+) (Test Example 12) per dish was transfected into HEK293 cells, using 81 μL of a transfection reagent (FUGENE® HD, Roche). At 24 hours after the transfection, the media were removed, and after washing three times with PBS, 1 mL of PBS was added. The cells were scraped with a cell scraper (Corning Inc.) and then recovered in polypropylene tubes. After centrifugation at 1200 rpm for 5 minutes, the supernatant was removed, 1504 of a cell lysate (50 mM Tris-HCl (pH8.0), 150 mM NaCl, 1% NP-40, 1 mM EDTA, and protease inhibitor cocktail complete) was added, and the cells were incubated on ice for 30 minutes and lysed. Each of the FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide which were present in the supernatant obtained after the centrifugation was purified using M2 antibody affinity gel (ANTI-FLAG M2 Affinity Gel; Sigma-Aldrich) in accordance with the method described in the product information document. A wash liquid (50 mM Tris-HCl (pH8.0), 150 mM NaCl, 1% NP-40, 1 mM EDTA, and protease inhibitor cocktail complete) and an eluate (20 mM Tris-HCl (pH7.4), 10 mM $MgCl_2$, 10 mM $MnCl_2$, and 0.5 mg/mL of FLAG peptide) were used for washing and elution, respectively, to give 100 μL of eluates. The eluates were subjected to immunoblotting using an anti-FGFR3 antibody (Cell Signaling Technology) and an anti-FLAG M2 antibody (Sigma-Aldrich) and silver staining, and then confirmed that FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide were obtained.

(3) Detection of the In Vitro Kinase Activity of FGFR3-TACC3 (N-FLAG) Fusion Polypeptide FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide, which were purified as described above were used to investigate their phosphorylating activity against a peptide substrate by using a kinase activity detection kit (HTRF KinEASE-TK; Cisbio). The reaction buffer was prepared by adding 1 mM (final concentration) of DTT and 5 mM (final concentration) of Mg to 5× kinase buffer enclosed in the kit using 1 μL of 1-fold, 3-fold and 10-fold diluted solutions of the above prepared eluates as enzyme solutions, respectively, in 384-well, low-volume black plate (Corning). Using 2.0 μM (final concentration) of TK Substrate enclosed in the kit as a substrate, the reaction was performed in a final volume of 5.0 μL at room temperature for 1 hour in each case of adding no ATP and adding 100 μM ATP (final concentration). After the reaction, Sa-XL665 solution and TK Antibody-Eu(K) solution were prepared in accordance with kit-recommended method and added each of 2.5 μL of the solutions. After the reaction was performed at room temperature for 1 hour, the HTRF counts (i.e., phosphorylation of the peptide substrate) were detected. As the results, it was showed that compared with ATP-free ones, the HTRF counts in ATP-added ones had increased about 38-fold, about 40-fold, and about 38-fold, respectively, in the case of adding 1 μL of 1-fold diluted solutions of the eluates described above including FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide, had increased about 27-fold, 34-fold, and 31-fold, respectively, in the case of adding 1 μL of 3-fold diluted solutions of the eluates, and had increased 5-fold, 18-fold, and 11-fold, respectively, in the case of adding 1 μL of 10-fold diluted solutions of the eluates.

As described above, the in vitro kinase activity of the respective fusion polypeptides could be detected by use of a kinase activity detection kit.

(4) Inhibitory Action of Compounds on the In Vitro Kinase Activity of FGFR3-TACC3 (N-FLAG) Fusion Polypeptide The inhibitory activity of the test compounds on the in vitro kinase activity of FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide was investigated using the kinase activity detection kit described above and 384-well plate of the same sort. The compounds were added so that the final concentrations were 100 nM, 10 nM, and 1 nM, and DMSO was added as a control so that the concentration was 0.1%. For FGFR3-TACC3_v1 (N-FLAG) fusion polypeptide, 1 μL of a 2-fold diluted solution of the eluate described above was added; for FGFR3-TACC3_v2 (N-FLAG) fusion polypeptide, 1 μL of a 3-fold diluted solution of the eluate described above was added; and for FGFR3-TACC3_v3 (N-FLAG) fusion polypeptide, 1 μL of a 3-fold diluted solution of the eluate described above was added. TK Substrate enclosed in the kit as a substrate was added in a final concentration of 2.0 μM, the reaction was performed at room temperature for 15 minutes. Then the reaction was performed in a final volume of 5.0 μL at room temperature for 60 minutes in each case of adding no ATP and adding 100 μM ATP (final concentration). After the other processes were performed by addition of each of 2.5 μL of Sa-XL665 solution and TK Antibody-Eu(K) solution prepared by using similar method to that described in (3) above, and the reaction was performed at room temperature for 1 hour, the HTRF counts were detected. Assuming that the phosphorylation counts with adding no ATP and adding ATP in the absence of the compounds (DMSO was added in a concentration of 0.1%, the concentration equal to the compounds) were 100% inhibition and 0% inhibition, respectively, the inhibition rates (%) of the kinase activity of FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide were calculated for the compounds, using the following formula:

[rate (%) of inhibiting kinase activity by compound]= (1−[phosphorylation count with adding compound and adding ATP−phosphorylation count with adding no compound and adding no ATP]/[phosphorylation count with adding no compound and adding ATP−phosphorylation count with adding no compound and adding no ATP])×100

As a result, as shown in Table 5, it was found out that some compounds of the present invention inhibit the phosphorylating activity of purified FGFR3-TACC3_v1 (N-FLAG) fusion polypeptide, purified FGFR3-TACC3_v2 (N-FLAG) fusion polypeptide, and purified FGFR3-TACC3_v3 (N-FLAG) fusion polypeptide against the peptide substrate.

TABLE 5

| Ex  |        | v1 | v2 | v3 |
|-----|--------|----|----|----|
| 56  | 100 nM | 92 | 94 | 93 |
|     | 10 nM  | 77 | 86 | 85 |
|     | 1 nM   | 49 | 33 | 47 |
| 113 | 100 nM | 92 | 94 | 96 |
|     | 10 nM  | 79 | 74 | 81 |
|     | 1 nM   | 28 | 24 | 35 |
| 116 | 100 nM | 95 | 95 | 96 |
|     | 10 nM  | 79 | 73 | 86 |
|     | 1 nM   | 31 | 22 | 41 |
| 122 | 100 nM | 94 | 95 | 97 |
|     | 10 nM  | 80 | 80 | 85 |
|     | 1 nM   | 34 | 27 | 45 |
| 248 | 100 nM | 86 | 78 | 91 |
|     | 10 nM  | 40 | 25 | 55 |
|     | 1 nM   | 7  | 6  | 30 |
| 299 | 100 nM | 94 | 95 | 96 |
|     | 10 nM  | 84 | 77 | 88 |
|     | 1 nM   | 35 | 20 | 47 |

Test Example 13

Isolation of FGFR3-BAIAP2L1 from Bladder Cancer Patient-Derived Cell Line SW780 cDNA was synthesized by reverse transcription reaction in RNA purified from bladder cancer patient-derived cell line SW780 (purchased from ATCC) using reverse transciptase (SuperScriptIII, Life Technologies, Corp.) and oligo (dT) primers (oligo(dT)20 primers, Life Technologies, Corp.) in accordance with the protocol of the kit.

Next, PCR (30 cycles of 98° C. for 15 seconds, 60° C. for 15 seconds, 68° C. for 5 minutes) was carried out using primers FGFR3-BAIAP2L1_cloning_F represented by SEQ ID No: 18 and FGFR3-BAIAP2L1_cloning_R represented by SEQ ID No: 19, the cDNA obtained above as a template, and DNA polymerase (KOD-plus-Ver. 2; Toyobo Co., Ltd.). Additional PCR (30 cycles of 98° C. for 15 seconds, 55° C. for 15 seconds, 68° C. for 4 minutes) was carried out using the PCR product described above which was diluted 10-fold as a template, primers FGFR3_BAIAP2L1_cloning_BamHI_F represented by SEQ ID No: 20 and FGFR3_BAIAP2L1_cloning_NotI_R represented by SEQ ID No: 21, and the same DNA polymerase as shown above. Electrophoresis performed after the PCR reaction showed that a PCR product of about 3.8 k bases was obtained. The PCR product was cloned into a cloning vector (TOPO XL PCR Cloning Kit; Life Technologies, Corp.), and the insert was sequenced by dideoxy sequencing (BigDye Terminator v3.1 Cycle Sequencing Kit; Life Technologies, Corp.). As a result, the product was found to be a transcript obtained by fusion of the region between the 5'-terminus of the CDS of FGFR3 (NM_001163213.1) registered in the NCBI and the 3' end of exon 18 to the region between the 5' end of exon 2 in the CDS of BAIAP2L1 (NM_018842.4) and the 3'-terminus of the CDS (FGFR3-BAIAP2L1). In the confirmed sequence, G at base position 3558 was replaced by A (SNPs registration No.: rs1045916), C at base position 3723 by T, and G at base position 3747 by A (SEQ ID No: 22). The polypeptide coded by SEQ ID No: 22 is shown in SEQ ID No: 23.

Test Example 14

Preparation of Retrovirus Solution of FGFR3-BAIAP2L1

To construct an expression plasmid expressing, as a protein, the ORF full length of FGFR3-BAIAP2L1, enzyme reaction was performed at 37° C. for 3 hours using the cloning vector described above and restriction enzyme BamHI, and restriction enzyme digested DNA fragments were obtained and purified. Further, enzyme reaction was performed at 37° C. for 3 hours using NotI and the DNA fragments, and restriction enzyme digested DNA fragments were obtained and purified. This ORF-containing DNA fragment was cloned into BamHI and NotI sites in the multicloning site of an expression vector (pMXs-puro; Cosmo Bio) to construct an expression plasmid (FGFR3-BAIAP2L1/pMXs-puro). The prepared FGFR3-BAIAP2L1/pMXs-puro was used to prepare a retrovirus solution in accordance with the method used in Test Example 9.

Test Example 15

Investigation of Anchorage-Independent Growth of FGFR3-BAIAP2L1

The virus solution prepared using FGFR3-BAIAP2L1/pMXs-puro in Test Example 14 was used to obtain NIH3T3 cells expressing FGFR3-BAIAP2L1 stably in accordance with the method used in Test Example 10 (designated as FGFR3-BAIAP2L1-expressing NIH3T3 cells).

To investigate the anchorage-independent growth-promoting ability of FGFR3-BAIAP2L1-expressing NIH3T3 cells, the same method as in Test Example 10 was applied. It was confirmed that the count of Mock/NIH3T3 cells did not increase between Day 1 and Day 4, while the count of FGFR3-BAIAP2L1-expressing NIH3T3 cells increased about 2.5-fold between Day 1 and Day 4. In light of the foregoing, it was shown that FGFR3-BAIAP2L1-expressing NIH3T3 cells exhibit anchorage-independent cell growth.

Test Example 16

Inhibitory Activity on Anchorage-Independent Cell Growth of FGFR3-BAIAP2L1-Expressing NIH3T3 Cells In a 96-well spheroid plate (Sumilon Celltight Spheroid 96U; Sumitomo Bakelite), FGFR3-BAIAP2L1-expressing NIH3T3 cells were seeded at 1×10³ cells per well in D-MEM medium containing 10% fetal bovine serum. A well supplemented with only medium was also prepared for a positive control. Culturing was performed overnight in the presence of 5% $CO_2$ at 37° C. followed by addition of test compounds (final concentrations: 100 nM, 10 nM, and 1 nM). As a negative control, DMSO used as a solvent for the compounds was added at the same concentration (0.1%) as in the case of addition of the compounds. Then, culturing was performed in the presence of 5% $CO_2$ at 37° C. for 4 days, and a cell counting reagent (CellTiter-Glo™ Luminescent Cell Viability Assay; Promega) was added and the resulting mixture was stirred for 20 minutes followed by measurement with a luminometer. Assuming that the values of the positive control and the negative control were 100% inhibition and 0% inhibition, respectively, the growth inhibition rate (%) was calculated for each compound. As shown in Table 6, it was found out that some compounds of the present invention inhibit the anchorage-independent growth of FGFR3-BAIAP2L1-expressing NIH3T3 cells.

The results described above showed that the growth of cancer cells and tumors that express FGFR3-BAIAP2L1 can be inhibited by the compounds of the present invention.

TABLE 6

| Ex | | FGFR3-BAIAP2L1-expressing NIH3T3 Cells |
|---|---|---|
| 56 | 100 nM | 90 |
| | 10 nM | 80 |
| | 1 nM | 24 |
| 113 | 100 nM | 89 |
| | 10 nM | 70 |
| | 1 nM | 14 |
| 116 | 100 nM | 87 |
| | 10 nM | 74 |
| | 1 nM | 15 |
| 122 | 100 nM | 90 |
| | 10 nM | 83 |
| | 1 nM | 17 |
| 248 | 100 nM | 82 |
| | 10 nM | 19 |
| | 1 nM | −3 |
| 299 | 100 nM | 91 |
| | 10 nM | 81 |
| | 1 nM | 15 |

A pharmaceutical composition which comprises one or more of the compounds of formula (I) or salts thereof, as active ingredient, can be prepared in a conventional manner by using an excipient commonly used in the art, more specifically, a pharmaceutical excipient, pharmaceutical carrier, or another additive.

Any mode of administration may be used: namely, either oral administration in the form of tablets, pills, capsules, granules, powders, solutions or the like, or parenteral administration in the form of injections (e.g., intraarticular, intravenous, or intramuscular injection), suppositories, eye drops, eye ointments, percutaneous solutions, ointments, percutaneous patches, transmucosal solutions, transmucosal patches, inhalants, intravesical instillation or the like.

Solid compositions used for oral administration include tablets, powders, granules, and the like. In these solid compositions, one or more active ingredients are mixed with at least one inert excipient. The compositions may also comprise inert additives such as lubricants, disintegrating agents, stabilizers, and/or solubilizers, as in usual cases. Tablets or pills may be coated with sugar or a gastrosoluble or enteric film, if needed.

Liquid compositions for oral administration include pharmaceutically acceptable emulsions, solutions, suspensions, syrups, elixirs, and the like, and comprise a commonly-used inert diluent such as purified water or ethanol. These liquid compositions may comprise auxiliaries (e.g., solubilizers, wetting agents, suspending agents), sweeteners, flavors, aromatics, and/or antiseptics, in addition to such an inert diluent.

Injections for parenteral administration include sterile aqueous or non-aqueous solutions, suspensions, or emulsions. Examples of aqueous solvents include injectable distilled water and physiological saline. Examples of non-aqueous solvents include alcohols such as ethanol. These compositions may further comprise isotonizing agents, antiseptics, wetting agents, emulsifiers, dispersants, stabilizers or solubilizers. They are sterilized, for example, by filtration through a bacteria-retaining filter, by incorporation of disinfectants, or by irradiation. Alternatively, they may be formulated into a sterile solid composition and reconstituted for use by being dissolved or suspended in sterile water or a sterile injectable solvent before use.

Formulations for external use include ointments, plasters, creams, jellies, cataplasms, sprays, lotions, eye drops, eye ointments, and the like. They include commonly-used ointment bases, lotion bases, aqueous or non-aqueous solutions, suspensions, emulsions, or the like.

Transmucosal formulations such as inhalants or transnasal formulations are used in solid, liquid, or semi-solid form and can be prepared in a conventionally known manner. For example, such formulations may be supplemented as appropriate with known excipients, and further with pH adjusters, antiseptics, surfactants, lubricants, stabilizers, thickeners, or the like. For their administration, an appropriate device for inhalation or insufflation may be used. For example, using a known device (e.g., a metered-dose inhalation device) or a nebulizer, the compound(s) may be administered alone or as a powder of a formulated mixture or as a solution or suspension in combination with a pharmaceutically acceptable carrier. Dry powder inhalators and the like may be for single or multiple administration use, and dry powders or powder-containing capsules may be used in such devices. Alternatively, they may be in the form of pressurized aerosol sprays or the like which use an appropriate propellant, for example, a preferred gas such as chlorofluoroalkane or carbon dioxide.

In general, for oral administration, the daily dosage is desirably about 0.001 to 100 mg/kg body weight, preferably 0.1 to 30 mg/kg body weight, more preferably 0.1 to 10 mg/kg body weight, given as a single dose or in 2 to 4 divided doses. For intravenous administration, the daily dosage is desirably about 0.0001 to 10 mg/kg body weight, given in one or several doses per day. Likewise, for transmucosal formulations, the daily dosage is about 0.001 to 100 mg/kg body weight, given in one or several doses per day. The dosage may be determined as appropriate for each case in consideration of symptom, age, sex, and the like.

The pharmaceutical composition of the present invention comprises one or more of the compounds of formula (I) or salts thereof, as active ingredients in an amount of 0.01 to 100 wt. % (0.01 to 50 wt. % in one embodiment), which varies depending on administration route, dosage form, administration site, or the types of excipients and additives.

The compounds of formula (I) can be used in combination with various therapeutic or prophylactic agents for diseases against which the compounds of formula (I) would be effective. In such combination therapy, drugs may be administered simultaneously or separately in succession or at desired time intervals. Formulations for simultaneous administration may be in either mixed form or separate form.

EXAMPLES

The processes for preparing the compounds of formula (I) are described in more detail with reference to the examples shown below. It should be noted that the present invention is not limited to the compounds described in the examples shown below. In addition, the processes for preparing the starting compounds are shown in preparation examples. Processes for preparing the compounds of formula (I) are not limited only to those actually described in the examples shown below, and the compounds of formula (I) may also be prepared by any combination of these processes or by any processes obvious to those skilled in the art.

In the examples, preparation examples and tables shown below, the following abbreviations are used as needed.

PEx: Preparation Example No., Ex: Example No., PSyn: Preparation Example No. of compound prepared in the same manner, Syn: Example No. of compound prepared in the same manner, Str: chemical structural formula (Me: methyl, Et: ethyl, $^i$Pr: isopropyl, $^t$Bu: tert-butyl, Boc: tert-butoxycarbonyl, Bn: benzyl, THP: tetrahydropyranyl), DAT: physical and chemical data, ESI+: m/z value in mass analysis (ionization method ESI, (M+H)$^+$ unless otherwise specified), ESI−: m/z value (ionization method ESI, (M−H)$^−$ unless otherwise specified), EI: m/z value in mass analysis (ionization method EI, (M)$^+$ unless otherwise specified), APCI/ESI+: m/z value in mass analysis (simultaneous measurement by ionization methods APCI and ESI, (M+H)$^+$ unless otherwise specified), NMR1: δ (ppm) in $^1$H-NMR in dimethyl sulfoxide-d$_6$, NMR2: δ (ppm) in $^1$H-NMR in CDCl$_3$, NMR3: δ (ppm) in $^1$H-NMR in CD$_3$OD, "M" in Preparation Example and Example: which indicates mol/L. "HCl" in a structural formula indicates hydrochloride and the number in front of the term "HCl" indicates molar ratio. For example, 2HCl means a dihydrochloride salt. The symbol "*" in the tables in Preparation Examples and Examples indicates that the compounds given the symbol are optically active substances.

Preparation Example 1

Under an argon atmosphere, to a mixture of 3-methoxy-4-[4-(4-methylpiperazin-1-yl)piperidin-1-yl]aniline (300 mg) and ethanol (6 mL), methanesulfonic acid (128 µL) was added followed by stirring at room temperature for 30 minutes. Subsequently, 5-bromo-2-chloropyrimidine (229 mg) was added thereto and the resulting mixture was stirred at 100° C. for 4 hours. Additional 5-bromo-2-chloropyrimidine (95 mg) was added thereto and the resulting mixture was stirred at 100° C. for 12 hours. To the reaction mixture, a saturated aqueous sodium hydrogen carbonate solution was added followed by extraction with chloroform. An organic layer obtained was dried over anhydrous sodium sulfate and then filtered. After the filtrate was concentrated under reduced pressure, the resulting residue was purified by basic silica gel column chromatography (ethyl acetate/methanol) to give 5-bromo-N-{3-methoxy-4-[4-(4-methylpiperazin-1-yl)piperidin-1-yl]phenyl}pyrimidin-2-amine (352 mg).

Preparation Example 2

To a mixture of 3-methoxy-4-[4-(4-methylpiperazin-1-yl)piperidin-1-yl]aniline (253 mg) and isopropanol (6 mL), methanesulfonic acid (162 µL) was added followed by stirring at room temperature for 30 minutes. After that, 2-chloro-5-iodopyrimidine (200 mg) was added thereto, and the resulting mixture was stirred at 90° C. for 12 hours and further stirred at 130° C. for 2 hours under microwave irradiation. To the reaction mixture, a saturated aqueous sodium hydrogen carbonate solution was added followed by extraction with chloroform. An organic layer obtained was dried over anhydrous sodium sulfate and then filtered. After the filtrate was concentrated under reduced pressure, the resulting residue was purified by silica gel column chromatography (chloroform/methanol) to give 5-iodo-N-{3-methoxy-4-[4-(4-methylpiperazin-1-yl)piperidin-1-yl]phenyl}pyrimidin-2-amine (282 mg).

Preparation Example 3

Under an argon atmosphere, a mixture of 1-ethynyl-3,5-dimethoxybenzene (3 g) and acetonitrile (30 mL) was ice cooled, and then sulfuryl chloride (3.15 mL) was added thereto followed by stirring at room temperature for 4 hours. Additional sulfuryl chloride (449 µL) was added thereto followed by stirring at room temperature for 12 hours. After the reaction mixture was concentrated under reduced pressure, ethyl acetate and a saturated aqueous sodium hydrogen carbonate solution were added to the resulting residue followed by stirring at room temperature for 30 minutes. The resulting solid was collected by filtration, washed with ethyl acetate, and then dried under reduced pressure to give 2,4-dichloro-3-ethynyl-1,5-dimethoxybenzene (1.99 g).

Preparation Example 4

A mixture of 1-ethynyl-3,5-dimethoxybenzene (4 g) and acetonitrile (80 mL) was ice cooled, and N-fluoro-N'-(chloromethyl)triethylenediamine bis(tetrafluoroborate) (19.4 g) was added thereto. The resulting mixture was gradually warmed and stirred at room temperature for 12 hours. To the reaction mixture, a saturated aqueous sodium hydrogen carbonate solution was added followed by extraction with ethyl acetate. An organic layer obtained was washed with saturated brine, and then dried over anhydrous sodium sulfate and filtered. After the filtrate was concentrated under reduced pressure, the resulting residue was purified by silica gel column chromatography (ethyl acetate/hexane) and subsequently purified by silica gel column chromatography (chloroform/hexane) to give 3-ethynyl-2,4-difluoro-1,5-dimethoxybenzene (798 mg, Preparation Example No. PEx. 4-1, which is described later) and 1-ethynyl-2-fluoro-3,5-dimethoxybenzene (375 mg, Preparation Example No. PEx. 4-2, which is described later).

Preparation Example 5

Under an argon atmosphere, a mixture of 1-ethynyl-2-fluoro-3,5-dimethoxybenzene (800 mg) and acetonitrile (8 mL) was ice cooled, and sulfuryl chloride (378 µL) was added thereto followed by stirring at room temperature for 12 hours. To the reaction mixture, ethyl acetate and a saturated aqueous sodium hydrogen carbonate solution were added followed by extraction with ethyl acetate. An organic layer obtained was washed with saturated brine, dried over anhydrous sodium sulfate, and then filtered. After the filtrate was concentrated under reduced pressure, the resulting residue was solidified with ethyl acetate/diisopropyl ether to give 2-chloro-3-ethynyl-4-fluoro-1,5-dimethoxybenzene (787 mg).

Preparation Example 6

To a mixture of 2,6-difluoro-3-methoxybenzaldehyde (500 mg), potassium carbonate (803 mg), and methanol (10 mL), dimethyl (1-diazo-2-oxopropyl)phosphonate (523 µL) was added at room temperature under an argon atmosphere followed by stirring for 5 hours. To the reaction mixture, water was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (ethyl acetate/hexane) to give 2-ethynyl-1,3-difluoro-4-methoxybenzene (452 mg).

Preparation Example 7

To a mixture of 2-amino-5-iodopyrimidine (1 g), 3-ethynyl-2,4-difluoro-1,5-dimethoxybenzene (897 mg), tetrakistriphenylphosphine palladium (261 mg), copper iodide (43 mg), and N,N-dimethylformamide (20 mL), N,N-diisopropylethylamine (1.55 mL) was added under an argon atmosphere followed by stirring at 80° C. for 1 hour. The reaction mixture was concentrated under reduced pressure, and to the obtained residue were added chloroform and water, and insoluble materials were removed by filtration through celite. After the filtrate was extracted with chloroform, the organic layer was washed with saturated brine, dried over anhydrous sodium sulfate, and then filtered. After the filtrate was concentrated under reduced pressure, the resulting residue was purified by silica gel column chromatography (chloroform/methanol) to give 5-[(2,6-difluoro-3,5-dimethoxyphenyl)ethynyl]pyrimidin-2-amine (1.07 g).

Preparation Example 8

To a mixture of 5-[(2,6-difluoro-3,5-dimethoxyphenyl)ethynyl]pyrimidin-2-amine (400 mg), methanol (4 mL), and tetrahydrofuran (4 mL), 10% palladium-carbon (73 mg) was added under an argon atmosphere. After the resulting mixture was stirred at 60° C. for 8 hours under a hydrogen atmosphere, insoluble materials were removed by filtration through celite. The filtrate was concentrated under reduced pressure to give 5-[(2,6-difluoro-3,5-dimethoxyphenyl)ethyl]pyrimidin-2-amine (402 mg).

Preparation Example 9

To a mixture of 5-[(2,6-difluoro-3,5-dimethoxyphenyl)ethyl]pyrimidin-2-amine (100 mg) and acetonitrile (2 mL) under an argon atmosphere were added copper chloride (II) (68 mg) and n-pentyl nitrite (69 µL), followed by stirring at 60° C. for 4 hours. To the reaction mixture, ethyl acetate was added and insoluble materials were removed by filtration. After the filtrate was concentrated under reduced pressure, the resulting residue was purified by silica gel column chromatography (ethyl acetate/hexane) to give 2-chloro-5-[2-(2,6-difluoro-3,5-dimethoxyphenyl)ethyl]pyrimidine (20 mg).

Preparation Example 10

A mixture of (2-chloropyrimidin-5-yl)methanol (120 mg), 3,5-dimethoxyphenol (186 mg), tributylphosphine (297 µL), and tetrahydrofuran (2.4 mL) was ice cooled, and 1,1'-(azodicarbonyl)dipiperidine (305 mg) was added thereto followed by stirring at room temperature for 12 hours. Insoluble materials were removed by filtration and the filtrate was concentrated under reduced pressure. The resulting residue was purified by silica gel column chromatography (ethyl acetate/hexane) to give 2-chloro-5-[(3,5-dimethoxyphenoxy)methyl]pyrimidine (119 mg).

Preparation Example 13

A mixture of 2-chloro-5-hydroxypyrimidine (278 mg), potassium carbonate (453 mg), and N,N-dimethylformamide (3 mL) was ice cooled, and 3,5-dimethoxybenzyl bromide (541 mg) was added thereto followed by stirring at room temperature for 7 hours. To the reaction mixture, water was added followed by extraction with ethyl acetate. An organic layer obtained was washed with saturated brine, dried over anhydrous magnesium sulfate, and then filtered. The resulting residue was purified by silica gel column chromatography (ethyl acetate/hexane) to give 2-chloro-5-[(3,5-dimethoxybenzyl)oxy]pyrimidine (360 mg).

Preparation Example 14

To a mixture of 2-chloro-5-[(3,5-dimethoxybenzyl)oxy]pyrimidine (4.17 g) and N,N-dimethylformamide (40 mL), N-chlorosuccinimide (4.05 g) was added followed by stirring at room temperature for 2 hours and stirring at 60° C. for 2 hours. To the reaction mixture, water was added, and the resulting solid was collected by filtration, washed with water, and then dried under reduced pressure. The obtained solid was suspended in ethyl acetate (40 mL) and heated to 80° C. The solid was collected by filtration, and then dried under reduced pressure to give 2-chloro-5-[(2,6-dichloro-3,5-dimethoxybenzyl)oxy]pyrimidine (3.99 g).

Preparation Example 15

A mixture of 2-chloro-5-hydroxypyrimidine (487 mg) and 1-(3,5-dimethoxyphenyl)ethanol (680 mg), tributylphosphine (1.37 mL), and tetrahydrofuran (14 mL) was ice cooled, and 1,1'-(azodicarbonyl)dipiperidine (1.4 g) was added thereto followed by stirring at room temperature for 12 hours and stirring at 50° C. for 3 hours. Insoluble materials were removed by filtration and the filtrate was concentrated under reduced pressure. The resulting residue was purified by silica gel column chromatography (ethyl acetate/hexane) to give 2-chloro-5-[1-(3,5-dimethoxyphenyl)ethoxy]pyrimidine (415 mg).

Preparation Example 16

A mixture of methyl 3,5-dimethoxybenzoate (1 g) and acetonitrile (20 mL) was ice cooled, and N-fluoro-N'-(chloromethyl)triethylenediamine bis(tetrafluoroborate) (4.09 g) was added thereto followed by stirring at room temperature overnight. To the reaction mixture, a saturated aqueous sodium hydrogen carbonate solution was added followed by extraction with ethyl acetate. An organic layer obtained was washed with saturated brine, added anhydrous sodium sulfate and basic silica gel followed by stirring for 30 minutes, and then filtered. After the filtrate was concentrated under reduced pressure, the resulting residue was purified by silica gel column chromatography (ethyl acetate/hexane) to give methyl 2,6-difluoro-3,5-dimethoxybenzoate (292 mg: Preparation Example 16-1) and methyl 2-fluoro-3,5-dimethoxybenzoate (232 mg: Preparation Example 16-2).

Preparation Example 17

A mixture of methyl 2,6-difluoro-3,5-dimethoxybenzoate (10 g) and tetrahydrofuran (50 mL) was ice cooled, and lithium borohydride (3.0M tetrahydrofuran solution, 43 mL) was added thereto followed by stirring at room temperature for 65 hours. The reaction mixture was ice cooled again, and additional lithium borohydride (3.0M tetrahydrofuran solution, 14 mL) was added thereto followed by stirring at room temperature for 22 hours. The reaction mixture was ice cooled and slowly added into ice water (300 mL). Further, concentrated hydrochloric acid (25 mL) was slowly added thereto, and the resulting mixture was stirred at room temperature for 1 hour and extracted with toluene/ethyl acetate (1:1). An organic layer obtained was washed with a saturated aqueous sodium hydrogen carbonate solution and saturated brine, dried over anhydrous sodium sulfate, and then filtered. The filtrate was concentrated under reduced pressure to give (2,6-difluoro-3,5-dimethoxyphenyl)methanol (8.67 g).

Preparation Example 18

A mixture of (2,6-difluoro-3,5-dimethoxyphenyl)methanol (1.71 g), triethylamine (2.57 mL), and tetrahydrofuran (34 mL) was ice cooled, and methanesulfonyl chloride (716 μL) was added thereto followed by stirring for 1 hour. To the reaction mixture, water was added followed by extraction with ethyl acetate. An organic layer obtained was washed with saturated brine, dried over anhydrous sodium sulfate, and then filtered. The filtrate was concentrated under reduced pressure to give 2,6-difluoro-3,5-dimethoxybenzyl methanesulfonate (2.32 g).

Preparation Example 19

To a mixture of 2-chloro-5-hydroxypyrimidine (4.38 g), potassium carbonate (9.27 g), and N,N-dimethylformamide (79 mL), 2,6-difluoro-3,5-dimethoxybenzyl methanesulfonate (7.89 g) was added followed by stirring at 60° C. for 1 hour. To the reaction mixture, water was added, and the resulting solid was collected by filtration, washed with water, and then dried under reduced pressure to give 2-chloro-5-[(2,6-difluoro-3,5-dimethoxybenzyl)oxy]pyrimidine (8.53 g).

Preparation Example 20

A mixture of 2,3,5,6-tetrafluoropyridine (1.5 g) and methanol (15 mL) was ice cooled, and sodium methoxide (4.03 g) was added thereto followed by stirring at room temperature for 2 hours and stirring at 50° C. overnight. To the reaction mixture, water was added followed by extraction with diethyl ether. An organic layer obtained was washed with saturated brine, dried over anhydrous sodium sulfate, and then filtered. The filtrate was concentrated under reduced pressure to give 3,5-difluoro-2,6-dimethoxypyridine (1.47 g).

Preparation Example 21

A mixture of diisopropylamine (745 μL) and tetrahydrofuran (5 mL) was cooled to −78° C., and n-butyl lithium (1.6M hexane solution, 3.02 mL) was added thereto followed by stirring at 0° C. for 30 minutes. The reaction mixture was cooled to −78° C., and a mixture of 3,5-difluoro-2,6-dimethoxypyridine (770 mg) and tetrahydrofuran (5 mL) was added thereto dropwise followed by stirring for 1 hour. After N,N-dimethylformamide (440 μL) was added thereto, the resulting mixture was warmed to room temperature and stirred for 1 hour. To the reaction mixture, water was added followed by extraction with ethyl acetate. An organic layer obtained was washed with saturated brine, dried over anhydrous sodium sulfate, and then filtered. The resulting residue was purified by silica gel column chromatography (ethyl acetate/hexane) to give 3,5-difluoro-2,6-dimethoxyisonicotinaldehyde (406 mg).

Preparation Example 22

A mixture of 3,5-difluoro-2,6-dimethoxyisonicotinaldehyde (400 mg) and methanol (4 mL) was ice cooled, and sodium borohydride (82 mg) was added thereto followed by stirring for 1 hour. To the reaction mixture, 1M hydrochloric acid was added followed by extraction with ethyl acetate. An organic layer obtained was washed with saturated brine, dried over anhydrous sodium sulfate, and then filtered. The filtrate was concentrated to give (3,5-difluoro-2,6-dimethoxypyridin-4-yl)methanol (403 mg).

Preparation Example 23

To a mixture of 2-chloro-5-[(2,6-dichloro-3,5-dimethoxybenzyl)oxy]pyrimidine (235 mg), tert-butyl 4-(4-amino-3-methoxyphenyl)piperidine-1-carboxylate (306 mg), 1,1'-binaphthalene-2,2'-diylbis(diphenylphosphine) (138 mg), cesium carbonate (660 mg), and dioxane (10 mL), palladium acetate (30 mg) was added at room temperature under an argon atmosphere. The resulting mixture was stirred at 100° C. for 3 hours. To the reaction mixture, water was added followed by extraction with ethyl acetate. An organic layer obtained was washed with saturated brine, dried over anhydrous magnesium sulfate, and then filtered. After the filtrate was concentrated under reduced pressure, the resulting residue was purified by silica gel column chromatography (ethyl acetate/hexane) to give tert-butyl 4-[4-({5-[(2,6-dichloro-3,5-dimethoxybenzyl)oxy]pyrimidin-2-yl}amino)-3-methoxyphenyl]piperidine-1-carboxylate (298 mg).

Preparation Example 24

To a mixture of 2-fluoro-5-nitrotoluene (500 mg), potassium carbonate (2.0 g), and N,N-dimethylformamide (15 mL), 4-piperidin-4-ylthiomorpholine 1,1-dioxide bistrifluoroacetate (2.16 g) was added followed by stirring at 80° C. for 20 hours. To the reaction mixture, water was added followed by extraction with ethyl acetate. An organic layer obtained was washed with saturated brine, dried over anhydrous magnesium sulfate, and then filtered. After the filtrate was concentrated under reduced pressure, the resulting residue was purified by silica gel column chromatography (chloroform/methanol) to give 4-[1-(2-methyl-4-nitrophenyl)piperidin-4-yl]thiomorpholine 1,1-dioxide (870 mg).

Preparation Example 25

To a mixture of 4-[1-(2-methyl-4-nitrophenyl)piperidin-4-yl]thiomorpholine 1,1-dioxide (1.5 g) and acetic acid (30 mL), 10% palladium-carbon (452 mg) was added under an argon atmosphere. After stirring for 13 hours under a hydrogen atmosphere, insoluble materials were removed by filtration through celite. The filtrate was concentrated under reduced pressure, and then a saturated aqueous sodium hydrogen carbonate solution was added to the resulting residue. The resulted solid was collected by filtration, washed with water, and then dried under reduced pressure to give 4-[4-(1,1-dioxidothiomorpholin-4-yl)piperidin-1-yl]-3-methylaniline (1.26 g).

Preparation Example 26

To a mixture of 1-chloro-2-(difluoromethoxy)-4-nitrobenzene (920 mg), potassium carbonate (1.7 g), and N,N-dimethylformamide (10 mL), 1-methyl-4-piperidin-4-ylpiperazine (1.13 g) was added followed by stirring at 100° C. overnight. The reaction mixture was concentrated under reduced pressure, and water was added to the resulting residue followed by extraction with ethyl acetate. An organic layer obtained was washed with saturated brine, dried over anhydrous magnesium sulfate, and then filtered. After the filtrate was concentrated under reduced pressure, the resulting residue was purified by silica gel column chromatography (chloroform/methanol/conc. aqueous ammonia solution) to give 1-{1-[2-(difluoromethoxy)-4-nitrophenyl]piperidin-4-yl}-4-methylpiperazine (1.38 g).

Preparation Example 27

To a mixture of 1-{1-[2-(difluoromethoxy)-4-nitrophenyl]piperidin-4-yl}-4-methylpiperazine (1.38 g) and ethanol (54 mL), 10% palladium-carbon (397 mg) was added under an argon atmosphere. After stirring for 1 hour under a hydrogen atmosphere, insoluble materials were removed by filtration through celite. The filtrate was concentrated under reduced pressure to give 3-(difluoromethoxy)-4-[4-(4-methylpiperazin-1-yl)piperidin-1-yl]aniline (1.25 g).

Preparation Example 28

A mixture of benzyl piperazine-1-carboxylate (10 g), 2,2,6,6-tetramethylpiperidin-4-one (7.05 g), and dichloromethane (100 mL) was ice cooled, and sodium triacetoxy borohydride (11.5 g) was added thereto followed by stirring at room temperature overnight. To the reaction mixture, a saturated aqueous sodium hydrogen carbonate solution was added followed by extraction with chloroform. An organic layer obtained was washed with saturated brine, dried over anhydrous sodium sulfate, and then filtered. After the filtrate was concentrated under reduced pressure, the resulting residue was purified by basic silica gel column chromatography (ethyl acetate/hexane) to give benzyl 4-(2,2,6,6-tetramethylpiperidin-4-yl)piperazine-1-carboxylate (7.18 g).

Preparation Example 29

To a mixture of benzyl 4-(2,2,6,6-tetramethylpiperidin-4-yl)piperazine-1-carboxylate (7.18 g) and ethanol (60 mL), 10% palladium-carbon (2.0 g) was added under an argon atmosphere. After stirring for 7 hours under a hydrogen atmosphere, insoluble materials were removed by filtration through celite. The filtrate was concentrated under reduced pressure to give 1-(2,2,6,6-tetramethylpiperidin-4-yl)piperazine (4.35 g).

Preparation Example 30

To a mixture of 2-chloro-5-[(2,3,5,6-tetrafluorobenzyl)oxy]pyrimidine (202 mg), tert-butyl 9-(4-amino-2-methoxyphenyl)-3,9-diazaspiro[5,5]undecane-3-carboxylate (311 mg), 2-(dicyclohexylphosphino)-2',4',6'-triisopropyl-1,1'-biphenyl (30 mg), potassium carbonate (134 mg), and tert-butanol (10 mL), tris(dibenzylideneacetone)dipalladium (19 mg) was added at room temperature under an argon atmosphere. The resulting mixture was stirred at 100° C. for 4 hours. Insoluble materials were removed by filtration and washed with ethyl acetate. The filtrate was concentrated under reduced pressure and the resulting residue was purified by silica gel column chromatography (ethyl acetate/hexane) to give tert-butyl 4-[4-({5-[(2,3,5,6-tetrafluorobenzyl)oxy]pyrimidin-2-yl}amino)-2-methoxyphenyl]-3,9-diazaspiro[5,5]undecane-3-carboxylate (259 mg).

Preparation Example 31

To a mixture of N-[3-(1,4-dioxa-8-azaspiro[4,5]dec-8-yl)phenyl]-5-[(2,3,5,6-tetrafluorobenzyl)oxy]pyrimidin-2-amine (596 mg), acetic acid (9 mL), and water (9 mL), concentrated hydrochloric acid (0.5 mL) was added followed by stirring at 80° C. for 7 hours. The reaction mixture was ice cooled, and a 1M aqueous sodium hydroxide solution (155 mL) and a saturated aqueous sodium hydrogen carbonate solution were added thereto, and then the resulting solid was collected by filtration. Chloroform was added thereto, and the resulting mixture was dried over anhydrous sodium sulfate and then filtered. The filtrate was concentrated under reduced pressure to give 1-[3-({5-[(2,3,5,6-tetrafluorobenzyl)oxy]pyrimidin-2-yl}amino)phenyl]piperidin-4-one (512 mg).

Preparation Example 32

A mixture of 2-[3-({5-[(2,3,5,6-tetrafluorobenzyl)oxy]pyrimidin-2-yl}amino)-1H-pyrazol-1-yl]ethanol (116 mg), triethylamine (84 μL), and tetrahydrofuran (4 mL) was ice cooled, and methanesulfonyl chloride (47 μL) was added thereto followed by stirring for 3 hours. To the reaction mixture, water was added followed by extraction with ethyl acetate. An organic layer obtained was washed with saturated brine, dried over anhydrous magnesium sulfate, and then filtered. The filtrate was concentrated under reduced pressure to give 2-[3-({5-[(2,3,5,6-tetrafluorobenzyl)oxy]pyrimidin-2-yl}amino)-1H-pyrazol-1-yl]ethyl methanesulfonate (129 mg).

Preparation Example 33

A mixture of 4-(4-nitro-1H-pyrazol-1-yl)piperidine (250 mg), 1-methylpiperidin-4-one (220 μL), and dichloromethane (5 mL) was ice cooled, and sodium triacetoxy borohydride (810 mg) was added thereto followed by stirring at room temperature for 4 hours. To the reaction mixture, a saturated aqueous sodium hydrogen carbonate solution was added followed by extraction with chloroform. An organic layer obtained was washed with saturated brine, dried over anhydrous magnesium sulfate, and then filtered. After the filtrate was concentrated under reduced pressure, the resulting residue was purified by silica gel column chromatography (chloroform/methanol/conc. aqueous ammonia solution) to give 1'-methyl-4-(4-nitro-1H-pyrazol-1-yl)-1,4'-bipiperidine (342 mg).

Preparation Example 34

To a mixture of 1-(2-chloro-4-nitrophenyl)-4-(1-methylpiperidin-4-yl)piperazine (3.7 g), ammonium chloride (352 mg), ethanol (94 mL), tetrahydrofuran (47 mL), and water (47 mL), iron powder (3.06 g) was added followed by stirring at 70° C. for 4 hours. After insoluble materials were removed by filtration, the filtrate was concentrated under reduced pressure. To the resulting residue, a saturated aqueous sodium hydrogen carbonate solution was added followed by extraction with ethyl acetate. An organic layer obtained was dried over anhydrous magnesium sulfate and then filtered. The filtrate was concentrated under reduced pressure to give 3-chloro-4-[4-(1-methylpiperidin-4-yl)piperazin-1-yl]aniline (1.03 g).

Preparation Example 35

To a mixture of (3R,5S)-1-(2-methoxy-4-nitrophenyl)-3,5-dimethylpiperazine (3.0 g), N,N-diisopropylethylamine (2.32 mL), di-tert-butyldicarbonate (2.71 g), and dioxane (20 mL), 4-dimethylaminopyridine (69 mg) was added followed by stirring at 80° C. overnight. To the reaction mixture, a saturated aqueous sodium hydrogen carbonate solution was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (ethyl acetate/hexane) to give tert-butyl (2R,6S)-4-(2-methoxy-4-nitrophenyl)-2,6-dimethylpiperazine-1-carboxylate (1.73 g).

Preparation Example 36

To a mixture of 2-(2-bromoethoxy)-1-chloro-4-nitrobenzene (3.0 g), cesium carbonate (5.23 g), N-methylpyrrolidone (30 mL), 1H-pyrazole (874 mg) was added followed by stirring at 60° C. for 6 hours. To the reaction mixture, water was added, and the resulting solid was collected by filtration. The solid was washed with water and dried under reduced pressure to give 1-[2-(2-chloro-5-nitrophenoxy)ethyl]-1H-pyrazole (2.57 g).

Preparation Example 37

To a mixture of 1-[2-(2-chloro-5-nitrophenoxy)ethyl]-1H-pyrazole (1.3 g), cesium carbonate (1.0 g), N-methylpyrrolidone (8 mL), cis-2,6-dimethylpiperazine (832 mg) was added followed by stirring at 130° C. overnight. To the reaction mixture, water was added, and the resulting solid was collected by filtration. The solid was washed with water and dried under reduced pressure to give (3R,5S)-3,5-dimethyl-1-{4-nitro-2-[2-(1H-pyrazol-1-yl)ethoxy]phenyl}piperazine (1.15 g).

Preparation Example 38

A mixture of 2-chloro-5-[(3,5-dimethoxybenzyl)oxy]pyridine (500 mg) and acetonitrile (10 mL) was ice cooled, and sulfuryl chloride (297 µL) was added thereto followed by stirring at room temperature for three days. After the reaction mixture was concentrated under reduced pressure, a saturated aqueous sodium hydrogen carbonate solution was added to the residue obtained. The resulting solid was collected by filtration, washed with water, and then dried under reduced pressure to give 2-chloro-5-[(2,6-dichloro-3,5-dimethoxybenzyl)oxy]pyridine (596 mg).

Preparation Example 39

To a mixture of 5-[(2,6-difluoro-3,5-dimethoxybenzyl)oxy]-N-[1-(tetrahydro-2H-pyran-2-yl)-1H-pyrazol-4-yl]pyrimidin-2-amine (3.6 g) and methanol (20 mL), a 4M hydrogen chloride/dioxane solution (40 mL) was added followed by stirring at room temperature for 6 hours. After the reaction mixture was concentrated under reduced pressure, a saturated aqueous sodium hydrogen carbonate solution was added to the residue obtained. The resulting solid was collected by filtration, washed with diethyl ether, and then dried under reduced pressure to give 5-[(2,6-difluoro-3,5-dimethoxybenzyl)oxy]-N-(1H-pyrazol-4-yl)pyrimidin-2-amine (2.9 g).

Preparation Example 40

To a mixture of 5-[(2,6-difluoro-3,5-dimethoxybenzyl)oxy]-N-(1H-pyrazol-4-yl)pyrimidin-2-amine (4.0 g), potassium carbonate (4.6 g), and N,N-dimethylformamide (80 mL), ethyl bromoacetate (2.4 mL) was added followed by stirring at 80° C. for 3 hours. To the reaction mixture, water was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (ethyl acetate/hexane) to give ethyl [4-({5-[(2,6-difluoro-3,5-dimethoxybenzyl)oxy]pyrimidin-2-yl}amino)-1H-pyrazol-1-yl]acetate (4.2 g).

Preparation Example 41

To a mixture of 5-[(2,6-difluoro-3,5-dimethoxybenzyl)oxy]-N-(1H-pyrazol-4-yl)pyrimidin-2-amine (50 mg), potassium carbonate (57 mg), and N,N-dimethylformamide (1 mL), [(4R)-2,2-dimethyl-1,3-dioxolan-4-yl]methyl 4-methylbenzenesulfonate (98 µL) was added followed by stirring at 60° C. for 1 hour and stirring at 110° C. for 4 days. To the reaction mixture, water was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (ethyl acetate/hexane) to give 5-[(2,6-difluoro-3,5-dimethoxybenzyl)oxy]-N-(1-{[(4S)-2,2-dimethyl-1,3-dioxolan-4-yl]methyl}-1H-pyrazol-4-yl)pyrimidin-2-amine (45 mg).

Preparation Example 111

To a mixture of 4-nitro-1H-pyrazole (500 mg), tert-butyl (3-endo)-3-[(methylsulfonyl)oxy]-8-azabicyclo[3,2,1]octane-8-carboxylate (1.35 g) and N-methylpyrrolidone (6 mL), cesium carbonate (2.16 g) was added followed by stirring at 100° C. for 6 hours. To the reaction mixture, water was added, and the resulting solid was collected by filtration, washed with water, and then dried under reduced pressure to give tert-butyl (3-exo)-3-(4-nitro-1H-pyrazol-1-yl)-8-azabicyclo[3,2,1]octane-8-carboxylate (1.07 g).

Preparation Example 118

A mixture of 4-nitro-1H-pyrazol (3 g), quinuclidin-3-ol (4.05 g), triphenylphosphine (9.05 g), and tetrahydrofuran (60 mL) was ice cooled, and diisopropyl azodicarboxylate (6.84 mL) was added thereto followed by stirring at room temperature overnight. After the reaction mixture was concentrated under reduced pressure, 1M hydrochloric acid (50 mL) was added to the resulting residue. The aqueous layer obtained was washed with ethyl acetate, and then a 1M aqueous sodium hydroxide solution (60 mL) was added for basification. After extraction with chloroform, an organic layer obtained was dried over anhydrous sodium sulfate and then filtered. The filtrate was concentrated under reduced pressure and then the resulting residue was purified by basic silica gel column chromatography (ethyl acetate) to give 3-(4-nitro-1H-pyrazol-1-yl)quinuclidine (5.15 g).

Preparation Example 133

A mixture of tert-butyl (4-amino-2-methoxyphenyl)[2-(4-methylpiperazin-1-yl)ethyl]carbamate (1.21 g) and tetrahydrofuran (24 mL) was ice cooled, and lithium aluminum hydride (629 mg) was added thereto followed by stirring for 1 hour under heating to reflux. To the reaction mixture, water (0.63 mL), a 1M aqueous sodium hydroxide solution (0.63 mL), and water (1.89 mL) in that order were added. After insoluble materials were removed by filtration through celite, the filtrate was extracted with ethyl acetate. An organic layer obtained was washed with saturated brine, dried over anhydrous magnesium sulfate, and then filtered. After the filtrate was concentrated under reduced pressure, the resulting residue was purified by basic silica gel column chromatography (chloroform/methanol) to give 2-methoxy-$N^1$-methyl-$N^1$-[2-(4-methylpiperazin-1-yl)ethyl]benzene-1,4-diamine (922 mg).

Preparation Example 138

To a mixture of 2-chloro-5-nitropyrimidine (798 mg), potassium carbonate (1.04 g), and N,N-dimethylformamide (16 mL), 1-methyl-4-(piperidin-4-yl)piperazine (1.1 g) was added followed by stirring at room temperature for 3 hours. To the reaction mixture, water was added followed by extraction with ethyl acetate. An organic layer obtained was washed with saturated brine, dried over anhydrous magnesium sulfate, and then filtered. After the filtrate was concentrated under reduced pressure, the resulting residue was purified by silica gel column chromatography (chloroform/methanol) to give 2-[4-(4-methylpiperazin-1-yl)piperidin-1-yl]-5-nitropyrimidine (542 mg).

Preparation Example 143

To a mixture of tert-butyl 4-(2-amino-1,3-thiazol-5-yl)piperidine-1-carboxylate (1.13 g) and ethyl acetate (8 mL), 4M hydrogen chloride/ethyl acetate solution (8 mL) was added followed by stirring at room temperature for 3 hours. The solvent was concentrated under reduced pressure to give 5-(piperidin-4-yl)-1,3-thiazol-2-amine hydrochloride (877 mg).

Preparation Example 144

To a mixture of 5-(piperidin-4-yl)-1,3-thiazol-2-amine hydrochloride (519 mg), dichloromethane (5 mL), and methanol (5 mL), 1H-benzotriazol-1-ylmethanol (423 mg), sodium acetate (388 mg), and sodium triacetoxy borohydride (1.0 g) in that order were added followed by stirring at room temperature for 2 hours. To the reaction mixture, a saturated aqueous sodium hydrogen carbonate solution and basic silica gel were added followed by concentration of the solvent under reduced pressure. The resulting residue was purified by basic silica gel column chromatography (chloroform/methanol) to give 5-(1-methylpiperidin-4-yl)-1,3-thiazol-2-amine (411 mg).

Preparation Example 145

A mixture of 5-nitropyridin-2(1H)-one (700 mg), (R)-2,2-dimethyl-1,3-dioxolane-4-methanol (661 mg), triphenylphosphine (1.97 g), and tetrahydrofuran (20 mL) was ice cooled, diisopropyl azodicarboxylate (1.49 mL) was added followed by stirring at room temperature for 5 hours. To the reaction mixture, water was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (hexane/ethyl acetate) to give (R)-2-[(2,2-dimethyl-1,3-dioxolan-4-yl)methoxy]-5-nitropyridine (541 mg).

Preparation Example 152

To a mixture of (S)-2,2-dimethyl-1,3-dioxolane-4-methanol (661 mg) and N,N-dimethylformamide (23 mL), sodium hydride (218 mg) was added followed by stirring at room temperature for 10 minutes. To the reaction mixture, 2-chloro-5-nitropyridine (793 mg) was added followed by stirring at room temperature for 2 hours. After water was added to the reaction mixture, extraction with ethyl acetate was performed. An organic layer obtained was washed with saturated brine, dried over anhydrous sodium sulfate, and then filtered. After the filtrate was concentrated under reduced pressure, the resulting residue was purified by silica gel column chromatography (hexane/ethyl acetate) to give (S)-2-[(2,2-dimethyl-1,3-dioxolan-4-yl)methoxy]-5-nitropyridine (810 mg).

Preparation Example 162

To a mixture of 2-[4-({5-[(2,6-difluoro-3,5-dimethoxybenzyl)oxy]pyrimidin-2-yl}amino)-1H-pyrazol-1-yl]ethyl methanesulfonate (320 mg) and N-methylpyrrolidone (6 mL), tert-butyl piperazine-1-carboxylate (1.31 g) was added followed by stirring at 80° C. overnight and additional stirring at 120° C. overnight. To the reaction mixture, water and a saturated aqueous sodium hydrogen carbonate solution were added followed by extraction with ethyl acetate. An organic layer obtained was washed with saturated brine, dried over anhydrous magnesium sulfate, and then filtered. After the filtrate was concentrated under reduced pressure, the resulting residue was purified by silica gel column chromatography (chloroform/methanol) and then solidified with ethyl acetate/diisopropyl ether to give tert-butyl 4-{2-[4-({5-[(2,6-difluoro-3,5-dimethoxybenzyl)oxy]pyrimidin-2-yl}amino)-1H-pyrazol-1-yl]ethyl}piperazine-1-carboxylate (202 mg).

Preparation Example 175

A mixture of 5-methyl-1H-pyrazol-3-amine (522 mg) and N,N-dimethylformamide (10 mL) was ice cooled, and sodium hydride (473 mg) was added thereto followed by stirring for 30 minutes. To the reaction mixture, 2-(2-bromoethoxy)tetrahydro-2H-pyran (893 μL) was added followed by stirring at room temperature for 12 hours. After saturated aqueous ammonium chloride solution was added to the reaction mixture, extraction with ethyl acetate was performed. An organic layer obtained was washed with saturated brine, dried over anhydrous sodium sulfate, and then filtered. After the filtrate was concentrated under reduced pressure, the resulting residue was purified by silica gel column chromatography (hexane/ethyl acetate) to give 5-methyl-1-[2-(tetrahydro-2H-pyran-2-yloxy)ethyl]-1H-pyrazol-3-amine (427 mg: Preparation Example 175-1) and 3-methyl-1-[2-(tetrahydro-2H-pyran-2-yloxy)ethyl]-1H-pyrazol-5-amine (199 mg: Preparation Example 175-2).

Preparation Example 176

To a mixture of 5-[2-(benzyloxy)ethyl]-3-(2,5-dimethyl-1H-pyrrol-1-yl)-1-methyl-1H-pyrazole (640 mg) and ethanol (9.7 mL), hydroxylamine (1.37 mL) and p-toluenesulfonic acid monohydrate (1.95 g) in that order were added followed by stirring at 95° C. overnight. The reaction mixture was concentrated under reduced pressure, and then water was added to the resulting residue followed by extraction with chloroform. An organic layer obtained was washed with saturated brine, dried over anhydrous magnesium sulfate, and then filtered. After the filtrate was concentrated under reduced pressure, the resulting residue was purified by silica gel column chromatography (chloroform/methanol) to give 5-[2-(benzyloxy)ethyl]-1-methyl-1H-pyrazol-3-amine (470 mg).

Preparation Example 183

To a mixture of (1-methyl-3-nitro-1H-pyrazol-5-yl)methanol (398 mg), 3,4-dihydro-2H-pyran (459 µL), and ethyl acetate (8 mL), p-toluenesulfonic acid monohydrate (96 mg) was added followed by stirring at room temperature for 1.5 hours. Additional 3,4-dihydro-2H-pyran (459 µL) and p-toluenesulfonic acid monohydrate (96 mg) were added thereto followed by stirring at room temperature for 1.5 hours. After water was added to the reaction mixture, extraction with ethyl acetate was performed. An organic layer obtained was washed with saturated brine, dried over anhydrous sodium sulfate, and then filtered. After the filtrate was concentrated under reduced pressure, the resulting residue was purified by silica gel column chromatography (hexane/ethyl acetate) to give 1-methyl-3-nitro-5-[(tetrahydro-2H-pyran-2-yloxy)methyl]-1H-pyrazole (487 mg).

Preparation Example 186

A mixture of 4-nitro-1H-pyrazole (300 mg), 2-phenyl-1,3-dioxan-5-ol (717 mg), triphenylphosphine (1.11 g) and tetrahydrofuran (4.5 mL) was ice cooled, and then diisopropyl azodicarboxylate (842 µL) was added thereto followed by stirring at room temperature for 12 hours. After the reaction mixture was concentrated under reduced pressure, the resulting residue was purified by silica gel chromatography (ethyl acetate/hexane) to give 4-nitro-1-(2-phenyl-1,3-dioxan-5-yl)-1H-pyrazol (121 mg).

Preparation Example 189

To a mixture of 5-nitropyridine-2-carbaldehyde (761 mg), 2-(piperazin-1-yl)ethanol (1.23 mL), acetic acid (570 µl), and dichloromethane (20 mL), sodium triacetoxy borohydride (2.23 g) was added followed by stirring at room temperature for 16 hours. To the reaction mixture, a saturated aqueous sodium hydrogen carbonate solution was added followed by extraction with chloroform/2-propanol. An organic layer obtained was washed with saturated brine, dried over anhydrous sodium sulfate, and then filtered. After the filtrate was concentrated under reduced pressure, the resulting residue was purified by silica gel column chromatography (chloroform/methanol) to give 2-{4-[(5-nitropyridin-2-yl)methyl]piperazin-1-yl}ethanol (726 mg).

Preparation Example 191

To a mixture of methyl 5-({5-[(2,6-difluoro-3,5-dimethoxybenzyl)oxy]pyrimidin-2-yl}amino)-1-(tetrahydro-2H-pyran-2-yl)-1H-pyrazole-3-carboxylate (871 mg), ethanol (8.7 mL), and tetrahydrofuran (8.7 mL), a 1M aqueous sodium hydroxide solution (3.45 mL) was added followed by stirring at 60° C. for 2 hours. To the reaction mixture, 1M hydrochloric acid was added, and the resulting solid was collected by filtration, washed with water, and then dried under reduced pressure to give 5-({5-[(2,6-difluoro-3,5-dimethoxybenzyl)oxy]pyrimidin-2-yl}amino)-1-(tetrahydro-2H-pyran-2-yl)-1H-pyrazole-3-carboxylic acid (846 mg).

Preparation Example 193

A mixture of 5-({5-[(2,6-difluoro-3,5-dimethoxybenzyl)oxy]pyrimidin-2-yl}amino)-1-(tetrahydro-2H-pyran-2-yl)-1H-pyrazole-3-carboxylic acid (300 mg) and dioxane (8.5 mL) was ice cooled, and 1,1'-carbonyldiimidazole (99 mg) was added thereto followed by stirring at room temperature for 2 hours and stirring at 60° C. for 2 hours. Additional 1,1'-carbonyldiimidazole (99 mg) was added thereto followed by stirring at 60° C. for 2 hours. Further, 1,1'-carbonyldiimidazole (297 mg) was added thereto followed by stirring at room temperature for 1 hour. The reaction mixture was ice cooled and sodium borohydride (230 mg) was added thereto followed by stirring at room temperature for 12 hours. Water was added to the reaction mixture and extraction with ethyl acetate was performed. An organic layer obtained was washed with saturated brine, dried over anhydrous sodium sulfate, and then filtered. After the filtrate was concentrated under reduced pressure, the resulting residue was purified by silica gel column chromatography (hexane/ethyl acetate) to give [5-({5-[(2,6-difluoro-3,5-dimethoxybenzyl)oxy]pyrimidin-2-yl}amino)-1-(tetrahydro-2H-pyran-2-yl)-1H-pyrazol-3-yl]methanol (126 mg).

Preparation Example 201

To a mixture of 1-methyl-3-nitro-1H-pyrazole-5-carbaldehyde (850 mg) and tetrahydrofuran (50 mL), methyl (triphenylphosphoranylidene)acetate (3.66 g) was added followed by stirring at 60° C. for 3 hours. After the reaction mixture was concentrated under reduced pressure, water was added to the resulting residue followed by extraction with chloroform. An organic layer obtained was washed with saturated brine, dried over anhydrous magnesium sulfate, and then filtered. After the filtrate was concentrated under reduced pressure, the residue obtained was washed with chloroform and the resulting solid was collected by filtration. The filtrate was concentrated under reduced pressure, and the resulting residue was purified by silica gel column chromatography (chloroform/methanol) and then combined with the solid obtained earlier to give methyl (E)-3-(1-methyl-3-nitro-1H-pyrazol-5-yl)acrylate (1.15 g).

Preparation Example 202

Under an argon atmosphere, to a mixture of methyl (E)-3-(1-methyl-3-nitro-1H-pyrazol-5-yl)acrylate (1.15 g) and ethanol (50 mL) was added 10% palladium-carbon (580 mg). After stirring under a hydrogen atmosphere in 1 atm for 12 hours and in 2.7 atm for 4 hours, insoluble materials were removed by filtration through celite. The resulting filtrate was concentrated under reduced pressure to give methyl 3-(3-amino-1-methyl-1H-pyrazol-5-yl)propanoate (955 mg).

Preparation Example 204

To a mixture of 2-[(tert-butoxycarybonyl)amino]-1,3-thiazole-5-carboxylic acid (500 mg), N-[3-(diethylamino)propyl]-N'-ethylcarbodiimide hydrochloride (589 mg), 1H-benzotriazol-1-ol (415 mg), and N,N-dimethylformamide (10 mL), 1-methylpiperazine (451 μL) was added followed by stirring at room temperature for 3 days. To the reaction mixture, water was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (chloroform/methanol) to give tert-butyl {5-[(4-methylpiperazin-1-yl)carbonyl]-1,3-thiazol-2-yl}carbamate (560 mg).

Preparation Example 205

A mixture of 4-aminopyridin-2(1H)-one (400 mg) and N-methylpyrrolidone (15 mL) was ice cooled, and sodium hydride (218 mg) was added thereto followed by stirring at room temperature for 30 minutes. To the reaction mixture, (S)-2,2-dimethyl-1,3-dioxolan-4-ylmethyl p-toluenesulfonate (1.14 g) and sodium iodide (109 mg) in that order were added followed by stirring at room temperature for 4 hours. After sodium hydride (218 mg) was added to the reaction mixture followed by stirring at 80° C. overnight. To the reaction mixture, a saturated aqueous ammonium chloride solution was added, and then the resulting mixture was saturated with sodium chloride, and extraction with methanol/chloroform was performed. An organic layer obtained was dried over anhydrous sodium sulfate and then filtered. The filtrate was concentrated under reduced pressure, and the resulting residue was purified by basic silica gel column chromatography (ethyl acetate/methanol) to give (R)-4-amino-1-[(2,2-dimethyl-1,3-dioxolan-4-yl)methyl]pyridin-2(1H)-one (136 mg).

Preparation Example 209

A mixture of [5-({5-[(2,6-difluoro-3,5-dimethoxybenzyl)oxy]pyrimidin-2-yl}amino)-1-(tetrahydro-2H-pyran-2-yl)-1H-pyrazol-3-yl]methanol (126 mg), triethylamine (147 μL), dichloromethane (6 mL), and tetrahydrofuran (6 mL) was ice cooled, and then methanesulfonyl chloride (82 μL) was added thereto followed by stirring at room temperature for 3 hours. To the reaction mixture, N,N-dimethylformamide (6 mL) was added followed by stirring at room temperature for 12 hours. Water was added to the reaction mixture and extraction with chloroform was performed. An organic layer obtained was washed with saturated brine, dried over anhydrous sodium sulfate, and then filtered. The filtrate was concentrated under reduced pressure to give N-[3-(chloromethyl)-1H-pyrazol-5-yl]-5-[(2,6-difluoro-3,5-dimethoxybenzyl)oxy]pyrimidin-2-amine (109 mg).

Preparation Example 210

To a mixture of tert-butyl {5-[(4-methylpiperazin-1-yl)carbonyl]-1,3-thiazol-2-yl}carbamate (560 mg) and ethyl acetate (8 mL) was added 4M hydrogen chloride/ethyl acetate solution (8 mL) followed by stirring at room temperature for 3 hours. After the reaction mixture was concentrated under reduced pressure, the resulted residue was purified by basic silica gel chromatography (methanol/chloroform) to give (2-amino-1,3-thiazol-5-yl)(4-methylpiperazin-1-yl)methanone (357 mg).

Preparation Example 211

To a mixture of (5-nitro-1H-pyrazol-3-yl)methanol (1.86 g), 3,4-dihydro-2H-pyran (4.7 mL), and acetonitrile (28 mL), trifluoroacetic acid (40 μL) was added followed by stirring at 70° C. for 3 hours. To the reaction mixture, a saturated aqueous sodium hydrogen carbonate solution was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (hexane/ethyl acetate) to give 5-nitro-1-(tetrahydro-2H-pyran-2-yl)-3-[(tetrahydro-2H-pyran-2-yloxy)methyl]-1H-pyrazole (3.98 g).

Preparation Example 214

A mixture of [5-({5-[(2,6-difluoro-3,5-dimethoxybenzyl)oxy]pyrimidin-2-yl}amino)-1H-pyrazol-3-yl]methanol (200 mg) and 1,2-dichloroethane (12 mL) was ice cooled, and manganese dioxide (442 mg) was added thereto followed by stirring at room temperature for 30 minutes and then stirring at 90° C. for 2 hours. After insoluble materials were removed by filtration, the filtrate was concentrated under reduced pressure to give 5-({5-[(2,6-difluoro-3,5-dimethoxybenzyl)oxy]pyrimidin-2-yl}amino)-1H-pyrazole-3-carbaldehyde (142 mg).

Preparation Example 229

A mixture of methyl 2-chloro-6-fluoro-3,5-dimethoxybenzoate (682 mg) and tetrahydrofuran (25 mL) was ice cooled, and lithium aluminum hydride (104 mg) was added thereto followed by stirring at room temperature for 3 hours. To the reaction mixture, diethylether was added for dilution under ice cooling, and then a saturated aqueous sodium sulfate solution was added thereto. Insoluble materials were separated by filtration and the filtrate was concentrated under reduced pressure. The resulting residue was purified by silica gel column chromatography (hexane/ethyl acetate) to give (2-chloro-6-fluoro-3,5-dimethoxyphenyl)methanol (363 mg).

Preparation Example 232

To a mixture of 2-bromo-5-nitroanisole (3.15 g), tert-butyl 3-(4,4,5,5-tetramethyl-1,3,2-dioxaborolan-2-yl)-8-azabicyclo[3.2.1]oct-2-ene-8-carboxylate (5.00 g), and dioxane (40 mL), [1,1'-bis(diphenylphosphino)ferrocene]palladium dichloride dichloromethane complex (554 mg) and potassium carbonate (2.81 g) in that order were added under an argon atmosphere followed by stirring at 80° C. for 21 hours. To the reaction mixture, water was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (hexane/ethyl acetate) to give tert-butyl 3-(2-methoxy-4-nitrophenyl)-8-azabicyclo[3.2.1]oct-2-ene-8-carboxylate (2.78 g).

Preparation Example 252

A mixture of tert-butyl 4,4-bis(acetoxymethyl)-1,4'-bipiperidin-1'-carboxylate (712 mg) and dichloromethane (6 mL) was ice cooled, and then trifluoroacetic acid (3 mL) was added thereto followed by stirring at room temperature for 3 hours. To the reaction mixture, a saturated aqueous sodium hydrogen carbonate solution was added followed by extraction with dichloromethane. An organic layer obtained was washed with brine, dried over anhydrous sodium sulfate, and then filtered. The filtrate was concentrated under reduced pressure to give 1,4'-bipiperidin-4,4-diylbis(methylene) diacetate (529 mg).

Preparation Example 255

A mixture of tert-butyl 4,4-bis(hydroxymethyl)piperidine-1-carboxylate (1.01 g), triethylamine (861 µL), and dichloromethane (10 mL) was ice cooled, and acetic anhydride (950 µL) was added thereto followed by stirring for 2 hours. To the reaction mixture, water was added followed by extraction with dichloromethane. An organic layer obtained was washed with saturated brine, dried over anhydrous sodium sulfate, and then filtered. After the filtrate was concentrated under reduced pressure, the resulting residue was purified by silica gel column chromatography (hexane/ethyl acetate) to give tert-butyl 4,4-bis(acetoxymethyl)piperidine-1-carboxylate (1.38 g).

Preparation Example 295

After a mixture of 2-[3-(2,5-dimethyl-1H-pyrrol-1-yl)-1-methyl-1H-pyrazol-5-yl]ethanol (630 mg), benzyl bromide (376 µL), and tetrahydrofuran (8 mL) was ice cooled, sodium hydride (173 mg) was added thereto followed by stirring at room temperature for 6 hours. To the reaction mixture, water was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (ethyl acetate/hexane) to give 5-[2-(benzyloxy)ethyl]-3-(2,5-dimethyl-1H-pyrrol-1-yl)-1-methyl-1H-pyrazole (640 mg).

Preparation Example 296

After a mixture of 3-(2,5-dimethyl-1H-pyrrol-1-yl)-1-methyl-1H-pyrazole (2 g) and tetrahydrofuran (60 mL) was cooled to −78° C., n-butyl lithium (1.6M hexane solution, 8.56 mL) was added thereto followed by stirring for 2 hours. To the reaction mixture, oxirane (1.1M tetrahydrofuran solution, 15.6 mL) and borontrifluoride tetrahydrofuran complex (1.51 mL) were added followed by stirring for 30 minutes. After that, the mixture obtained was warmed to room temperature and stirred for 6 hours. To the reaction mixture, a saturated aqueous ammonium chloride solution was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (ethyl acetate/hexane) to give 2-[3-(2,5-dimethyl-1H-pyrrol-1-yl)-1-methyl-1H-pyrazol-5-yl]ethanol (630 mg).

The compounds shown in Tables 7 to 62 below were prepared in the same manner as in the preparation examples described above. Tables 7 to 62 also show the processes for preparing the compounds of the preparation examples and the structures and physical and chemical data of the compounds.

Example 1

To a mixture of 5-bromo-N-{3-methoxy-4-[4-(4-methylpiperazin-1-yl)piperidin-1-yl]phenyl}pyrimidin-2-amine (104 mg), 1-ethynyl-3,5-dimethoxybenzene (37 mg), tetrakistriphenylphosphine palladium (13 mg), copper iodide (4 mg), and N,N-dimethylformamide (2 mL), triethylamine (157 µL) was added under an argon atmosphere followed by stirring at 120° C. for 30 minutes. Further, a mixture of 1-ethynyl-3,5-dimethoxybenzene (146 mg) and N,N-dimethylformamide (1 mL) was added thereto followed by stirring at 120° C. for 2 hours. The reaction mixture was diluted with ethyl acetate, and insoluble materials were removed by filtration through celite. After the filtrate was concentrated under reduced pressure, the resulting residue was purified by silica gel column chromatography (chloroform/methanol) and subsequently purified by basic silica gel column chromatography (ethyl acetate/methanol), and then solidified with ethyl acetate to give 5-[(3,5-dimethoxyphenyl)ethynyl]-N-{3-methoxy-4-[4-(4-methylpiperazin-1-yl)piperidin-1-yl]phenyl}pyrimidin-2-amine (23 mg).

Example 2

To a mixture of 5-[(3,5-dimethoxyphenyl)ethynyl]-N-{3-methoxy-4-[4-(4-methylpiperazin-1-yl)piperidin-1-yl]phenyl}pyrimidin-2-amine (72 mg), methanol (2 mL), and tetrahydrofuran (2 mL), 10% palladium-carbon (25 mg) was added under an argon atmosphere. After stirring for 4 hours under a hydrogen atmosphere (3 atm), insoluble materials were removed by filtration through celite. After the filtrate was concentrated under reduced pressure, the resulting residue was purified by silica gel column chromatography (chloroform/methanol) and then solidified with diethyl ether to give 5-[2-(3,5-dimethoxyphenyl)ethyl]-N-{3-methoxy-4-[4-(4-methylpiperazin-1-yl)piperidin-1-yl]phenyl}pyrimidin-2-amine (17 mg).

Example 3

To a mixture of 5-iodo-N-{3-methoxy-4-[4-(4-methylpiperazin-1-yl)piperidin-1-yl]phenyl}pyrimidin-2-amine (100 mg), 2,4-dichloro-3-ethynyl-1,5-dimethoxybenzene (55 mg), tetrakistriphenylphosphine palladium (23 mg), copper iodide (2 mg), and N,N-dimethylformamide (2 mL), N,N-diisopropylethylamine (67 µL) was added under an argon atmosphere followed by stirring at 100° C. for 4 hours. The reaction mixture was diluted with ethyl acetate, and insoluble materials were removed by filtration through celite. To the filtrate, a saturated aqueous sodium hydrogen carbonate solution was added followed by extraction with ethyl acetate. An organic layer obtained was washed with brine, dried over anhydrous sodium sulfate, and then filtered. After the filtrate was concentrated under reduced pressure, the resulting residue was purified by silica gel column chromatography (chloroform/methanol) and subsequently purified by basic silica gel column chromatography (ethyl acetate/methanol), and then solidified with ethyl acetate to give 5-[(2,6-dichloro-3,5-dimethoxyphenyl)ethynyl]-N-{3-methoxy-4-[4-(4-methylpiperazin-1-yl)piperidin-1-yl]phenyl}pyrimidin-2-amine (56 mg).

Example 4

To a mixture of 5-[(2,6-dichloro-3,5-dimethoxyphenyl)ethynyl]-N-{3-methoxy-4-[4-(4-methylpiperazin-1-yl)piperidin-1-yl]phenyl}pyrimidin-2-amine (92 mg) and ethyl acetate (6 mL), a 4M hydrogen chloride/ethyl acetate solution (1 mL) was added followed by stirring at room temperature for 4 hours. The resulting solid was collected by filtration and dried under reduced pressure to give 5-[(2,6- dichloro-3,5-dimethoxyphenyl)ethynyl]-N-{3-methoxy-4-[4-(4-methylpiperazin-1-yl)piperidin-1-yl]phenyl}pyrimidin-2-amine trihydrochloride (101 mg).

Example 5

A mixture of 5-[2-(3,5-dimethoxyphenyl)ethyl]-N-{3-methoxy-4-[4-(4-methylpiperazin-1-yl)piperidin-1-yl]phenyl}pyrimidin-2-amine (131 mg) and acetonitrile (1.3 mL) was ice cooled, and then sulfuryl chloride (41 µL) was added thereto followed by stirring at room temperature for 12 hours. After the reaction mixture was concentrated under reduced pressure, the resulting residue was purified by silica gel column chromatography (chloroform/methanol) and then washed with diisopropyl ether to give N-{2-chloro-5-methoxy-4-[4-(4-methylpiperazin-1-yl)piperidin-1-yl]phenyl}-5-[2-(2,6-dichloro-3,5-dimethoxyphenyl)ethyl]pyrimidin-2-amine (29 mg).

Example 6

Under an argon atmosphere, a mixture of 5-[(2,6-difluoro-3,5-dimethoxyphenyl)ethynyl]-N-{3-methoxy-4-[4-(1-methylpiperidin-4-yl)piperazin-1-yl]phenyl}pyrimidin-2-amine (164 mg), 4-methylbenzenesulfonyl hydrazide (2.63 g), and 1,2-dimethoxyethane (3 mL) was stirred at 110° C., and a mixture of sodium acetate (1.16 g) and water (1 mL) was added thereto. After 2 hours, 4-methylbenzenesulfonyl hydrazide (1.32 g) was added thereto, and then an additional mixture of sodium acetate (581 mg) and water (1 mL) was added thereto followed by stirring at 110° C. for 2 hours. To the reaction mixture, a saturated aqueous sodium hydrogen carbonate solution was added followed by extraction with chloroform. An organic layer obtained was dried over anhydrous magnesium sulfate and then filtered. The filtrate was concentrated under reduced pressure, and the resulting residue was purified by basic silica gel column chromatography (ethyl acetate/methanol/conc. aqueous ammonia solution) and then solidified with ethyl acetate/diisopropyl ether to give 5-[2-(2,6-difluoro-3,5-dimethoxyphenyl)ethyl]-N-{3-methoxy-4-[4-(1-methylpiperidin-4-yl)piperazin-1-yl]phenyl}pyrimidin-2-amine (114 mg).

Example 7

A mixture of 5-[(2,6-difluoro-3,5-dimethoxyphenyl)ethynyl]-N-[3-methoxy-4-(4-methylpiperazin-1-yl)phenyl]pyrimidin-2-amine (100 mg), tetrahydrofuran (5 mL), and methanol (5 mL) was reacted using H-Cube (trademark) (10% palladium-carbon, 0.5 mL/min, 50° C., 1 atm). The reaction mixture was concentrated under reduced pressure, and the resulting residue was purified by silica gel column chromatography (chloroform/methanol) and then solidified with ethyl acetate/diisopropyl ether to give 5-[2-(2,6-difluoro-3,5-dimethoxyphenyl)ethyl]-N-[3-methoxy-4-(4-methylpiperazin-1-yl)phenyl]pyrimidin-2-amine (29 mg).

Example 8

To a mixture of ethyl [4-({5-[(2,6-difluoro-3,5-dimethoxybenzyl)oxy]pyrimidin-2-yl}amino)-1H-pyrazol-1-yl]acetate (292 mg), tetrahydrofuran (6 mL), and ethanol (6 mL), a 1M aqueous sodium hydroxide solution (1.3 mL) was added at room temperature followed by stirring for 5 hours. The reaction mixture was neutralized with 1M hydrochloric acid and the resulting solid was collected by filtration. The solid was washed with water and dried under reduced pressure to give [4-({5-[(2,6-difluoro-3,5-dimethoxybenzyl)oxy]pyrimidin-2-yl}amino)-1H-pyrazol-1-yl]acetic acid (267 mg).

Example 9

To a mixture of 2-chloro-5-[2-(2,6-difluoro-3,5-dimethoxyphenyl)ethyl]pyrimidine (56 mg), 1-(1-methylpiperidin-4-yl)-1H-pyrazol-4-amine (48 mg), 1,1'-binaphthalene-2,2'-diylbis(diphenylphosphine) (33 mg), cesium carbonate (174 mg), and dioxane (2.2 mL), palladium acetate (8 mg) was added at room temperature under an argon atmosphere followed by stirring at 100° C. for 4 hours. To the reaction mixture, water was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (chloroform/methanol) and then solidified with ethyl acetate/diisopropyl ether to give 5-[2-(2,6-difluoro-3,5-dimethoxyphenyl)ethyl]-N-[1-(1-methylpiperidin-4-yl)-1H-pyrazol-4-yl]pyrimidin-2-amine (43 mg).

Example 10

To a mixture of 1-(bromomethyl)-2,6-difluorobenzene (14 mg), 2-chloro-5-hydroxypyrimidine (9.1 mg), and N,N-dimethylformamide (1 mL), potassium carbonate (16 mg) was added followed by stirring at room temperature overnight. To the reaction mixture, water was added followed by extraction with chloroform. An organic layer obtained was concentrated under reduced pressure. To the resulting residue, a mixture of 3-methoxy-4-[4-(4-methylpiperazin-1-yl)piperidin-1-yl]aniline (30 mg), cesium carbonate (65 mg), palladium acetate-X-Phos (Pd:P=1:2) ChemDose (trademark) tablet, and tert-butyl alcohol (0.5 mL) was added followed by stirring at 120° C. overnight under a nitrogen atmosphere. To the reaction mixture, water was added followed by extraction with chloroform. An organic layer obtained was concentrated under reduced pressure. The resulting residue was purified by HPLC (0.1% aqueous formic acid solution/methanol) to give 5-[(2,6-difluorobenzyl)oxy]-N-{3-methoxy-4-[4-(4-methylpiperazin-1-yl)piperidin-1-yl]phenyl}pyrimidin-2-amine (17 mg).

Example 11

To a mixture of 5-[(2,6-difluoro-3,5-dimethoxybenzyl)oxy]-N-(1-{[(4S)-2,2-dimethyl-1,3-dioxolan-4-yl]methyl}-1H-pyrazol-4-yl)pyrimidin-2-amine (45 mg) and tetrahydrofuran (2 mL), 1M hydrochloric acid (1 mL) was added followed by stirring at 50° C. for 3 hours. To the reaction mixture, a saturated aqueous sodium hydrogen carbonate solution was added followed by extraction with chloroform. An organic layer obtained was washed with saturated brine, dried over anhydrous sodium sulfate, and then filtered. The filtrate was concentrated under reduced pressure, and the resulting residue was purified by silica gel column chromatography (chloroform/methanol) and then solidified with ethyl acetate to give (2S)-3-[4-({5-[(2,6-difluoro-3,5-dimethoxybenzyl)oxy]pyrimidin-2-yl}amino)-1H-pyrazol-1-yl]propane-1,2-diol (27 mg).

Example 12

A mixture of tert-butyl 4-[4-({5-[(2,6-dichloro-3,5-dimethoxybenzyl)oxy]pyrimidin-2-yl}amino)-3-methoxyphenyl]piperidin-1-carboxylate (298 mg) and chloroform (6 mL) was ice cooled, and trifluoroacetic acid (1 mL) was added thereto followed by stirring at room temperature for 4 hours. After the reaction mixture was ice cooled, a 1M aqueous sodium hydroxide solution (10 mL) and a saturated aqueous sodium hydrogen carbonate solution were added thereto for basification followed by extraction with chloroform. An organic layer obtained was washed with saturated brine, dried over anhydrous magnesium sulfate, and then filtered. The filtrate was concentrated under reduced pressure to give a crude product (273 mg). Further, the crude product (60 mg) was purified by silica gel chromatography (chloroform/methanol/conc. aqueous ammonia solution), and then solidified with ethyl acetate/diisopropyl ether to give 5-[(2,6-dichloro-3,5-dimethoxybenzyl)oxy]-N-[2-methoxy-4-(piperidin-4-yl)phenyl]pyrimidin-2-amine (23 mg).

Example 13

To a mixture of 5-[(2,6-dichloro-3,5-dimethoxybenzyl)oxy]-N-[2-methoxy-4-(piperidin-4-yl)phenyl]pyrimidin-2-amine (63 mg), dichloromethane (2 mL), and methanol (1 mL), 1H-benzotriazol-1-ylmethanol (20 mg) was added followed by stirring at room temperature for 1 hour. Subsequently, sodium triacetoxy borohydride (51 mg) was added thereto followed by stirring at room temperature for 2 hours. To the reaction mixture, a saturated aqueous sodium hydrogen carbonate solution was added and extraction with chloroform was performed. An organic layer obtained was washed with saturated brine, dried over anhydrous magnesium sulfate, and then filtered. The filtrate was concentrated under reduced pressure, and the resulting residue was purified by silica gel column chromatography (chloroform/methanol/conc. aqueous ammonia solution) and then solidified with ethyl acetate/diisopropyl ether to give 5-[(2,6-dichloro-3,5-dimethoxybenzyl)oxy]-N-[2-methoxy-4-(1-methylpiperidin-4-yl)phenyl]pyrimidin-2-amine (28 mg).

Example 14

To a mixture of 5-[(2,6-dichloro-3,5-dimethoxybenzyl)oxy]-N-[1-(piperidin-4-yl)-1H-pyrazol-4-yl]pyrimidin-2-amine (200 mg), ethanol (3 mL), and N,N-dimethylformamide (3 mL), 2,2-dimethyloxyrane (112 μL) was added followed by stirring at room temperature overnight. To the reaction mixture, a saturated aqueous sodium hydrogen carbonate solution was added followed by extraction with ethyl acetate. An organic layer obtained was washed with saturated brine, dried over anhydrous sodium sulfate, and then filtered. The filtrate was concentrated under reduced pressure, and the resulting residue was purified by basic silica gel column chromatography (ethyl acetate) and then solidified with ethyl acetate to give 1-{4-[4-({5-[(2,6-dichloro-3,5-dimethoxybenzyl)oxy]pyrimidin-2-yl}amino)-1H-pyrazol-1-yl]piperidin-1-yl}-2-methylpropan-2-ol (93 mg).

Example 15

A mixture of 5-[(2,6-dichloro-3,5-dimethoxybenzyl)oxy]-N-[1-(piperidin-4-yl)-1H-pyrazol-4-yl]pyrimidin-2-amine (150 mg), triethylamine (131 μL), and dichloromethane (4 mL) was ice cooled, and cyclopropanecarbonyl chloride (29 μL) was added thereto followed by stirring at room temperature overnight. To the reaction mixture, a saturated aqueous sodium hydrogen carbonate solution was added followed by extraction with chloroform. An organic layer obtained was washed with saturated brine, dried over anhydrous sodium sulfate, and then filtered. The filtrate was concentrated under reduced pressure, and the resulting residue was solidified with ethyl acetate to give cyclopropyl {4-[4-({5-[(2,6-dichloro-3,5-dimethoxybenzyl)oxy]pyrimidin-2-yl}amino)-1H-pyrazol-1-yl]piperidin-1-yl}methanone (159 mg).

Example 16

To a mixture of 5-[(2,6-dichloro-3,5-dimethoxybenzyl)oxy]-N-[1-(piperidin-4-yl)-1H-pyrazol-4-yl]pyrimidin-2-amine (150 mg), potassium carbonate (130 mg), and N,N-dimethylformamide (4 mL), 2-bromoethyl methyl ether (32 μL) was added followed by stirring at room temperature overnight and stirring at 60° C. for 3 hours. Additional 2-bromoethyl methyl ether (12 μL) was added thereto followed by stirring at 60° C. for 4 hours. To the reaction mixture, water was added followed by extraction with ethyl acetate. An organic layer obtained was washed with saturated brine, dried over anhydrous sodium sulfate, and then filtered. The filtrate was concentrated under reduced pressure, and the resulting residue was purified by basic silica gel column chromatography (ethyl acetate/hexane) and then solidified with ethyl acetate to give 5-[(2,6-dichloro-3,5-dimethoxybenzyl)oxy]-N-{1-[1-(2-methoxyethyl)piperidin-4-yl]-1H-pyrazol-4-yl}pyrimidin-2-amine (41 mg).

Example 17

To a mixture of ethyl 1-methyl-5-({5-[(2,3,5,6-tetrafluorobenzyl)oxy]pyrimidin-2-yl}amino)-1H-pyrazol-3-carboxylate (663 mg), ethanol (6.6 mL), and tetrahydrofuran (6.6 mL), a 1M aqueous sodium hydroxide solution (3.2 mL) was added followed by stirring at room temperature for 4 hours. To the reaction mixture, 1M hydrochloric acid (3.2 mL) was added, and the resulting solid was collected by filtration, washed with water, and dried under reduced pressure to give 1-methyl-5-({5-[(2,3,5,6-tetrafluorobenzyl)oxy]pyrimidin-2-yl}amino)-1H-pyrazol-3-carboxylic acid (464 mg).

Example 18

To a mixture of 1-methyl-5-({5-[(2,3,5,6-tetrafluorobenzyl)oxy]pyrimidin-2-yl}amino)-1H-pyrazol-3-carboxylic acid (100 mg), 1-methylpiperazine (83 μL), 1H-benzotriazol-1-ol (68 mg), and N,N-dimethylformamide (2 mL), N-[3-(diethylamino)propyl]-N'-ethylcarbodiimide hydrochloride (97 mg) was added followed by stirring at room temperature overnight. To the reaction mixture, a saturated aqueous sodium hydrogen carbonate solution was added followed by extraction with ethyl acetate. An organic layer obtained was washed with saturated brine, dried over anhydrous magnesium sulfate, and then filtered. The filtrate was concentrated under reduced pressure and the resulting residue was purified by silica gel column chromatography (chloroform/methanol/conc. aqueous ammonia solution) to give (4-methylpiperazin-1-yl)[1-methyl-5-({5-[(2,3,5,6-tetrafluorobenzyl)oxy]pyrimidin-2-yl}amino)-1H-pyrazol-3-yl]methanone (79 mg).

Example 19

A mixture of tert-butyl 4-[4-({5-[(2,3,5,6-tetrafluorobenzyl)oxy]pyrimidin-2-yl}amino)-2-methoxyphenyl]-3,9-diazaspiro[5,5]undecane-3-carboxylate (232 mg) and dichloromethane (3 mL) was ice cooled, and trifluoroacetic acid (0.5 mL) was added thereto followed by stirring at room temperature for 1 hour. After the reaction mixture was concentrated under reduced pressure, ethyl acetate and a saturated aqueous sodium hydrogen carbonate solution were added to the resulting residue. The resulting solid was collected by filtration, washed with ethyl acetate, and then dried under reduced pressure to give N-[4-(3,9-diazaspiro[5,5]undec-3-yl)-3-methoxyphenyl]-5-[(2,3,5,6-tetrafluorobenzyl)oxy]pyrimidin-2-amine (167 mg).

Example 20

To a mixture of 2-[3-({5-[(2,3,5,6-tetrafluorobenzyl)oxy]pyrimidin-2-yl}amino)-1H-pyrazol-1-yl]ethyl methanesulfonate (160 mg) and N-methylpyrrolidone (6 mL), 1-methylpiperazine (382 µL) was added followed by stirring at 80° C. for 2 hours. To the reaction mixture, water and a saturated aqueous sodium hydrogen carbonate solution were added followed by extraction with ethyl acetate. An organic layer obtained was washed with saturated brine, dried over anhydrous sodium sulfate, and then filtered. The filtrate was concentrated under reduced pressure, and the resulting residue was purified by silica gel column chromatography (chloroform/methanol/conc. aqueous ammonia solution) and then solidified with ethyl acetate/diisopropyl ether to give N-{1-[2-(4-methylpiperazin-1-yl)ethyl]-1H-pyrazol-3-yl}-5-[(2,3,5,6-tetrafluorobenzyl)oxy]pyrimidin-2-amine (64 mg).

Example 21

A mixture of N-[3-methoxy-4-(4-methylpiperazin-1-yl)phenyl]-5-[(2,3,5,6-tetrafluorobenzyl)oxy]pyrimidin-2-amine (100 mg) and chloroform (4 mL) was ice cooled, and m-chloroperbenzoic acid (43 mg) was added thereto followed by stirring at 4 to 10° C. for 3 hours and stirring at room temperature for 2 hours. To the reaction mixture, an aqueous sodium thiosulfate solution was added, and the resulting mixture was stirred at room temperature for 1 hour followed by extraction with chloroform. An organic layer obtained was washed with saturated brine, dried over anhydrous magnesium sulfate, and then filtered. The filtrate was concentrated under reduced pressure, and the resulting residue was purified by basic silica gel column chromatography (chloroform/methanol) and then solidified with ethyl acetate/diisopropyl ether to give N-[3-methoxy-4-(4-methyl-4-oxidopiperazin-1-yl)phenyl]-5-[(2,3,5,6-tetrafluorobenzyl)oxy]pyrimidin-2-amine (16 mg).

Example 22

To a mixture of 2-chloro-5-[(2,6-dichloro-3,5-dimethoxybenzyl)oxy]pyridine (100 mg), 3-methoxy-4-[(4-methylpiperazin-1-yl)piperidin-1-yl]aniline (87 mg), 2-(dicyclohexylphosphino)-2',4',6'-triisopropyl-1,1'-biphenyl (27 mg), sodium tert-butoxide (41 mg), and N-methylpyrrolidone (3 mL), palladium acetate (6.4 mg) was added under an argon atmosphere followed by stirring at 160° C. for 2 hours under microwave irradiation. To the reaction mixture, water was added followed by extraction with ethyl acetate. An organic layer obtained was washed with saturated brine, dried over anhydrous sodium sulfate, and then filtered. The filtrate was concentrated under reduced pressure, and the resulting residue was purified by basic silica gel column chromatography (chloroform/methanol) to give 5-[(2,6-dichloro-3,5-dimethoxybenzyl)oxy]-N-{3-methoxy-4-[4-(4-methylpiperazin-1-yl)piperidin-1-yl]phenyl}pyridin-2-amine (27 mg).

Example 23

A mixture of 5-[(2,6-difluoro-3,5-dimethoxybenzyl)oxy]-N-(1H-pyrazol-4-yl)pyrimidin-2-amine (200 mg), cesium carbonate (215 mg), (2S)-2-methyloxylane (128 mg), and N-methylpyrrolidone (4 mL) was stirred at 130° C. for 30 minutes under microwave irradiation. To the reaction mixture, a saturated aqueous sodium hydrogen carbonate solution was added followed by extraction with ethyl acetate. An organic layer obtained was washed with saturated brine, dried over anhydrous magnesium sulfate, and then filtered. The filtrate was concentrated under reduced pressure, and the resulting residue was purified by silica gel column chromatography (ethyl acetate/hexane) and then washed with ethyl acetate/diisopropyl ether to give (2S)-1-[4-({5-[(2,6-difluoro-3,5-dimethoxybenzyl)oxy]pyrimidin-2-yl}amino)-1H-pyrazol-1-yl]propan-2-ol (171 mg).

Example 24

To a mixture of [4-({5-[(2,6-difluoro-3,5-dimethoxybenzyl)oxy]pyrimidin-2-yl}amino)-1H-pyrazol-1-yl]acetic acid (50 mg), ammonium chloride (25 mg), triethylamine (66 µL), 1H-benzotriazol-1-ol (32 mg) and N,N-dimethylformamide (1 mL) was added N-[3-(diethylamino)propyl]-N'-ethylcarbodiimide hydrochloride (45 mg) followed by stirring at room temperature for 12 hours. To the reaction mixture, water was added followed by extraction with ethyl acetate. An organic layer obtained was concentrated under reduced pressure, and the resulted residue was solidified with diisopropyl ether to give 2-[4-({5-[(2,6-difluoro-3,5-dimethoxybenzyl)oxy]pyrimidin-2-yl}amino)-1H-pyrazol-1-yl]acetamide (48 mg).

Example 64

To a mixture of 5-[(2,6-dichloro-3,5-dimethoxybenzyl)oxy]-N-[2-methoxy-4-(piperidin-4-yl)phenyl]pyrimidin-2-amine (62 mg), acetone (118 µL), and dichloromethane (3 mL), sodium triacetoxy borohydride (51 mg) was added followed by stirring at room temperature overnight. To the reaction mixture, a saturated aqueous sodium hydrogen carbonate solution was added followed by extraction with chloroform. An organic layer obtained was washed with saturated brine, dried over anhydrous magnesium sulfate, and then filtered. After the filtrate was concentrated under reduced pressure, the resulting residue was purified by silica gel column chromatography (chloroform/methanol/conc. aqueous ammonia solution) and then solidified with ethyl acetate/diisopropyl ether to give 5-[(2,6-dichloro-3,5-dimethoxybenzyl)oxy]-N-[4-(1-isopropylpiperidin-4-yl)-2-methoxyphenyl]pyrimidin-2-amine (14 mg).

Example 106

To a mixture of 5-[(2,6-difluoro-3,5-dimethoxybenzyl)oxy]-N-{4-(piperazin-1-yl)-3-[2-(1H-pyrazol-1-yl)ethoxy]phenyl}pyrimidin-2-amine (229 mg), formaldehyde (37% aqueous solution, 164 µL), acetic acid (231 µL), and dichloromethane (6 mL), sodium triacetoxy borohydride (257 mg) was added followed by stirring at room temperature overnight. To the reaction mixture, a saturated aqueous sodium hydrogen carbonate solution was added followed by extraction with chloroform. An organic layer obtained was washed with saturated brine, dried over anhydrous sodium sulfate, and then filtered. After the filtrate was concentrated under reduced pressure, the resulting residue was purified by basic silica gel column chromatography (ethyl acetate/methanol) and then solidified with ethyl acetate/diisopropyl ether to give 5-[(2,6-difluoro-3,5-dimethoxybenzyl)oxy]-N-{4-(4-methylpiperazin-1-yl)-3-[2-(1H-pyrazol-1-yl)ethoxy]phenyl}pyrimidin-2-amine (72 mg).

Example 120

To a mixture of 1-[3-({5-[(2,3,5,6-tetrafluorobenzyl)oxy]pyrimidin-2-yl}amino)phenyl]piperidin-4-one (209 mg), 1-methylpiperazine (103 μL), and dichloromethane (4 mL), sodium triacetoxy borohydride (298 mg) was added followed by stirring at room temperature overnight. To the reaction mixture, a saturated aqueous sodium hydrogen carbonate solution was added followed by extraction with chloroform. An organic layer obtained was washed with saturated brine, dried over anhydrous sodium sulfate, and then filtered. After the filtrate was concentrated under reduced pressure, the resulting residue was purified by silica gel column chromatography (chloroform/methanol/conc. aqueous ammonia solution) and then solidified with ethyl acetate/diisopropyl ether to give N-{3-[4-(4-methylpiperazin-1-yl)piperidin-1-yl]phenyl}-5-[(2,3,5,6-tetrafluorobenzyl)oxy]pyrimidin-2-amine (98 mg).

Example 161

To a mixture of 5-[(2,6-difluoro-3,5-dimethoxybenzyl)oxy]-N-[4-(piperidin-4-yl)phenyl]pyrimidin-2-amine (52 mg), glycolic acid (26 mg), 1H-benzotriazol-1-ol (31 mg), and N,N-dimethylformamide (1 mL), N-[3-(diethylamino)propyl]-N'-ethylcarbodiimide hydrochloride (44 mg) was added followed by stirring at room temperature for 2 days. To the reaction mixture, a saturated aqueous sodium hydrogen carbonate solution was added followed by extraction with ethyl acetate. An organic layer obtained was washed with saturated brine, dried over anhydrous magnesium sulfate, and then filtered. After the filtrate was concentrated under reduced pressure, the resulting residue was purified by silica gel column chromatography (chloroform/methanol) and then solidified with ethyl acetate/diisopropyl ether to give 1-{4-[4-({5-[(2,6-difluoro-3,5-dimethoxybenzyl)oxy]pyrimidin-2-yl}amino)phenyl]piperidin-1-yl}-2-hydroxyethanone (10 mg).

Example 162

To a mixture of 5-[(2,6-difluoro-3,5-dimethoxybenzyl)oxy]-N-{3-[4-(4-methylpiperazin-1-yl)piperidin-1-yl]phenyl}pyrimidin-2-amine (123 mg) and ethanol (3 ml), fumaric acid (26 mg) was added followed by heating to reflux. To the reaction mixture, water was added followed by stirring at room temperature overnight, and the resulting solid was collected by filtration. The solid was washed with ethanol and then dried under reduced pressure to give 5-[(2,6-difluoro-3,5-dimethoxybenzyl)oxy]-N-{3-[4-(4-methylpiperazin-1-yl)piperidin-1-yl]phenyl}pyrimidin-2-amine hemifumarate (82 mg).

Example 166

To a mixture of tert-butyl 4-[4-({5-[2-(2,6-difluoro-3,5-dimethoxyphenyl)ethyl]pyrimidin-2-yl}amino)-1H-pyrazol-1-yl]piperidine-1-carboxylate (276 mg) and ethyl acetate (2 mL), a 4M hydrogen chloride/ethyl acetate solution (2 mL) was added followed by stirring at room temperature for 3 hours. After the reaction mixture was concentrated under reduced pressure, a saturated aqueous sodium hydrogen carbonate solution was added to the resulting residue followed by extraction with ethyl acetate. An organic layer obtained was washed with saturated brine, dried over anhydrous sodium sulfate, and then filtered. After the filtrate was concentrated under reduced pressure, the resulting residue was purified by basic silica gel column chromatography (chloroform/methanol) and then solidified with ethyl acetate/diisopropyl ether to give 5-[2-(2,6-difluoro-3,5-dimethoxyphenyl)ethyl]-N-[1-(piperidin-4-yl)-1H-pyrazol-4-yl]pyrimidin-2-amine (119 mg).

Example 190

To a mixture of tert-butyl {2-[4-({5-[(2,6-difluoro-3,5-dimethoxybenzyl)oxy]pyrimidin-2-yl}amino)-1H-pyrazol-1-yl]ethyl}carbamate (101 mg) and ethyl acetate (2 mL), a 4M hydrogen chloride/ethyl acetate solution (2 mL) was added followed by stirring at room temperature for 3 hours. The resulting solid was collected by filtration and then dried under reduced pressure to give N-[1-(2-aminoethyl)-1H-pyrazol-4-yl]-5-[(2,6-difluoro-3,5-dimethoxybenzyl)oxy]pyrimidin-2-amine trihydrochloride (100 mg).

Example 212

To a mixture of 5-[(2,6-difluoro-3,5-dimethoxybenzyl)oxy]-N-{1-[3-(tetrahydro-2H-pyran-2-yloxy)propyl]-1H-pyrazol-4-yl}pyrimidin-2-amine (1.6 g), tetrahydrofuran (6.9 mL), and water (3.4 mL), acetic acid (13.8 mL) was added followed by stirring at 70° C. for 2 days. After the reaction mixture was concentrated under reduced pressure, a saturated aqueous sodium hydrogen carbonate solution was added to the resulting residue followed by extraction with chloroform. An organic layer obtained was dried over anhydrous magnesium sulfate and then filtered. The filtrate was concentrated under reduced pressure, and the resulting residue was dissolved in methanol (30 mL). Potassium carbonate (656 mg) was added thereto followed by stirring at 60° C. for 5 hours. To the reaction mixture, water was added and extraction with chloroform was performed. An organic layer obtained was dried over anhydrous magnesium sulfate and then filtered. The filtrate was concentrated under reduced pressure to give 3-[4-({5-[(2,6-difluoro-3,5-dimethoxybenzyl)oxy]pyrimidin-2-yl}amino)-1H-pyrazol-1-yl]propan-1-ol (510 mg).

Example 213

To a mixture of 5-[(2,6-difluoro-3,5-dimethoxybenzyl)oxy]-N-{6-[(2-phenyl-1,3-dioxan-5-yl)oxy]pyridin-3-yl}pyrimidin-2-amine (335 mg) and acetic acid (10 mL), water (2 mL) was added followed by stirring at 60° C. for 16 hours. After the solvent was concentrated under reduced pressure, a saturated aqueous sodium hydrogen carbonate solution was added to the resulting residue followed by extraction with chloroform. An organic layer obtained was washed with saturated brine, dried over anhydrous sodium sulfate, and then filtered. After the filtrate was concentrated under reduced pressure, the resulting residue was purified by silica gel column chromatography (chloroform/methanol) and then solidified with ethyl acetate to give 2-{[5-({5-[(2, 6-difluoro-3,5-dimethoxybenzyl)oxy]pyrimidin-2-yl}amino)pyridin-2-yl]oxy}propane-1,3-diol (92 mg).

Example 214

To a mixture of 5-[(2,6-difluoro-3,5-dimethoxybenzyl)oxy]-N-{6-[2-(tetrahydro-2H-pyran-2-yloxy)ethoxy]pyridin-3-yl}pyrimidin-2-amine (1.49 g) and methanol (5 mL), a 4M hydrogen chloride/dioxane solution (5 mL) was added followed by stirring at room temperature for 2 hours. After the reaction mixture was concentrated under reduced pressure, a saturated aqueous sodium hydrogen carbonate solution was added to the resulting residue followed by extraction with chloroform. An organic layer obtained was washed with saturated brine, dried over anhydrous sodium sulfate, and then filtered. The filtrate was concentrated under reduced pressure, and the resulted residue was solidified with ethyl acetate. The solid was collected by filtration to give 2-{[5-({5-[(2,6-difluoro-3,5-dimethoxybenzyl)oxy]pyrimidin-2-yl}amino)pyridin-2-yl]oxy}ethanol (452 mg). Further the filtrate was purified by silica gel column chromatography (chloroform/methanol) to give the product (701 mg).

Example 217

To a mixture of 1-[5-({5-[(2,6-difluoro-3,5-dimethoxybenzyl)oxy]pyrimidin-2-yl}amino)pyridin-2-yl]piperidin-4-one (256 mg), 2-aminoethanol (131 μL), acetic acid (200 μL), and dichloromethane (9.3 mL), sodium triacetoxy borohydride (243 mg) was added followed by stirring at room temperature overnight. To the reaction mixture, a saturated aqueous sodium hydrogen carbonate solution was added followed by extraction with chloroform/2-propanol. An organic layer obtained was washed with saturated brine, dried over anhydrous sodium sulfate, and then filtered. After the filtrate was concentrated under reduced pressure, the resulting residue was purified by basic silica gel column chromatography (chloroform/methanol) and then solidified with ethyl acetate to give 2-({1-[5-({5-[(2,6-difluoro-3,5-dimethoxybenzyl)oxy]pyrimidin-2-yl}amino)pyridin-2-yl]piperidin-4-yl}amino)ethanol (137 mg).

Example 239

A mixture of N-{5-[2-(benzyloxy)ethyl]-1-methyl-1H-pyrazol-3-yl}-5-[(2,6-difluoro-3,5-dimethoxybenzyl)oxy]pyrimidin-2-amine (283 mg) and dichloromethane (47 mL) was cooled to −78° C., and boron tribromide (1.0M dichloromethane solution, 830 μL) was added thereto followed by stirring at −78° C. for 1 hour and stirring at 0° C. for 1 hour. To the reaction mixture, a saturated aqueous sodium hydrogen carbonate solution was added followed by extraction with chloroform. An organic layer obtained was washed with saturated brine, dried over anhydrous magnesium sulfate, and then filtered. After the filtrate was concentrated under reduced pressure, the resulting residue was purified by silica gel column chromatography (chloroform/methanol) to give 2-[3-({5-[(2,6-difluoro-3,5-dimethoxybenzyl)oxy]pyrimidin-2-yl}amino)-1-methyl-1H-pyrazol-5-yl]ethanol (38 mg).

Example 246

A mixture of 5-({5-[(2,6-difluoro-3,5-dimethoxybenzyl)oxy]pyrimidin-2-yl}amino)-1-methyl-1H-pyrazol-3-carboxylic acid (320 mg) and dioxane (6 mL) was ice cooled, and 1,1'-carbonyldiimidazole (616 mg) was added thereto followed by stirring at room temperature for 2 hours. To the reaction mixture, sodium borohydride (287 mg) was added followed by stirring at room temperature for 12 hours. To the reaction mixture, water and chloroform were added, and insoluble materials were removed by filtration through celite, and then the filtrate was extracted with chloroform. An organic layer obtained was washed with saturated brine, dried over anhydrous sodium sulfate, and then filtered. After the filtrate was concentrated under reduced pressure, the resulting residue was purified by silica gel column chromatography (hexane/ethyl acetate) to give [5-({5-[(2,6-difluoro-3,5-dimethoxybenzyl)oxy]pyrimidin-2-yl}amino)-1-methyl-1H-pyrazol-3-yl]methanol (125 mg).

Example 253

To a mixture of 5-({5-[(2,6-difluoro-3,5-dimethoxybenzyl)oxy]pyrimidin-2-yl}amino)-1-(2-hydroxyethyl)pyridin-2(1H)-one (90 mg), triethylamine (50 μL), and dichloromethane (3 mL), methanesulfonyl chloride (20 μL) was added followed by stirring at room temperature for 1 hour. To the reaction mixture, 1-methylpiperazine (50 μL) and N,N-dimethylformamide (3 mL) were added followed by stirring at 50° C. for 20 hours. To the reaction mixture, water was added and extraction with ethyl acetate was performed. An organic layer obtained was washed with saturated brine, dried over anhydrous sodium sulfate, and then filtered. After the filtrate was concentrated under reduced pressure, the resulting residue was purified by basic silica gel column chromatography (ethyl acetate/chloroform) and then solidified with diethyl ether to give 5-({5-[(2,6-difluoro-3,5-dimethoxybenzyl)oxy]pyrimidin-2-yl}amino)-1-[2-(4-methylpiperazin-1-yl)ethyl]pyridin-2(1H)-one (28 mg).

Example 254

To a mixture of 2-chloro-5-[(2,6-difluoro-3,5-dimethoxybenzyl)oxy]pyrimidine (270 mg), 1-(1-methylpiperidin-4-yl)-1H-imidazol-4-amine (231 mg), 1,1'-binaphthalene-2,2'-diylbis(diphenylphosphine) (80 mg), cesium carbonate (556 mg), and dioxane (5.4 mL), palladium acetate (19 mg) was added under an argon atmosphere followed by stirring at 150° C. for 30 minutes under microwave irradiation. To the reaction mixture, water was added followed by extraction with chloroform. An organic layer obtained was washed with saturated brine, dried over anhydrous sodium sulfate, and then filtered. After the filtrate was concentrated under reduced pressure, the resulting residue was purified by silica gel column chromatography (chloroform/methanol) and then solidified with ethanol/diethyl ether to give 5-[(2,6-difluoro-3,5-dimethoxybenzyl)oxy]-N-[1-(1-methylpiperidin-4-yl)-1H-imidazol-4-yl]pyrimidin-2-amine (241 mg).

Example 278

To a mixture of 2-chloro-5-[(2-fluoro-3,5-dimethoxybenzyl)oxy]pyrimidine (200 mg), 2-(4-amino-1H-pyrazol-1-yl)ethanol (170 mg), 4,5-bis(diphenylphosphino)-9,9-dimethylxanthene (39 mg), cesium carbonate (655 mg), and dioxane (4 mL), tris(dibenzylideneacetone)dipalladium (31 mg) was added under an argon atmosphere followed by stirring at 80° C. overnight. To the reaction mixture, water was added followed by extraction with ethyl acetate. An organic layer obtained was washed with saturated brine, dried over anhydrous sodium sulfate, and then filtered. After the filtrate was concentrated under reduced pressure, the resulting residue was purified by basic silica gel column chromatography (ethyl acetate/methanol) and then solidified with ethanol to give 2-[4-({5-[(2-fluoro-3,5-dimethoxybenzyl)oxy]pyrimidin-2-yl}amino)-1H-pyrazol-1-yl]ethanol (58 mg).

Example 282

To a mixture of 5-({5-[(2,6-difluoro-3,5-dimethoxybenzyl)oxy]pyrimidin-2-yl}amino)-1H-pyrazol-3-carbaldehyde (100 mg), morpholine (67 μL), and N,N-dimethylformamide (2 mL), sodium triacetoxy borohydride (243 mg) was added followed by stirring at room temperature for 12 hours. To the reaction mixture, a saturated aqueous sodium hydrogen carbonate solution was added followed by extraction with chloroform. An organic layer obtained was washed with saturated brine, dried over anhydrous sodium sulfate, and then filtered. After the filtrate was concentrated under reduced pressure, the resulting residue was purified by basic silica gel column chromatography (chloroform/methanol) and purified by silica gel column chromatography (chloroform/methanol) and then solidified with ethanol/diisopropyl ether to give 5-[(2,6-difluoro-3,5-dimethoxybenzyl)oxy]-N-[3-(morpholin-4-ylmethyl)-1H-pyrazol-5-yl]pyrimidin-2-amine (42 mg).

Example 286

To a mixture of 2-chloro-5-[(2,6-dichloro-3,5-dimethoxybenzyl)oxy]pyrimidine (159 mg), 3-methoxy-4-(1-methylpiperidin-4-yl)aniline (100 mg), and tert-butanol (5 mL), tris(dibenzylideneacetone)dipalladium (13 mg), 2-(dicyclohexylphosphino)-2',4',6'-triisopropyl-1,1'-biphenyl (20 mg), and potassium carbonate (88 mg) were added under an argon atmosphere followed by stirring at 100° C. for 8 hours. Insoluble materials were removed by filtration, washed with ethyl acetate, and then the filtrate was concentrated under reduced pressure. The resulting residue was purified by silica gel column chromatography (chloroform/methanol) to give 5-[(2,6-dichloro-3,5-dimethoxybenzyl)oxy]-N-[3-methoxy-4-(1-methylpiperidin-4-yl)phenyl]pyrimidin-2-amine (35 mg).

Example 302

To a mixture of 2-{4-[4-({5-[(2,6-difluoro-3,5-dimethoxybenzyl)oxy]pyrimidin-2-yl}amino)phenyl]piperazin-1-yl}ethyl methanesulfonate (100 mg) and methanol (3 mL), sodium methoxide (25% methanol solution, 3 mL) was added followed by stirring at 90° C. for 15 minutes under microwave irradiation. After the reaction mixture was concentrated under reduced pressure, water was added to the resulting residue followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (chloroform/methanol) to give 5-[(2,6-difluoro-3,5-dimethoxybenzyl)oxy]-N-{4-[4-(2-methoxyethyl)piperazin-1-yl]phenyl}pyrimidin-2-amine (46 mg).

Example 315

To a mixture of {1'-[4-({15-[(2,6-difluoro-3,5-dimethoxybenzyl)oxy]pyrimidin-2-yl}amino)-2-methoxyphenyl]-1,4'-bipiperidine-4,4-diyl}bis(methylene)diacetate (46 mg) and methanol (3 mL), sodium methoxide (25% methanol solution, 0.2 mL) was added followed by stirring at room temperature for 14 hours. The reaction mixture was concentrated under reduced pressure, and the resulting residue was purified by silica gel column chromatography (chloroform/methanol) to give {1'-[4-({5-[(2,6-difluoro-3,5-dimethoxybenzyl)oxy]pyrimidin-2-yl}amino)-2-methoxyphenyl]-1,4'-bipiperidine-4,4-diyl}dimethanol (34 mg).

Example 336

A mixture of ethyl 4-[4-({5-[(2,6-difluoro-3,5-dimethoxybenzyl)oxy]pyrimidin-2-yl}amino)-2-fluorophenyl]butanoate (150 mg) and tetrahydrofuran (3 mL) was ice cooled, and lithium aluminum hydride (11 mg) was added thereto followed by stirring at room temperature for 3 hours. The reaction mixture was diluted with diethyl ether under ice cooling and then a saturated aqueous sodium sulfate solution was added thereto. Insoluble materials were separated by filtration and the filtrate was concentrated under reduced pressure. The resulting residue was purified by silica gel column chromatography (chloroform/methanol) to give 4-[4-({5-[(2,6-difluoro-3,5-dimethoxybenzyl)oxy]pyrimidin-2-yl}amino)-2-fluorophenyl]butan-1-ol (70 mg).

Example 349

A mixture of ethyl 4-[4-({5-[(2,6-difluoro-3,5-dimethoxybenzyl)oxy]pyrimidin-2-yl}amino)-2-fluorophenyl]butanoate (150 mg) and tetrahydrofuran (3 mL) was ice cooled, and then methyl magnesium bromide (1.0M tetrahydrofuran solution, 1.2 mL) was added thereto followed by stirring for 3 hours. To the reaction mixture, a saturated aqueous ammonium chloride solution was added followed by extraction with ethyl acetate. An organic layer obtained was washed with saturated brine, dried over anhydrous sodium sulfate, and then filtered. After the filtrate was concentrated under reduced pressure, the resulting residue was purified by silica gel column chromatography (chloroform/methanol) to give 5-[4-({5-[(2,6-difluoro-3,5-dimethoxybenzyl)oxy]pyrimidin-2-yl}amino)-2-fluorophenoxy]-2-methylpentan-2-ol (104 mg).

Example 356

To a mixture of 2-(4-aminophenoxy)-2-methylpropionic acid (14.6 mg), cesium carbonate (49 mg), 2-chloro-5-[(2,6-difluoro-3,5-dimethoxybenzyl)oxy]pyrimidine (15.8 mg) and tert-butanol (0.5 mL) was added palladium(II) acetate-2-(dicyclohexylphosphino)-2',4',6'-triisopropyl-1,1'-biphenyl (Pd:P 1:2) ChemDose (trademark) tablet under a nitrogen atmosphere followed by stirring at 120° C. overnight. To the reaction mixture, water was added followed by extraction with chloroform (2 mL), and then the solvent was concentrated under reduced pressure. The resulting residue was purified by HPLC (0.1% aqueous formic acid solution/methanol) to give 2-[4-({5-[(2,6-difluoro-3,5-dimethoxybenzyl)oxy]pyrimidin-2-yl}amino)phenoxy]-2-methylpropionic acid (0.7 mg).

Example 375

To a mixture of 4-amino-1-(1-tert-butoxycarbonyl-azetidin-3-yl)-1H-pyrazole (17.9 mg), cesium carbonate (49 mg), 2-chloro-5-[(2,6-difluoro-3,5-dimethoxybenzyl)oxy]pyrimidine (15.8 mg), tert-butanol (0.34 mL) and N,N-dimethylformamide (0.16 mL) was added palladium(II) acetate-2-(dicyclohexylphosphino)-2',4',6'-triisopropyl-1,1'- biphenyl (Pd:P 1:2) ChemDose (trademark) tablet under a nitrogen atmosphere followed by stirring at 120° C. overnight. To the reaction mixture, water was added followed by extraction with chloroform (2 mL), and then the solvent was concentrated under reduced pressure. To the resulting residue, ethanol (1 mL) and a 4M hydrogen chloride/ethyl acetate solution (0.5 mL) were added followed by stirring at room temperature overnight. After that, the solvent was concentrated under reduced pressure. The resulting residue was purified by HPLC (0.1% aqueous formic acid solution/methanol) to give N-[1-(azetidin-3-yl)-1H-pyrazol-4-yl]-5-[(2,6-difluoro-3,5-dimethoxybenzyl)oxy]pyrimidin-2-amine (1.7 mg).

In the same manner as in the examples shown above, the compounds shown in Tables 63 to 137 below were prepared. Tables 63 to 137 show the structures of the compounds of the examples and Tables 138 to 156 show the preparation processes and physical and chemical data of the compounds of the examples.

TABLE 7

| PEx | PSyn | Str | DAT |
|---|---|---|---|
| 1 | 1 | | APCI/ESI+: 461, 463 |
| 2 | 2 | | APCI/ESI+: 509 |
| 3 | 3 | | NMR2: 3.68 (1H, s), 3.92 (6H, s), 6.58 (1H, s) |
| 4-1 | 4 | | APCI/ESI+: 199 |
| 4-2 | 4 | | APCI/ESI+: 181 |
| 5 | 5 | | NMR2: 3.60 (1H, S), 3.89 (3H, S), 3.91 (3H, S), 6.61 (1H, d, J = 7.5 Hz) |

TABLE 8

| PEx | PSyn | Str | DAT |
|---|---|---|---|
| 6 | 6 | 2,6-difluoro-3-methoxyphenylacetylene | EI: 168 |
| 7 | 7 | 5-((2,6-difluoro-3,5-dimethoxyphenyl)ethynyl)pyrimidin-2-amine | APCI/ESI+: 292 |
| 8 | 8 | 5-(2-(2,6-difluoro-3,5-dimethoxyphenyl)ethyl)pyrimidin-2-amine | APCI/ESI+: 296 |
| 9 | 9 | 2-chloro-5-(2-(2,6-difluoro-3,5-dimethoxyphenyl)ethyl)pyrimidine | APCI/ESI+: 315 |
| 10 | 10 | 2-chloro-5-((3,5-dimethoxyphenoxy)methyl)pyrimidine | APCI/ESI+: 281 |

TABLE 9

| PEx | PSyn | Str | DAT |
|---|---|---|---|
| 13 | 13 | 2-chloro-5-((3,5-dimethoxybenzyl)oxy)pyrimidine | APCI/ESI+: 281 |
| 14 | 14 | 2-chloro-5-((2,6-dichloro-3,5-dimethoxybenzyl)oxy)pyrimidine | APCI/ESI+: 349 |
| 15 | 15 | 2-chloro-5-(1-(3,5-dimethoxyphenyl)ethoxy)pyrimidine | ESI+: 295 |
| 16-1 | 16 | methyl 2,6-difluoro-3,5-dimethoxybenzoate | ESI+: 233 |
| 16-2 | 16 | methyl 2-fluoro-3,5-dimethoxybenzoate | ESI+: 215 |

TABLE 10

| PEx | PSyn | Str | DAT |
|---|---|---|---|
| 17 | 17 | (2,6-difluoro-3,5-dimethoxyphenyl)methanol | ESI+: 205 |
| 18 | 18 | 2,6-difluoro-3,5-dimethoxybenzyl methanesulfonate | NMR2: 3.04 (3H, s), 3.88 (6H, s), 5.34 (2H, s), 6.72 (1H, t, J = 8.2 Hz) |

TABLE 10-continued
| PEx | PSyn | Str | DAT |
|---|---|---|---|
| 19 | 19 | | APCI/ESI+: 317 |
| 20 | 20 | | APCI/ESI+: 176 |
| 21 | 21 | | NMR2: 4.03 (6H, s), 10.3 (1H, s) |
| 22 | 22 | | APCI/ESI+: 206 |
| 23 | 23 | | APCI/ESI+: 619 |
TABLE 11
| PEx | PSyn | Str | DAT |
|---|---|---|---|
| 24 | 24 | | ESI+: 354 |
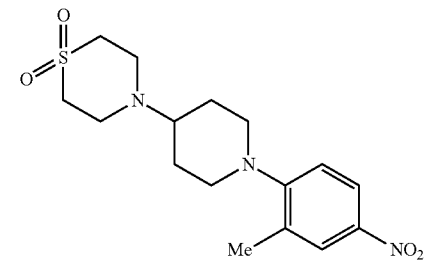 [SMILES: Cc1cc(N)ccc1N1CCC(N2CCS(=O)(=O)CC2)CC1]

TABLE 11-continued
| PEx | PSyn | Str | DAT |
|---|---|---|---|
| 25 | 25 | 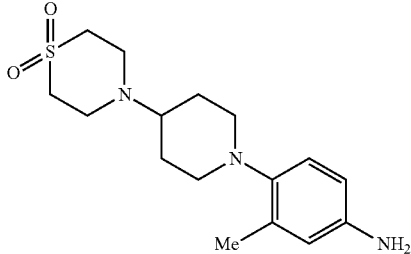 | ESI+: 324 |
| 26 | 26 | 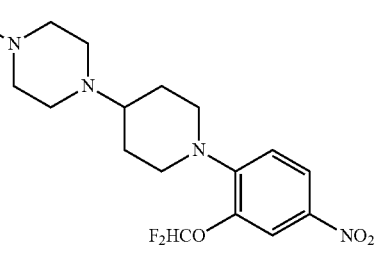 | ESI+: 371 |
| 27 | 27 | 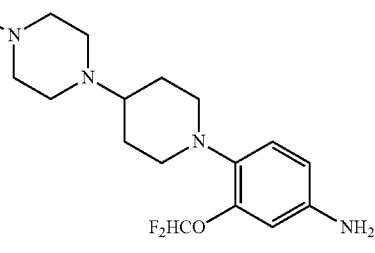 | APCI/ESI+: 341 |
| 28 | 28 | 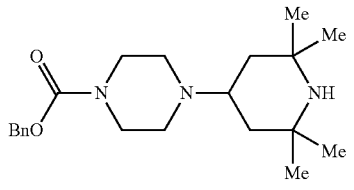 [SMILES: CC1(C)CC(N2CCN(C(=O)OCc3ccccc3)CC2)CC(C)(C)N1] | NMR2: 1.10-1.19 (2H, m), 1.12 (6H, s), 1.19 (6H, s), 1.69-1.76 (2H, m), 2.27 (1H, brs), 2.55-2.59 (4H, m), 2.76-2.87 (1H, m), 3.48-3.55 (4H, m), 5.13 (2H, s), 7.23-7.40 (5H, m) |
| 29 | 29 | 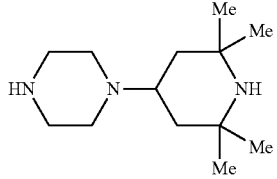 [SMILES: CC1(C)CC(N2CCNCC2)CC(C)(C)N1] | APCI/ESI+: 226 |
TABLE 12
| PEx | PSyn | Str | DAT |
|---|---|---|---|
| 30 | 30 | 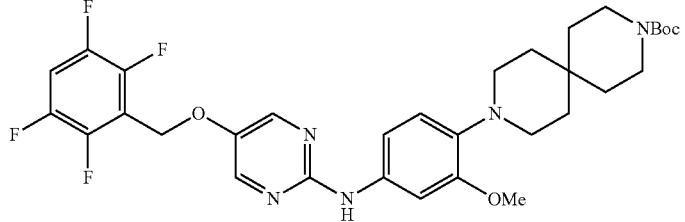 [SMILES: COc1cc(Nc2ncc(OCc3c(F)c(F)cc(F)c3F)cn2)ccc1N1CCC2(CCN(C(=O)OC(C)(C)C)CC2)CC1] | ESI+: 632 |

TABLE 12-continued

| PEx | PSyn | Str | DAT |
|---|---|---|---|
| 31 | 31 | | ESI+: 447 |
| 32 | 32 | | APCI/ESI+: 462 |
| 33 | 33 | | APCI/ESI+: 294 |
| 34 | 34 | | ESI+: 309 |
| 35 | 35 | | APCI/ESI+: 366 |

TABLE 13

| PEx | PSyn | Str | DAT |
|---|---|---|---|
| 36 | 36 | | APCI/ESI+: 268 |

TABLE 13-continued

| PEx | PSyn | Str | DAT |
|---|---|---|---|
| 37 | 37 | | APCI/ESI+: 346 |
| 38 | 38 | | APCI/ESI+: 348 |
| 39 | 39 | | APCI/ESI+: 364 |
| 40 | 40 | | APCI/ESI+: 450 |
| 41 | 41 | | APCI/ESI+: 478 |

TABLE 14

| PEx | PSyn | Str | DAT |
|---|---|---|---|
| 42 | 2 | | APCI/ESI+: 497 |

TABLE 14-continued

| PEx | PSyn | Str | DAT |
|---|---|---|---|
| 43 | 2 | (structure: 5-iodo-N-[2-methoxy-4-(4-(4-methylpiperazin-1-yl)piperidin-1-yl)phenyl]pyrimidin-2-amine) | APCI/ESI+: 509 |
| 44 | 6 | (structure: 2,6-difluoro-phenylacetylene) | EI: 138 |
| 45 | 6 | (structure: 2,3,5,6-tetrafluoro-phenylacetylene) | EI: 174 |
| 46 | 14 | (structure: 2-chloro-5-[1-(2,6-dichloro-3,5-dimethoxyphenyl)ethoxy]pyrimidine) | APCI/ESI+: 363 |
| 47 | 18 | (structure: (3,5-difluoro-2,6-dimethoxypyridin-4-yl)methyl methanesulfonate) | APCI/ESI+: 284 |

TABLE 15

| PEx | PSyn | Str | DAT |
|---|---|---|---|
| 48 | 19 | (structure: 2-chloro-5-[(3,5-difluoro-2,6-dimethoxypyridin-4-yl)methoxy]pyrimidine) | APCI/ESI+: 318 |

TABLE 15-continued
| PEx | PSyn | Str | DAT |
|---|---|---|---|
| 49 | 13 | 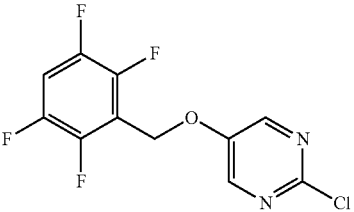 [SMILES: Fc1cc(F)c(F)c(COc2cnc(Cl)nc2)c1F] | APCI/ESI+: 293 |
| 50 | 24 | 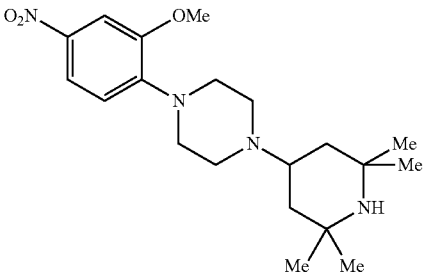 [SMILES: COc1cc([N+](=O)[O-])ccc1N1CCN(C2CC(C)(C)NC(C)(C)C2)CC1] | NMR2: 1.06-1.26 (14H, m), 1.77-1.84 (2H, m), 2.74-2.91 (6H, m), 3.22-3.31 (4H, m), 3.95 (3H, s), 6.88 (1H, d, J = 8.8 Hz), 7.70 (1H, s), 7.86 (1H, d, J = 8.8 Hz) |
| 51 | 27 | 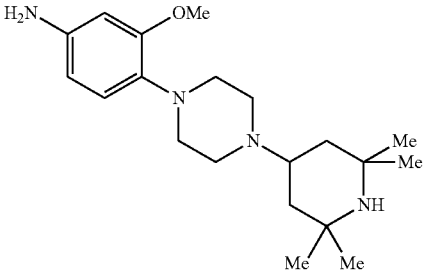 | APCI/ESI+: 347 |
| 52 | 23 | 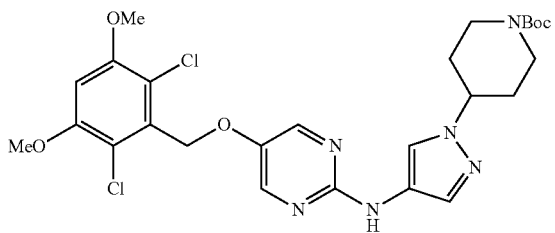 [SMILES: COc1cc(OC)c(Cl)c(COc2cnc(Nc3cnn(C4CCN(C(=O)OC(C)(C)C)CC4)c3)nc2)c1Cl] | APCI/ESI+: 579 |
| 53 | 23 | 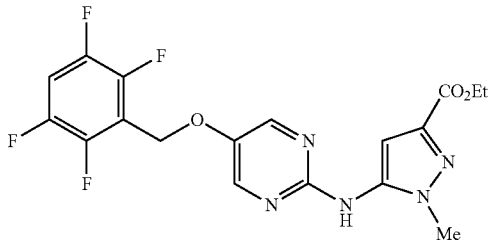 [SMILES: CCOC(=O)c1cc(Nc2ncc(OCc3c(F)c(F)cc(F)c3F)cn2)n(C)n1] | APCI/ESI+: 426 |

TABLE 16

| PEx | PSyn | Str | DAT |
|---|---|---|---|
| 54 | 24 | 2-(4-nitro-2-methoxyphenyl)-9-Boc-2,9-diazaspiro[5.5]undecane | NMR2: 1.47-1.71 (17H, m), 3.17-3.20 (4H, m), 3.40-3.43 (4H, m), 3.95 (3H, s), 6.89 (1H, d, J = 8.8 Hz), 7.69 (1H, d, J = 2.7 Hz), 7.85 (1H, dd, J = 8.8, 2.4 Hz) |
| 55 | 27 | 2-(4-amino-2-methoxyphenyl)-9-Boc-2,9-diazaspiro[5.5]undecane | NMR2: 1.46-1.87 (13H, m), 2.88-2.90 (4H, m), 3.38-3.41 (4H, m), 3.73-3.81 (6H, m), 6.23-6.26 (2H, m), 6.78 (1H, d, J = 8.1 Hz) |
| 56 | 24 | 1-(4-nitro-2-methylphenyl)-4-hydroxy-4-(pyrrolidin-1-ylmethyl)piperidine | ESI+: 320 |
| 57 | 27 | 1-(4-amino-2-methylphenyl)-4-hydroxy-4-(pyrrolidin-1-ylmethyl)piperidine | ESI+: 290 |
| 58 | 23 | pyrimidine with 2,3,5,6-tetrafluorobenzyloxy and anilino-piperidine-dioxolane | ESI+: 491 |

TABLE 17

| PEx | PSyn | Str | DAT |
|---|---|---|---|
| 59 | 23 | pyrimidine with 2,3,5,6-tetrafluorobenzyloxy and anilino-(N-Boc-piperidinyloxy) | ESI+: 549 |

TABLE 17-continued

| PEx | PSyn | Str | DAT |
|---|---|---|---|
| 60 | 24 | | NMR2: 1.45 (9H, s), 3.84 (3H, s), 4.10 (4H, s), 4.26 (4H, s), 6.22 (1H, d, J = 9.0 Hz), 7.60 (1H, d, J = 2.4 Hz), 7.82 (1H, dd, J = 8.8, 2.4 Hz) |
| 61 | 27 | | NMR2: 1.44 (9H, s), 3.40 (2H, brs), 3.74 (3H, s), 3.87 (4H, s), 4.05 (4H, s), 6.21-6.31 (3H, m) |
| 62 | 30 | | ESI+: 576 |
| 63 | 27 | | APCI/ESI+: 264 |
| 64 | 33 | | APCI/ESI+: 281 |
| 65 | 27 | | ESI+: 251 |

TABLE 18

| PEx | PSyn | Str | DAT |
|---|---|---|---|
| 66 | 24 | | ESI+: 330 |
| 67 | 27 | | ESI+: 300 |
| 68 | 27 | | ESI+: 311 |
| 69 | 24 | | ESI+: 3392 |

TABLE 18-continued

| PEx | PSyn | Str | DAT |
|---|---|---|---|
| 70 | 24 | (structure: 4-nitro-2-methoxyphenyl attached to (3R,5S)-3,5-dimethylpiperazine NH) | APCI/ESI+: 266 |
| 71 | 27 | (structure: 4-amino-2-methoxyphenyl attached to (3R,5S)-3,5-dimethyl-N-Boc-piperazine) | APCI/ESI+: 336 |

TABLE 19

| PEx | PSyn | Str | DAT |
|---|---|---|---|
| 72 | 23 | (structure: 3,6-dimethoxy-2,5-difluorobenzyloxy-pyrimidin-2-ylamino-3-methoxyphenyl-(3R,5S)-3,5-dimethyl-N-Boc-piperazine) | APCI/ESI+: 616 |
| 73 | 28 | (structure: 1-Cbz-piperidin-4-yl attached to (3R,5S)-3,5-dimethylpiperazine NH) | APCI/ESI+: 332 |
| 74 | 35 | (structure: 1-Cbz-piperidin-4-yl attached to (3R,5S)-3,5-dimethyl-N-Boc-piperazine) | APCI/ESI+: 432 |
| 75 | 29 | (structure: piperidin-4-yl attached to (3R,5S)-3,5-dimethyl-N-Boc-piperazine) | APCI/ESI+: 298 |
| 76 | 24 | (structure: 4-nitro-2-methoxyphenyl-piperidin-4-yl-(3R,5S)-3,5-dimethyl-N-Boc-piperazine) | APCI/ESI+: 449 |

TABLE 19-continued
| PEx | PSyn | Str | DAT |
|---|---|---|---|
| 77 | 27 | 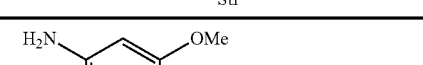 | APCI/ESI+: 419 |
TABLE 20
| PEx | PSyn | Str | DAT |
|---|---|---|---|
| 78 | 23 | (structure) | APCI/ESI+: 699 |
| 79 | 24 | (structure) | NMR2: 1.23 (6H, d, J = 6.3 Hz), 2.44-2.50 (2H, m), 3.50-3.52 (2H, m), 3.85-3.90 (2H, m), 3.95 (3H, s), 6.85 (1H, d, J = 9.0 Hz), 7.71 (1H, d, J = 2.4 Hz), 7.85 (1H, dd, J = 8.8, 2.7 Hz) |
| 80 | 27 | (structure) | NMR2: 1.20 (6H, d, J = 6.3 Hz), 2.27-2.32 (2H, m), 3.15-3.18 (2H, m), 3.49 (2H, brs), 3.82-3.93 (5H, m), 6.23-6.27 (2H, m), 6.74 (1H, d, J = 8.1 Hz) |
| 81 | 30 | (structure) | ESI+: 656 |

TABLE 20-continued

| PEx | PSyn | Str | DAT |
|---|---|---|---|
| 82 | 30 | (structure) | ESI+: 600 |

TABLE 21

| PEx | PSyn | Str | DAT |
|---|---|---|---|
| 83 | 24 | (structure) | ESI+: 349 |
| 84 | 27 | (structure) | ESI+: 319 |
| 85 | 28 | (structure) | ESI+: 338 |
| 86 | 27 | (structure) | ESI+: 308 |
| 87 | 35 | (structure) | APCI/ESI+: 446 |
| 88 | 27 | (structure) | APCI/ESI+: 416 |

TABLE 22

| PEx | PSyn | Str | DAT |
|---|---|---|---|
| 89 | 23 | (structure) | APCI/ESI+: 696 |

TABLE 22-continued
| PEx | PSyn | Str | DAT |
|---|---|---|---|
| 90 | 37 | 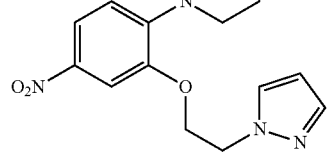 | APCI/ESI+: 418 |
| 91 | 27 | 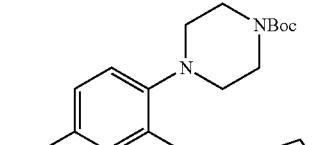 | APCI/ESI+: 388 |
| 92 | 23 | 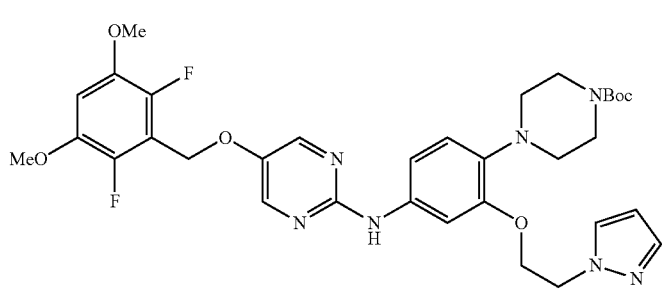 | APCI/ESI+: 668 |
| 93 | 36 | 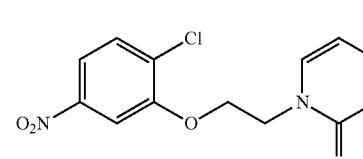 | APCI/ESI+: 295 |
TABLE 23
| PEx | PSyn | Str | DAT |
|---|---|---|---|
| 94 | 37 | | APCI/ESI+: 373 |

TABLE 23-continued
| PEx | PSyn | Str | DAT |
|---|---|---|---|
| 95 | 35 | 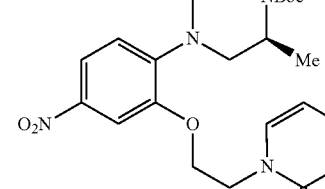 | APCI/ESI+: 473 |
| 96 | 27 | 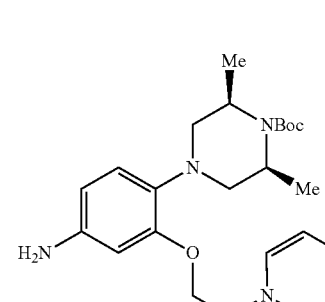 | APCI/ESI+: 443 |
| 97 | 23 | 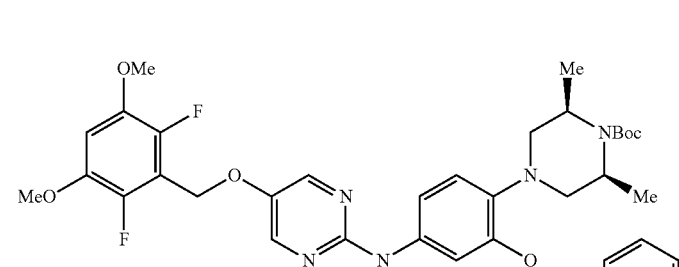 | ESI+: 723 |
TABLE 24
| PEx | PSyn | Str | DAT |
|---|---|---|---|
| 98 | 30 | 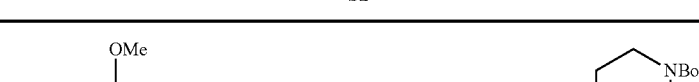 | ESI+: 688 |

TABLE 24-continued
| PEx | PSyn | Str | DAT |
|---|---|---|---|
| 99 | 30 | 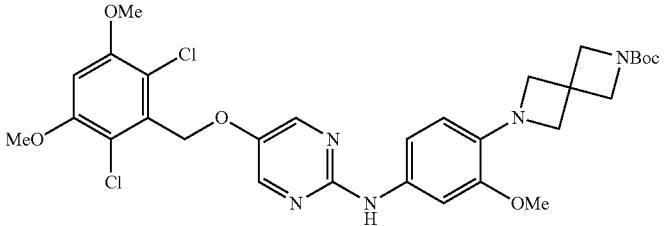 [SMILES: COc1cc(Nc2ncc(OCc3c(Cl)c(OC)cc(OC)c3Cl)cn2)ccc1N1CC2(CN(C(=O)OC(C)(C)C)C2)C1] | ESI+: 632 |
| 100 | 13 | 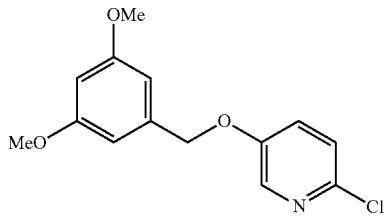 [SMILES: COc1cc(COc2ccc(Cl)nc2)cc(OC)c1] | APCI/ESI+: 280 |
| 101 | 2 | 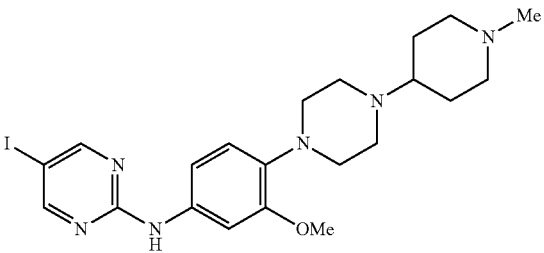 [SMILES: COc1cc(Nc2ncc(I)cn2)ccc1N1CCN(C2CCN(C)CC2)CC1] | APCI/ESI+: 509 |
| 102 | 2 | 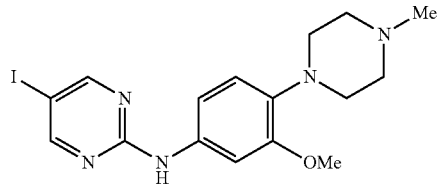 [SMILES: COc1cc(Nc2ncc(I)cn2)ccc1N1CCN(C)CC1] | APCI/ESI+: 426 |
| 103 | 2 | 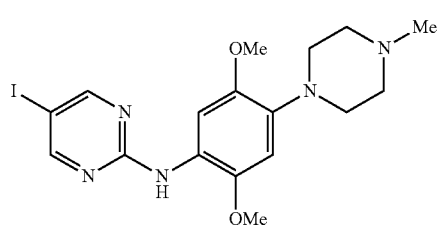 [SMILES: COc1cc(N2CCN(C)CC2)c(OC)cc1Nc1ncc(I)cn1] | APCI/ESI+: 456 |
TABLE 25
| PEx | PSyn | Str | DAT |
|---|---|---|---|
| 104 | 32 | 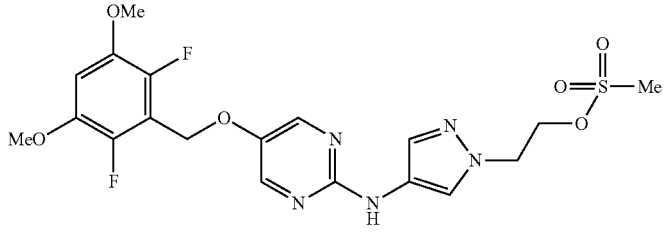 [SMILES: COc1cc(OC)c(F)c(COc2cnc(Nc3cnn(CCOS(C)(=O)=O)c3)nc2)c1F] | APCI/ESI+: 486 |

TABLE 25-continued
| PEx | PSyn | Str | DAT |
|---|---|---|---|
| 105 | 23 | 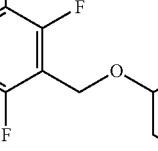 | APCI/ESI+: 448 |
| 106 | 41 | | APCI/ESI+: 478 |
| 107 | 19 | | ESI+: 317 |
| 108 | 32 | | APCI/ESI+: 462 |
TABLE 26
| PEx | PSyn | Str | DAT |
|---|---|---|---|
| 109 | 23 | 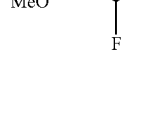 | APCI/ESI+: 545 |
| 110 | 31 | | APCI/ESI+: 501 |

TABLE 26-continued

| PEx | PSyn | Str | DAT |
|-----|------|-----|-----|
| 111 | 111 | | NMR2: 1.50 (9H, s), 1.72-1.81 (2H, m), 1.95-2.24 (6H, m), 4.32-4.49 (2H, m), 4.61-4.72 (1H, m), 8.06 (1H, s), 8.12 (1H, s) |
| 112 | 27 | | NMR2: 1.49 (9H, s), 1.71-1.81 (2H, m), 1.90-2.12 (6H, m), 2.87 (2H, brs), 4.20-4.45 (2H, m), 4.50-4.61 (1H, m), 6.98 (1H, s), 7.12 (1H, s) |

TABLE 27

| PEx | PSyn | Str | DAT |
|-----|------|-----|-----|
| 113 | 23 | | APCI/ESI+: 605 |
| 114 | 23 | | APCI/ESI+: 523 |
| 115 | 23 | | APCI/ESI+: 547 |
| 116 | 23 | | ESI+: 557 |

TABLE 27-continued
| PEx | PSyn | Str | DAT |
|---|---|---|---|
| 117 | 23 | 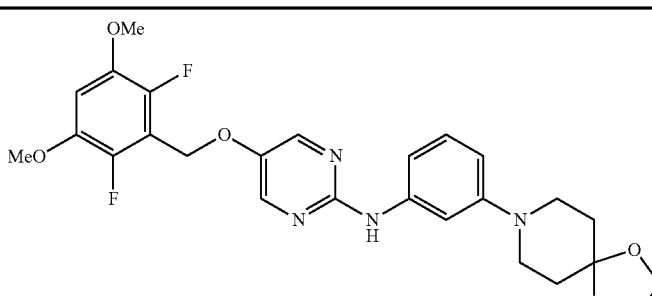 | APCI/ESI+: 515 |
TABLE 28
| PEx | PSyn | Str | DAT |
|---|---|---|---|
| 118 | 118 | | APCI/ESI+: 223 |
| 119 | 27 | | APCI/ESI+: 193 |
| 120 | 23 | | APCI/ESI+: 558 |
| 121 | 23 | | APCI/ESI+: 576 |
| 122 | 23 | | APCI/ESI+: 614 |

TABLE 28-continued
| PEx | PSyn | Str | DAT |
|---|---|---|---|
| 123 | 23 | 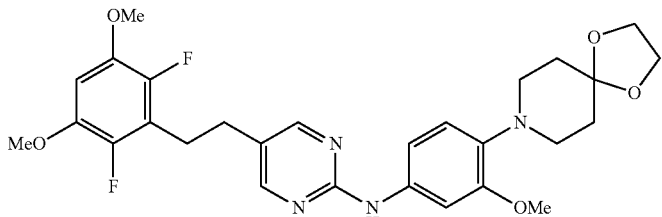 | APCI/ESI+: 543 |
TABLE 29
| PEx | PSyn | Str | DAT |
|---|---|---|---|
| 124 | 31 | 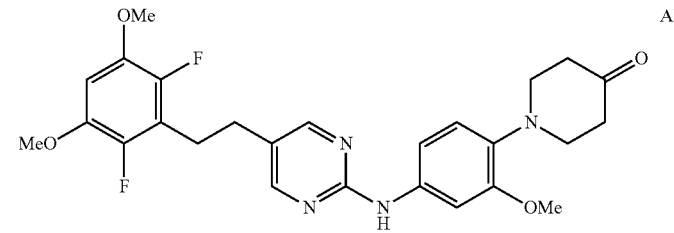 | APCI/ESI+: 499 |
| 125 | 24 | 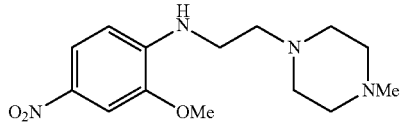 | APCI/ESI+: 295 |
| 126 | 17 | 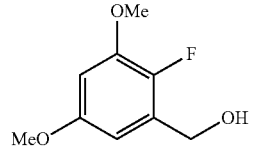 [SMILES: COc1cc(CO)c(F)c(OC)c1] | NMR2: 1.74-1.80 (1H, m), 3.79 (3H, s), 3.86 (3H, s), 4.74 (2H, dd, J = 6.2, 1.2 Hz), 6.47 (1H, dd, J = 7.0, 3.0 Hz), 6.51 (1H, dd, J = 4.8, 3.0 Hz) |
| 127 | 23 | 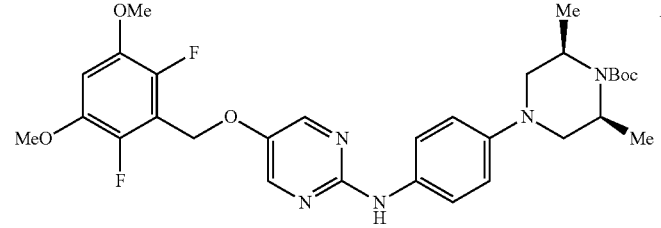 | APCI/ESI+: 586 |
| 128 | 35 | 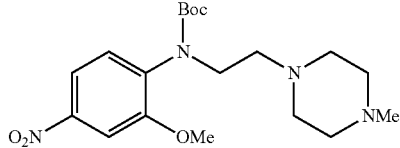 | APCI/ESI+: 395 |
| 129 | 27 | 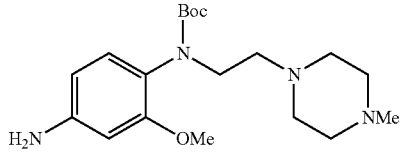 [SMILES: COc1cc([N+](=O)[O-])ccc1N(CCN1CCN(C)CC1)C(=O)OC(C)(C)C] | APCI/ESI+: 365 |

TABLE 30

| PEx | PSyn | Str | DAT |
|---|---|---|---|
| 130 | 27 | | APCI/ESI+: 265 |
| 131 | 18 | | NMR2: 3.01 (3H, s), 3.79 (3H, s), 3.87 (3H, s), 5.26 (2H, d, J = 1.6 Hz), 6.47 (1H, dd, J = 4.7, 3.0 Hz), 6.57 (1H, d, J = 7.0, 3.0 Hz) |
| 132 | 19 | | APCI/ESI+: 299 |
| 133 | 133 | | APCI/ESI+: 279 |
| 134 | 31 | | APCI/ESI+: 471 |

TABLE 31

| PEx | PSyn | Str | DAT |
|---|---|---|---|
| 135 | 23 | | APCI/ESI+: 450 |

TABLE 31-continued
| PEx | PSyn | Str | DAT |
|---|---|---|---|
| 136 | 23 | 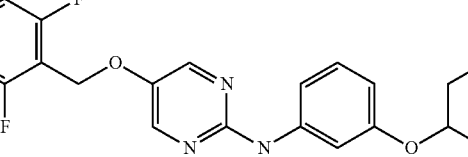 | APCI/ESI+: 573 |
| 137 | 23 | 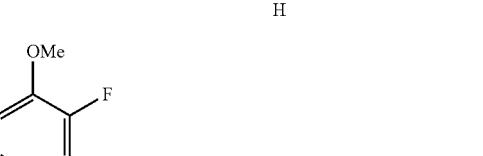 | APCI/ESI+: 545 |
| 138 | 138 | 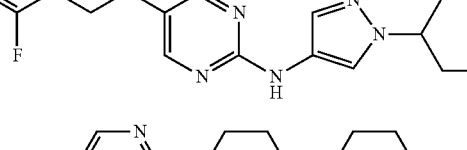 | APCI/ESI+: 307 |
| 139 | 27 | 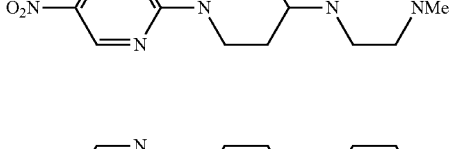 | APCI/ESI+: 277 |
| 140 | 27 | 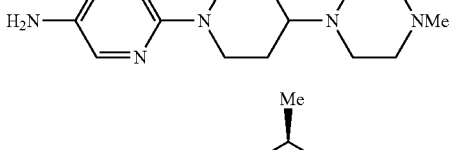 | APCI/ESI+: 208 |
TABLE 32
| PEx | PSyn | Str | DAT |
|---|---|---|---|
| 141 | 24 | | APCI/ESI+: 320 |
| 142 | 27 | | APCI/ESI+: 290 |
| 143 | 143 | | ESI+: 184 |

TABLE 32-continued
| PEx | PSyn | Str | DAT |
|---|---|---|---|
| 144 | 144 |  | ESI+: 198 |
| 145 | 145 | | ESI+: 255 |
| 146 | 189 | | ESI+: 671 |
| 147 | 40 | | APCI/ESI+: 507 |
TABLE 33
| PEx | PSyn | Str | DAT |
|---|---|---|---|
| 148 | 27 | * 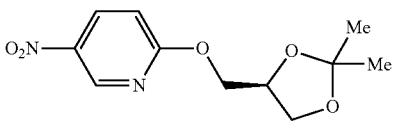 [SMILES: CC1(C)OC[C@@H](COc2ccc([N+](=O)[O-])cn2)O1] | APCI/ESI+: 225 |
| 149 | 143 | 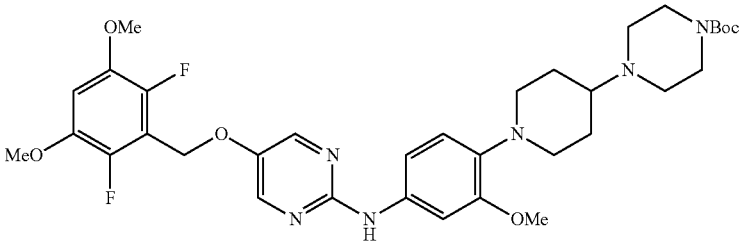 [SMILES: COc1cc(Nc2ncc(OCc3c(F)c(OC)cc(OC)c3F)cn2)ccc1N1CCC(N2CCN(C(=O)OC(C)(C)C)CC2)CC1] | APCI/ESI+: 197 |
| 150 | 23 | * 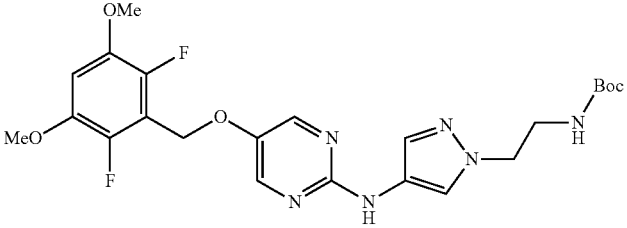 [SMILES: COc1cc(OC)c(F)c(COc2cnc(Nc3cnn(CCNC(=O)OC(C)(C)C)c3)nc2)c1F] | APCI/ESI+: 505 |

TABLE 33-continued

| PEx | PSyn | Str | DAT |
|---|---|---|---|
| 151 | 40 | (structure) | ESI+: 575 |
| 152 | 152 | * (structure) | ESI+: 255 |
| 153 | 27 | * (structure) | ESI+: 225 |
| 154 | 152 | (structure) | ESI+: 303 |

TABLE 34

| PEx | PSyn | Str | DAT |
|---|---|---|---|
| 155 | 27 | (structure) | ESI+: 273 |
| 156 | 24 | (structure) | APCI/ESI+: 336 |
| 157 | 27 | (structure) | APCI/ESI+: 306 |

TABLE 34-continued

| PEx | PSyn | Str | DAT |
|---|---|---|---|
| 158 | 40 | | APCI/ESI+: 464 |
| 159 | 40 | | APCI/ESI+: 464 |
| 160 | 40 | | APCI/ESI+: 478 |

TABLE 35

| PEx | PSyn | Str | DAT |
|---|---|---|---|
| 161 | 40 | | APCI/ESI+: 464 |
| 162 | 162 | | ESI+: 576 |
| 163 | 23 | | APCI/ESI+: 505 |

TABLE 35-continued
| PEx | PSyn | Str | DAT |
|---|---|---|---|
| 164 | 111 | 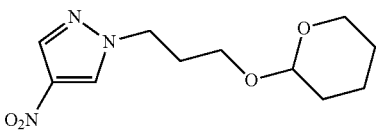 | ESI+: 256 |
| 165 | 152 | 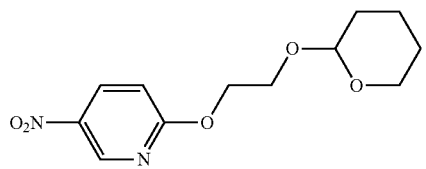 | ESI+: 269 |
| 166 | 27 | 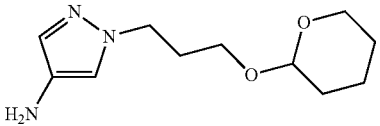 [SMILES: O=[N+]([O-])c1cnn(CCCOC2CCCCO2)c1] | ESI+: 226 |
TABLE 36
| PEx | PSyn | Str | DAT |
|---|---|---|---|
| 167 | 27 | 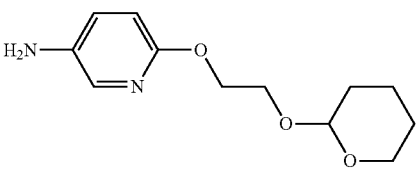 [SMILES: Nc1ccc(OCCOC2CCCCO2)nc1] | APCI/ESI+: 155(-THP) |
| 168 | 23 | 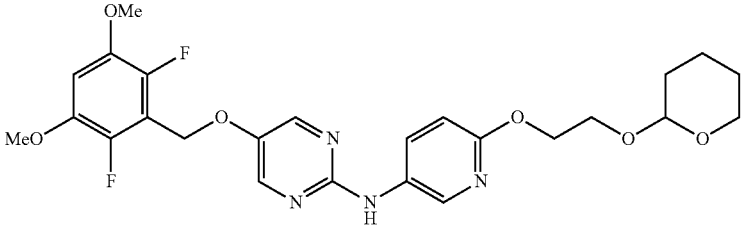 [SMILES: COc1cc(OC)c(F)c(COc2cnc(Nc3ccc(OCCOC4CCCCO4)nc3)nc2)c1F] | APCI/ESI+: 519 |
| 169 | 23 | 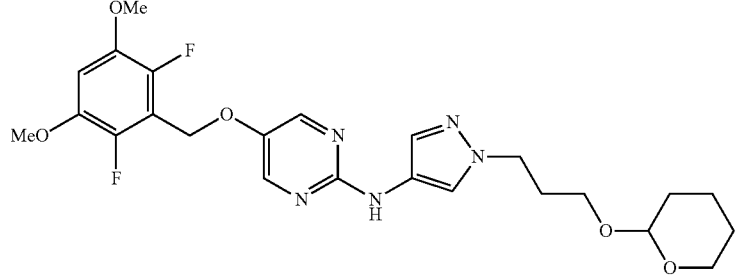 [SMILES: COc1cc(OC)c(F)c(COc2cnc(Nc3cnn(CCCOC4CCCCO4)c3)nc2)c1F] | ESI+: 506 |
| 170 | 23 | 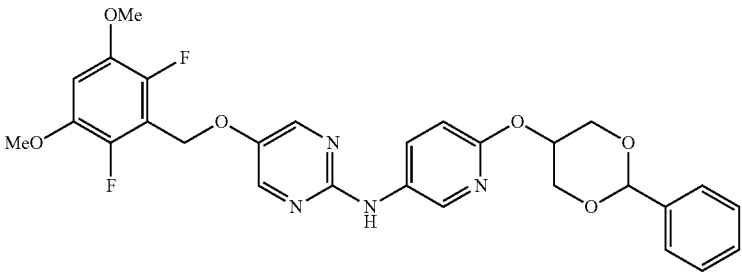 [SMILES: COc1cc(OC)c(F)c(COc2cnc(Nc3ccc(OC4COC(c5ccccc5)OC4)nc3)nc2)c1F] | APCI/ESI+: 553 |

TABLE 36-continued
| PEx | PSyn | Str | DAT |
|---|---|---|---|
| 171 | 23 | 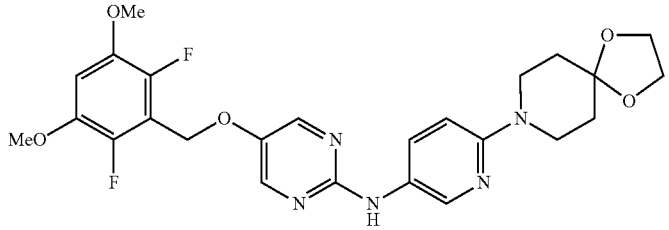 [SMILES: COc1cc(OC)c(F)c(COc2cnc(Nc3ccc(N4CCC5(CC4)OCCO5)nc3)nc2)c1F] | APCI/ESI+: 516 |
TABLE 37
| PEx | PSyn | Str | DAT |
|---|---|---|---|
| 172 | 32 | | ESI+: 500 |
| 173 | 31 | | APCI/ESI+: 472 |
| 174 | 40 | | ESI+: 561 |
| 175-1 | 175 | | APCI/ESI+: 226 |
| 175-2 | 175 | | APCI/ESI+: 226 |

TABLE 37-continued
| PEx | PSyn | Str | DAT |
|---|---|---|---|
| 176 | 176 | 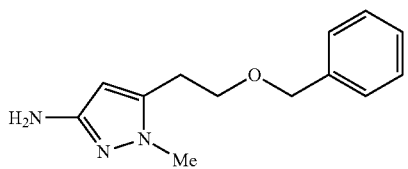 [SMILES: Cn1nc(N)cc1CCOCc1ccccc1] | ESI+: 232 |
TABLE 38
| PEx | PSyn | Str | DAT |
|---|---|---|---|
| 177 | 23 | 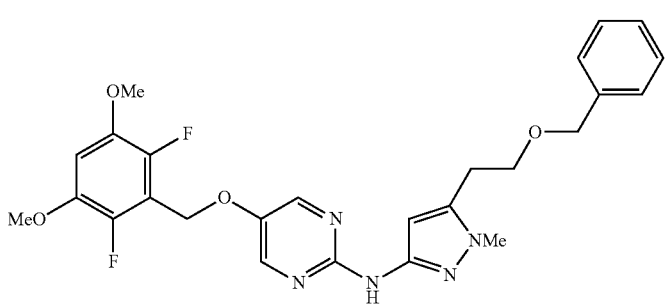 [SMILES: COc1cc(OC)c(F)c(COc2cnc(Nc3cc(CCOCc4ccccc4)n(C)n3)nc2)c1F] | ESI+: 512 |
| 178 | 23 | 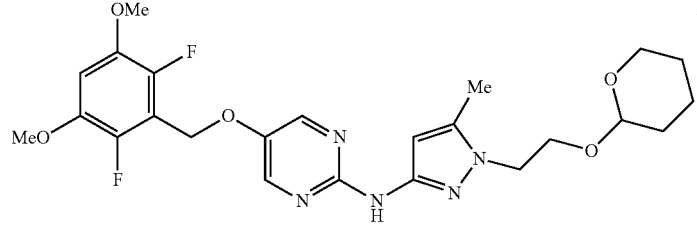 [SMILES: COc1cc(OC)c(F)c(COc2cnc(Nc3cc(C)n(CCOC4CCCCO4)n3)nc2)c1F] | APCI/ESI+: 506 |
| 179 | 23 | 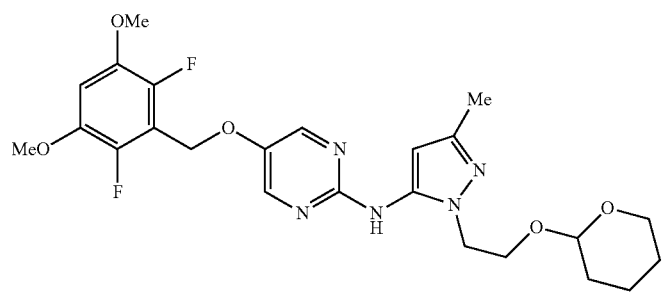 [SMILES: COc1cc(OC)c(F)c(COc2cnc(Nc3cc(C)nn3CCOC3CCCCO3)nc2)c1F] | APCI/ESI+: 506 |
| 180 | 23 | 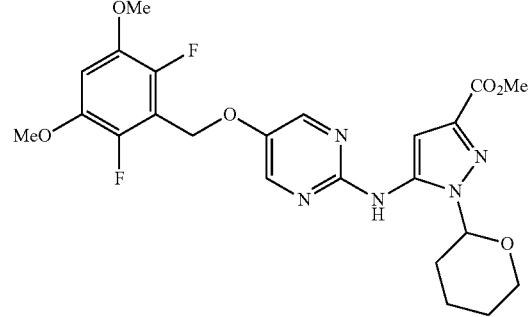 [SMILES: COC(=O)c1cc(Nc2ncc(OCc3c(F)c(OC)cc(OC)c3F)cn2)n(C2CCCCO2)n1] | APCI/ESI+: 506 |

TABLE 39

| PEx | PSyn | Str | DAT |
|---|---|---|---|
| 181 | 23 | (structure) | APCI/ESI+: 450 |
| 182 | 27 | (structure) | ESI+: 226 |
| 183 | 183 | (structure) | APCI/ESI+: 242 |
| 184 | 27 | (structure) | APCI/ESI+: 212 |
| 185 | 23 | (structure) | APCI/ESI+: 492 |
| 186 | 186 | (structure) | APCI/ESI+: 276 |
| 187 | 27 | (structure) | APCI/ESI+: 246 |

TABLE 40
| PEx | PSyn | Str | DAT |
|---|---|---|---|
| 188 | 23 | 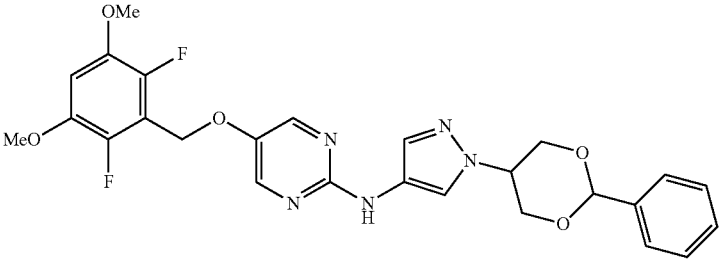 [SMILES: COc1cc(OC)c(F)c(COc2cnc(Nc3cnn(C4COC(c5ccccc5)OC4)c3)nc2)c1F] | APCI/ESI+: 526 |
| 189 | 189 | 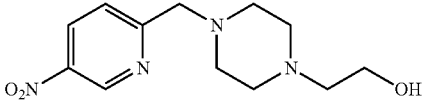 | APCI/ESI+: 267 |
| 190 | 27 | 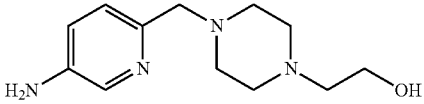 [SMILES: O=[N+]([O-])c1ccc(CN2CCN(CCO)CC2)nc1] | APCI/ESI+: 237 |
| 191 | 191 | 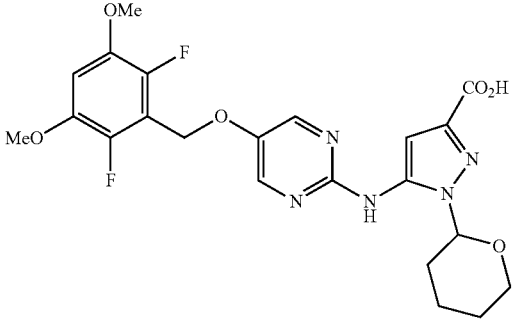 [SMILES: COc1cc(OC)c(F)c(COc2cnc(Nc3cc(C(=O)O)nn3C3CCCCO3)nc2)c1F] | APCI/ESI−: 490 |
| 192 | 27 + 23 | 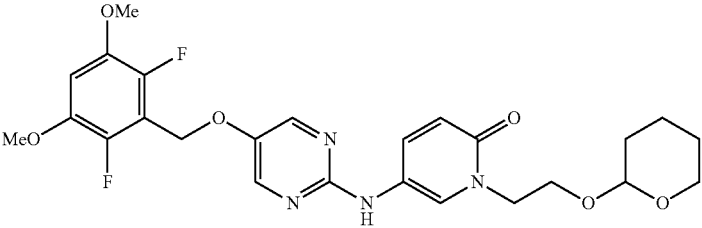 [SMILES: COc1cc(OC)c(F)c(COc2cnc(Nc3ccc(=O)n(CCOC4CCCCO4)c3)nc2)c1F] | APCI/ESI+: 435(-THP) |
TABLE 41
| PEx | PSyn | Str | DAT |
|---|---|---|---|
| 193 | 193 | 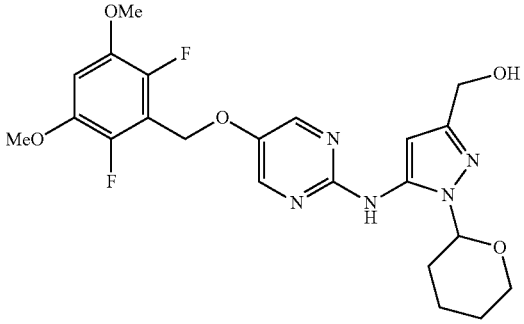 [SMILES: COc1cc(OC)c(F)c(COc2cnc(Nc3cc(CO)nn3C3CCCCO3)nc2)c1F] | APCI/ESI+: 478 |

TABLE 41-continued

| PEx | PSyn | Str | DAT |
|---|---|---|---|
| 194 | 175 | (structure) | APCI/ESI+: 239 |
| 195 | 32 | (structure) | NMR2: 2.96(3 H, s), 3.85(3H, s), 3.89(6H, s), 5.16 (2H, s), 5.25(2 H, s), 6.68(1H, t, J = 8.0 Hz), 6.91 (1H, s), 7.63(1H, brs), 8.24(2H, s) |
| 196 | 193 | (structure) | APCI/ESI+: 158 |
| 197 | 214 | (structure) | NMR1: 4.22(3 H, s), 7.77(1H, s), 9.91(1H, s) |
| 198 | 144 | (structure) | APCI/ESI+: 211 |

TABLE 42

| PEx | PSyn | Str | DAT |
|---|---|---|---|
| 199 | 27 | (structure) | APCI/ESI+: 181 |
| 200 | 23 | (structure) | ESI+: 519 |
| 201 | 201 | (structure) | ESI+: 212 |
| 202 | 202 | (structure) | ESI+: 184 |

TABLE 42-continued

| PEx | PSyn | Str | DAT |
|---|---|---|---|
| 203 | 23 | (structure) | ESI+: 464 |
| 204 | 204 | (structure) | APCI/ESI+: 327 |
| 205 | 205 | (structure) | ESI+: 225 |

TABLE 43

| PEx | PSyn | Str | DAT |
|---|---|---|---|
| 206 | 205 | (structure) | ESI+: 225 |
| 207 | 23 | (structure) | ESI+: 505 |
| 208 | 23 | (structure) | ESI+: 505 |
| 209 | 209 | (structure) | APCI/ESI+: 412 |

TABLE 43-continued
| PEx | PSyn | Str | DAT |
|---|---|---|---|
| 210 | 210 | 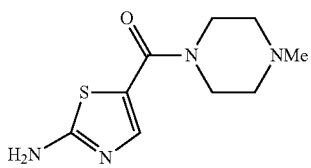 [SMILES: CN1CCN(C(=O)c2cnc(N)s2)CC1] | APCI/ESI+: 227 |
TABLE 44
| PEx | PSyn | Str | DAT |
|---|---|---|---|
| 211 | 211 | | NMR2: 1.36-1.94(9H, m), 1.99-2.07(1H, m), 2.09-2.20(1H, m), 2.35-2.54(1H, m), 3.44-3.75(2H, m), 3.78-4.04(2H, m), 4.51-4.72(2H, m), 4.78-4.90(1H, m), 5.52-5.65(1H, m), 6.87-6.94(1H, m) |
| 212 | 27 | | NMR2: 1.31-1.94(10H, m), 2.00-2.11(1H, m), 2.29-2.44(1H, m), 3.27-3.77(4H, m), 3.81-3.97(1H, m), 4.00-4.11(1H, m), 4.47-4.59(1H, m), 4.61-4.73(2H, m), 5.20-5.33(1H, m), 5.66(1H, s) |
| 213 | 23 | | APCI/ESI+: 562 |
| 214 | 214 | | APCI/ESI+: 392 |

TABLE 45

| PEx | PSyn | Str | DAT |
|---|---|---|---|
| 215 | 214 | | APCI/ESI+: 406 |
| 216 | 204 | | APCI/ESI+: 324 |
| 217 | 27 | | APCI/ESI+: 294 |
| 218 | 23 | | APCI/ESI+: 574 |

TABLE 46

| PEx | PSyn | Str | DAT |
|---|---|---|---|
| 219 | 32 | | ESI+: 500 |

TABLE 46-continued

| PEx | PSyn | Str | DAT |
|---|---|---|---|
| 220 | 27 | H2N-C6H3(OMe)-N(azetidine-oxetane spiro) | ESI+: 221 |
| 221 | 24 | O2N-C6H3(OMe)-N(azetidine-oxetane spiro) | ESI+: 251 |
| 222 | 27 | H2N-C6H3(OMe)-N(piperidine)-NH-CH(Me)-CH(Me)(OH)* | ESI+: 294 |
| 223 | 28 | O2N-C6H3(OMe)-N(piperidine)-NH-CH(Me)-CH(Me)(OH)* | ESI+: 324 |
| 224 | 24 | O2N-C6H3(OMe)-N(piperidin-4-one) | NMR2: 2.64(4 H, t, J = 6.0 Hz), 3.54(4H, t, J = 6.0 Hz), 3.99(3H, s), 6.93(1H, d, J = 8.8 Hz), 7.75(1H, d, J = 2.4 Hz), 7.88 (1H, dd, J = 8.8, 2.4 Hz) |

TABLE 47

| PEx | PSyn | Str | DAT |
|---|---|---|---|
| 225 | 27 | H2N-C6H3(OMe)-N(piperidine)-NH-CH(iPr)-CH(Me)(OH)* | ESI+: 322 |
| 226 | 28 | O2N-C6H3(OMe)-N(piperidine)-NH-CH(iPr)-CH(Me)(OH)* | ESI+: 352 |
| 227 | 13 | 2,5-di(OMe)-3-Cl-6-F-benzyl-O-(2-chloropyrimidin-5-yl) | EI: 332 |

TABLE 47-continued

| PEx | PSyn | Str | DAT |
|---|---|---|---|
| 228 | 18 | 2-chloro-6-fluoro-3,5-dimethoxybenzyl methanesulfonate | EI: 298 |
| 229 | 229 | (2-chloro-6-fluoro-3,5-dimethoxyphenyl)methanol | EI: 220 |
| 230 | 30 | pyrimidine derivative with NBoc-azabicyclic and methoxyaniline | ESI+: 613 |

30

TABLE 48

| PEx | PSyn | Str | DAT |
|---|---|---|---|
| 231 | 27 | H₂N-aryl-OMe with NBoc-azabicyclic | ESI+: 333 |
| 232 | 232 | O₂N-aryl-OMe with NBoc-azabicyclic (alkene) | ESI+: 361 |
| 233 | 27 | H₂N-aryl-OMe-piperidine-NH-CMe₂-OH | ESI+: 294 |
| 234 | 28 | O₂N-aryl-OMe-piperidine-NH-CMe₂-OH | ESI+: 324 |

TABLE 48-continued

| PEx | PSyn | Str | DAT |
|---|---|---|---|
| 235 | 30 | (structure) | ESI+: 616 |
| 236 | 27 | (structure) | ESI+: 294 |
| 237 | 28 | (structure) | ESI+: 324 |

TABLE 49

| PEx | PSyn | Str | DAT |
|---|---|---|---|
| 238 | 32 | (structure) | ESI+: 580 |
| 239 | 27 | (structure) * | ESI+: 336 |
| 240 | 28 | (structure) * | ESI+: 366 |
| 241 | 27 | (structure) | EI: 248 |
| 242 | 24 | (structure) | ESI+: 279 |

TABLE 49-continued
| PEx | PSyn | Str | DAT |
|---|---|---|---|
| 243 | 30 | 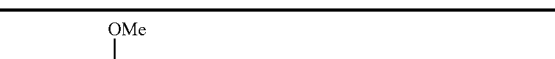 | ESI+: 588 |
TABLE 50
| PEx | PSyn | Str | DAT |
|---|---|---|---|
| 244 | 19 | | NMR2: 3.94(6H, s), 5.35(2H, s), 6.62(1H, s), 7.24 (1H, d, J = 8.8 Hz), 7.31(1H, dd, J = 8.8, 3.2 Hz), 8.16(1H, d, J = 3.2 Hz) |
| 245 | 30 | | ESI+: 680 |
| 246 | 27 | | ESI+: 400 |
| 247 | 30 | | ESI+: 430 |
| 248 | 19 | | NMR2: 3.94(6H, s), 5.63(2H, s), 6.63(1H, s), 8.02 (1H, s), 8.15(1H, s) |

TABLE 51
| PEx | PSyn | Str | DAT |
|---|---|---|---|
| 249 | 30 | 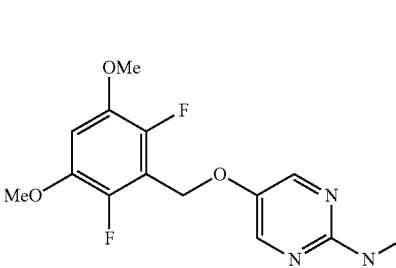 | ESI+: 714 |
| 250 | 27 | 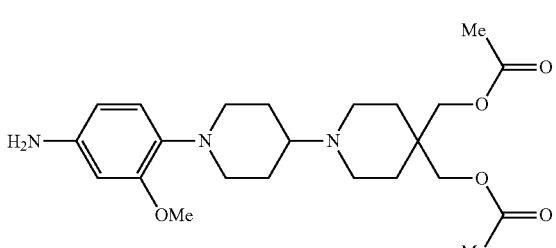 | NMR2: 1.93-1.96(6H, m), 2.06-2.09(2H, m), 2.08 (6H, s), 2.54-2.60 (3H, m), 2.95-2.97 (4H, m), 3.42-3.45 (2H, m), 3.81(3H, s), 4.06(4H, s), 6.22-6.26(2H, m), 6.74 (1H, d, J = 8.0 Hz) |
| 251 | 24 | 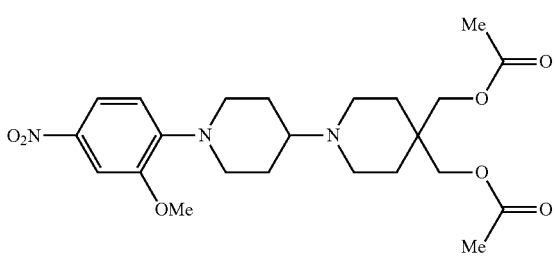 [SMILES: COc1cc(N)ccc1N1CCC(N2CCC(COC(C)=O)(COC(C)=O)CC2)CC1] | ESI+: 464 |
| 252 | 252 | 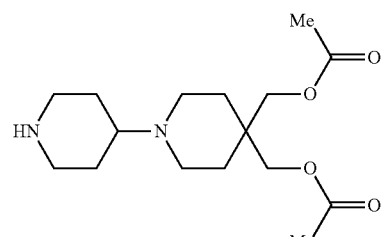 | ESI+: 313 |
TABLE 52
| PEx | PSyn | Str | DAT |
|---|---|---|---|
| 253 | 28 |  | ESI+: 413 |

TABLE 52-continued
| PEx | PSyn | Str | DAT |
|---|---|---|---|
| 254 | 252 | 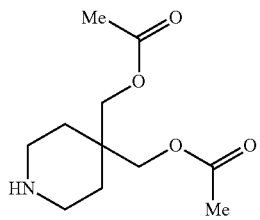 [SMILES: CC(=O)OCC1(COC(C)=O)CCNCC1] | ESI+: 230 |
| 255 | 255 | 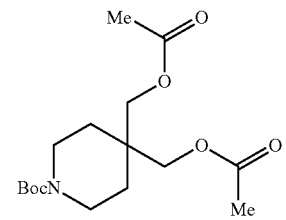 | NMR2: 1.46-1.52(13H, m), 2.07 (6H, s), 3.40-3.43 (4H, m), 4.03(4H, s) |
| 256 | 27 | 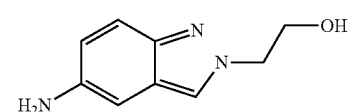 | NMR3: 3.97(2H, t, J = 5.2 Hz), 4.42(2H, t, J = 5.2 Hz), 6.85(1H, dd, J = 2.0, 0.8 Hz), 6.92(1H, dd, J = 8.8, 2.0 Hz), 7.41(1H, dd, J = 8.8, 0.8 Hz), 7.89(1H, d, J = 0.8 Hz) |
TABLE 53
| PEx | PSyn | Str | DAT |
|---|---|---|---|
| 257 | 40 | 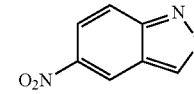 | NMR2: 2.91(1H, t, J = 6.0 Hz), 4.15-4.19(2H, m), 4.61 (2H, t, J = 4.8 Hz), 7.74 (1H, d, J = 9.2 Hz), 8.11(1H, dd, J = 9.2, 2.0 Hz), 8.29 (1H, s), 8.73 (1H, d, J = 2.4 Hz) |
| 258 | 27 | 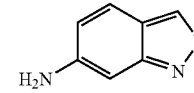 | NMR3: 3.95(2H, t, J = 5.6 Hz), 4.37 (2H, t, J = 5.6 Hz), 6.65(1H, dd, J = 8.8, 2.0 Hz), 6.72 (1H, m), 7.44(1H, dd, J = 8.8, 0.8 Hz), 7.99(1H, s) |
| 259 | 40 | 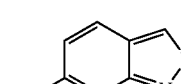 | NMR2: 2.87(1H, t, J = 6.0 Hz), 4.17-4.20(2H, m), 4.62 (2H, t, J = 4.8 Hz), 7.77(1H, dd, J = 9.2, 0.8 Hz), 7.91 (1H, dd, J = 9.2, 2.0 Hz), 8.13(1H, s), 8.67-8.68(1H, m) |
TABLE 54
| PEx | PSyn | Str | DAT |
|---|---|---|---|
| 260 | 30 | 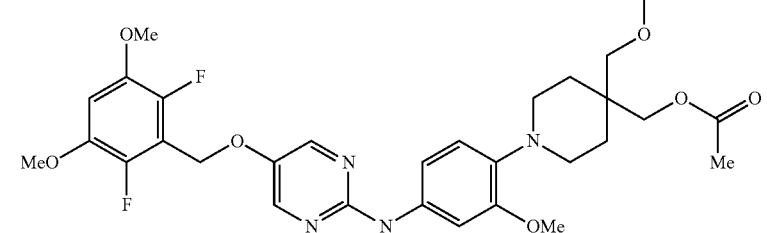 | ESI+: 631 |

TABLE 54-continued

| PEx | PSyn | Str | DAT |
|---|---|---|---|
| 261 | 27 | (structure) | ESI+: 351 |
| 262 | 24 | (structure) | ESI+: 381 |
| 263 | 30 | (structure) | ESI+: 482 |

TABLE 55

| PEx | PSyn | Str | DAT |
|---|---|---|---|
| 264 | 30 | (structure) | ESI+: 522 |
| 265 | 27 | (structure) | ESI+: 264 [M + Na]+ |
| 266 | 19 | (structure) | EI: 271 |

TABLE 55-continued
| PEx | PSyn | Str | DAT |
|---|---|---|---|
| 267 | 30 | 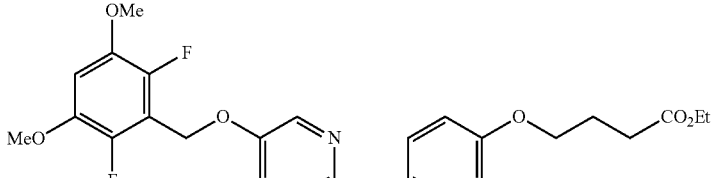 | ESI+: 522 |
| 268 | 27 | 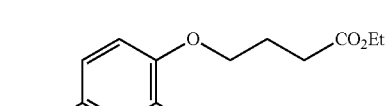 | ESI+: 242 |
| 269 | 30 | 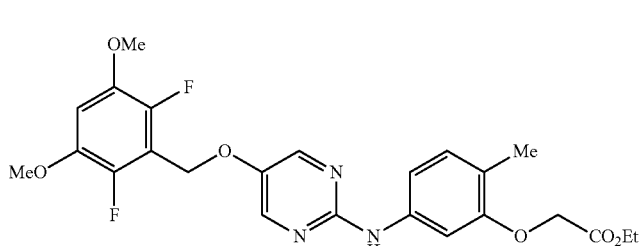 | ESI+: 490 |
TABLE 56
| PEx | PSyn | Str | DAT |
|---|---|---|---|
| 270 | 27 | 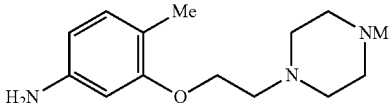 | NMR2: 2.09(3H, s), 2.29 (3H, s), 2.48-2.65(8H, m), 2.83(2H, t, J = 5.6 Hz), 3.54(2H, brs), 4.06 (2H, t, J = 5.6 Hz), 6.20-6.22(2H, m), 6.88(1H, d, J = 8.4 Hz) |
| 271 | 36 | 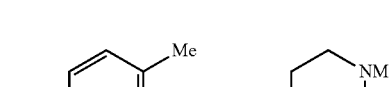 | NMR2: 2.30-2.66(14H, m), 2.89(2H, t, J = 5.4 Hz), 4.19(2H, t, J = 5.6 Hz), 7.24(1H, d, J = 8.0 Hz), 7.66(1H, d, J = 2.0 Hz), 7.75(1H, dd, J = 8.0, 2.0 Hz) |
| 272 | 30 | 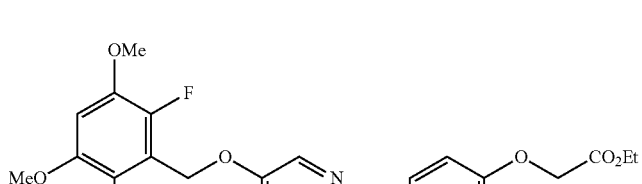 | ESI+: 490 |
TABLE 57
| PEx | PSyn | Str | DAT |
|---|---|---|---|
| 273 | 27 |  | NMR3: 1.75-1.83(2H, m), 1.95-2.01(6H, m), 2.53-2.59 (2H, m), 2.86-2.99(7H, m), 3.81(3H, s), 4.45(4H, s), 6.27(1H, dd, J = 8.4, 2.4 Hz), 6.42(1H, d, J = 2.4 Hz), 6.78(1H, d, J = 8.0 Hz) |

TABLE 57-continued

| PEx | PSyn | Str | DAT |
|---|---|---|---|
| 274 | 24 | O₂N-C₆H₃(OMe)-N(piperidine)-N(spiro-oxetane-piperidine) | NMR2: 1.69-1.79(2H, m), 1.85-1.90(6H, m), 2.43-2.49 (5H, m), 2.67-2.73(2H, m), 3.73-3.76(2H, m), 3.94(3H, s), 4.41(4H, s), 6.87(1H, d, J = 8.8 Hz), 7.69(1H, d, J = 2.4 Hz), 7.84 (1H, dd, J = 8.8, 2.4 Hz). |
| 275 | 252 | HN-piperidine-N-spiro-oxetane | ESI+: 211 |
| 276 | 28 | BocN-piperidine-N-spiro-oxetane | ESI+: 311 |

TABLE 58

| PEx | PSyn | Str | DAT |
|---|---|---|---|
| 277 | 30 | MeO/OMe/F substituted benzyl-O-pyrimidine-NH-C₆H₃(F)-O-(CH₂)₄-Cl | EI: 497 |
| 278 | 27 | H₂N-C₆H₃(F)-O-(CH₂)₄-Cl | EI: 217 |
| 279 | 36 | MeO/OMe/F substituted benzyl-O-pyrimidine-NH-C₆H₃(F)-O-(CH₂)₄-N(piperazine)NBoc | ESI+: 648 |
| 280 | 27 | H₂N-C₆H₄-N(piperidine)-NH-CH₂-CH(OH)-Me | ESI+: 250 |
| 281 | 28 | O₂N-C₆H₄-N(piperidine)-NH-CH₂-CH(OH)-Me | ESI+: 280 |

TABLE 58-continued
| PEx | PSyn | Str | DAT |
|---|---|---|---|
| 282 | 30 | | ESI+: 518 |
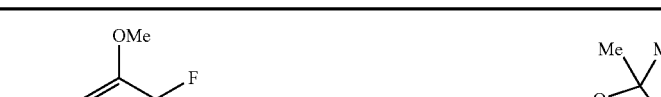
TABLE 59
| PEx | PSyn | Str | DAT |
|---|---|---|---|
| 283 | 27 | | ESI+: 238 |
| 284 | 19 | | EI: 267 |
| 285 | 27 | | ESI+: 197 |
| 286 | 30 | | ESI+: 506 |
| 287 | 27 | | ESI+: 264 |
| 288 | 28 | | ESI+: 294 |
| 289 | 30 | | ESI+: 631 |

TABLE 60

| PEx | PSyn | Str | DAT |
|---|---|---|---|
| 290 | 27 | (structure) | NMR2: 1.14-1.16(2H, m), 1.45(9H, s), 1.63-1.87(5H, m), 2.70-2.71 (2H, m), 3.48-3.49(2H, m), 3.81 (3H, s), 3.95-4.07(4H, m), 6.21 (1H, dd, J = 8.0, 2.4 Hz), 6.30(1H, d, J = 2.4 Hz), 6.71(1H, d, J = 8.4 Hz) |
| 291 | 13 | (structure) | NMR2: 1.18-1.22(2H, m), 1.48(9H, s), 1.59(2H, br-s), 1.69-1.75(3H, m), 1.82-1.87(2H, m), 2.71-2.73 (2H, m), 3.95(3H, s), 4.16(2H, t, J = 6.4 Hz), 6.89(1H, d, J = 8.8 Hz), 7.74(1H, d, J = 2.4 Hz), 7.89 (1H, dd, J = 8.8, 2.4 Hz) |
| 292 | 19 | (structure) | NMR2: 2.22(3H, s), 3.89(3H, s), 3.93(3H, s), 5.33(2H, s), 6.57 (1H, s), 8.37(2H, s) |
| 293 | 18 | (structure) | EI: 294 |

TABLE 61

| PEx | PSyn | Str | DAT |
|---|---|---|---|
| 294 | 229 | (structure) | NMR2: 1.85(1H, t, J = 6.4 Hz), 2.26(3H, s), 3.84(3H, s), 3.90(3H, s), 4.86(2H, d, J = 6.4 Hz), 6.49(1H, s) |
| 295 | 295 | (structure) | ESI+: 310 |
| 296 | 296 | (structure) | ESI+: 220 |

TABLE 61-continued
| PEx | PSyn | Str | DAT |
|---|---|---|---|
| 297 | 27 | 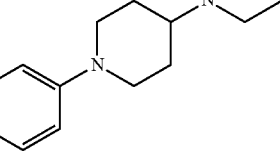 | ESI+: 336 |
| 298 | 35 | 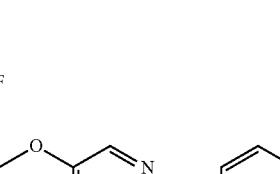 | ESI+: 366 |
TABLE 62
| PEx | PSyn | Str | DAT |
|---|---|---|---|
| 299 | 28 | 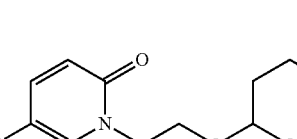 | ESI+: 266 |
| 300 | 23 | | APCI/ESI+: 558 |
| 301 | 175 | | APCI/ESI−: 268 |
| 302 | 23 |  | ESI+: 476 |

TABLE 62-continued

| PEx | PSyn | Str | DAT |
|---|---|---|---|
| 303 | 24 | 4-methoxy-1-(4-methoxy-2-nitrophenyl)piperidine structure | ESI+: 267 |
| 304 | 27 | 4-(4-methoxypiperidin-1-yl)-3-methoxyaniline structure | ESI+: 237 |

TABLE 63

| Ex | Str |
|---|---|
| 1 | Structure with 3,5-dimethoxyphenyl ethynyl pyrimidine linked via NH to methoxyphenyl-piperidine-N-methylpiperazine |
| 2 | Structure with 3,5-dimethoxyphenethyl pyrimidine linked via NH to methoxyphenyl-piperidine-N-methylpiperazine |
| 3 | Structure with 2,6-dichloro-3,5-dimethoxyphenyl ethynyl pyrimidine linked via NH to methoxyphenyl-piperidine-N-methylpiperazine |

TABLE 63-continued
| Ex | Str |
|---|---|
| 4 | 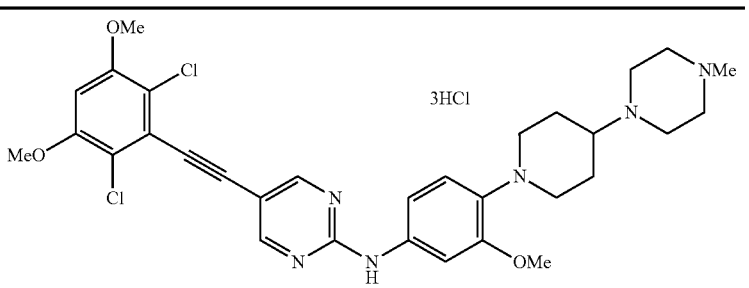 |
| 5 | 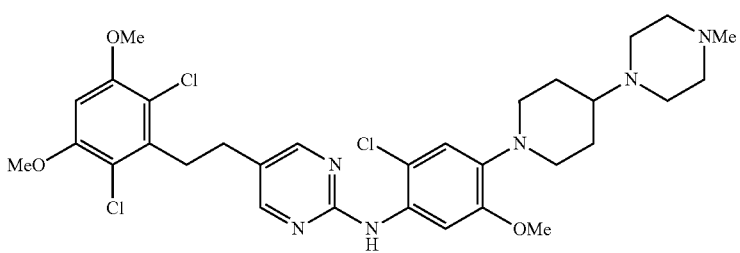 [SMILES: COc1cc(Nc2ncc(CCc3c(Cl)c(OC)cc(OC)c3Cl)cn2)c(Cl)cc1N1CCC(N2CCN(C)CC2)CC1] |
TABLE 63
| Ex | Str |
|---|---|
| 6 | 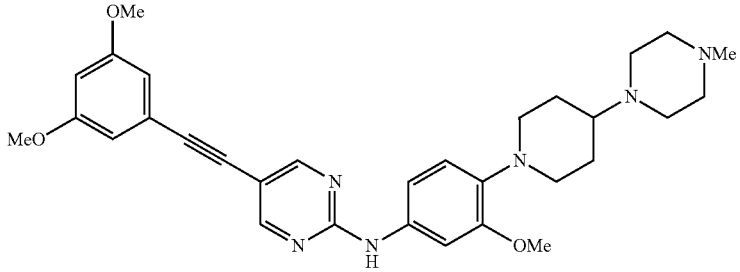 [SMILES: COc1cc(C#Cc2cnc(Nc3ccc(N4CCC(N5CCN(C)CC5)CC4)c(OC)c3)nc2)cc(OC)c1] |
| 7 | 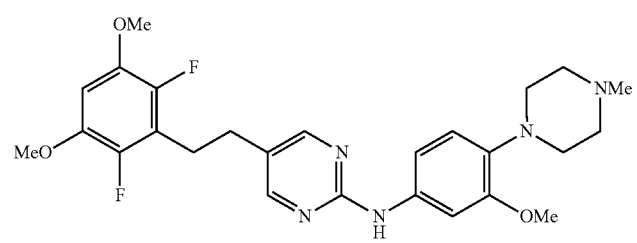 [SMILES: COc1cc(Nc2ncc(CCc3c(F)c(OC)cc(OC)c3F)cn2)ccc1N1CCN(C)CC1] |
| 8 | 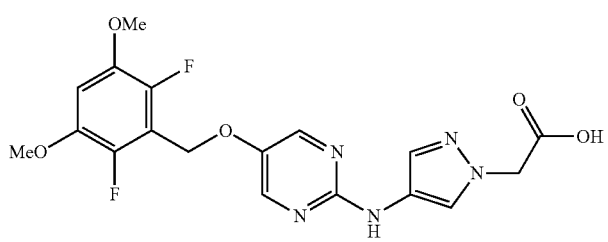 [SMILES: COc1cc(OC)c(F)c(COc2cnc(Nc3cnn(CC(=O)O)c3)nc2)c1F] |

TABLE 63-continued

| Ex | Str |
|---|---|
| 9 | (structure) |
| 10 | (structure) |
| 11 | (structure) |

TABLE 65

| Ex | Str |
|---|---|
| 12 | (structure) |
| 13 | (structure) |

TABLE 65-continued

| Ex | Str |
|---|---|
| 14 | (structure: 2,5-dichloro-3,6-dimethoxybenzyl ether of pyrimidine-NH-pyrazole-piperidine-CH2-C(Me)2-OH) |
| 15 | (structure: 2,5-dichloro-3,6-dimethoxybenzyl ether of pyrimidine-NH-pyrazole-piperidine-N-C(O)-cyclopropyl) |
| 16 | (structure: 2,5-dichloro-3,6-dimethoxybenzyl ether of pyrimidine-NH-pyrazole-piperidine-CH2CH2-OMe) |

TABLE 66

| Ex | Str |
|---|---|
| 17 | (structure: 2,3,5,6-tetrafluorobenzyl ether of pyrimidine-NH-(1-methyl-pyrazole-3-carboxylic acid)) |
| 18 | (structure: 2,3,5,6-tetrafluorobenzyl ether of pyrimidine-NH-(1-methyl-pyrazole-3-C(O)-4-methylpiperazine)) |

TABLE 66-continued

| Ex | Str |
|---|---|
| 19 | |
| 20 | |
| 21 | |

TABLE 67

| Ex | Str |
|---|---|
| 22 | |
| 23 | |
| 24 | |

TABLE 67-continued

| Ex | Str |
|---|---|
| 25 | (structure: 3,5-dimethoxy-2,6-difluorophenyl-ethynyl-pyrimidine-NH-(3-methoxy-4-(4-(4-methylpiperazin-1-yl)piperidin-1-yl)phenyl)) |
| 26 | (structure: 3,5-dimethoxy-2,6-difluorophenyl-ethynyl-pyrimidine-NH-(3-methoxy-4-(4-(4-methylpiperazin-1-yl)piperidin-1-yl)phenyl), 3HCl) |

TABLE 68

| Ex | Str |
|---|---|
| 27 | (structure: 3,5-dimethoxy-2,6-difluorophenyl-ethyl-pyrimidine-NH-(3-methoxy-4-(4-(4-methylpiperazin-1-yl)piperidin-1-yl)phenyl)) |
| 28 | (structure: 3,5-dimethoxy-2,6-difluorophenyl-ethyl-pyrimidine-NH-(2,5-dimethoxy-4-(4-(4-methylpiperazin-1-yl))phenyl), 2HCl) |
| 29 | (structure: 3,5-dimethoxy-2,6-difluorophenyl-ethynyl-pyrimidine-NH-(3-methoxy-4-(4-(1-methylpiperidin-4-yl)piperazin-1-yl)phenyl)) |

TABLE 68-continued

| Ex | Str |
|---|---|
| 30 | (structure: 3,6-dimethoxy-2,5-difluorophenyl-ethynyl-pyrimidin-2-yl-NH-(3-methoxy-4-(4-methylpiperazin-1-yl)phenyl)) |
| 31 | (structure: 3,6-dimethoxy-2,5-difluorophenyl-ethynyl-pyrimidin-2-yl-NH-(2,5-dimethoxy-4-(4-methylpiperazin-1-yl)phenyl)) |

TABLE 69

| Ex | Str |
|---|---|
| 32 | (structure: 3,6-dimethoxy-2,5-difluorophenyl-ethynyl-pyrimidin-2-yl-NH-(3-fluoro-4-(4-(4-methylpiperazin-1-yl)piperidin-1-yl)phenyl)) |
| 33 | (structure: 3,6-dimethoxy-2,5-difluorophenyl-ethyl-pyrimidin-2-yl-NH-(3-fluoro-4-(4-(4-methylpiperazin-1-yl)piperidin-1-yl)phenyl)) |
| 34 | (structure: 3,6-dimethoxy-2,5-difluorophenyl-ethynyl-pyrimidin-2-yl-NH-(2-methoxy-4-(4-(4-methylpiperazin-1-yl)piperidin-1-yl)phenyl)) |

TABLE 69-continued
| Ex | Str |
|---|---|
| 35 | 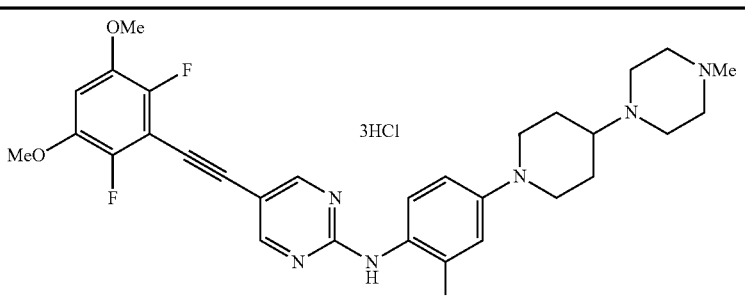 |
| 36 | 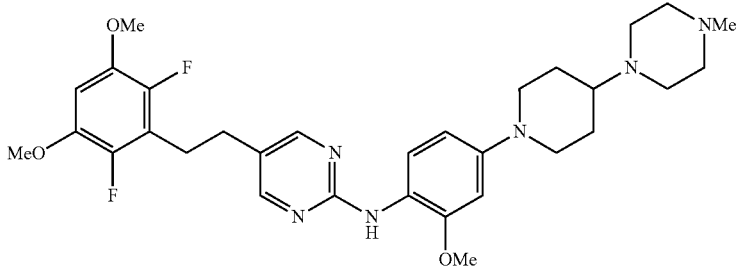 [SMILES: COc1cc(N2CCC(N3CCN(C)CC3)CC2)ccc1Nc1ncc(CCc2c(F)c(OC)cc(OC)c2F)cn1] |
TABLE 70
| Ex | Str |
|---|---|
| 37 | 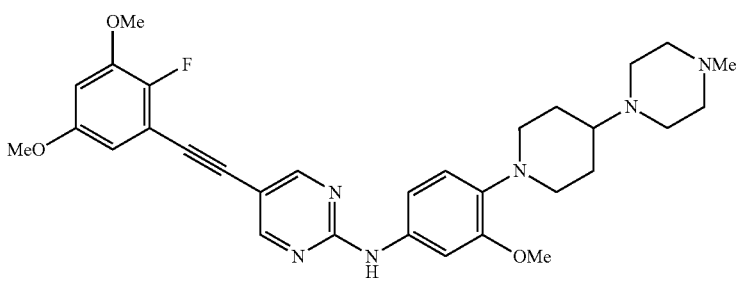 [SMILES: COc1cc(C#Cc2cnc(Nc3ccc(N4CCC(N5CCN(C)CC5)CC4)c(OC)c3)nc2)c(F)c(OC)c1] |
| 38 | 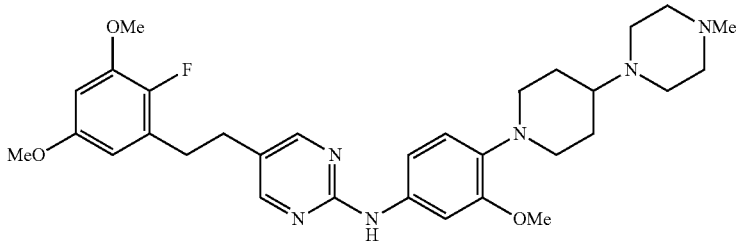 [SMILES: COc1cc(CCc2cnc(Nc3ccc(N4CCC(N5CCN(C)CC5)CC4)c(OC)c3)nc2)c(F)c(OC)c1] |
| 39 | 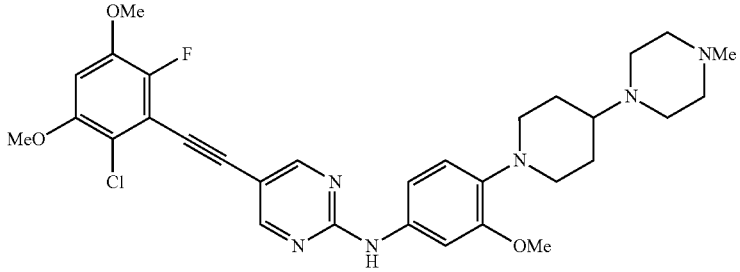 |

TABLE 70-continued
| Ex | Str |
|---|---|
| 40 | 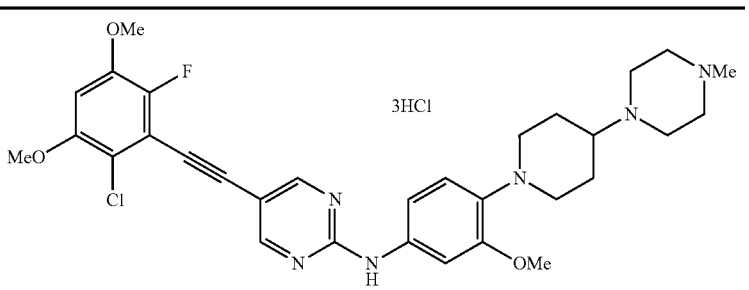 |
| 41 | 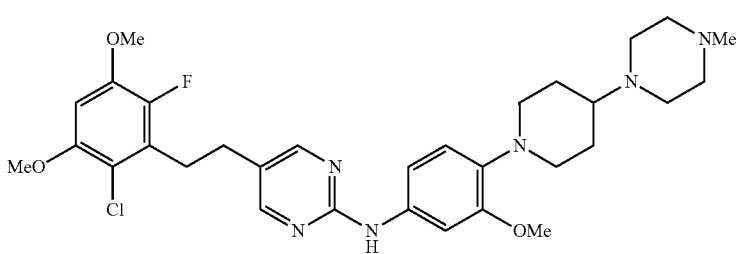 |
TABLE 71
| Ex | Str |
|---|---|
| 42 | 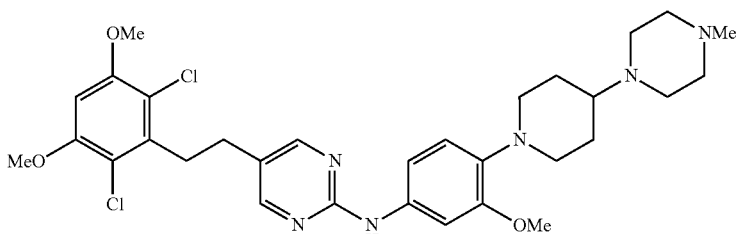 |
| 43 | 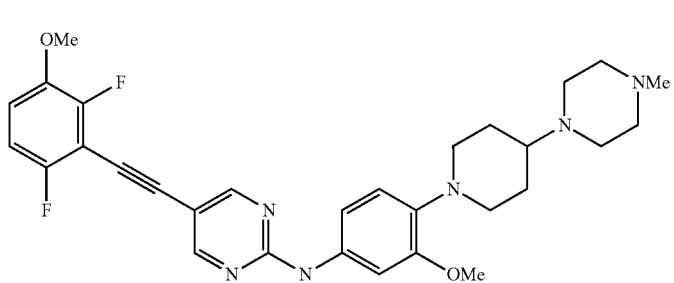 |
| 44 | 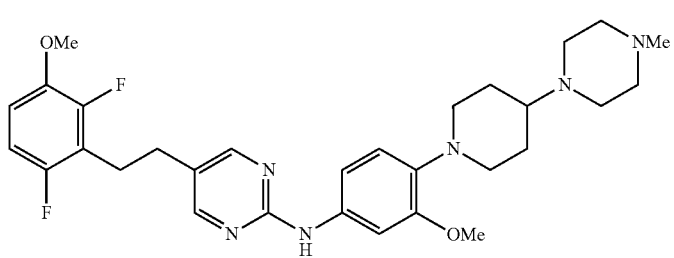 [SMILES: COc1cc(Nc2ncc(CCc3c(F)ccc(OC)c3F)cn2)ccc1N1CCC(N2CCN(C)CC2)CC1] |

TABLE 71-continued

| Ex | Str |
|---|---|
| 45 | (structure) |
| 46 | (structure) |

TABLE 72

| Ex | Str |
|---|---|
| 47 | (structure) |
| 48 | (structure) |
| 49 | (structure) |

TABLE 72-continued

| Ex | Str |
|---|---|
| 50 | |
| 51 | |

TABLE 73

| Ex | Str |
|---|---|
| 52 | |
| 53 | |
| 54 | |

TABLE 73-continued
| Ex | Str |
|---|---|
| 55 | 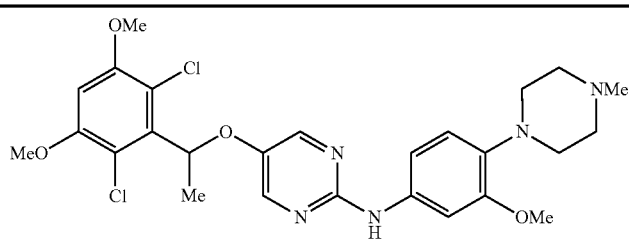 |
| 56 | 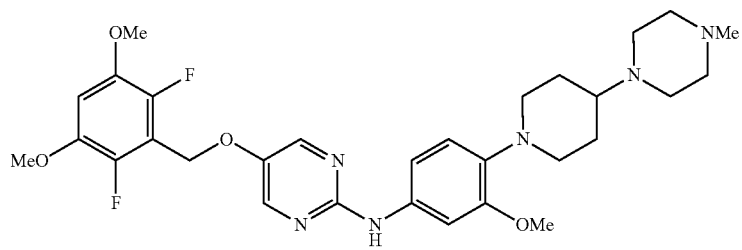 |
TABLE 74
| Ex | Str |
|---|---|
| 57 | 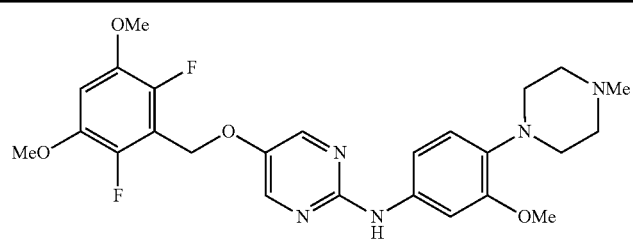 |
| 58 | 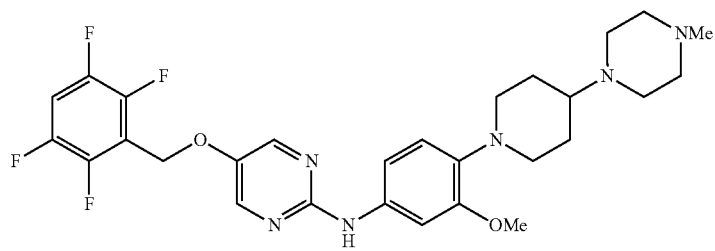 [SMILES: COc1cc(Nc2ncc(OCc3c(F)c(F)cc(F)c3F)cn2)ccc1N1CCC(N2CCN(C)CC2)CC1] |
| 59 | 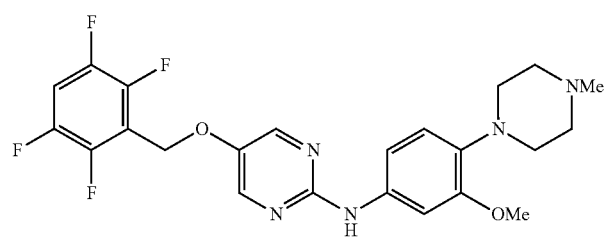 [SMILES: COc1cc(Nc2ncc(OCc3c(F)c(F)cc(F)c3F)cn2)ccc1N1CCN(C)CC1] |

TABLE 74-continued
| Ex | Str |
|---|---|
| 60 | 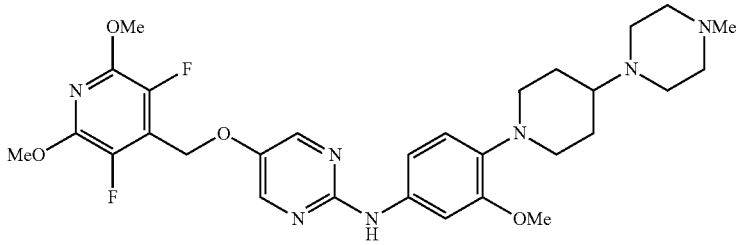 [SMILES: COc1cc(Nc2ncc(OCc3c(F)c(OC)nc(OC)c3F)cn2)ccc1N1CCC(N2CCN(C)CC2)CC1] |
| 61 | 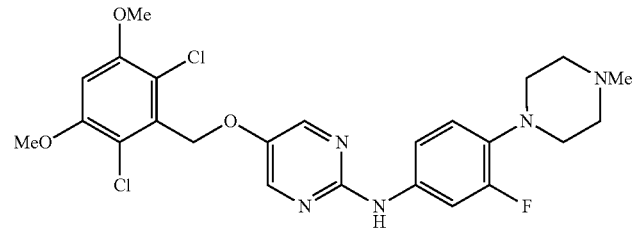 [SMILES: COc1cc(OC)c(Cl)c(COc2cnc(Nc3ccc(N4CCN(C)CC4)c(F)c3)nc2)c1Cl] |
TABLE 75
| Ex | Str |
|---|---|
| 62 | 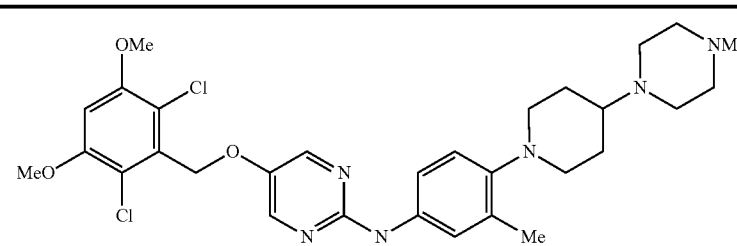 |
| 63 | 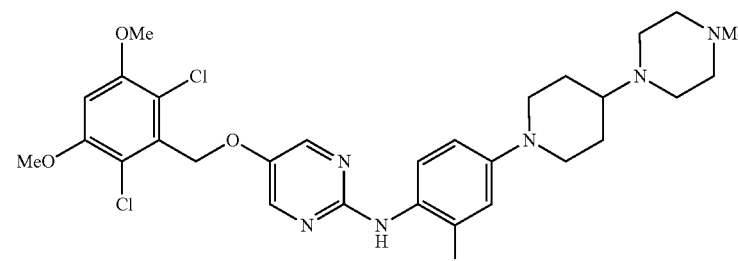 |
| 64 | 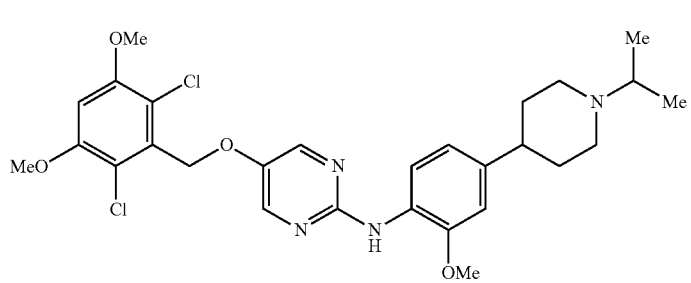 [SMILES: COc1cc(C2CCN(C(C)C)CC2)ccc1Nc1ncc(OCc2c(Cl)c(OC)cc(OC)c2Cl)cn1] |

TABLE 75-continued

| Ex | Str |
|---|---|
| 65 | |
| 66 | |

TABLE 76

| Ex | Str |
|---|---|
| 67 | |
| 68 | |
| 69 | |

TABLE 76-continued
| Ex | Str |
|---|---|
| 70 | 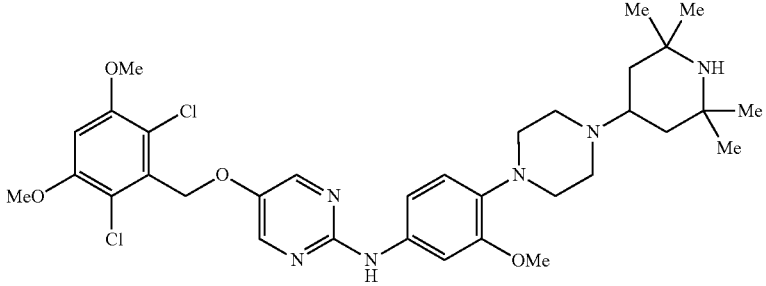 [SMILES: COc1cc(Nc2ncc(OCc3c(Cl)c(OC)cc(OC)c3Cl)cn2)ccc1N1CCN(C2CC(C)(C)NC(C)(C)C2)CC1] |
| 71 | 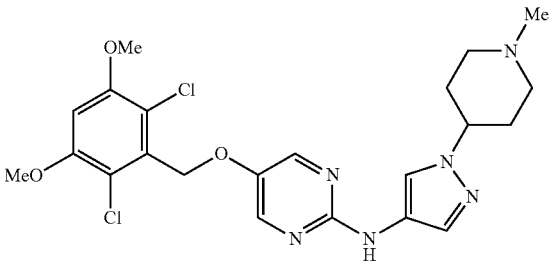 [SMILES: COc1cc(OC)c(Cl)c(COc2cnc(Nc3cnn(C4CCN(C)CC4)c3)nc2)c1Cl] |
TABLE 77
| Ex | Str |
|---|---|
| 72 | 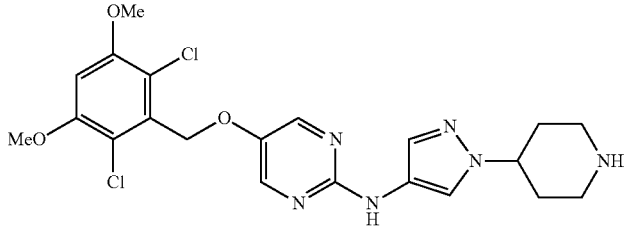 [SMILES: COc1cc(OC)c(Cl)c(COc2cnc(Nc3cnn(C4CCNCC4)c3)nc2)c1Cl] |
| 73 | 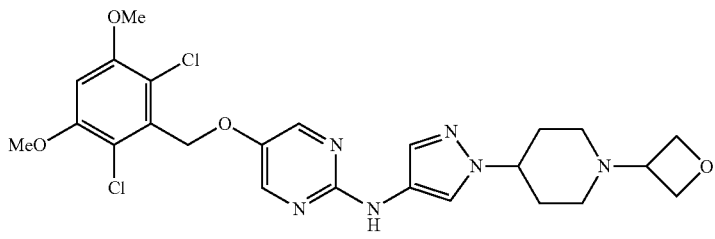 [SMILES: COc1cc(OC)c(Cl)c(COc2cnc(Nc3cnn(C4CCN(C5COC5)CC4)c3)nc2)c1Cl] |
| 74 | 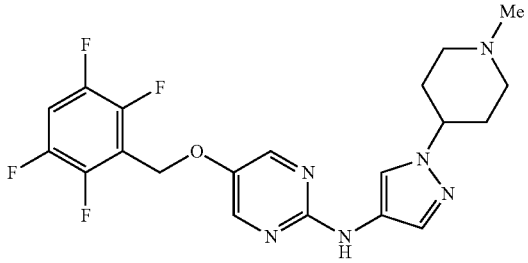 [SMILES: CN1CCC(n2cc(Nc3ncc(OCc4c(F)c(F)cc(F)c4F)cn3)cn2)CC1] |

TABLE 77-continued

| Ex | Str |
|---|---|
| 75 | (structure) |
| 76 | (structure) |

TABLE 78

| Ex | Str |
|---|---|
| 77 | (structure) |
| 78 | (structure) |
| 79 | (structure) |

TABLE 78-continued

| Ex | Str |
|---|---|
| 80 | (structure) |
| 81 | (structure) |

TABLE 79

| Ex | Str |
|---|---|
| 82 | (structure) |
| 83 | (structure) |

197
198
TABLE 79-continued
| Ex | Str |
|---|---|
| 84 | 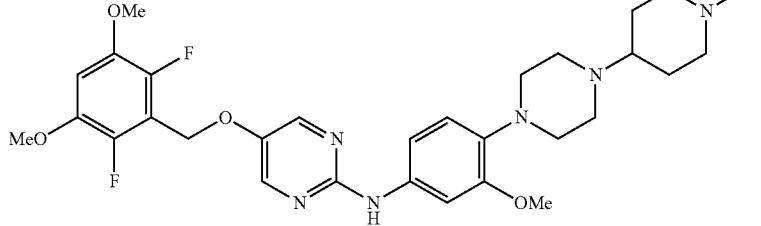 |
| 85 | 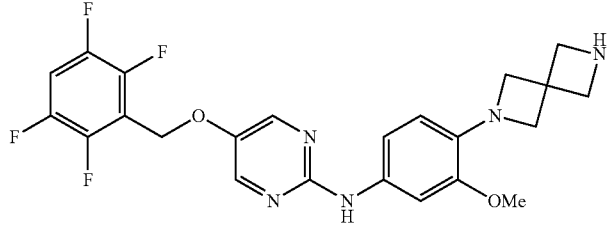 [SMILES: COc1cc(Nc2ncc(OCc3c(F)c(F)cc(F)c3F)cn2)ccc1N1CC2(CNC2)C1] |
TABLE 80
| Ex | Str |
|---|---|
| 86 | 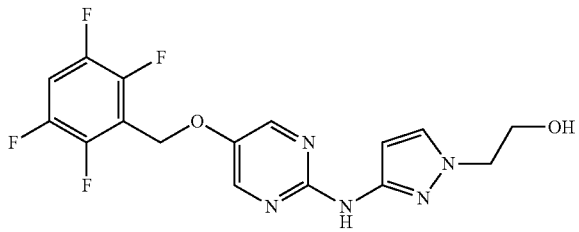 [SMILES: OCCn1ccc(Nc2ncc(OCc3c(F)c(F)cc(F)c3F)cn2)n1] |
| 87 | 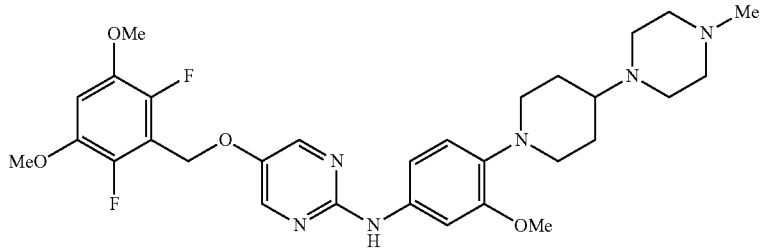 [SMILES: COc1cc(Nc2ncc(OCc3c(F)c(OC)cc(OC)c3F)cn2)ccc1N1CCC(N2CCN(C)CC2)CC1] |
| 88 | 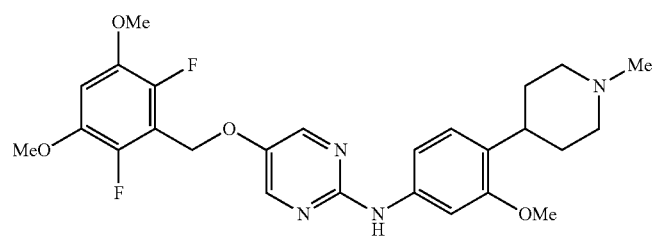 [SMILES: COc1cc(Nc2ncc(OCc3c(F)c(OC)cc(OC)c3F)cn2)ccc1C1CCN(C)CC1] |

TABLE 80-continued

| Ex | Str |
|---|---|
| 89 | (structure) |
| 90 | (structure) |

TABLE 81

| Ex | Str |
|---|---|
| 91 | (structure) |
| 92 | (structure) |
| 93 | (structure) |

TABLE 81-continued

| Ex | Str |
|---|---|
| 94 | (structure) |
| 95 | (structure) |

TABLE 82

| Ex | Str |
|---|---|
| 96 | (structure) |
| 97 | (structure) |
| 98 | (structure) |
| 99 | (structure) |

TABLE 82-continued
| Ex | Str |
|----|-----|
| 100 | 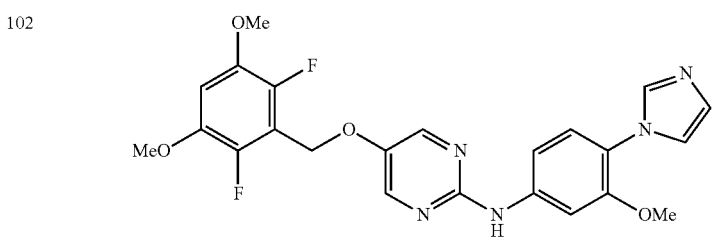 |
15
TABLE 83
| Ex | Str |
|----|-----|
| 101 | 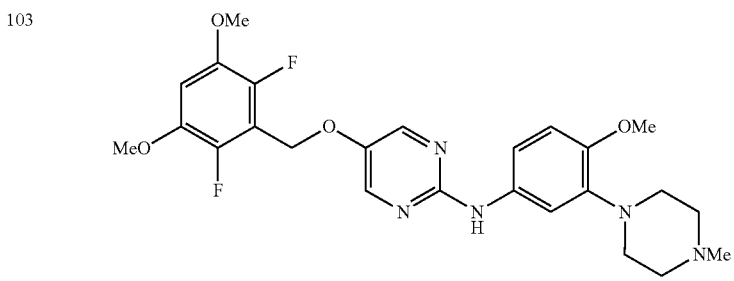 * |
| 102 | |
| 103 | 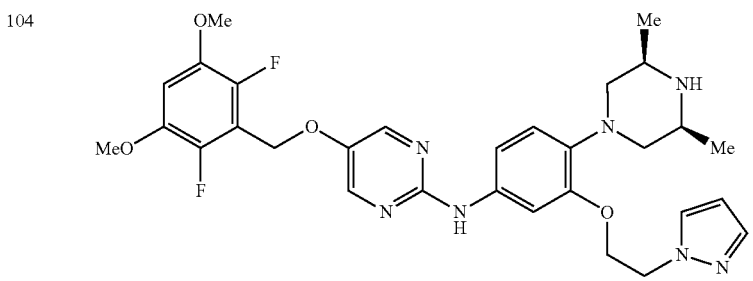 |
| 104 | |

TABLE 83-continued

| Ex | Str |
|---|---|
| 105 | (structure) |

TABLE 84

| Ex | Str |
|---|---|
| 106 | (structure) |
| 107 | (structure) |
| 108 | (structure) |
| 109 | (structure) |

TABLE 84-continued

| Ex | Str |
|---|---|
| 110 | |

TABLE 85

| Ex | Str |
|---|---|
| 111 | |
| 112 | |
| 113 | |
| 114 | |

TABLE 85-continued
| Ex | Str |
|---|---|
| 115 | 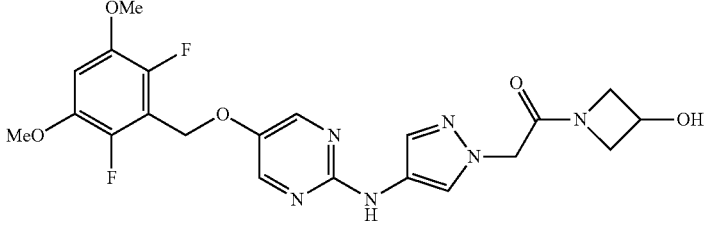 [SMILES: COc1cc(OC)c(F)c(COc2cnc(Nc3cnn(CC(=O)N4CC(O)C4)c3)nc2)c1F] |
TABLE 86
| Ex | Str |
|---|---|
| 116 | |
| 117 | |
| 118 | |
| 119 | |

TABLE 86-continued
| Ex | Str |
|---|---|
| 120 | 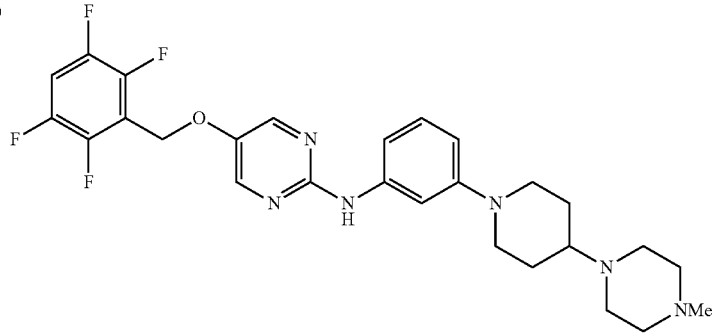 |
TABLE 87
| Ex | Str |
|---|---|
| 121 | 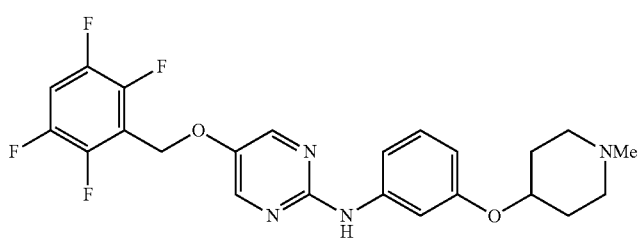 [SMILES: CN1CCC(Oc2cccc(Nc3ncc(OCc4c(F)c(F)cc(F)c4F)cn3)c2)CC1] |
| 122 | 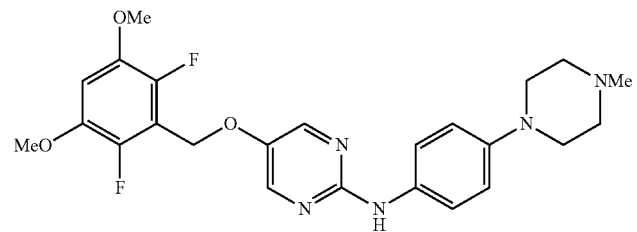 |
| 123 | 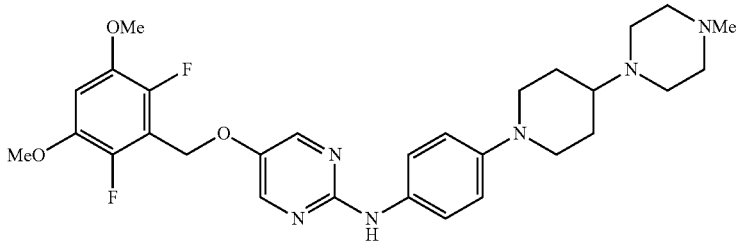 [SMILES: COc1cc(OC)c(F)c(COc2cnc(Nc3ccc(N4CCC(N5CCN(C)CC5)CC4)cc3)nc2)c1F] |
| 124 | 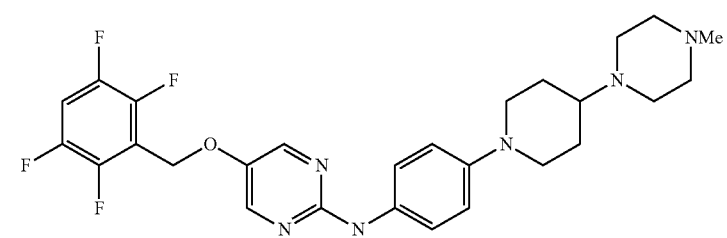 |

TABLE 87-continued
| Ex | Str |
|---|---|
| 125 | 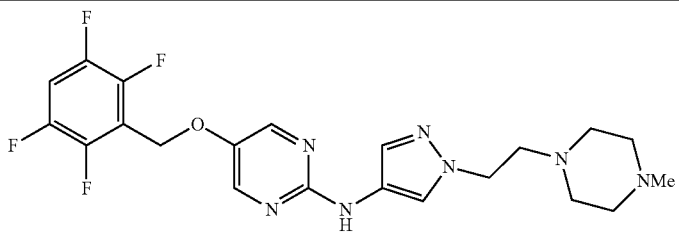 |
TABLE 88
| Ex | Str |
|---|---|
| 126 | 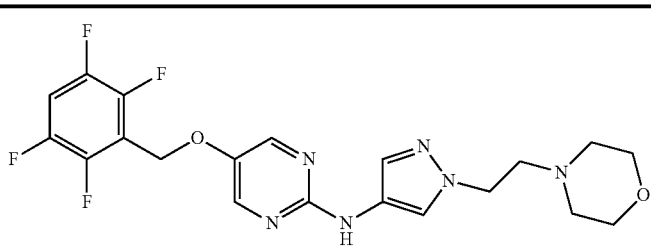 |
| 127 | 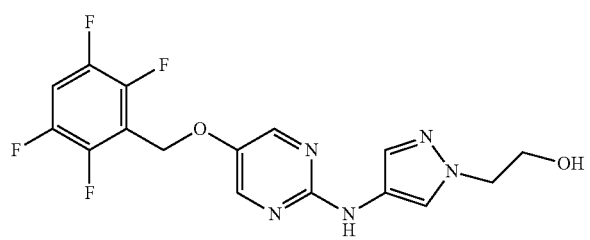 [SMILES: OCCn1cc(Nc2ncc(OCc3c(F)c(F)cc(F)c3F)cn2)cn1] |
| 128 | 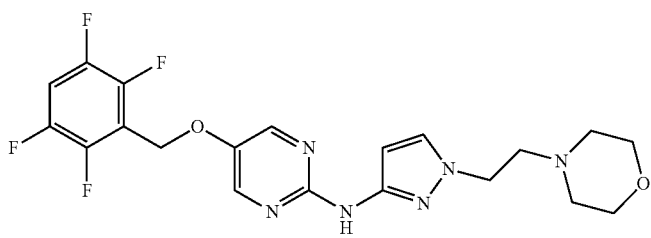 [SMILES: Fc1cc(F)c(F)c(COc2cnc(Nc3ccn(CCN4CCOCC4)n3)nc2)c1F] |
| 129 | 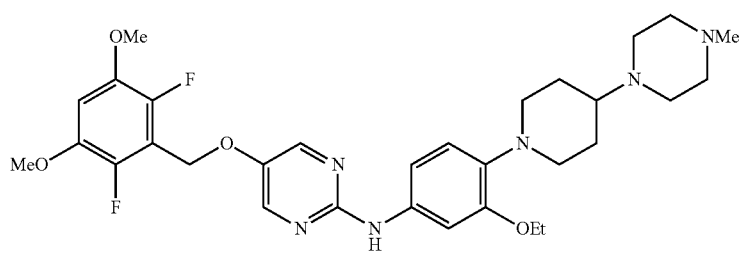 [SMILES: CCOc1cc(Nc2ncc(OCc3c(F)c(OC)cc(OC)c3F)cn2)ccc1N1CCC(N2CCN(C)CC2)CC1] |

TABLE 88-continued
| Ex | Str |
|---|---|
| 130 | 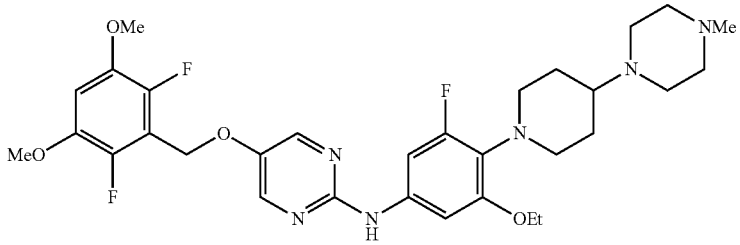 [SMILES: CCOc1cc(Nc2ncc(OCc3c(F)c(OC)cc(OC)c3F)cn2)cc(F)c1N1CCC(N2CCN(C)CC2)CC1] |
TABLE 89
| Ex | Str |
|---|---|
| 131 | 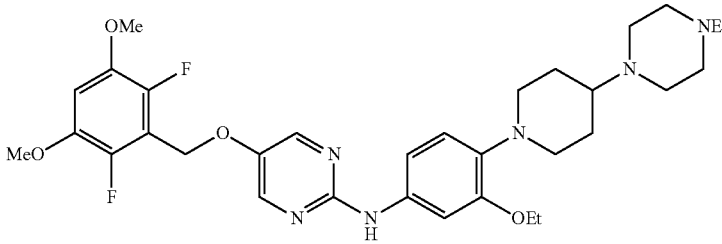 |
| 132 | 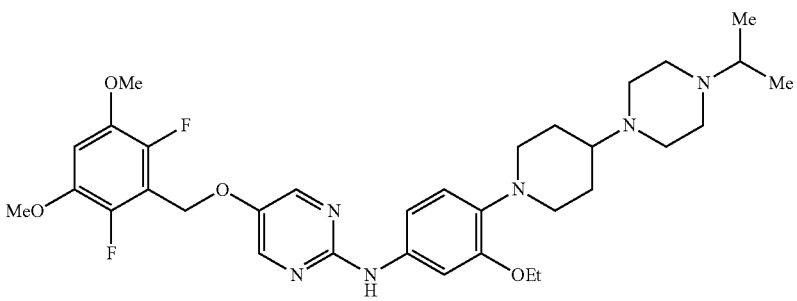 [SMILES: CCOc1cc(Nc2ncc(OCc3c(F)c(OC)cc(OC)c3F)cn2)ccc1N1CCC(N2CCN(C(C)C)CC2)CC1] |
| 133 | 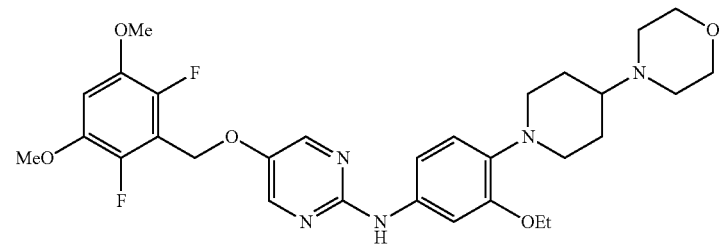 [SMILES: CCOc1cc(Nc2ncc(OCc3c(F)c(OC)cc(OC)c3F)cn2)ccc1N1CCC(N2CCOCC2)CC1] |
| 134 | 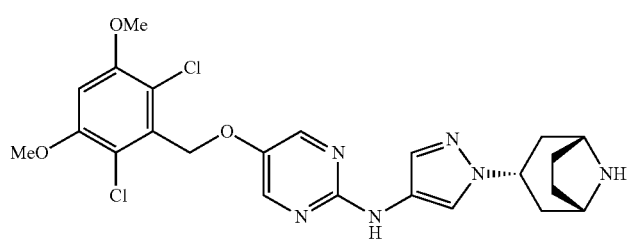 [SMILES: COc1cc(OC)c(Cl)c(COc2cnc(Nc3cnn([C@@H]4C[C@H]5CC[C@@H](C4)N5)c3)nc2)c1Cl] |

TABLE 89-continued

| Ex | Str |
|---|---|
| 135 | (structure) |

TABLE 90

| Ex | Str |
|---|---|
| 136 | (structure) |
| 137 | (structure) |
| 138 | (structure) |
| 139 | (structure) |
| 140 | (structure) |

TABLE 91

| Ex | Str |
|---|---|
| 141 | (structure) |
| 142 | (structure) |
| 143 | (structure) |
| 144 | (structure) 3HCl |
| 145 | (structure) |

TABLE 92

| Ex | Str |
|---|---|
| 146 | (structure) |

TABLE 92-continued
| Ex | Str |
|----|-----|
| 147 | 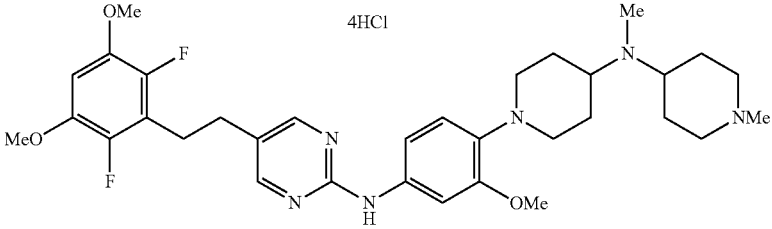 [SMILES: COc1cc(Nc2ncc(CCc3c(F)c(OC)cc(OC)c3F)cn2)ccc1N1CCC(N(C)C2CCN(C)CC2)CC1] 4HCl |
| 148 | 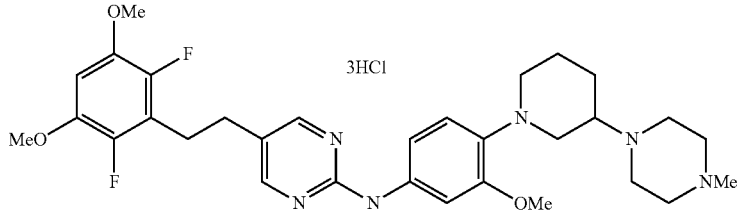 3HCl |
| 149 | 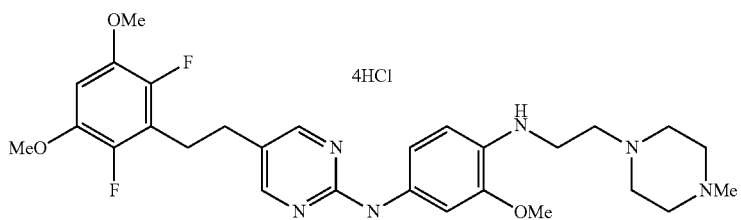 4HCl |
| 150 | 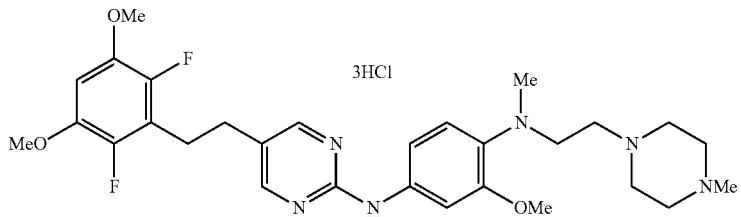 3HCl |
| 151 | 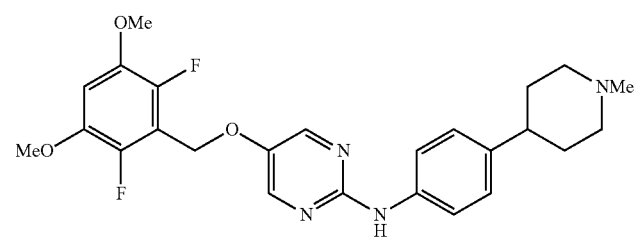 [SMILES: COc1cc(OC)c(F)c(COc2cnc(Nc3ccc(C4CCN(C)CC4)cc3)nc2)c1F] |
TABLE 93
| Ex | Str |
|----|-----|
| 152 | 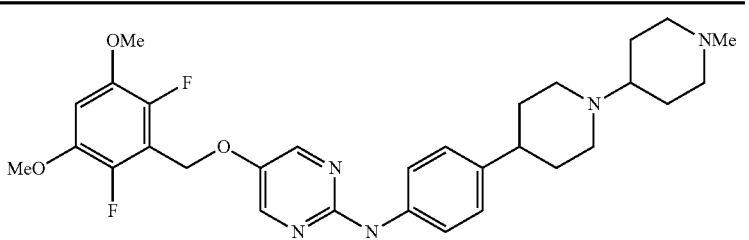 |

TABLE 93-continued

| Ex | Str |
|---|---|
| 153 | (structure) |
| 154 | (structure) |
| 155 | (structure) |
| 157 | (structure) |

TABLE 94

| Ex | Str |
|---|---|
| 158 | (structure) |

TABLE 94-continued

| Ex | Str |
|---|---|
| 159 | (structure) |
| 160 | (structure) |
| 161 | (structure) |
| 162 | (structure) |

TABLE 95

| Ex | Str |
|---|---|
| 165 | (structure) |

TABLE 95-continued

| Ex | Str |
|---|---|
| 166 | (structure) |
| 167 | (structure) |
| 168 | (structure) |
| 169 | (structure) |

TABLE 96

| Ex | Str |
|---|---|
| 170 | (structure) |

TABLE 96-continued

| Ex | Str |
|---|---|
| 171 | |
| 172 | |
| 173 | |
| 174 | |

TABLE 97

| Ex | Str |
|---|---|
| 175 | |

TABLE 97-continued

| Ex | Str |
|----|-----|
| 176 | |
| 177 | |
| 178 | |
| 179 | |

TABLE 98

| Ex | Str |
|----|-----|
| 180 | |

TABLE 98-continued

| Ex | Str |
|---|---|
| 181 | (structure) |
| 182 | (structure) |
| 183 | (structure) |
| 184 | (structure) |

TABLE 99

| Ex | Str |
|---|---|
| 185 | (structure) |

TABLE 99-continued

| Ex | Str |
|---|---|
| 186 | (structure) |
| 187 | (structure) |
| 188 | (structure) |
| 189 | (structure) |

TABLE 100

| Ex | Str |
|---|---|
| 190 | (structure) 3HCl |
| 191 | (structure) |

TABLE 100-continued

| Ex | Str |
|---|---|
| 192 | |
| 193 | |
| 194 | |

TABLE 101

| Ex | Str |
|---|---|
| 195 | |
| 196 | |

TABLE 101-continued
| Ex | Str |
|---|---|
| 197 | 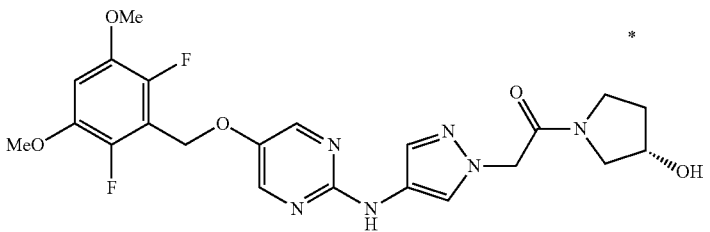 [SMILES: COc1cc(OC)c(F)c(COc2cnc(Nc3cnn(CC(=O)N4CC[C@H](O)C4)c3)nc2)c1F] |
| 198 | |
| 199 | |
TABLE 102
| Ex | Str |
|---|---|
| 200 | 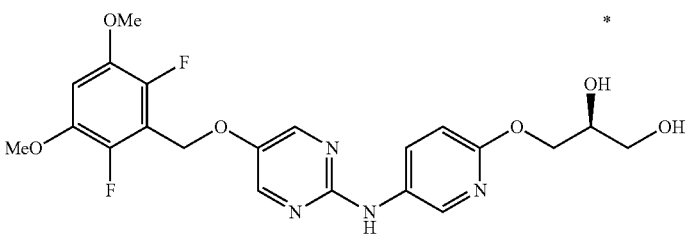 [SMILES: COc1cc(OC)c(F)c(COc2cnc(Nc3ccc(OC[C@@H](O)CO)nc3)nc2)c1F] |
| 201 | |

TABLE 102-continued

| Ex | Str |
|---|---|
| 202 | (structure: 3,6-dimethoxy-2,5-difluorobenzyl ether linked to pyrimidine-NH-pyrazole-CH₂CH₂-(1-methylpiperidin-4-yl)) |
| 203 | (structure: 3,6-dimethoxy-2,5-difluorobenzyl ether linked to pyrimidine-NH-pyrazole-CH₂CH₂-(4-methyl-1,4-diazepan-1-yl)) |
| 204 | (structure: 3,6-dimethoxy-2,5-difluorobenzyl ether linked to pyrimidine-NH-pyrazole-CH₂CH₂-N(Me)₂) |

TABLE 103

| Ex | Str |
|---|---|
| 205 | * (structure: 3,6-dimethoxy-2,5-difluorobenzyl ether linked to pyrimidine-NH-pyridine-O-CH₂-CH(OH)-CH₂OH) |
| 206 | 2HCl (structure: 3,6-dimethoxy-2,5-difluorobenzyl ether linked to pyrimidine-NH-pyrazole-CH₂CH₂-(3-hydroxyazetidin-1-yl)) |
| 207 | 3HCl (structure: 3,6-dimethoxy-2,5-difluorobenzyl ether linked to pyrimidine-NH-pyrazole-CH₂CH₂-piperazin-1-yl) |

TABLE 103-continued
| Ex | Str |
|---|---|
| 208 | 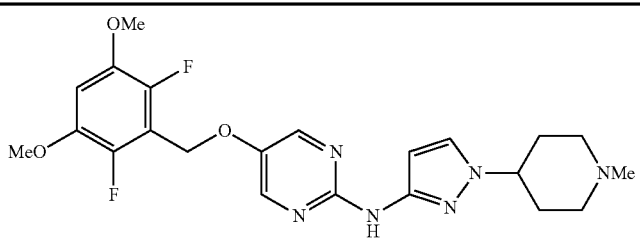 |
| 209 | 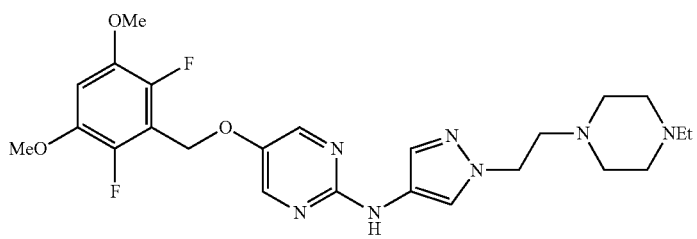 |
TABLE 104
| Ex | Str |
|---|---|
| 210 | 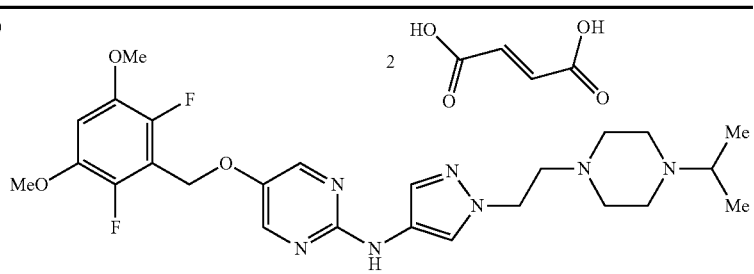 |
| 211 | 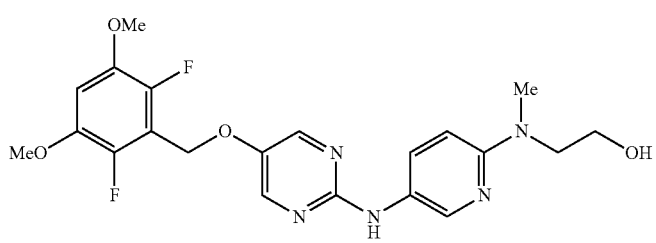 [SMILES: COc1cc(OC)c(F)c(COc2cnc(Nc3ccc(N(C)CCO)nc3)nc2)c1F] |
| 212 | 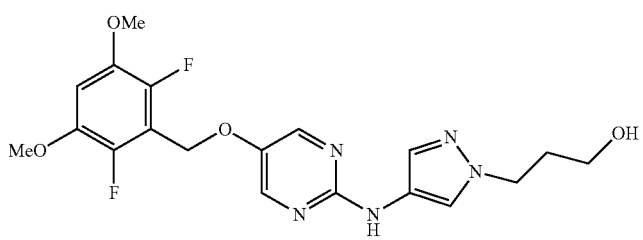 [SMILES: COc1cc(OC)c(F)c(COc2cnc(Nc3cnn(CCCO)c3)nc2)c1F] |

TABLE 104-continued

| Ex | Str |
|---|---|
| 213 | (structure) |
| 214 | (structure) |

TABLE 105

| Ex | Str |
|---|---|
| 215 | (structure) |
| 216 | (structure) |
| 217 | (structure) |
| 218 | (structure) |

TABLE 105-continued

| Ex | Str |
|---|---|
| 219 | (structure) |

TABLE 106

| Ex | Str |
|---|---|
| 220 | (structure) |
| 221 | (structure) |
| 222 | (structure) |
| 223 | (structure) |
| 224 | (structure) |

TABLE 107

| Ex | Str |
|---|---|
| 225 | (structure) |
| 226 | (structure) |
| 227 | (structure) |
| 228 | (structure) |
| 229 | (structure) |

TABLE 108

| Ex | Str |
|---|---|
| 230 | (structure) |

TABLE 108-continued
| Ex | Str |
|---|---|
| 231 | 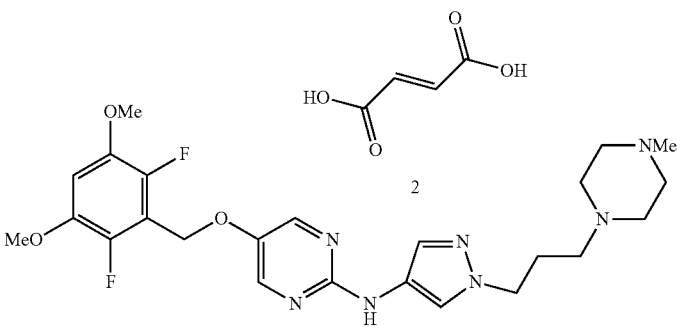 [SMILES: COc1cc(OC)c(F)c(COc2cnc(Nc3cnn(CCCN4CCN(C)CC4)c3)nc2)c1F ; O=C(O)/C=C/C(=O)O] |
| 232 | 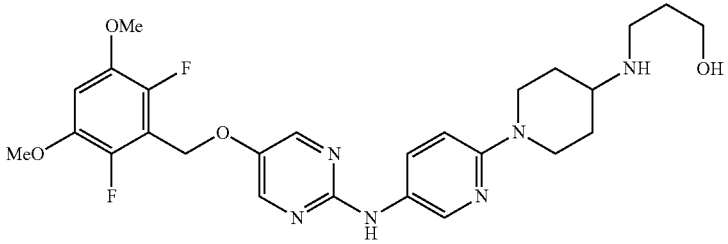 [SMILES: COc1cc(OC)c(F)c(COc2cnc(Nc3ccc(N4CCC(NCCCO)CC4)nc3)nc2)c1F] |
| 233 | 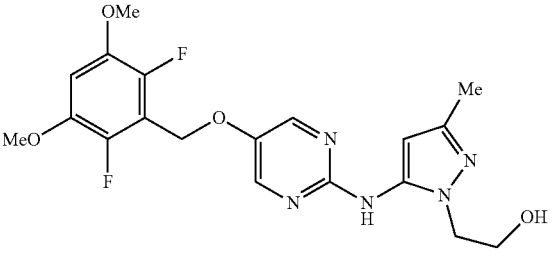 [SMILES: COc1cc(OC)c(F)c(COc2cnc(Nc3cc(C)nn3CCO)nc2)c1F] |
| 234 | 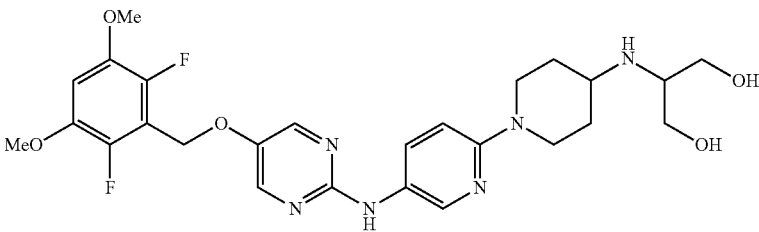 [SMILES: COc1cc(OC)c(F)c(COc2cnc(Nc3ccc(N4CCC(NC(CO)CO)CC4)nc3)nc2)c1F] |
TABLE 109
| Ex | Str |
|---|---|
| 235 | 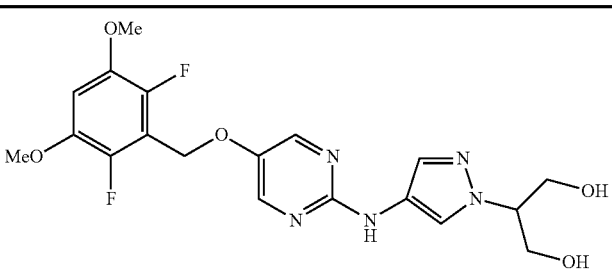 |

TABLE 109-continued
| Ex | Str |
|---|---|
| 236 | 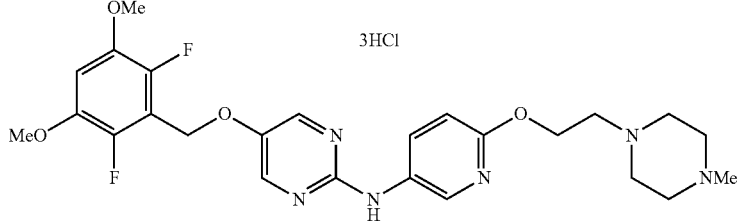 [SMILES: COc1cc(OC)c(F)c(COc2cnc(Nc3ccc(OCCN4CCN(C)CC4)nc3)nc2)c1F] |
| 237 | 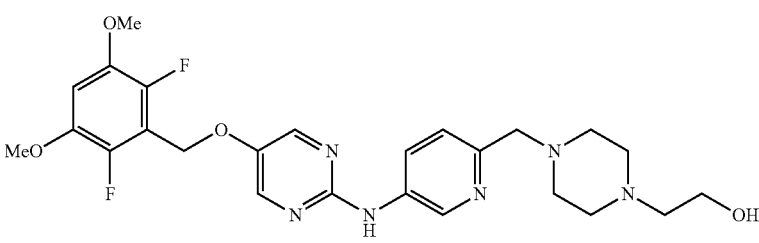 [SMILES: COc1cc(OC)c(F)c(COc2cnc(Nc3ccc(CN4CCN(CCO)CC4)nc3)nc2)c1F] |
| 238 | 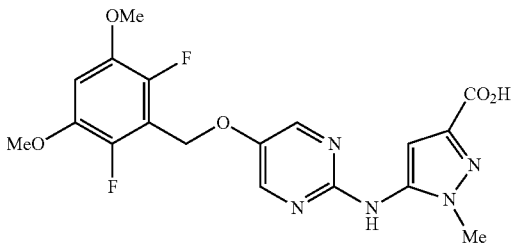 [SMILES: COc1cc(OC)c(F)c(COc2cnc(Nc3cc(C(=O)O)nn3C)nc2)c1F] |
| 239 | 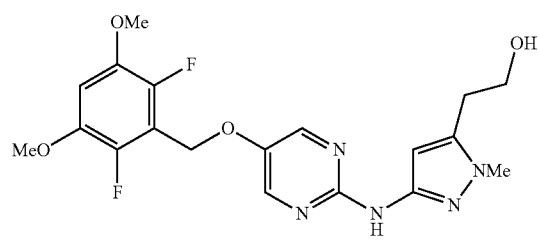 [SMILES: COc1cc(OC)c(F)c(COc2cnc(Nc3cc(CCO)n(C)n3)nc2)c1F] |
TABLE 110
| Ex | Str |
|---|---|
| 240 | 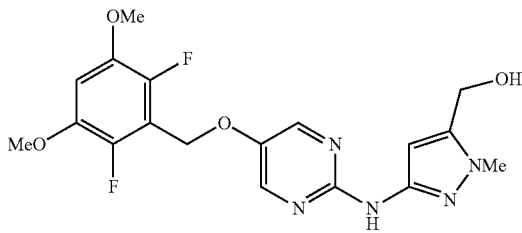 [SMILES: COc1cc(OC)c(F)c(COc2cnc(Nc3cc(CO)n(C)n3)nc2)c1F] |

US 9,464,077 B2
TABLE 110-continued
| Ex | Str |
|---|---|
| 241 | 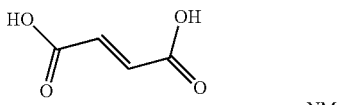 |
| 242 | 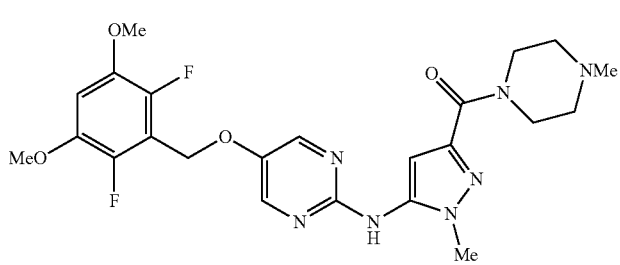 [SMILES: COc1cc(OC)c(F)c(COc2cnc(Nc3cc(C(=O)N4CCN(C)CC4)nn3C)nc2)c1F] |
| 243 | 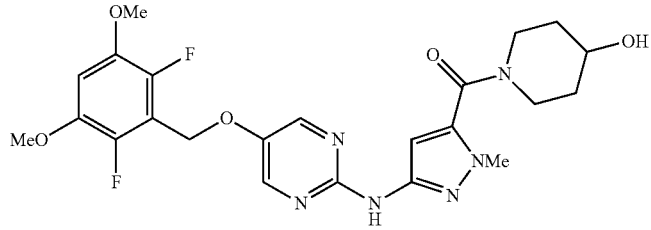 [SMILES: COc1cc(OC)c(F)c(COc2cnc(Nc3cc(C(=O)N4CCC(O)CC4)n(C)n3)nc2)c1F] |
| 244 | 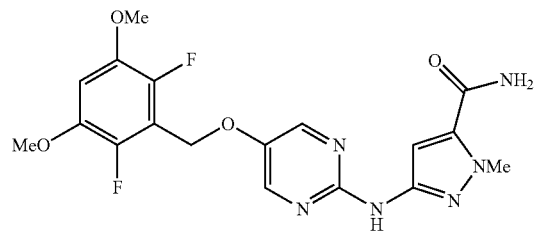 [SMILES: COc1cc(OC)c(F)c(COc2cnc(Nc3cc(C(N)=O)n(C)n3)nc2)c1F] |
TABLE 111
| Ex | Str |
|---|---|
| 245 | 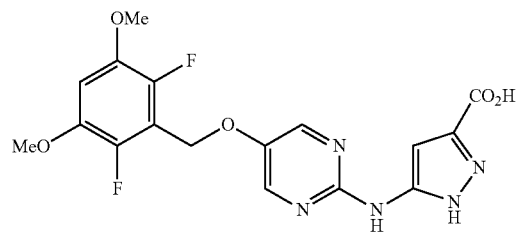 [SMILES: COc1cc(OC)c(F)c(COc2cnc(Nc3cc(C(=O)O)n[nH]3)nc2)c1F] |

TABLE 111-continued

| Ex | Str |
|---|---|
| 246 | (structure: 2,5-dimethoxy-3,6-difluorobenzyl ether linked to pyrimidine-NH-pyrazole with CH2OH and N-Me) |
| 247 | (structure: 2,5-dimethoxy-3,6-difluorobenzyl ether linked to pyrimidine-NH-pyridinone with N-CH2CH2OH) |
| 248 | (structure: 2,5-dimethoxy-3,6-difluorobenzyl ether linked to pyrimidine-NH-pyrazole with CH2-N-methylpiperazine and N-Me) |
| 249 | (structure: 2,5-dimethoxy-3,6-difluorobenzyl ether linked to pyrimidine-NH-pyrazole with CH2-(4-hydroxypiperidine) and N-Me; 2HCl) |

TABLE 112

| Ex | Str |
|---|---|
| 250 | (structure: 2,5-dimethoxy-3,6-difluorobenzyl ether linked to pyrimidine-NH-pyridine-piperidine-N-oxetane) |
| 251 | (structure: 2,5-dimethoxy-3,6-difluorobenzyl ether linked to pyrimidine-NH-pyridinone with N-CH2CH2OH) |

TABLE 112-continued
| Ex | Str |
|---|---|
| 252 | 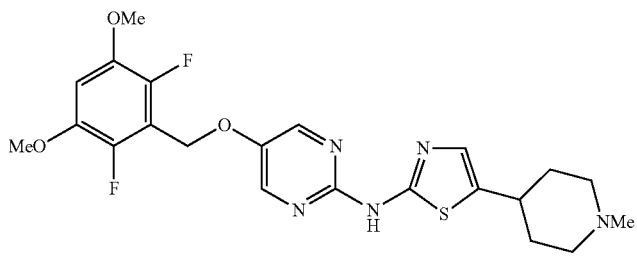 [SMILES: COc1cc(OC)c(F)c(COc2cnc(Nc3ncc(C4CCN(C)CC4)s3)nc2)c1F] |
| 253 | 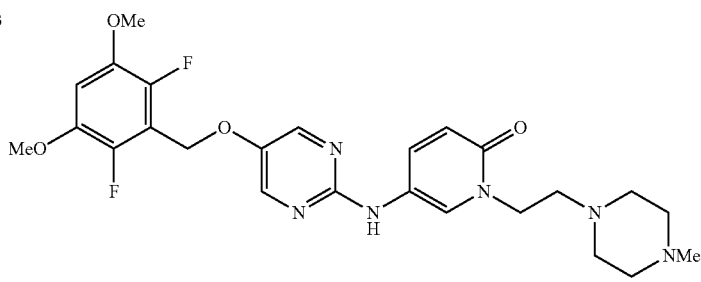 |
| 254 | 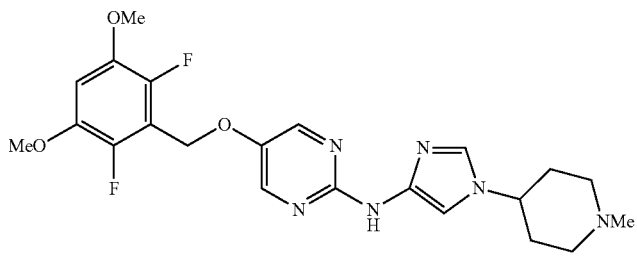 [SMILES: COc1cc(OC)c(F)c(COc2cnc(Nc3cn(C4CCN(C)CC4)cn3)nc2)c1F] |
TABLE 113
| Ex | Str |
|---|---|
| 255 | 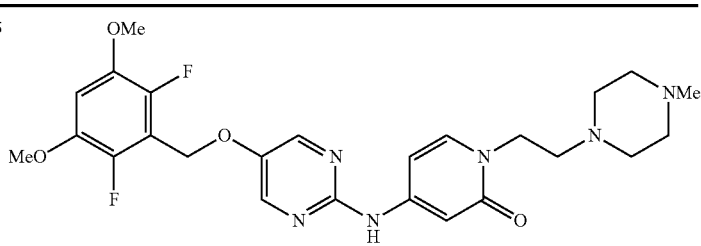 |
| 256 | 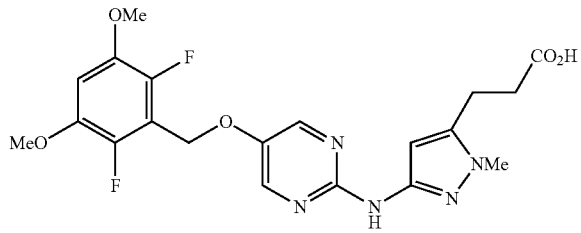 [SMILES: COc1cc(OC)c(F)c(COc2cnc(Nc3cc(CCC(=O)O)n(C)n3)nc2)c1F] |

TABLE 113-continued
| Ex | Str |
|---|---|
| 257 | 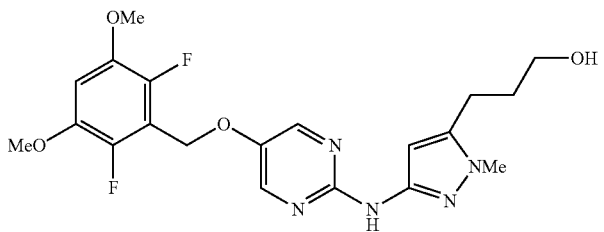 [SMILES: COc1cc(OC)c(F)c(COc2cnc(Nc3cc(CCCO)n(C)n3)nc2)c1F] |
| 258 | 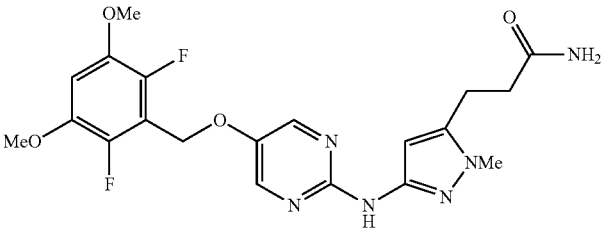 [SMILES: COc1cc(OC)c(F)c(COc2cnc(Nc3cc(CCC(N)=O)n(C)n3)nc2)c1F] |
| 259 | 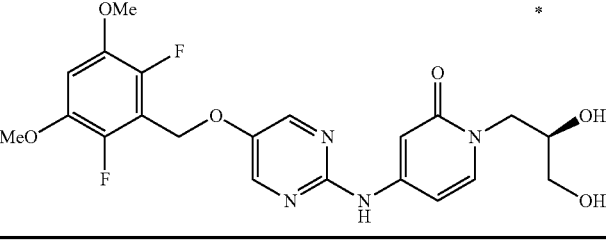 |
TABLE 114
| Ex | Str |
|---|---|
| 260 | 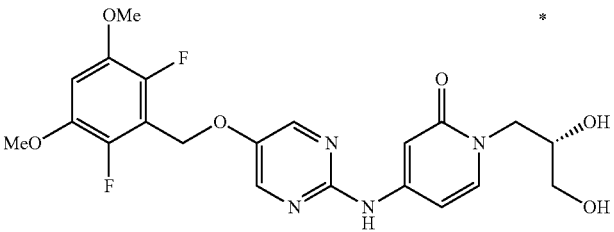 [SMILES: COc1cc(OC)c(F)c(COc2cnc(Nc3ccn(C[C@H](O)CO)c(=O)c3)nc2)c1F] |
| 261 | 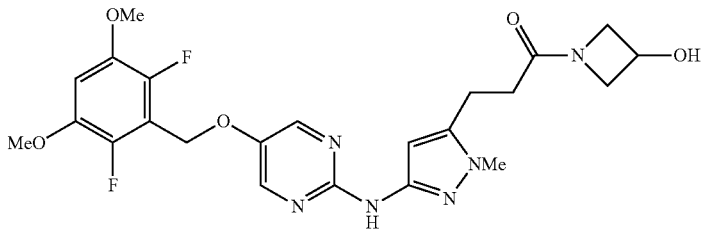 [SMILES: COc1cc(OC)c(F)c(COc2cnc(Nc3cc(CCC(=O)N4CC(O)C4)n(C)n3)nc2)c1F] |
| 262 | 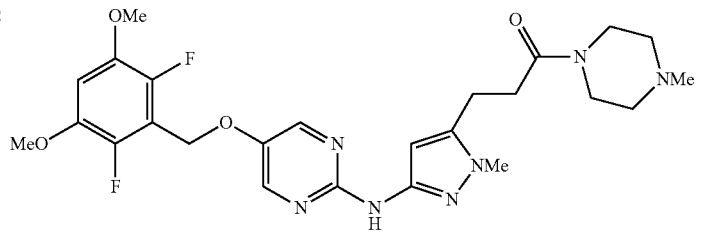 |

TABLE 114-continued
| Ex | Str |
|---|---|
| 263 | 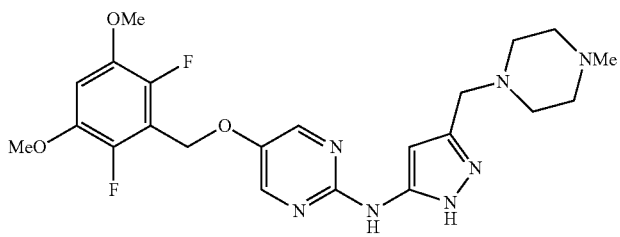 [SMILES: COc1cc(OC)c(F)c(COc2cnc(Nc3cc(CN4CCN(C)CC4)n[nH]3)nc2)c1F] |
| 264 | 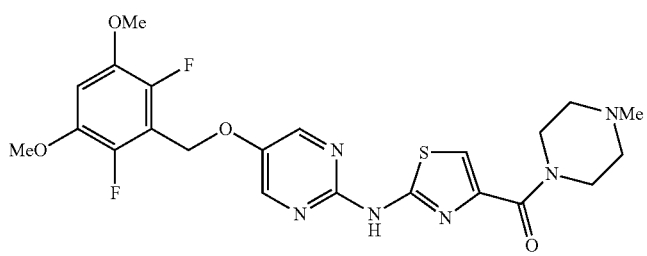 [SMILES: COc1cc(OC)c(F)c(COc2cnc(Nc3nc(C(=O)N4CCN(C)CC4)cs3)nc2)c1F] |
TABLE 115
| Ex | Str |
|---|---|
| 265 | 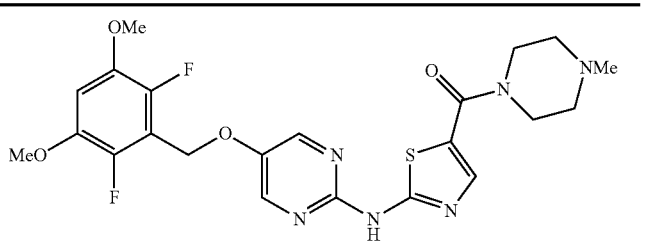 |
| 266 | 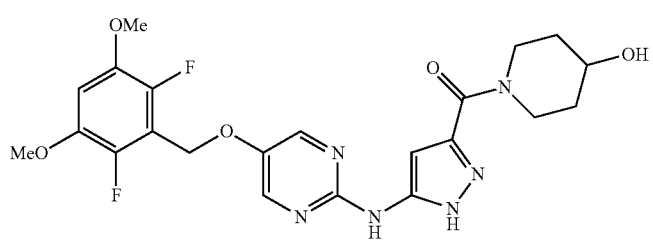 [SMILES: COc1cc(OC)c(F)c(COc2cnc(Nc3cc(C(=O)N4CCC(O)CC4)n[nH]3)nc2)c1F] |
| 267 | 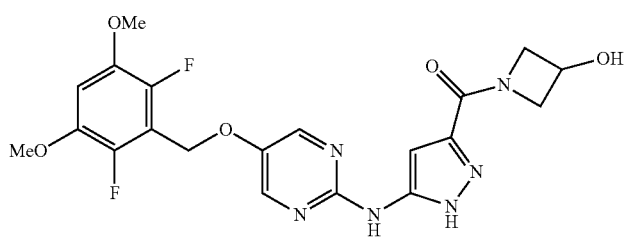 [SMILES: COc1cc(OC)c(F)c(COc2cnc(Nc3cc(C(=O)N4CC(O)C4)n[nH]3)nc2)c1F] |

TABLE 115-continued
| Ex | Str |
|---|---|
| 268 | 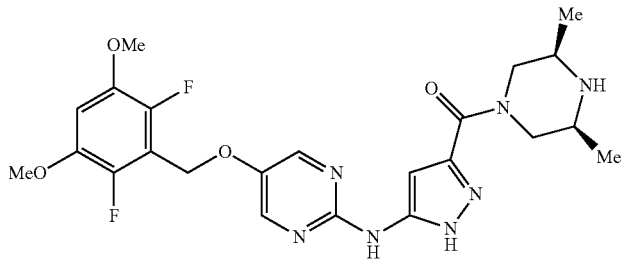 [SMILES: COc1cc(OC)c(F)c(COc2cnc(Nc3cc(C(=O)N4C[C@@H](C)N[C@@H](C)C4)n[nH]3)nc2)c1F] |
| 269 | 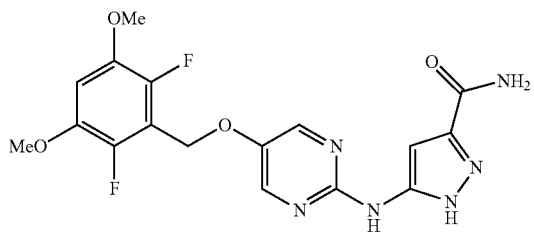 [SMILES: COc1cc(OC)c(F)c(COc2cnc(Nc3cc(C(N)=O)n[nH]3)nc2)c1F] |
TABLE 116
| Ex | Str |
|---|---|
| 270 | 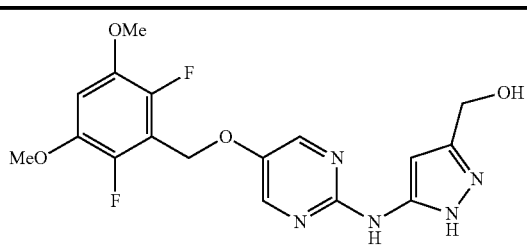 |
| 271 | 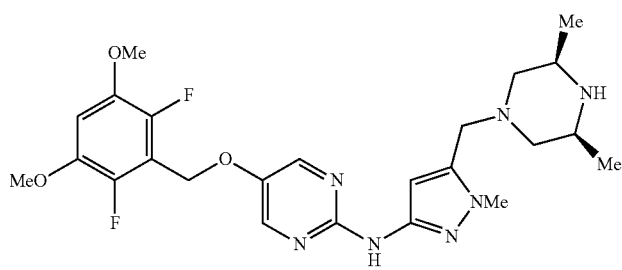 [SMILES: COc1cc(OC)c(F)c(COc2cnc(Nc3cc(CN4C[C@@H](C)N[C@@H](C)C4)n(C)n3)nc2)c1F] |
| 272 | 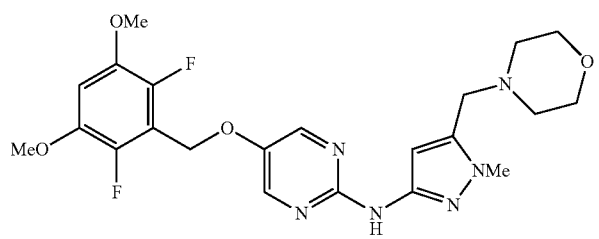 [SMILES: COc1cc(OC)c(F)c(COc2cnc(Nc3cc(CN4CCOCC4)n(C)n3)nc2)c1F] |

TABLE 116-continued
| Ex | Str |
|---|---|
| 273 | 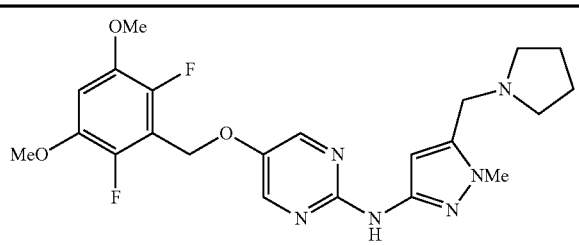 |
| 274 | 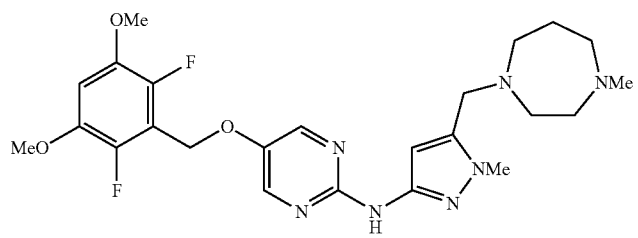 [SMILES: COc1cc(OC)c(F)c(COc2cnc(Nc3cc(CN4CCCN(C)CC4)n(C)n3)nc2)c1F] |
TABLE 117
| Ex | Str |
|---|---|
| 275 | 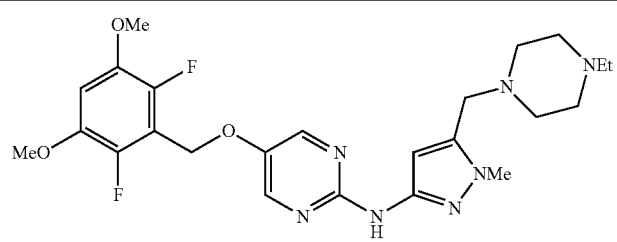 |
| 276 | 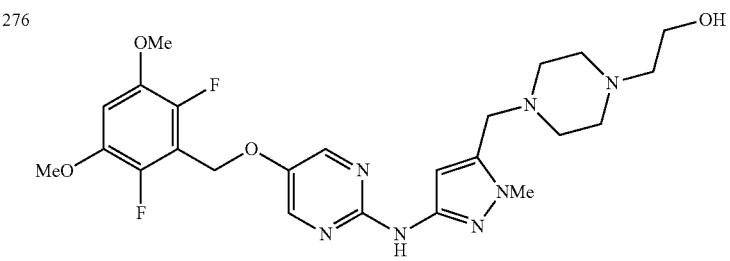 |
| 277 | 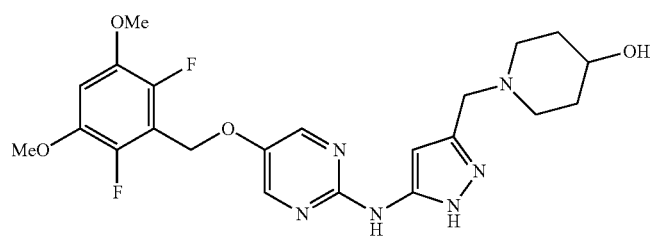 [SMILES: COc1cc(OC)c(F)c(COc2cnc(Nc3cc(CN4CCC(O)CC4)n[nH]3)nc2)c1F] |

TABLE 117-continued
| Ex | Str |
|---|---|
| 278 | 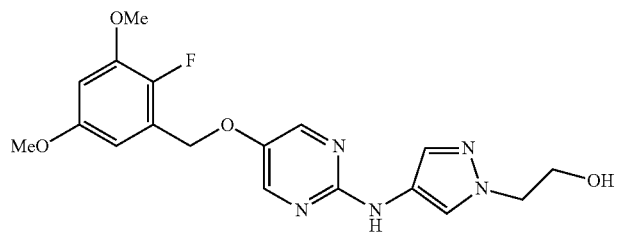 [SMILES: COc1cc(COc2cnc(Nc3cnn(CCO)c3)nc2)c(F)c(OC)c1] |
| 279 | 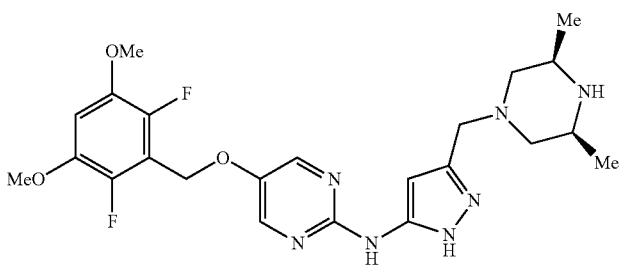 [SMILES: COc1cc(OC)c(F)c(COc2cnc(Nc3cc(CN4C[C@@H](C)N[C@@H](C)C4)n[nH]3)nc2)c1F] |
TABLE 118
| Ex | Str |
|---|---|
| 280 | 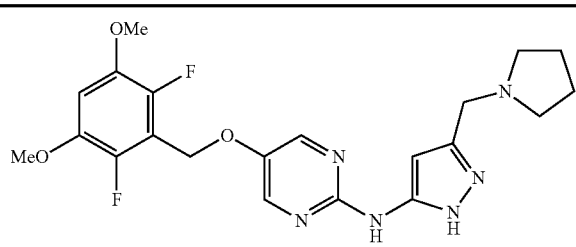 |
| 281 | 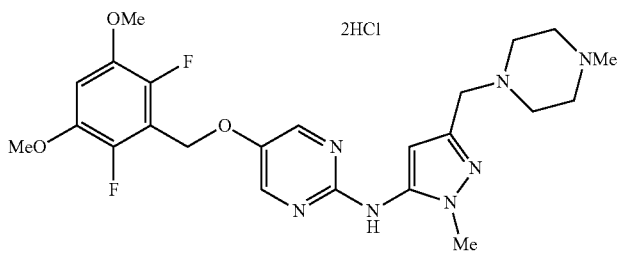 [SMILES: COc1cc(OC)c(F)c(COc2cnc(Nc3cc(CN4CCN(C)CC4)nn3C)nc2)c1F] |
| 282 | 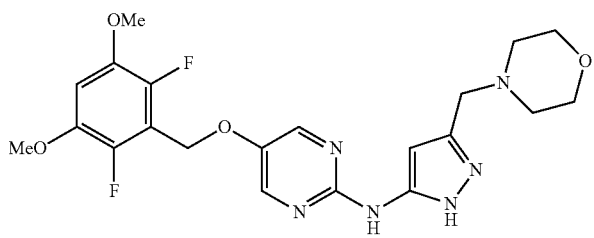 [SMILES: COc1cc(OC)c(F)c(COc2cnc(Nc3cc(CN4CCOCC4)n[nH]3)nc2)c1F] |

TABLE 118-continued

| Ex | Str |
|---|---|
| 283 | (structure) |
| 284 | (structure) |

TABLE 119

| Ex | Str |
|---|---|
| 285 | (structure) |
| 286 | (structure) |
| 287 | (structure) |

TABLE 119-continued
| Ex | Str |
|---|---|
| 288 | 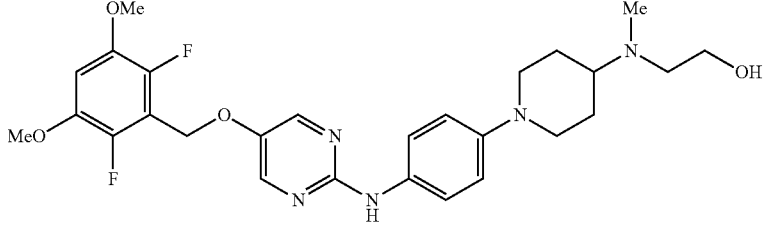 [SMILES: COc1cc(OC)c(F)c(COc2cnc(Nc3ccc(N4CCC(N(C)CCO)CC4)cc3)nc2)c1F] |
| 289 | 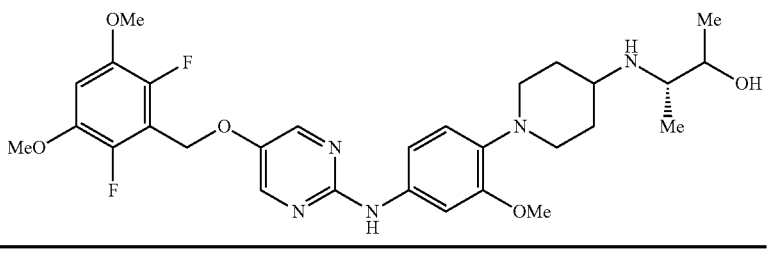 |
TABLE 120
| Ex | Str |
|---|---|
| 290 | 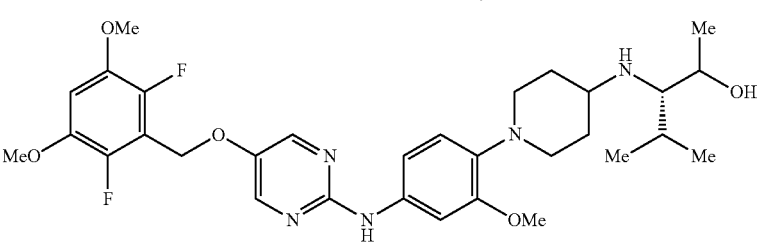 |
| 291 | 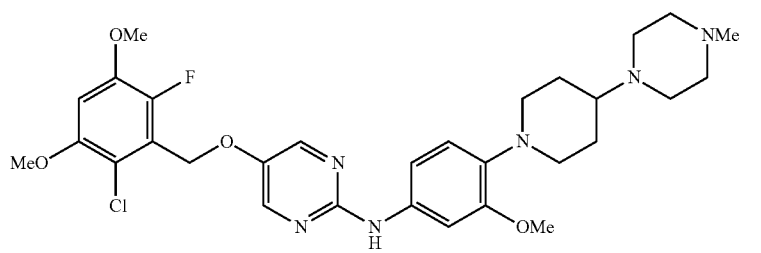 |
| 292 | 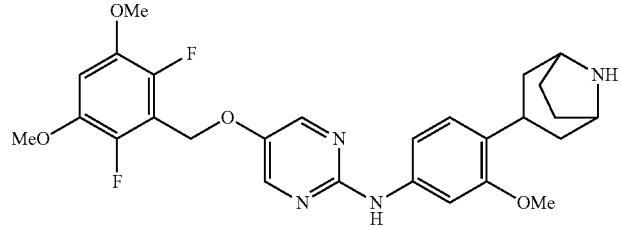 [SMILES: COc1cc(Nc2ncc(OCc3c(F)c(OC)cc(OC)c3F)cn2)ccc1C1CC2CCC(C1)N2] |

TABLE 120-continued

| Ex | Str |
|---|---|
| 293 | (structure) |
| 294 | (structure) |

TABLE 121

| Ex | Str |
|---|---|
| 295 | (structure) |
| 296 | (structure) |
| 297 | (structure) |
| 298 | (structure) |

TABLE 121-continued
| Ex | Str |
|---|---|
| 299 | 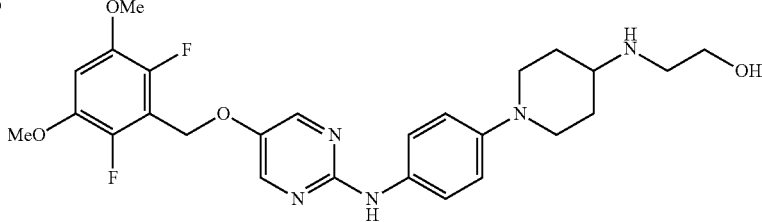 |
| 300 | 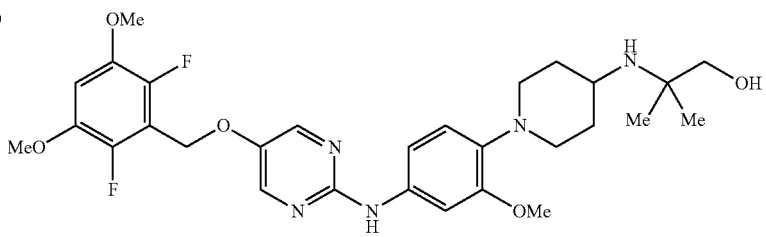 [SMILES: COc1cc(Nc2ncc(OCc3c(F)c(OC)cc(OC)c3F)cn2)ccc1N1CCC(NC(C)(C)CO)CC1] |
TABLE 122
| Ex | Str |
|---|---|
| 301 | 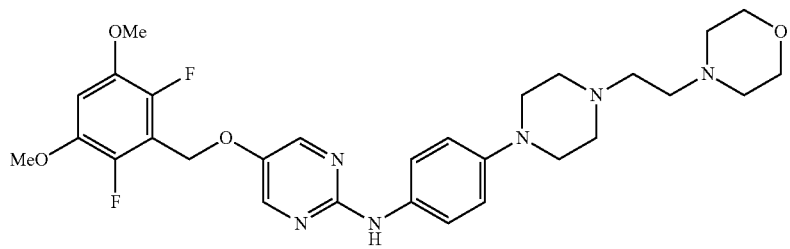 [SMILES: COc1cc(OC)c(F)c(COc2cnc(Nc3ccc(N4CCN(CCN5CCOCC5)CC4)cc3)nc2)c1F] |
| 302 | 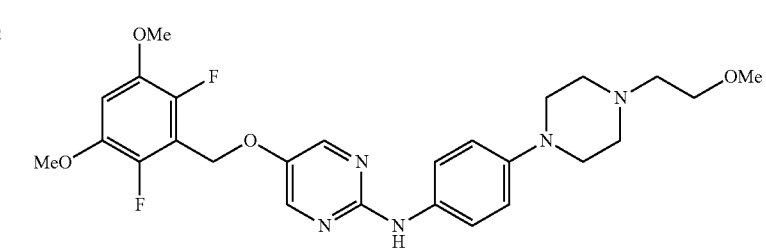 |
| 303 | 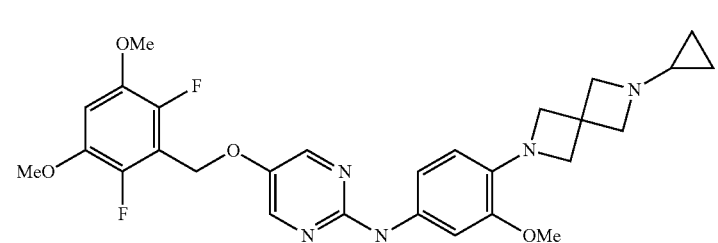 |

TABLE 122-continued
| Ex | Str |
|---|---|
| 304 | 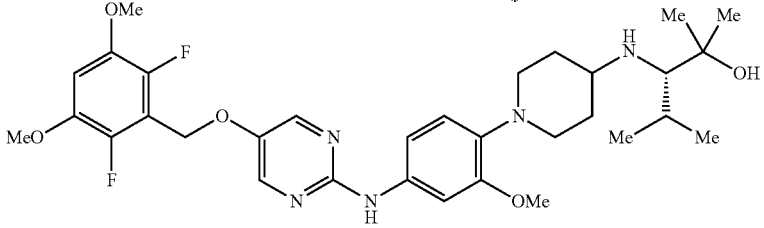 |
| 305 | 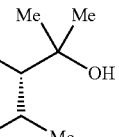 |
TABLE 123
| Ex | Str |
|---|---|
| 306 | 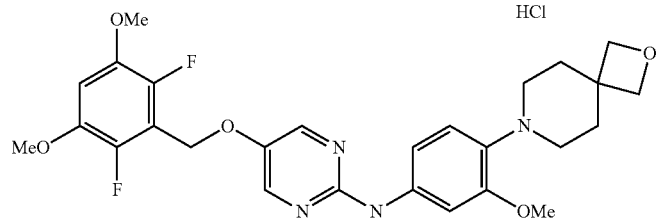 |
| 307 | 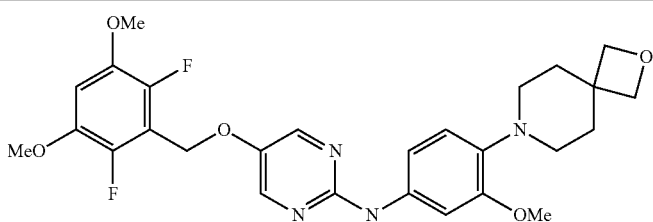 |
| 308 | 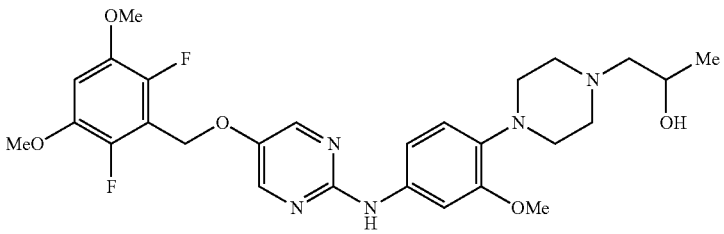 [SMILES: COc1cc(Nc2ncc(OCc3c(F)c(OC)cc(OC)c3F)cn2)ccc1N1CCN(CC(C)O)CC1] |

TABLE 123-continued
| Ex | Str |
|---|---|
| 309 | 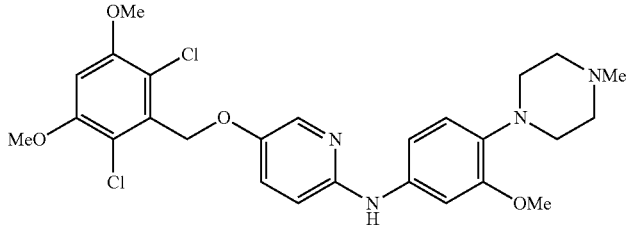 [SMILES: COc1cc(Nc2ccc(OCc3c(Cl)c(OC)cc(OC)c3Cl)cn2)ccc1N1CCN(C)CC1] |
| 310 | 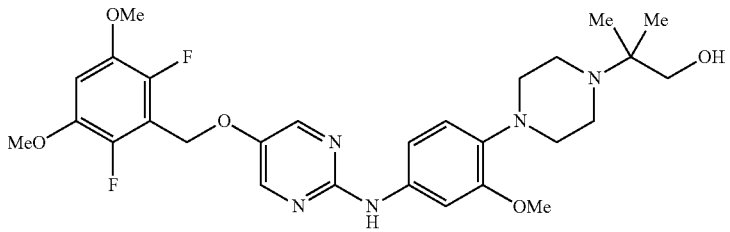 [SMILES: COc1cc(Nc2ncc(OCc3c(F)c(OC)cc(OC)c3F)cn2)ccc1N1CCN(C(C)(C)CO)CC1] |
TABLE 124
| Ex | Str |
|---|---|
| 311 | 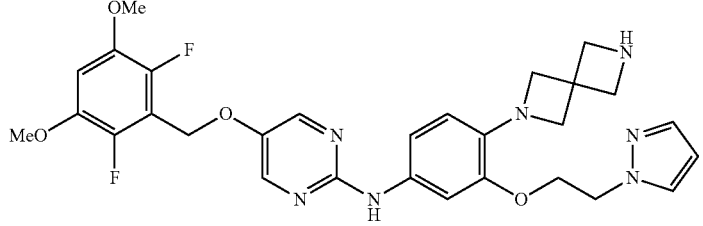 [SMILES: COc1cc(OC)c(F)c(COc2cnc(Nc3ccc(N4CC5(CNC5)C4)c(OCCn4cccn4)c3)nc2)c1F] |
| 312 | 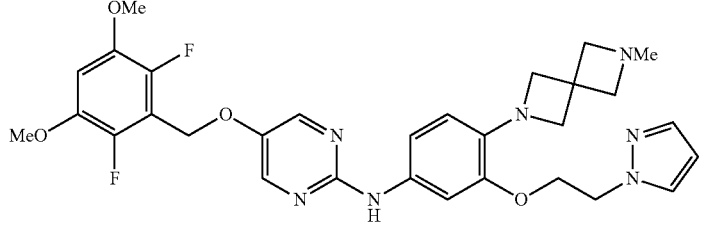 [SMILES: COc1cc(OC)c(F)c(COc2cnc(Nc3ccc(N4CC5(CN(C)C5)C4)c(OCCn4cccn4)c3)nc2)c1F] |
| 313 | 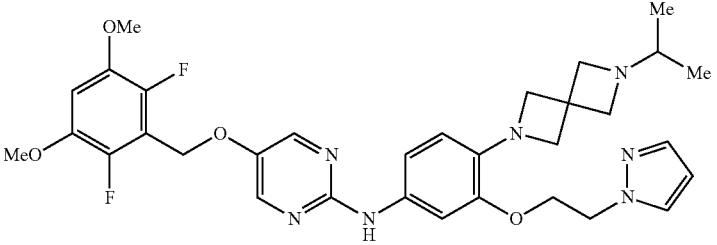 [SMILES: COc1cc(OC)c(F)c(COc2cnc(Nc3ccc(N4CC5(C4)CN(C(C)C)C5)c(OCCn4cccn4)c3)nc2)c1F] |
| 314 | 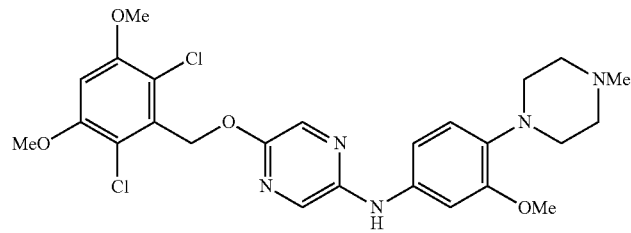 [SMILES: COc1cc(Nc2cnc(OCc3c(Cl)c(OC)cc(OC)c3Cl)cn2)ccc1N1CCN(C)CC1] |

TABLE 124-continued

| Ex | Str |
|---|---|
| 315 | (structure) |

TABLE 125

| Ex | Str |
|---|---|
| 316 | (structure) |
| 317 | (structure) |
| 318 | (structure) |
| 319 | (structure) |

TABLE 125-continued
| Ex | Str |
|---|---|
| 320 | 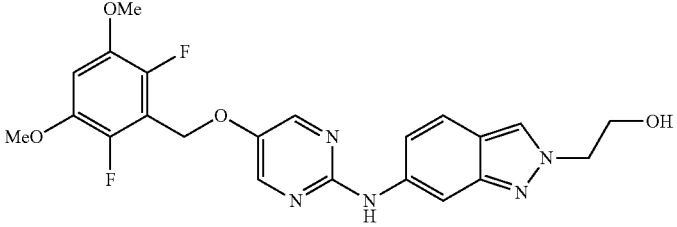 [SMILES: COc1cc(OC)c(F)c(COc2cnc(Nc3ccc4cn(CCO)nc4c3)nc2)c1F] |
TABLE 126
| Ex | Str |
|---|---|
| 321 | 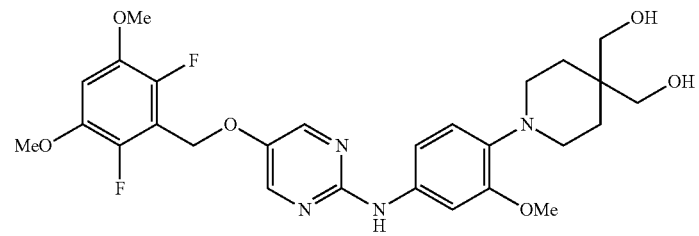 [SMILES: COc1cc(Nc2ncc(OCc3c(F)c(OC)cc(OC)c3F)cn2)ccc1N1CCC(CO)(CO)CC1] |
| 322 | 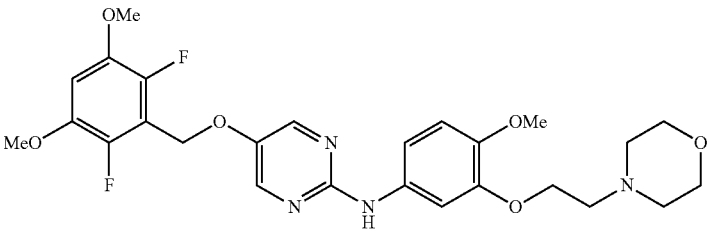 [SMILES: COc1ccc(Nc2ncc(OCc3c(F)c(OC)cc(OC)c3F)cn2)cc1OCCN1CCOCC1] |
| 323 | 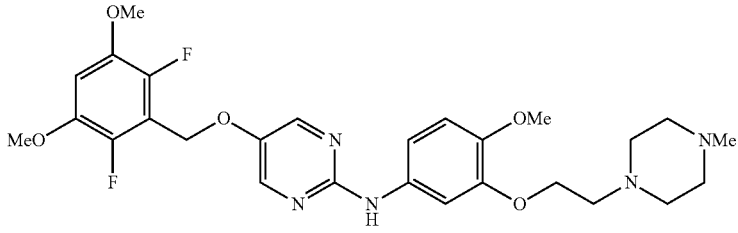 [SMILES: COc1ccc(Nc2ncc(OCc3c(F)c(OC)cc(OC)c3F)cn2)cc1OCCN1CCN(C)CC1] |
| 324 | 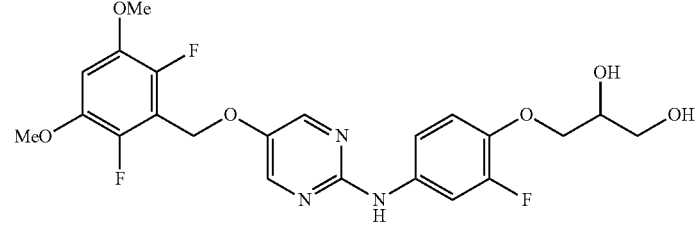 [SMILES: COc1cc(OC)c(F)c(COc2cnc(Nc3ccc(OCC(O)CO)c(F)c3)nc2)c1F] |
| 325 | 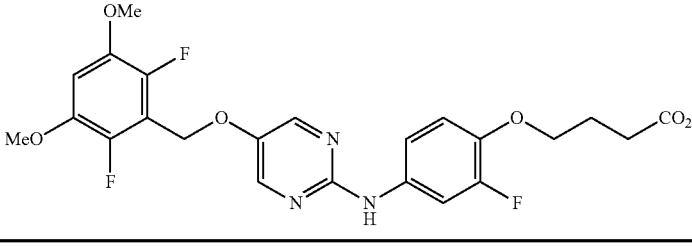 |

TABLE 127
| Ex | Str |
|---|---|
| 326 | 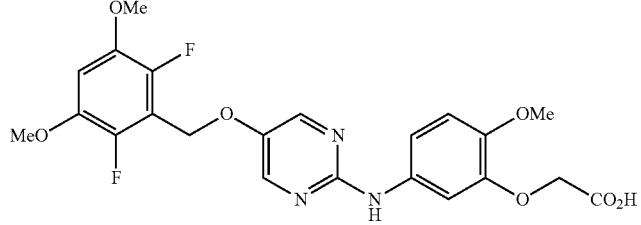 [SMILES: COc1ccc(Nc2ncc(OCc3c(F)c(OC)cc(OC)c3F)cn2)cc1OCC(=O)O] |
| 327 | 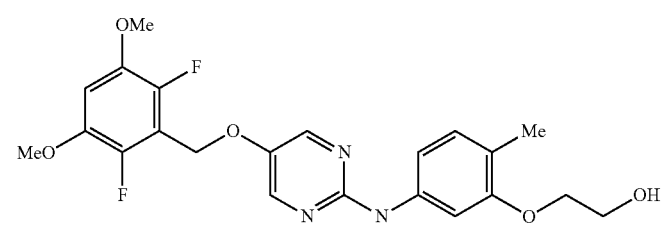 |
| 328 | 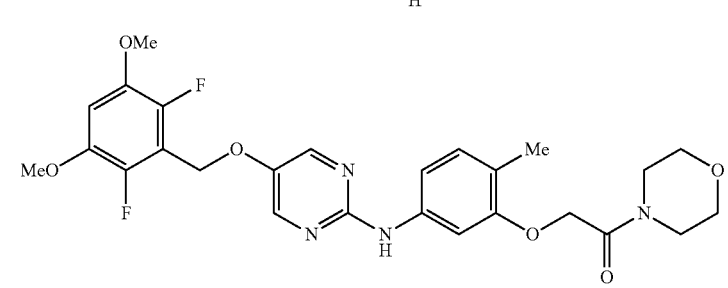 |
| 329 | 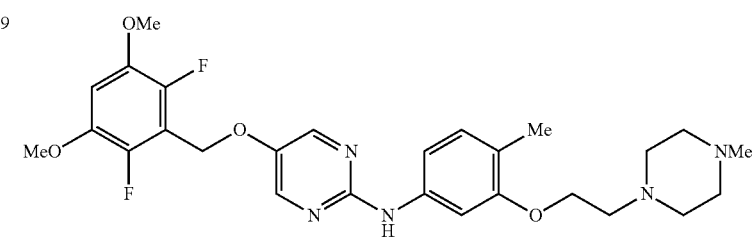 |
| 330 | 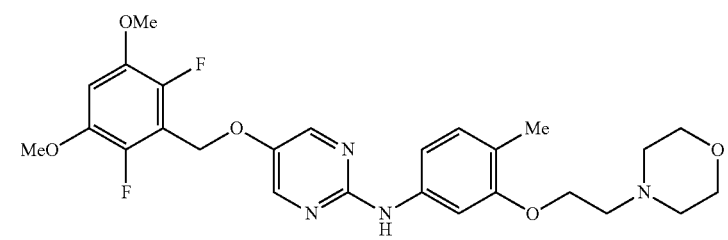 [SMILES: COc1cc(OC)c(F)c(COc2cnc(Nc3ccc(C)c(OCCN4CCOCC4)c3)nc2)c1F] |
TABLE 128
| Ex | Str |
|---|---|
| 331 | 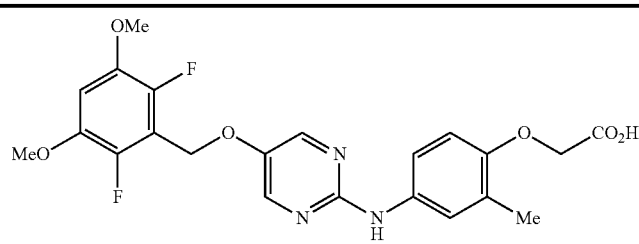 |

TABLE 128-continued
| Ex | Str |
|---|---|
| 332 | 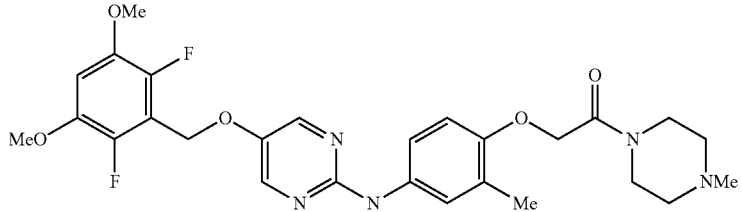 |
| 333 | 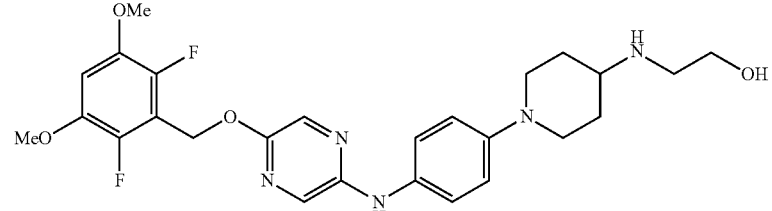 |
| 334 | 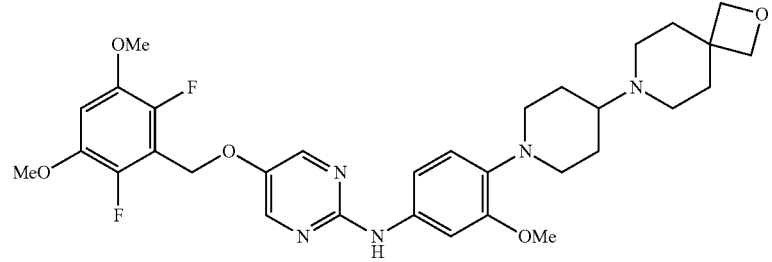 [SMILES: COc1cc(Nc2ncc(OCc3c(F)c(OC)cc(OC)c3F)cn2)ccc1N1CCC(N2CCC3(CC2)COC3)CC1] |
| 335 | 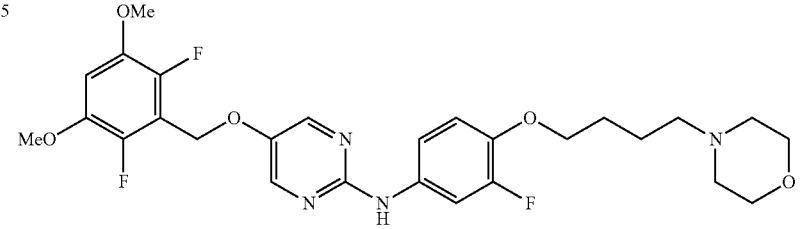 |
| 336 | 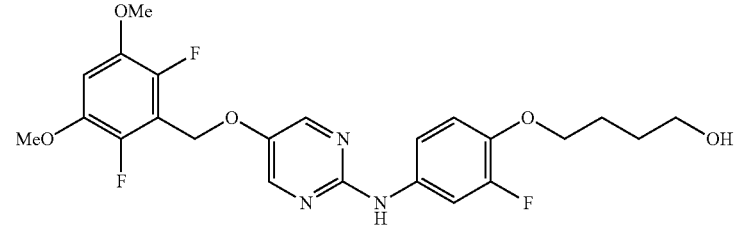 [SMILES: COc1cc(OC)c(F)c(COc2cnc(Nc3ccc(OCCCCO)c(F)c3)nc2)c1F] |
TABLE 129
| Ex | Str |
|---|---|
| 337 | 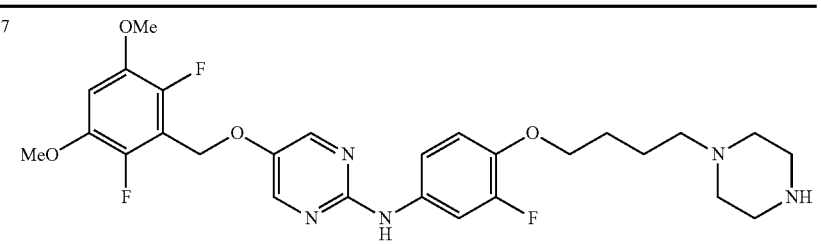 |

TABLE 129-continued

| Ex | Str |
|---|---|
| 338 | (structure) |
| 339 | (structure) |
| 340 | (structure) |
| 341 | (structure) |
| 342 | (structure) |

TABLE 130

| Ex | Str |
|---|---|
| 343 | (structure) |

TABLE 130-continued

| Ex | Str |
|---|---|
| 344 | (structure) |
| 345 | (structure) |
| 346 | (structure) |
| 347 | (structure) |
| 348 | (structure) |

TABLE 131

| Ex | Str |
|---|---|
| 349 | (structure) |

TABLE 131-continued

| Ex | Str |
|---|---|
| 350 | (structure) |
| 351 | (structure) |
| 352 | (structure) |
| 353 | (structure) |

TABLE 132

| Ex | Str |
|---|---|
| 354 | (structure) |

TABLE 132-continued

| Ex | Str |
|---|---|
| 355 | (structure) |
| 356 | (structure) |
| 357 | (structure) |
| 358 | (structure) |
| 359 | (structure) |

TABLE 133

| Ex | Str |
|---|---|
| 360 | (structure) |

TABLE 133-continued
| Ex | Str |
|---|---|
| 361 | |
| 362 | |
| 363 | |
| 364 | |
| 365 | |
TABLE 134
| Ex | Str |
|---|---|
| 366 | 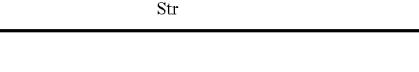 |

TABLE 134-continued
| Ex | Str |
|---|---|
| 367 | 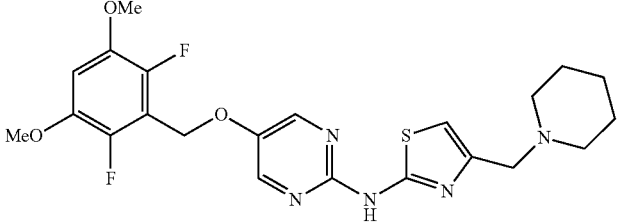 [SMILES: COc1cc(OC)c(F)c(COc2cnc(Nc3nc(CN4CCCCC4)cs3)nc2)c1F] |
| 368 | 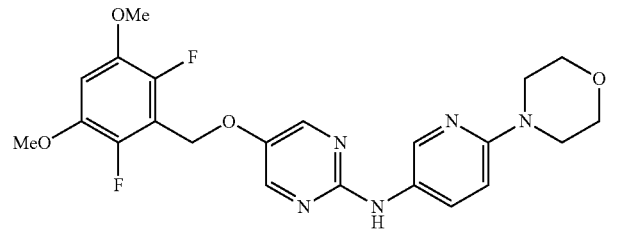 [SMILES: COc1cc(OC)c(F)c(COc2cnc(Nc3ccc(N4CCOCC4)nc3)nc2)c1F] |
| 369 | 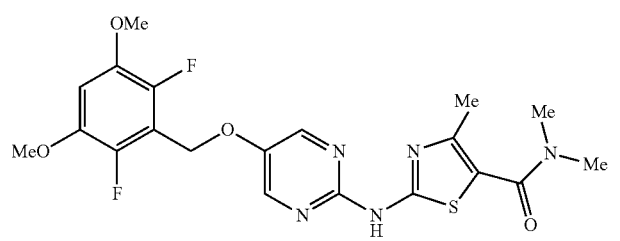 [SMILES: COc1cc(OC)c(F)c(COc2cnc(Nc3nc(C)c(C(=O)N(C)C)s3)nc2)c1F] |
| 370 | 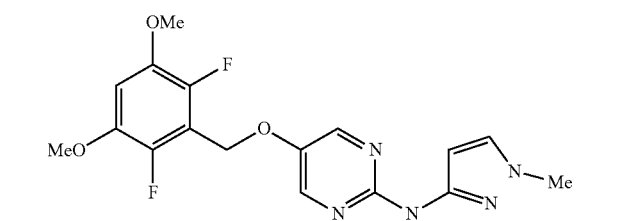 |
| 371 | 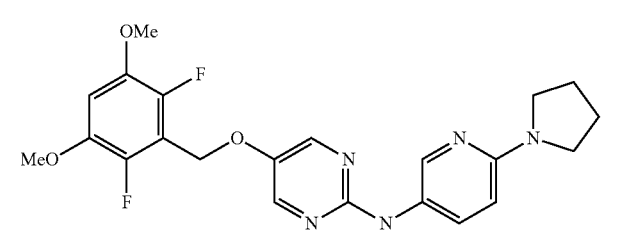 |
TABLE 135
| Ex | Str |
|---|---|
| 372 | 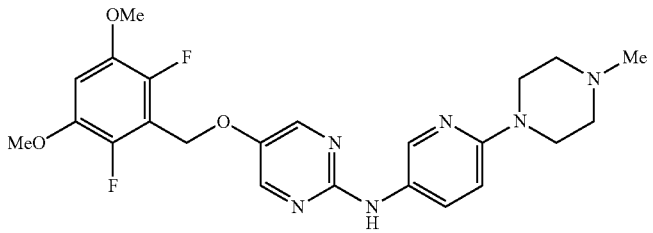 [SMILES: COc1cc(OC)c(F)c(COc2cnc(Nc3ccc(N4CCN(C)CC4)nc3)nc2)c1F] |

TABLE 135-continued

| Ex | Str |
|---|---|
| 373 | (structure) |
| 374 | (structure) |
| 375 | (structure) |
| 376 | (structure) |
| 377 | (structure) |

TABLE 136

| Ex | Str |
|---|---|
| 378 | (structure) |

TABLE 136-continued
| Ex | Str |
|---|---|
| 379 | 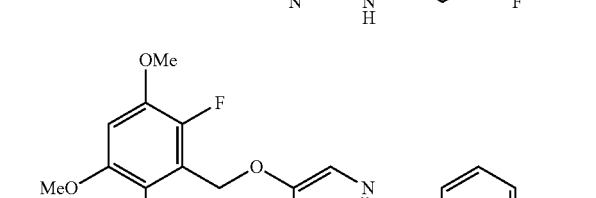 |
| 380 | 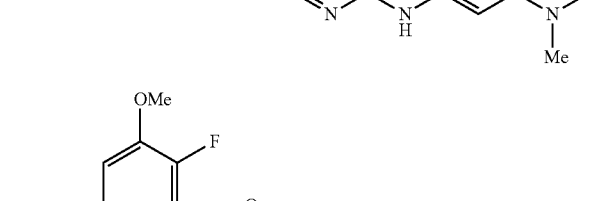 |
| 381 | 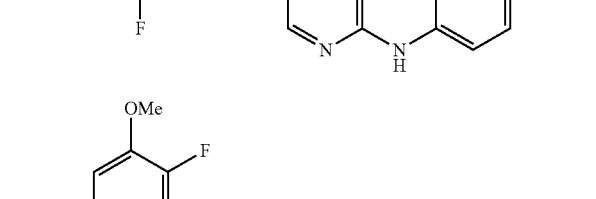 |
| 382 | 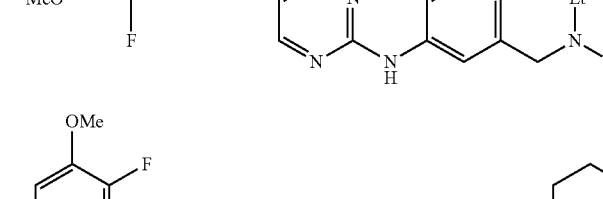 |
| 383 | 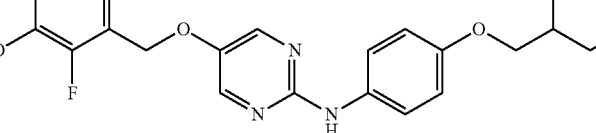 |
TABLE 137
| Ex | Str |
|---|---|
| 384 | 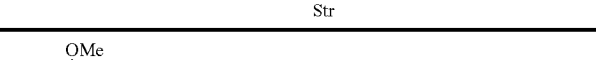 |

TABLE 137-continued

| Ex | Str |
|---|---|
| 385 | (structure: 3,5-dimethoxy-2,6-difluorobenzyl ether linked to pyrimidine-NH-(3-fluoro-4-morpholinophenyl)) |
| 386 | (structure: 3,5-dimethoxy-2,6-difluorobenzyl ether linked to pyrimidine-NH-(3-morpholinophenyl)) |
| 387 | (structure: 3,5-dimethoxy-2,6-difluorobenzyl ether linked to pyrimidine-NH-(3-methoxy-4-(oxetan-3-yloxy)phenyl)) |
| 388 | (structure: 3,5-dimethoxy-2,6-difluorobenzyl ether linked to pyrimidine-NH-(3-methoxy-4-(4-methoxypiperidin-1-yl)phenyl)) |

TABLE 138

| Ex | Syn | DAT |
|---|---|---|
| 1 | 1 | ESI+: 543<br>NMR1: 1.49-1.61(2H, m), 1.77-1.85(2H, m), 2.19(3H, s), 2.22-2.71(11H, m), 3.28-3.43(2H, m), 3.76(3H, s), 3.77(6H, s), 6.55(1H, t, J = 2.3 Hz), 6.69(2H, d, J = 2.3 Hz), 6.83(1H, d, J = 8.6 Hz), 7.27(1H, dd, J = 8.6, 2.3 Hz), 7.31(1H, d, J = 2.3 Hz), 8.61(2H, s), 9.79(1H, s) |
| 2 | 2 | ESI+: 547<br>NMR1: 1.46-1.59(2H, m), 1.74-1.83(2H, m), 2.14(3H, s), 2.19-2.54(11H, m), 2.71-2.82(4H, m), 3.26-3.36(2H, m), 3.70(6H, s), 3.74(3H, s), 6.30(1H, t, J = 2.3 Hz), 6.38(2H, d, J = 2.3 Hz), 6.79(1H, d, J = 8.6 Hz), 7.24(1H, dd, J = 8.6, 2.3 Hz), 7.35(1H, d, J = 2.3 Hz), 8.26(2H, s), 9.22(1H, s) |
| 3 | 3 | ESI+: 611 |
| 4 | 4 | ESI+: 611 |
| 5 | 5 | ESI+: 649, 651 |
| 6 | 6 | ESI+: 583 |
| 7 | 7 | ESI+: 500<br>NMR1: 2.21(3H, s), 2.35-2.59(4H, m), 2.66-2.76(2H, m), 2.81-3.00(6H, m), 3.74(3H, s), 3.81(6H, s), 6.78(1H, d, J = 8.4 Hz), 6.85(1H, t, J = 8.4 Hz), 7.24(1H, dd, J = 8.4, 2.4 Hz), 7.36(1H, d, J = 2.4 Hz), 8.18(2H, s), 9.26(1H, s) |
| 8 | 8 | APCI/ESI+: 422 |
| 9 | 9 | APCI/ESI+: 459 |
| 10 | 10 | ESI+: 525 |
| 11 | 11 | ESI+: 438<br>NMR1: 3.28-3.37(2H, m), 3.72-3.80(1H, m), 3.83-3.91(7H, m), 4.15(1H, dd, J = 13.8, 4.1 Hz), 4.67(1H, t, J = 5.6 Hz), 4.91(1H, d, J = 5.3 Hz), 5.14(2H, s), 7.06(1H, t, J = 8.4 Hz), 7.45(1H, d, J = 0.6 Hz), 7.87(1Hd, J = 0.6 Hz), 8.26(2H, s), 9.21(1H, s) |
| 12 | 12 | ESI+: 519 |

TABLE 139

| Ex | Syn | DAT |
|---|---|---|
| 13 | 13 | ESI+: 533 |
| 14 | 14 | ESI+: 551 |

TABLE 139-continued

| Ex | Syn | DAT |
|---|---|---|
| 15 | 15 | ESI+: 547 |
| 16 | 16 | ESI+: 537 |
| 17 | 17 | APCI/ESI+: 398 |
| 18 | 18 | ESI+: 480 |
| 19 | 19 | ESI+: 532<br>NMR1: 1.59-1.61(8H, m), 2.84-2.86(4H, m), 3.04-3.05(4H, m), 3.74(3H, s), 5.26(2H, s), 6.82(1H, d, J = 8.4 Hz), 7.24(1H, d, J = 8.4 Hz), 7.32(1H, s), 7.97-8.03(1H, m), 8.34(2H, s), 8.53(1H, brs), 9.27(1H, s) |
| 20 | 20 | ESI+: 466 |
| 21 | 21 | ESI+: 494 |
| 22 | 22 | ESI+: 616 |
| 23 | 23 | ESI+: 422<br>NMR1: 0.97-1.05(3H, m), 3.87(6H, s), 3.92-3.96(3H, m), 4.82-4.86(1H, m), 5.14(2H, s), 7.06(1H, t, J = 8.4 Hz), 7.44(1H, d, J = 0.6 Hz), 7.86(1H, d, J = 0.6 Hz), 8.26(2H, s), 9.21(1H, s) |
| 24 | 24 | ESI+: 421<br>NMR1: 3.87(6H, s), 4.69(2H, s), 5.15(2H, s), 7.06(1H, t, J = 8.4 Hz), 7.19(1H, brs), 7.34(1H, brs), 7.46(1H, s), 7.89(1H, s), 8.26(2H, s), 9.26(1H, s) |
| 25 | 3 | ESI+: 579 |
| 26 | 4 | ESI+: 579 |

TABLE 140

| Ex | Syn | DAT |
|---|---|---|
| 27 | 2 | ESI+: 583<br>NMR1: 1.46-1.59(2H, m), 1.74-1.82(2H, m), 2.14(3H, s), 2.18-2.58(11H, m), 2.65-2.75(2H, m), 2.84-2.93(2H, m), 3.24-3.38(2H, m), 3.74(3H, s), 3.81(6H, s), 6.79(1H, d, J = 8.8 Hz), 6.85(1H, t, J = 8.4 Hz), 7.23(1H, dd, J = 8.8, 2.4 Hz), 7.34(1H, d, J = 2.4 Hz), 8.17(2H, s), 9.25(1H, s) |
| 28 | 7 + 4 | ESI+: 530 |
| 29 | 3 | ESI+: 579 |
| 30 | 3 | ESI+: 496 |
| 31 | 3 | ESI+: 526 |
| 32 | 3 | ESI+: 567 |
| 33 | 6 | APCI/ESI+: 571<br>NMR1: 1.48-1.61(2H, m), 1.77-1.87(2H, m), 2.13(3H, s), 2.20-2.64(11H, m), 2.69-2.76(2H, m), 2.85-2.93(2H, m), 3.81(6H, s), 6.85(1H, t, J = 8.4 Hz), 6.95(1H, dd, J = 9.9, 9.0 Hz), 7.32(1H, dd, J = 8.8, 1.8 Hz), 7.65(1H, dd, J = 15.2, 2.4 Hz), 8.21(2H, s), 9.50(1H, s) |
| 34 | 3 | ESI+: 579 |
| 35 | 4 | ESI+: 579 |
| 36 | 7 | ESI+: 583 |
| 37 | 3 | ESI+: 561 |
| 38 | 6 | ESI+: 565 |

TABLE 141

| Ex | Syn | DAT |
|---|---|---|
| 39 | 3 | ESI+: 595 |
| 40 | 4 | ESI+: 595 |
| 41 | 6 | ESI+: 599 |
| 42 | 6 | ESI+: 615 |
| 43 | 3 | ESI+: 549 |
| 44 | 6 | ESI+: 553 |
| 45 | 3 | ESI+: 519 |
| 46 | 6 | ESI+: 523 |
| 47 | 3 | ESI+: 555 |
| 48 | 6 | ESI+: 559 |
| 49 | 9 | ESI+: 549 |
| 50 | 9 | ESI+: 549<br>NMR1: 1.43-1.62(2H, m), 1.68-1.87(2H, m), 2.14(3H, s), 2.17-2.70(11H, m), 3.23-3.35(2H, m), 3.74(6H, s), 3.74(3H, s), 5.07(2H, s), 6.46(1H, t, J = 2.4 Hz), 6.60(2H, d, J = 2.4 Hz), 6.78(1H, d, J = 8.6 Hz), 7.23(1H, dd, J = 8.6, 2.2 Hz), 7.32(1H, d, J = 2.2 Hz), 8.29(2H, s), 9.15(1H, s) |
| 51 | 9 | ESI+: 466 |
| 52 | 9 | ESI+: 617<br>NMR1: 1.40-1.60(2H, m), 1.73-1.84(2H, m), 2.14(3H, s), 2.17-2.70(11H, m), 3.24-3.36(2H, m), 3.75(3H, s), 3.94(6H, s), 5.29(2H, s), 6.79(1H, d, J = 8.6 Hz), 7.00(1H, s), 7.24(1H, dd, J = 8.6, 2.3 Hz), 7.33(1H, d, J = 2.3 Hz), 8.32(2H, s), 9.21(1H, s) |
| 53 | 9 | ESI+: 534 |

TABLE 142

| Ex | Syn | DAT |
|---|---|---|
| 54 | 9 | ESI+: 631 |
| 55 | 9 | ESI+: 548 |
| 56 | 9 | ESI+: 585<br>NMR1: 1.45-1.60(2H, m), 1.73-1.84(2H, m), 2.14(3H, s), 2.17-2.58(11H, m), 3.24-3.36(2H, m), 3.75(3H, s), 3.87(6H, s), 5.16(2H, s), 6.79(1H, d, J = 8.8 Hz), 7.07(1H, t, J = 8.4 Hz), 7.24(1H, dd, J = 8.8, 2.4 Hz), 7.32(1H, d, J = 2.4 Hz), 8.29(2H, s), 9.21(1H, s) |
| 57 | 9 | ESI+: 502<br>NMR1: 2.21(3H, s), 2.37-2.53(4H, m), 2.83-2.94(4H, m), 3.75(3H, s), 3.87(6H, s), 5.16(2H, s), 6.79(1H, d, J = 8.4 Hz), 7.07(1H, t, J = 8.4 Hz), 7.25(1H, dd, J = 8.4, 2.4 Hz), 7.34(1H, d, J = 2.4 Hz), 8.30(2H, s), 9.23(1H, s) |
| 58 | 9 | ESI+: 561 |
| 59 | 9 | ESI+: 478 |
| 60 | 9 | ESI+: 586 |
| 61 | 9 | ESI+: 522 |
| 62 | 9 | ESI+: 601 |
| 63 | 9 | ESI+: 601 |
| 64 | 64 | ESI+: 561 |
| 65 | 64 | ESI+: 616 |
| 66 | 9 | ESI+: 572 |

TABLE 143

| Ex | Syn | DAT |
|---|---|---|
| 67 | 9 | ESI+: 636 |
| 68 | 9 | ESI+: 653 |
| 69 | 9 | ESI+: 605 |
| 70 | 9 | APCI/ESI+: 659 |
| 71 | 9 | ESI+: 493<br>NMR1: 1.80-2.12(6H, m), 2.19(3H, s), 2.77-2.89(2H, m), 3.94(6H, s), 3.98-4.10(1H, m), 5.27(2H, s), 7.00(1H, s), 7.46(1H, s), 7.88(1H, s), 8.28(2H, s), 9.19(1H, s) |
| 72 | 12 | ESI+: 479<br>NMR1: 1.66-1.78(2H, m), 1.85-1.95(2H, m), 2.50-2.61(2H, m), 2.98-3.06(2H, m), 3.94(6H, s), 4.06-4.16(1H, m), 5.27(2H, s), 7.00(1H, s), 7.45(1H, s), 7.87(1H, s), 8.29(2H, s), 9.19(1H, s) |
| 73 | 64 | ESI+: 535 |
| 74 | 9 | ESI+: 437 |
| 75 | 9 | ESI+: 549 |
| 76 | 64 | ESI+: 546 |
| 77 | 64 | ESI+: 574<br>NMR2: 1.07(6H, d, J = 6.8 Hz), 1.51-1.72(8H, m), 2.51(4H, t, J = 5.2 Hz), 2.69-2.73(1H, m), 2.95(4H, t, J = 5.2 Hz), 3.87(3H, s), 5.14(2H, d, J = 1.2 Hz), 6.91-7.03(3H, m), 7.10-7.15(1H, m), 7.20(1H, d, J = 2.4 Hz), 8.20(2H, s) |
| 78 | 286 | ESI+: 546<br>NMR2: 1.67-1.71(4H, m), 1.76-1.78(4H, m), 2.31(3H, s), 2.54(2H, s), 2.71-2.72(4H, m), 2.85-3.00(4H, m), 5.14(2H, s), 6.84(1H, s), |

TABLE 143-continued

| Ex | Syn | DAT |
|---|---|---|
|  |  | 7.05-7.15(2H, m), 7.30(1H, brs), 7.34-7.60 (1H, m), 8.19(2H, s) |
| 79 | 64 | ESI+: 490<br>NMR2: 2.43(3H, s), 3.56(4H, brs), 3.81(3H, s), 3.96(4H, s), 5.14(2H, s), 6.41(1H, d, J = 8.3 Hz), 6.81(1H, brs), 6.93(1H, dd, J = 8.3, 2.4 Hz), 7.10-7.12(2H, m), 8.17(2H, s) |
| 80 | 64 | ESI+: 518<br>NMR2: 0.95(6H, d, J = 5.4 Hz), 2.30(1H, brs), 3.37(4H, brs), 3.80-3.94(7H, m), 5.14(2H, s), 6.41(1H, d, J = 8.1 Hz), 6.81(1H, brs), 6.93(1H, d, J = 8.5 Hz), 7.11-7.14(2H, m), 8.17(2H, s). |
| 81 | 9 | ESI+: 461<br>NMR1: 1.83-2.07(6H, m), 2.19(3H, s), 2.78-2.88(2H, m), 3.87(6H, s), 3.98-4.09(1H, m), 5.14(2H, s), 7.07(1H, t, J = 8.4 Hz), 7.45(1H, s), 7.88(1H, s), 8.25(2H, s), 9.19(1H, s) |

TABLE 144

| Ex | Syn | DAT |
|---|---|---|
| 82 | 9 | ESI+: 544 |
| 83 | 9 | ESI+: 531 |
| 84 | 9 | ESI+: 585<br>NMR1: 1.34-1.50(2H, m), 1.68-1.89(4H, m), 2.07-2.19(4H, m), 2.47-2.64(4H, m), 2.73-2.95(6H, m), 3.74(3H, s), 3.87(6H, s), 5.16(2H, s), 6.78(1H, d, J = 8.6 Hz), 7.07(1H, t, J = 8.4 Hz), 7.25(1H, dd, J = 8.6, 2.2 Hz), 7.33(1H, d, J = 2.2 Hz), 8.29(2H, s), 9.22(1H, s) |
| 85 | 19 | ESI+: 476 |
| 86 | 9 | ESI+: 384 |
| 87 | 9 | ESI+: 569<br>NMR1: 1.45-1.63(2H, m), 1.75-1.88(2H, m), 2.14(3H, s), 2.16-2.70(14H, m), 2.92-3.08(2H, m), 3.87(6H, s), 5.16(2H, s), 6.92(1H, d, J = 8.4 Hz), 7.07(1H, t, J = 8.4 Hz), 7.40-7.50(2H, m), 8.28(2H, s), 9.19(1H, s) |
| 88 | 9 | ESI+: 501 |
| 89 | 9 | ESI+: 580 |
| 90 | 9 | ESI+: 591 |
| 91 | 9 | ESI+: 589 |
| 92 | 12 | ESI+: 516<br>NMR1: 0.96(6H, d, J = 6.4 Hz), 1.98-2.10(2H, m), 2.82-2.95(2H, m), 3.06-3.15(2H, m), 3.74(3H, s), 3.87(6H, s), 5.16(2H, s), 6.76(1H, d, J = 8.8 Hz), 7.07(1H, t, J = 8.4 Hz), 7.24(1H, dd, J = 8.8, 2.4 Hz), 7.32(1H, d, J = 2.4 Hz), 8.29(2H, s), 9.21(1H, s) |

TABLE 145

| Ex | Syn | DAT |
|---|---|---|
| 93 | 12 | ESI+: 599 |
| 94 | 286 | ESI+: 517 |
| 95 | 12 | ESI+: 556<br>NMR2: 1.76-1.81(8H, m), 2.97(4H, brs), 3.15(4H, brs), 3.88(9H, s), 5.14(2H, s), 6.67(1H, t, J = 8.2 Hz), 6.88-6.90(2H, m), 7.01(1H, dd, J = 8.4, 2.4 Hz), 8.20(2H, s), 9.26(1H, brs) |
| 96 | 64 | ESI+: 570<br>NMR2: 1.62-1.68(8H, m), 2.32(3H, s), 2.43-2.45(4H, m), 2.94-2.97(4H, m), 3.88(9H, s), 5.14(2H, s), 6.67(1H, t, J = 8.2 Hz), 6.88-7.00(3H, m), 7.21-7.22(1H, m), 8.19(2H, t, J = 2.2 Hz) |
| 97 | 12 | ESI+: 500<br>NMR2: 3.81-4.01(17H, m), 5.13(2H, s), 6.40(1H, d, J = 8.3 Hz), 6.64-6.68(1H, m), 6.77(1H, d, J = 7.1 Hz), 6.92(1H, d, J-8.5 Hz), 7.12(1H, brs), 8.17(2H, s) |
| 98 | 64 | ESI+: 514<br>NMR2: 2.38(3H, s), 3.47-3.58(4H, m), 3.81-3.94(13H, m), 5.13(2H, s), 6.40(1H, d, J = 8.5 Hz), 6.64-6.68(1H, m), 6.78(1H, brs), 6.92(1H, dd, J = 8.5, 2.0 Hz), 7.12(1H, d, J = 2.7 Hz), 8.17(2H, s) |
| 99 | 64 | ESI+: 542<br>NMR2: 0.90-0.94(6H, m), 2.10(1H, brs), 3.40-3.96(17H, m), 5.13(2H, s), 6.41(1H, d, J = 8.3 Hz), 6.66(1H, d, J = 8.0 Hz), 6.76(1H, brs), 6.91-6.93(1H, m), 7.13(1H, brs), 8.17(2H, s) |
| 100 | 286 | ESI+: 599<br>NMR2: 1.66-1.69(4H, m), 2.29(3H, s), 2.30(2H, s), 2.40(3H, s), 2.45(4H, brs), 2.70(4H, brs), 2.84-2.87(2H, m), 2.96-3.01(2H, m), 3.88(6H, s), 5.13(2H, s), 6.67(1H, t, J = 8.2 Hz), 6.87(1H, s), 7.04(1H, d, J = 8.8 Hz), 7.29(1H, d, J = 2.8 Hz), 7.34(1H, d, J = 8.4 Hz), 8.18(2H, s) |
| 101 | 286 | ESI+: 588<br>NMR3: 1.08(3H, d, J = 6.4 Hz), 1.12(3H, s), 1.20(3H, s), 1.49-1.52(1H, m), 1.64-1.66(1H, m), 1.94-1.96(1H, m), 2.03-2.04(1H, m), 2.59-2.68(4H, m), 3.29-3.34(2H, m), 3.87(9H, s), 5.15(2H, d, J = 2.0 Hz), 6.89-6.93(2H, m), 7.10-7.13(1H, m), 7.37(1H, d, J = 2.0 Hz), 8.19(2H, d, J = 2.0 Hz) |

TABLE 146

| Ex | Syn | DAT |
|---|---|---|
| 102 | 286 | ESI+: 470 |
| 103 | 9 | ESI+: 502 |
| 104 | 19 | ESI+: 596 |
| 105 | 12 | ESI+: 568 |
| 106 | 106 | ESI+: 582 |
| 107 | 12 | ESI+: 623 |
| 108 | 19 | ESI+: 588<br>NMR2: 1.76-1.81(8H, m), 2.96-2.97(4H, m), 3.15-3.16(4H, m), 3.88(3H, s), 3.94(6H, s), 5.33(2H, s), 6.61(1H, s), 6.89-6.91(2H, m), 7.01(1H, dd, J = 8.0, 2.4 Hz), 7.22-7.26(1H, m), 8.23(2H, s) |
| 109 | 19 | ESI+: 532 |

TABLE 147

| Ex | Syn | DAT |
|---|---|---|
| 110 | 64 | ESI+: 546<br>NMR2: 2.36(3H, brs), 3.45-3.50(4H, m), 3.81(3H, s), 3.93(10H, s), 5.32(2H, s), 6.40(1H, d, J = 8.5 Hz), 6.60(1H, s), 6.76(1H, brs), 6.92-6.95(1H, m), 7.14(1H, s), 8.20(2H, s) |
| 111 | 4 | ESI+: 649 |
| 112 | 10 | ESI+: 543 |
| 113 | 9 | ESI+: 408<br>NMR1: 3.69(2H, dd, J = 11.0, 5.6 Hz), 3.87(6H, s), 4.07(2H, t, J = 5.6 Hz), 4.83(1H, t, J = 5.4 Hz), 5.14(2H, s), 7.07(1H, t, J = 8.4 Hz), 7.45(1H, d, J = 0.6 Hz), 7.88(1H, d, J = 0.6 Hz), 8.26(2H s), 9.20(1H, s) |
| 114 | 20 | ESI+: 490<br>NMR1: 2.13(3H, s), 2.17-2.54(8H, m), 2.66(2H, t, J = 6.8 Hz), 3.87(6H, s), 4.14(2H, t, J = 6.8 Hz), 5.14(2H, s), 7.06(1H, t, J = 8.4 Hz), 7.43(1H, d, J = 0.6 Hz), 7.89(1H, d, J = 0.6 Hz), 8.25(2H, s), 9.20(1H, s) |
| 115 | 18 | ESI+: 477<br>NMR1: 3.58-3.65(1H, m), 3.75-3.84(1H, m), 3.87(6H, s), 4.04-4.10(1H, m), 4.17-4.24(1H, m), 4.41-4.49(1H, m), 4.78(2H, s), 5.15(2H, s), 5.72(1H, s), 7.07(1H, t, J = 8.4 Hz), 7.46(1H, d, J = 0.4 Hz), 7.88(1H, d, J = 0.4 Hz), 8.26(2H, s), 9.27(1H, s) |

TABLE 147-continued

| Ex | Syn | DAT |
| --- | --- | --- |
| 116 | 11 | ESI+: 438<br>NMR1: 3.23-3.38(2H, m), 3.72-3.80(1H, m), 3.84-3.96(7H, m), 4.15(1H, dd, J = 13.8, 4.1 Hz), 4.67(1H, t, J = 5.6 Hz), 4.91(1H, d, J = 5.3 Hz), 5.14(2H, s), 7.06(1H, t, J = 8.4 Hz), 7.45(1H, d, J = 0.6 Hz), 7.87(1H, d, J = 0.6 Hz), 8.26(2H, s), 9.21(1H, s) |
| 117 | 286 | ESI+: 502 |
| 118 | 9 | ESI+: 463 |
| 119 | 12 | APCI/ESI+: 449 |
| 120 | 120 | ESI+: 531 |
| 121 | 13 | ESI+: 463 |
| 122 | 9 | ESI+: 472<br>NMR1: 2.21(3H, s), 2.41-2.48(4H, m), 2.98-3.08(4H, m), 3.87(6H, s), 5.15(2H, s), 6.81-6.90(2H, m), 7.07(1H, t, J = 8.4 Hz), 7.47-7.55(2H, m), 8.26(2H, s), 9.15(1H, s) |

TABLE 148

| Ex | Syn | DAT |
| --- | --- | --- |
| 123 | 9 | ESI+: 555 |
| 124 | 9 | ESI+: 531 |
| 125 | 20 | ESI+: 466 |
| 126 | 20 | ESI+: 453 |
| 127 | 9 | APCI/ESI+: 384 |
| 128 | 20 | ESI+: 453 |
| 129 | 9 | ESI+: 599 |
| 130 | 9 | ESI+: 603 |
| 131 | 120 | ESI+: 599 |
| 132 | 120 | ESI+: 613 |
| 133 | 120 | ESI+: 572 |
| 134 | 12 | ESI+: 505 |
| 135 | 9 | ESI+: 499 |
| 136 | 12 | ESI+: 423 |
| 137 | 12 | ESI+: 447 |
| 138 | 9 | ESI+: 573 |
| 139 | 9 | ESI+: 470 |
| 140 | 9 | ESI+: 505 |
| 141 | 120 | ESI+: 597 |
| 142 | 12 | ESI+: 458 |
| 143 | 12 | ESI+: 476 |
| 144 | 166 + 4 | ESI+: 514 |
| 145 | 12 | ESI+: 486 |
| 146 | 12 | ESI+: 457 |
| 147 | 13 + 4 | ESI+: 611 |
| 148 | 9 + 4 | ESI+: 583 |
| 149 | 9 + 4 | ESI+: 543 |
| 150 | 9 + 4 | ESI+: 557 |
| 151 | 13 | ESI+: 471 |
| 152 | 64 | ESI+: 554 |
| 153 | 9 | ESI+: 567 |

TABLE 149

| Ex | Syn | DAT |
| --- | --- | --- |
| 154 | 9 | ESI+: 474 |
| 155 | 9 | ESI+: 487 |
| 157 | 15 | ESI+: 499 |
| 158 | 16 | ESI+: 501 |
| 159 | 64 | ESI+: 541 |
| 160 | 17 | ESI+: 422 |
| 161 | 161 | ESI+: 515 |
| 162 | 120 + 162 | ESI+: 555 |
| 165 | 9 | ESI+: 487 |
| 166 | 166 | ESI+: 445 |
| 167 | 18 | ESI+: 504 |
| 168 | 12 + 162 | ESI+: 473 |
| 169 | 18 | ESI+: 465 |
| 170 | 13 + 162 | ESI+: 487 |
| 171 | 9 | ESI+: 557 |

TABLE 149-continued

| Ex | Syn | DAT |
| --- | --- | --- |
| 172 | 18 | ESI+: 491 |
| 173 | 20 | ESI+: 477 |
| 174 | 20 | ESI+: 504 |
| 175 | 23 | ESI+: 436 |
| 176 | 9 | ESI+: 461 |
| 177 | 9 | ESI+: 556 |
| 178 | 9 | ESI+: 488 |

TABLE 150

| Ex | Syn | DAT |
| --- | --- | --- |
| 179 | 9 | APCI/ESI+: 487 |
| 180 | 18 | ESI+: 465 |
| 181 | 18 | ESI+: 509 |
| 182 | 9 | ESI+: 483 |
| 183 | 9 | ESI+: 570 |
| 184 | 23 | ESI+: 422 |
| 185 | 9 | ESI+: 556 |
| 186 | 17 | ESI+: 448 |
| 187 | 166 | ESI+: 458 |
| 188 | 16 | ESI+: 422 |
| 189 | 16 | ESI+: 378 |
| 190 | 190 | APCI/ESI+: 407 |
| 191 | 64 | ESI+: 555 |
| 192 | 106 | ESI+: 502 |
| 193 | 19 | ESI+: 571 |
| 194 | 12 | ESI+: 475 |
| 195 | 9 | ESI+: 586 |
| 196 | 18 | ESI+: 491 |
| 197 | 18 | ESI+: 491 |
| 198 | 18 | ESI+: 505 |

TABLE 151

| Ex | Syn | DAT |
| --- | --- | --- |
| 199 | 18 | ESI+: 504 |
| 200 | 18 | ESI+: 518 |
| 201 | 11 | ESI+: 465 |
| 202 | 13 | ESI+: 489 |
| 203 | 20 | ESI+: 504 |
| 204 | 20 | ESI+: 435 |
| 205 | 11 | ESI+: 465 |
| 206 | 20 + 4 | ESI+: 463 |
| 207 | 12 + 4 | ESI+: 476 |
| 208 | 9 | ESI+: 461 |
| 209 | 20 | ESI+: 504 |
| 210 | 20 + 162 | ESI+: 518 |
| 211 | 9 | ESI+: 448 |
| 212 | 212 | ESI+: 422 |
| 213 | 213 | ESI+: 465 |
| 214 | 214 | ESI+: 435 |
| 215 | 12 | ESI+: 461 |
| 216 | 120 | ESI+: 531 |
| 217 | 217 | ESI+: 517 |
| 218 | 17 | ESI+: 436 |
| 219 | 17 | ESI+: 450 |
| 220 | 17 | ESI+: 436 |
| 221 | 17 | ESI+: 450 |
| 222 | 18 | ESI+: 491 |
| 223 | 18 | ESI+: 505 |
| 224 | 18 | ESI+: 491 |
| 225 | 18 | ESI+: 505 |
| 226 | 13 | ESI+: 475 |

TABLE 152

| Ex | Syn | DAT |
| --- | --- | --- |
| 227 | 18 | ESI+: 495 |
| 228 | 18 | ESI+: 479 |

TABLE 152-continued

| Ex | Syn | DAT |
|---|---|---|
| 229 | 9 | ESI+: 503 |
| 230 | 214 | ESI+: 422 |
| 231 | 20 + 162 | ESI+: 504 |
| 232 | 217 | ESI+: 531 |
| 233 | 214 | ESI+: 422 |
| 234 | 217 | ESI+: 547 |
| 235 | 213 | ESI+: 438 |
| 236 | 9 + 4 | ESI+: 517 |
| 237 | 9 | ESI+: 517 |
| 238 | 17 | APCI/ESI+: 422 |
| 239 | 239 | ESI+: 422 |
| 240 | 214 | ESI+: 408 |
| 241 | 20 + 162 | ESI+: 504 |
| 242 | 18 | ESI+: 504 |
| 243 | 18 | ESI+: 505 |
| 244 | 24 | ESI+: 421 |
| 245 | 214 | ESI+: 408 |
| 246 | 246 | APCI/ESI+: 408 |
| 247 | 214 | ESI+: 435 |
| 248 | 20 | ESI+: 490<br>NMR1: 2.14(3H, s), 2.18-2.53(8H, m), 3.45(2H, s), 3.67(3H, s), 3.87(6H, s), 5.15(2H, s), 6.46(1H, s), 7.06(1H, t, J = 8.4 Hz), 8.26(2H, s), 9.42(1H, s) |
| 249 | 20 + 4 | ESI+: 491 |
| 250 | 64 | ESI+: 514 |
| 251 | 214 | ESI+: 435 |
| 252 | 9 | ESI+: 478 |
| 253 | 253 | ESI+: 517 |
| 254 | 254 | ESI+: 461 |
| 255 | 253 | ESI+: 517 |
| 256 | 17 | ESI+: 450 |

TABLE 153

| Ex | Syn | DAT |
|---|---|---|
| 257 | 246 | ESI+: 436 |
| 258 | 24 | ESI+: 449 |
| 259 | 11 | ESI+: 465 |
| 260 | 11 | ESI+: 465 |
| 261 | 18 | ESI+: 505 |
| 262 | 18 | ESI+: 532 |
| 263 | 20 | ESI+: 476 |
| 264 | 254 | ESI+: 507 |
| 265 | 254 | ESI+: 507 |
| 266 | 18 | ESI+: 491 |
| 267 | 18 | ESI+: 463 |
| 268 | 18 | ESI+: 504 |
| 269 | 24 | ESI+: 407 |
| 270 | 214 | APCI/ESI+: 394 |
| 271 | 20 | ESI+: 504 |
| 272 | 20 | ESI+: 477 |
| 273 | 20 | ESI+: 461 |
| 274 | 20 | ESI+: 504 |
| 275 | 20 | ESI+: 504 |
| 276 | 20 | ESI+: 520 |
| 277 | 20 | ESI+: 477 |
| 278 | 278 | ESI+: 390 |
| 279 | 20 | ESI+: 490 |
| 280 | 282 | ESI+: 447 |
| 281 | 282 + 4 | ESI+: 490 |
| 282 | 282 | ESI+: 463 |
| 283 | 282 | ESI+: 490 |
| 284 | 282 | ESI+: 506 |
| 285 | 214 | ESI+: 490 |
| 286 | 286 | ESI+: 533 |

TABLE 154

| Ex | Syn | DAT |
|---|---|---|
| 287 | 286 | ESI+: 501 |
| 288 | 286 | ESI+: 530 |
| 289 | 286 | ESI+: 574 |

TABLE 154-continued

| Ex | Syn | DAT |
|---|---|---|
| 290 | 286 | ESI+: 602 |
| 291 | 286 | ESI+: 601 |
| 292 | 12 | ESI+: 513 |
| 293 | 64 | ESI+: 527 |
| 294 | 64 | ESI+: 555 |
| 295 | 286 | ESI+: 574<br>NMR3: 1.23(6H, s), 1.61-1.64(2H, m), 1.97-1.99(2H, m), 2.57-2.62(5H, m), 3.31-3.34(2H, m), 3.87(9H, s), 5.16(2H, t, J = 1.6 Hz), 6.89-6.94(2H, m), 7.11(1H, dd, J = 8.8, 2.4 Hz), 7.36(1H, d, J = 2.4 Hz), 8.20(2H, s) |
| 296 | 16 | ESI+: 544 |
| 297 | 286 | ESI+: 532 |
| 298 | 286 | ESI+: 502<br>NMR2: 2.61(2H, t, J = 5.6 Hz), 2.69(4H, t, J = 4.8 Hz), 3.16(4H, t, J = 4.8 Hz), 3.66(2H, t, J = 5.6 Hz), 3.88(6H, s), 5.13(2H, s), 6.66(1H, t, J = 8.0 Hz), 6.80(1H, br-s), 6.92(2H, d, J = 9.2 Hz), 7.43(2H, d, J = 9.2 Hz), 8.18(2H, s) |
| 299 | 12 | ESI+: 516<br>NMR2: 1.67-1.69(2H, m), 2.06-2.09(2H, m), 2.70-2.81(3H, m), 2.98(2H, t, J = 5.2 Hz), 3.60(2H, d, J = 12.4 Hz), 3.76-3.77(2H, m), 3.88(6H, s), 5.13(2H, s), 6.66(1H, t, J = 8.0 Hz), 6.82(1H, s), 6.92(2H, d, J = 8.8 Hz), 7.41(2H, d, J = 8.8 Hz), 8.18(2H, s) |
| 300 | 286 | ESI+: 574 |
| 301 | 16 | ESI+: 571 |
| 302 | 302 | ESI+: 516 |
| 303 | 64 | ESI+: 540 |
| 304 | 286 | ESI+: 616 |
| 305 | 4 | ESI+: 529 |
| 306 | 286 | ESI+: 529 |
| 307 | 16 | ESI+: 546 |
| 308 | 12 | ESI+: 488 |
| 309 | 286 | ESI+: 533 |
| 310 | 336 | ESI+: 560 |
| 311 | 12 | ESI+: 580 |
| 312 | 64 | ESI+: 594 |
| 313 | 64 | ESI+: 622 |
| 314 | 286 | ESI+: 534 |

TABLE 155

| Ex | Syn | DAT |
|---|---|---|
| 315 | 315 | ESI+: 630 |
| 316 | 286 | ESI+: 585 |
| 317 | 286 | ESI+: 458 |
| 318 | 286 | ESI+: 458 |
| 319 | 286 | ESI+: 458 |
| 320 | 286 | ESI+: 458 |
| 321 | 315 | ESI+: 547 |
| 322 | 16 | ESI+: 533 |
| 323 | 16 | ESI+: 546 |
| 324 | 11 | ESI+: 482 |
| 325 | 17 | ESI+: 494 |
| 326 | 17 | ESI−: 460 |
| 327 | 286 | ESI+: 448 |
| 328 | 18 | ESI+: 531 |
| 329 | 286 | ESI+: 530 |
| 330 | 286 | ESI+: 517 |
| 331 | 17 | ESI−: 460 |
| 332 | 18 | ESI+: 544 |
| 333 | 286 | ESI+: 516 |
| 334 | 286 | ESI+: 612 |
| 335 | 16 | ESI+: 549 |
| 336 | 336 | ESI+: 480 |
| 337 | 12 | ESI+: 548 |
| 338 | 286 | ESI+: 530 |
| 339 | 11 | ESI+: 478 |
| 340 | 286 | ESI+: 408 |
| 341 | 286 | ESI+: 490 |
| 342 | 286 | ESI+: 477 |
| 343 | 17 | ESI−: 476 |

TABLE 155-continued

| Ex | Syn | DAT |
|---|---|---|
| 344 | 286 | ESI+: 438<br>NMR1: 3.26-3.40(2H, m), 3.76-3.78(1H, m), 3.87(6H, s), 3.89-3.94(1H, m), 4.15(1H, dd, J = 14.0, 4.0 Hz), 4.71(1H, t, J = 5.6 Hz), 4.95(1H, d, J = 5.2 Hz), 5.27(2H, s), 7.05(1H, t, J = 8.4 Hz), 7.41(1H, s), 7.74(1H, d, J = 1.6 Hz), 7.84(1H, d, J = 1.6 Hz), 7.88(1H, s), 8.95(1H, brs) |
| 345 | 64 | ESI+: 562 |
| 346 | 286 | ESI+: 544 |
| 347 | 18 | ESI+: 563 |
| 348 | 18 | ESI+: 521 |
| 349 | 349 | ESI+: 508 |

TABLE 156

| Ex | Syn | DAT |
|---|---|---|
| 350 | 18 | ESI+: 576 |
| 351 | 286 | ESI+: 473 |
| 352 | 286 | ESI+: 422 |
| 353 | 12 | ESI+: 531 |
| 354 | 64 | ESI+: 545 |
| 355 | 286 | ESI+: 597 |
| 356 | 356 | ESI+: 476 |
| 357 | 356 | ESI+: 446 |
| 358 | 356 | ESI+: 446 |
| 359 | 356 | ESI+: 460 |
| 360 | 356 | ESI+: 473 |
| 361 | 356 | ESI+: 486 |
| 362 | 356 | ESI+: 432 |
| 363 | 356 | ESI+: 418 |
| 364 | 356 | ESI+: 432 |
| 365 | 356 | ESI+: 418 |
| 366 | 356 | ESI+: 466 |
| 367 | 356 | ESI+: 478 |
| 368 | 356 | ESI+: 460 |
| 369 | 356 | ESI+: 466 |
| 370 | 356 | ESI+: 378 |
| 371 | 356 | ESI+: 444 |
| 372 | 356 | ESI+: 473 |

TABLE 156-continued

| Ex | Syn | DAT |
|---|---|---|
| 373 | 375 | ESI+: 459 |
| 374 | 375 | ESI+: 433 |
| 375 | 375 | ESI+: 419 |
| 376 | 356 | ESI+: 458 |
| 377 | 356 | ESI+: 447 |
| 378 | 356 | ESI+: 471 |
| 379 | 356 | ESI+: 490 |
| 380 | 356 | ESI+: 417 |
| 381 | 375 | ESI+: 403 |
| 382 | 356 | ESI+: 459 |
| 383 | 356 | ESI+: 501 |
| 384 | 356 | ESI+: 519 |
| 385 | 356 | ESI+: 477 |
| 386 | 356 | ESI+: 459 |
| 387 | 356 | ESI+: 476 |
| 388 | 286 | ESI+: 517 |

INDUSTRIAL APPLICABILITY

The compound of formula (I) or a salt thereof according to the present invention has inhibitory action on FGFR1, FGFR2, and/or FGFR3, particularly, mutant FGFR3, and can be used as a therapeutic agent for various cancers related to FGFR1, FGFR2, and/or FGFR3, such as lung cancer and hormone therapy-resistant breast cancer, stomach cancer, triple negative breast cancer, endometrial cancer, and bladder cancer, particularly as a therapeutic agent for mutant FGFR3-positive bladder cancer.

SEQUENCE LISTING FREE TEXT

The numerical heading <223> in the Sequence Listing shown below contains an explanation of "Artificial Sequence". More specifically, the base sequences represented by SEQ ID NOs: 7, 8, 17, 20, and 21 in the Sequence Listing are artificially synthesized primer sequences. The base sequence represented by SEQ ID NO: 24 in the Sequence Listing is an artificially synthesized FLAG tag sequence.

The invention claimed is:

1. A compound of formula (I) or a salt thereof:

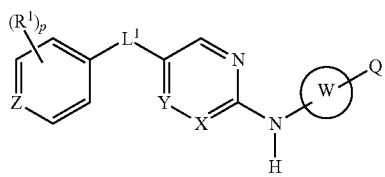

wherein
X is N;
Y is CH;
$L^1$ is ethylene or methylene-O—;
Z is CH;
each $R^1$ is independently lower alkyl optionally substituted with halogen, —O-(lower alkyl optionally substituted with halogen), halogen, cyano, or —N(lower alkyl)$_2$;
p is an integer of from 2 to 4;
ring W is an optionally substituted aromatic carbocyclic ring, an optionally substituted aromatic heterocyclic ring, or an optionally substituted non-aromatic heterocyclic ring;
Q is -$L^2$-$R^2$ or $R^3$;
$L^2$ is an optionally substituted aromatic heterocyclic ring or an optionally substituted non-aromatic heterocyclic ring;
$R^2$ is a non-aromatic heterocyclic group optionally substituted with lower alkyl, optionally substituted cycloalkyl, lower alkyl optionally substituted with at least one selected from the group consisting of —OH and —O-lower alkyl, —C(O)—$R^0$, —C(O)-optionally substituted cycloalkyl, —NH—$R^0$, —N(lower alkyl)-$R^0$, an -$L^3$-optionally substituted non-aromatic heterocyclic group, or H;
$R^0$ is lower alkyl optionally substituted with —OH;
$L^3$ is a bond, —NH—, —N(lower alkyl)-, or lower alkylene; and
$R^3$ is:
a lower alkyl optionally substituted with at least one selected from the group consisting of —C(O)OH, —OH, —O—$R^0$, amino optionally substituted with one or two $R^0$, carbamoyl optionally substituted with one or two $R^0$, an optionally substituted aromatic heterocyclic group, an optionally substituted non-aromatic heterocyclic group, and a —C(O)— optionally substituted non-aromatic heterocyclic group,
—O-(lower alkyl optionally substituted with at least one selected from the group consisting of —C(O)OH, —OH, —O—$R^0$, carbamoyl optionally substituted with one or two $R^0$, an optionally substituted non-aromatic heterocyclic group, and a —C(O)-optionally substituted non-aromatic heterocyclic group), —NH-(lower alkyl optionally substituted with at least one selected from the group consisting of —OH, a non-aromatic heterocyclic group optionally substituted with lower alkyl, and carbamoyl optionally substituted with one or two $R^0$),
—N(lower alkyl)-(lower alkyl optionally substituted with at least one selected from the group consisting of —OH, a non-aromatic heterocyclic group optionally substituted with lower alkyl, and carbamoyl optionally substituted with one or two $R^0$),
—C(O)OH,
—C(O)-optionally substituted non-aromatic heterocyclic group,
—O-(a non-aromatic heterocyclic group optionally substituted with lower alkyl), or carbamoyl optionally substituted with one or two $R^0$.

2. The compound or salt thereof according to claim 1, wherein
each $R^1$ is independently —O-lower alkyl or halogen;
p is 2 or 4; and
ring W is an optionally substituted aromatic carbocyclic ring or an optionally substituted aromatic heterocyclic ring.

3. The compound or salt thereof according to claim 2, wherein
p is 4; and
ring W is an optionally substituted benzene ring or optionally substituted pyrazole.

4. The compound or salt thereof according to claim 1, wherein Q is -$L^2$-$R^2$;
$L^2$ is an optionally substituted non-aromatic heterocyclic ring; and
$R^2$ is lower alkyl optionally substituted with at least one selected from the group consisting of —OH and —O-lower alkyl, —NH-(lower alkyl optionally substituted with —OH), an optionally substituted non-aromatic heterocyclic group, -lower alkylene-(an optionally substituted non-aromatic heterocyclic group), or H.

5. The compound or salt thereof according to claim 4, wherein p is 4;
$L^2$ is piperazine optionally substituted with one or more methyl, piperidine optionally substituted with one or more methyl, or 3,9-diazaspiro[5.5]undecane; and
$R^2$ is piperazine optionally substituted with methyl, piperidine optionally substituted with methyl, 2-hydroxyethylamino, or H.

6. The compound or salt thereof according to claim 5, wherein each $R^1$ is independently —O-methyl or F;
$L^1$ is -methylene-O—;
ring W is a benzene ring optionally substituted with —O-methyl;
$L^2$ is piperidine or 4-methylpiperazine; and
$R^2$ is 4-methylpiperazine, 2-hydroxyethylamino, or H.

7. The compound or salt thereof according to claim 1, wherein ring W is optionally substituted pyrazole;
Q is $R^3$; and R³ is lower alkyl substituted with at least one selected from the group consisting of —C(O)OH, carbamoyl optionally substituted with one or two R⁰, —OH, an optionally substituted non-aromatic heterocyclic group, and —C(O)-(an optionally substituted non-aromatic heterocyclic group).

8. The compound or salt thereof according to claim 7, wherein p is 4; and
R³ is lower alkyl substituted with at least one selected from the group consisting of —OH, a non-aromatic heterocyclic group optionally substituted with lower alkyl, and —C(O)-(a non-aromatic heterocyclic group optionally substituted with —OH).

9. The compound or salt thereof according to claim 8, wherein each R¹ is independently —O-methyl or F;
L¹ is -methylene-O—;
ring W is pyrazole optionally substituted with methyl; and
R³ is 2-hydroxyethyl, 2,3-dihydroxypropyl, or 4-methyl-piperazin-1-ylmethyl.

10. The compound or salt thereof according to claim 1, wherein the compound is selected from the group consisting of:
  5-[2-(2,6-difluoro-3,5-dimethoxyphenyl)ethyl]-N-[3-methoxy-4-(4-methylpiperazin-1-yl)phenyl]pyrimidin-2-amine,
  (2S)-3-[4-({5-[(2,6-difluoro-3,5-dimethoxybenzyl)oxy]pyrimidin-2-yl}amino)-1H-pyrazol-1-yl]propane-1,2-diol,
  5-[2-(2,6-difluoro-3,5-dimethoxyphenyl)ethyl]-N-{3-methoxy-4-[4-(4-methylpiperazin-1-yl)piperidin-1-yl]phenyl}pyrimidin-2-amine,
  5-[2-(2,6-difluoro-3,5-dimethoxyphenyl)ethyl]-N-{3-fluoro-4-[4-(4-methylpiperazin-1-yl)piperidin-1-yl]phenyl}pyrimidin-2-amine,
  5-[(2,6-difluoro-3,5-dimethoxybenzyl)oxy]-N-{3-methoxy-4-[4-(4-methylpiperazin-1-yl)piperidin-1-yl]phenyl}pyrimidin-2-amine,
  5-[(2,6-difluoro-3,5-dimethoxybenzyl)oxy]-N-[3-methoxy-4-(4-methylpiperazin-1-yl)phenyl]pyrimidin-2-amine,
  5-[(2,6-dichloro-3,5-dimethoxybenzyl)oxy]-N-[1-(1-methylpiperidin-4-yl)-1H-pyrazol-4-yl]pyrimidin-2-amine,
  5-[(2,6-dichloro-3,5-dimethoxybenzyl)oxy]-N-[1-(piperidin-4-yl)-1H-pyrazol-4-yl]pyrimidin-2-amine,
  5-[(2,6-difluoro-3,5-dimethoxybenzyl)oxy]-N-{3-methoxy-4-[4-(1-methylpiperidin-4-yl)piperazin-1-yl]phenyl}pyrimidin-2-amine,
  5-[(2,6-difluoro-3,5-dimethoxybenzyl)oxy]-N-{3-methyl-4-[4-(4-methylpiperazin-1-yl)piperidin-1-yl]phenyl}pyrimidin-2-amine,
  5-[(2,6-difluoro-3,5-dimethoxybenzyl)oxy]-N-{4-[(3R,5S)-3,5-dimethylpiperazin-1-yl]-3-methoxyphenyl}pyrimidin-2-amine,
  N-[4-(3,9-diazaspiro[5.5]undec-3-yl)-3-methoxyphenyl]-5-[(2,6-difluoro-3,5-dimethoxybenzyl)oxy]pyrimidin-2-amine,
  2-[4-({5-[(2,6-difluoro-3,5-dimethoxybenzyl)oxy]pyrimidin-2-yl}amino)-1H-pyrazol-1-yl]ethanol,
  5-[(2,6-difluoro-3,5-dimethoxybenzyl)oxy]-N-{1-[2-(4-methylpiperazin-1-yl)ethyl]-1H-pyrazol-4-yl}pyrimidin-2-amine,
  2-[4-({5-[(2,6-difluoro-3,5-dimethoxybenzyl)oxy]pyrimidin-2-yl}amino)-1H-pyrazol-1-yl]-1-(3-hydroxyazetidin-1-yl)ethanone,
  (2R)-3-[4-({5-[(2,6-difluoro-3,5-dimethoxybenzyl)oxy]pyrimidin-2-yl}amino)-1H-pyrazol-1-yl]propane-1,2-diol,
  2-({1-[4-({5-[(2,6-difluoro-3,5-dimethoxybenzyl)oxy]pyrimidin-2-yl}amino)phenyl]piperidin-4-yl}amino)ethanol,
  5-[(2,6-difluoro-3,5-dimethoxybenzyl)oxy]-N-{1-methyl-5-[(4-methylpiperazin-1-yl)methyl]-1H-pyrazol-3-yl}pyrimidin-2-amine, and
  5-[(2,6-difluoro-3,5-dimethoxybenzyl)oxy]-N-[4-(4-methylpiperazin-1-yl)phenyl]pyrimidin-2-amine.

11. The compound or salt thereof according to claim 10, wherein the compound is
  5-[(2,6-difluoro-3,5-dimethoxybenzyl)oxy]-N-{3-methoxy-4-[4-(4-methylpiperazin-1-yl)piperidin-1-yl]phenyl}pyrimidin-2-amine.

12. The compound or salt thereof according to claim 10, wherein the compound is
  2-[4-({5-[(2,6-difluoro-3,5-dimethoxybenzyl)oxy]pyrimidin-2-yl}amino)-1H-pyrazol-1-yl]ethanol.

13. The compound or salt thereof according to claim 10, wherein the compound is
  (2R)-3-[4-({5-[(2,6-difluoro-3,5-dimethoxybenzyl)oxy]pyrimidin-2-yl}amino)-1H-pyrazol-1-yl]propane-1,2-diol.

14. The compound or salt thereof according to claim 10, wherein the compound is
  2-({1-[4-({5-[(2,6-difluoro-3,5-dimethoxybenzyl)oxy]pyrimidin-2-yl}amino)phenyl]piperidin-4-yl}amino)ethanol.

15. The compound or salt thereof according to claim 10, wherein the compound is
  5-[(2,6-difluoro-3,5-dimethoxybenzyl)oxy]-N-{1-methyl-5-[(4-methylpiperazin-1-yl)methyl]-1H-pyrazol-3-yl}pyrimidin-2-amine.

16. The compound or salt thereof according to claim 10, wherein the compound is
  5-[(2,6-difluoro-3,5-dimethoxybenzyl)oxy]-N-[4-(4-methylpiperazin-1-yl)phenyl]pyrimidin-2-amine.

17. A pharmaceutical composition, comprising:
  a compound or salt thereof according to claim 10 and
  a pharmaceutically acceptable excipient.

18. The pharmaceutical composition according to claim 17, wherein the compound is suitable for treatment of mutant FGFR3-positive cancer.

19. A method of manufacturing a pharmaceutical composition, the method comprising:
  manufacturing the pharmaceutical composition with the compound or salt thereof according to claim 10,
  wherein the pharmaceutical composition is suitable for treatment of mutant FGFR3-positive cancer.

20. A method of treating mutant FGFR3-positive cancer, the method comprising:
  administering an effective amount of the compound or salt thereof according to claim 10 to a subject in need thereof.

* * * * *